US010046043B2

(12) United States Patent
Granoff et al.

(10) Patent No.: US 10,046,043 B2
(45) Date of Patent: *Aug. 14, 2018

(54) GNA1870-BASED VESICLE VACCINES FOR BROAD SPECTRUM PROTECTION AGAINST DISEASES CAUSED BY *NEISSERIA MENINGITIDIS*

(71) Applicant: CHILDREN'S HOSPITAL & RESEARCH CENTER AT OAKLAND, Oakland, CA (US)

(72) Inventors: Dan M. Granoff, Berkeley, CA (US); Victor Chen-Hsi Hou, Bethlehem, PA (US)

(73) Assignee: CHILDREN'S HOSPITAL & RESEARCH CENTER AT OAKLAND, Oakland, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/237,495

(22) Filed: Aug. 15, 2016

(65) Prior Publication Data

US 2017/0065699 A1 Mar. 9, 2017

Related U.S. Application Data

(63) Continuation of application No. 14/688,594, filed on Apr. 16, 2015, now Pat. No. 9,452,208, which is a continuation of application No. 11/795,739, filed as application No. PCT/US2006/002523 on Jan. 23, 2005, now Pat. No. 9,034,345.

(60) Provisional application No. 60/647,911, filed on Jan. 27, 2005.

(51) Int. Cl.
  *A61K 39/095* (2006.01)
  *A61K 39/00* (2006.01)
  *A61K 9/127* (2006.01)
  *C07K 14/22* (2006.01)

(52) U.S. Cl.
  CPC ............ *A61K 39/095* (2013.01); *A61K 9/127* (2013.01); *C07K 14/22* (2013.01); *A61K 2039/522* (2013.01); *A61K 2039/575* (2013.01); *Y10S 530/825* (2013.01)

(58) Field of Classification Search
  None
  See application file for complete search history.

(56) References Cited

U.S. PATENT DOCUMENTS

| | | | |
|---|---|---|---|
| 4,601,903 A | 7/1986 | Frasch | |
| 4,727,136 A | 2/1988 | Jennings et al. | |
| 5,597,572 A | 1/1997 | Huergo et al. | |
| 5,705,161 A | 1/1998 | Van Der Ley et al. | |
| 5,747,653 A | 5/1998 | Huergo et al. | |
| 6,180,111 B1 | 1/2001 | Stein et al. | |
| 6,482,807 B1 | 11/2002 | Van Der Ley et al. | |
| 6,936,261 B2 | 8/2005 | Granoff et al. | |
| 8,273,360 B2 | 9/2012 | Pizza et al. | |
| 8,476,032 B2 | 7/2013 | Granoff et al. | |
| 8,968,748 B2 | 3/2015 | Granoff et al. | |
| 9,034,345 B2 | 5/2015 | Granoff et al. | |
| 9,452,208 B2 * | 9/2016 | Granoff | A61K 39/095 |
| 2003/0021812 A1 | 1/2003 | Robinson et al. | |
| 2003/0215469 A1 | 11/2003 | Robinson et al. | |
| 2004/0126389 A1 | 7/2004 | Berthet et al. | |
| 2004/0167068 A1 * | 8/2004 | Zlotnick | C07K 14/22 424/130.1 |
| 2006/0166344 A1 * | 7/2006 | Pizza | A61K 39/095 435/183 |
| 2006/0171957 A1 | 8/2006 | Pizza | |
| 2006/0216307 A1 | 9/2006 | Berthet et al. | |
| 2006/0240045 A1 | 10/2006 | Berthet et al. | |
| 2006/0251670 A1 | 11/2006 | Comanducci et al. | |
| 2009/0035328 A1 | 2/2009 | Granoff | |

FOREIGN PATENT DOCUMENTS

| | | |
|---|---|---|
| EP | 0449958 | 3/1995 |
| EP | 1208214 | 11/2006 |
| WO | WO 1990006696 | 6/1990 |
| WO | WO 1996029412 | 9/1996 |
| WO | WO 1998002547 | 1/1998 |
| WO | WO 1998056901 | 12/1998 |
| WO | WO 1999024578 | 5/1999 |
| WO | WO 1999036544 | 7/1999 |
| WO | WO 1999057280 | 11/1999 |
| WO | WO 1999061053 | 12/1999 |
| WO | WO 2000066791 | 2/2000 |
| WO | WO 2000022430 | 4/2000 |
| WO | WO 2000025811 | 5/2000 |
| WO | WO 2000026384 | 5/2000 |
| WO | WO 2001009350 | 2/2001 |
| WO | WO 2001034642 | 5/2001 |
| WO | WO 2001037863 | 5/2001 |
| WO | WO 2001052885 | 7/2001 |
| WO | WO 2001091788 | 12/2001 |
| WO | WO 2002009746 | 2/2002 |
| WO | WO 2002028888 | 4/2002 |
| WO | WO 2002009643 | 5/2002 |
| WO | WO 2002062378 | 8/2002 |
| WO | WO 2002062380 | 8/2002 |
| WO | WO 2003010194 | 2/2003 |
| WO | WO 2003051379 | 6/2003 |
| WO | WO 2003105890 | 12/2003 |
| WO | WO 2004002523 | 1/2004 |
| WO | WO 2004014417 | 2/2004 |
| WO | WO 2004014418 | 2/2004 |
| WO | WO 2004014419 | 2/2004 |
| WO | WO 2004015099 | 2/2004 |
| WO | WO 2004019977 | 3/2004 |
| WO | WO 2004048404 | 6/2004 |

OTHER PUBLICATIONS

Adu-Bobie et al. In: Abstracts of the 14th International Pathogenic Neisseria Conference, (Ed) Apicella MA et al., Milwaukee, Wisconsin, USA, p. 212, Sep. 5-10, 2004.*

(Continued)

*Primary Examiner* — S. Devi
(74) *Attorney, Agent, or Firm* — Shweta Chandra; Bozicevic, Field & Francis LLP

(57) ABSTRACT

The present invention generally provides methods and compositions for eliciting an immune response against *Neisseria* spp. bacteria in a subject, particularly against a *Neisseria meningitidis* serogroup B strain.

12 Claims, 20 Drawing Sheets

(56) References Cited

OTHER PUBLICATIONS

50 Fed. Reg. 162, Guidelines for Production of Meningocotal Polysaccharide Vaccines Docket No. 84D-0263, Notice of Availability Published Aug. 21, 1985.

Artenstein MS, et al, "Prevention of meningococcal disease by group C polysaccharide vaccine." N Engl J Med 1970;282:417-20.

Ashton, F. E. et al., 1938, "A New Serogroup (L) of *Neisseria meningitdis*"*J. Clin. Microbiol.* 17: 722-727.

Baker, M. G., et al. A 10 year serogroup B meningococcal disease epidemic in New Zealand: descriptive epidemiology, 1991-2000. J Paediatr Child Health. 2001, vol. 37, pp. S13-19.

Balmer P, et al, "Serologic correlates of protection for evaluating the response to meningococcal vaccines," Expert Rev Vaccines 2004;3:77-87.

Beernink & Granoff (2008) "Bactericidal antibody responses induced by meningococcal recombinant chimeric factor H-binding protein vaccines" *Infect. Immun.* 76(6):2568-2575.

Beernink et al, Rapid genetic grouping of factor h-binding protein (genome-derived neisserial antigen 1870), a promising group B meningococcal vaccine candidate. Clin Vaccine Immunol 2006;13:758-63.

Beernink, et al. "Prevalence of factor H-binding protein variants and NadA among meningococcal group B isolates from the United States: implications for the development of a multicomponent group B vaccine" J Infect Dis 2007;195:1472-1479.

Bjerre et al, Complement activation induced by purified Neisseria meningitidis lipopolysaccharide (LPS), outer membrane vesicles, whole bacteria, and an LPS-free mutant. J Infect Dis 2002;185:220-8.

Bjune (1991) "Results of an efficacy trial with an outer membrane vesicle vaccine against systemic serogroup B meningococcal disease in Norway" *NIPH Ann.* 14(2):125-130.

Bjune, et al. (1991) "Effect of outer membrane vesicle vaccine against group B meningococcal disease in Norway" *LANCET* 338(8775):1093-1096.

Bonvehi et al. Three doses of an experimental detoxified L3-derived lipooligosaccharide meningococcal vaccine offer good safety but low immunogenicity in healthy young adults. Clin. Vaccine Immunol., Jul. 21, 2010 doi:10.1128/CVI.00129-10.

Borrow et al, Neisseria meningitidis group B correlates of protection and assay standardization—international meeting report Emory University, Atlanta, Georgia, United States, Mar. 16-17, 2005. Vaccine 2006;24:5093-107.

Borrow, et al., 2001, "Serological Basis for Use of Meningococcal Serogroup C Conjugate Vaccines in the U.K.:Reevaluation of Correlates of Protection", *Infection and Immunity*, 69(3):1568-1573.

Branham, S. E., 1956, "Milestones in the History of Meningocogus", *Canadian Journal of Microbiology*, 2:175-188.

Braun et al, Proinflammatory responses to lipo-oligosaccharide of Neisseria meningitidis immunotype strains in relation to virulence and disease. J Infect Dis 2002;185:1431-8.

Campagne et al. 2000, "Safety and immunogenicity of three doses of a *Neisseria meningitides* A + C diphtheria conjugate vaccine in infants from Niger", *Pediatric Infectious Disease Journal*, 19(2):144-150.

Cantini et al, Solution structure of the immunodominant domain of protective antigen GNA1870 of Neisseria meningetidis. J Biol Chem 2006;281:7220-7 (Epub Dec. 31, 2005).

Cartwright K et al, 1999, "Immunogenicity and reactogenicity in UK infants of a novel meningococcal vesicle vaccine containing multiple class 1 (PorA) outer membrane proteins", *Vaccine*, 17:2612-2619.

Cartwright, K., et al. Meningococcal disease in Europe: epidemiology, mortality, and prevention with conjugate vaccines. Report of a European advisory board meeting in Vienna, Austria, Oct. 6-8, 2000. Vaccine. 2001, vol. 19, pp. 4347-4356.

Christodoulides, M., et al. Immunization with recombinant class 1 outer-membrane protein from *Neisseria meningitidis*: influence of liposomes and adjuvants on antibody avidity, recognition of a native protein and the induction of a bactericidal immune response against meningococci. Microbiology. 1998. vol. 144, pp. 3027-3037.

Claassen et al, Production, characterization, and control of a Neisseria meningitides hexavalent class 1 outer membrane protein containing a vesicle vaccine. Vaccine 1996;14(10)1001-8.

De Groot, A. S., et al. Genome derived vaccines. Expert Rev Vaccines. 2004, vol. 3, pp. 59-76.

De Kleijn et al, 2000, "Immunogenicity and safety of a hexavalent meningococcal outermembrane-vesicle vaccine in children of 2-3 and 7-8 years of age" *Vaccine*, 18(15):1456-1466.

De Wals P, et al, "Effectiveness of a mass immunization campaign against serogroup C meningococcal disease in Quebec," Jama 2001;285:177-81.

Densen P., "Interaction of complement with Neisseria meningitidis and Neisseria gonorrhoeae," Clin Microbiol Rev 1989;2 Suppl:S11-7.

Desmond, N., et al. Getting to grips with an epidemic. Nurs N Z. 2004, vol. 10, p. 2.

Devi S. J. et al, 1996 Binding diversity of monoclonal antibodies to alpha(2-->8) polysialic acid conjugated to outer membrane vesicle via adipic acid dihydrazide. FEMS Immunol Med Microbial. Jul. 1996;14(4):211-20.

Devoe et al, Release of endotoxin in the form of cell wall blebs during in vitro growth of Neisseria meningitidis. J Exp Med 1973;138:1156-67.

Ding, et al. 1981, "Three new serogroups of *Neisseria meningitidis*", J. Biol. Stand. 9: 307-315.

European Patent Application No. 08831589.0. Extended European Search Report dated Dec. 10, 2010, 8 pages.

European Patent Application No. 11182969.3. European Search Report dated Feb. 23, 2012, 12 pages.

Ferrari et al, Outer membrane vesicles from group B Neisseria meningitidis Deltagna33 mutant: Proteomic and immunological comparison with detergent-derived outer membrane vesicles. Proteomics 2006;6:1856-66.

Figueroa JE, et al, "Infectious diseases associated with complement deficiencies," Clin Microbiol Rev 1991;4:359-95.

Fijen CA, et al, "Complement deficiencies in patients over ten years old with meningococcal disease due to uncommon serogroups," Lancet 1989;2:585-8.

Findlow et al, Comparison and correlation of neisseria meningitidis serogroup B immunologic assay results and human antibody responses following three doses of the Norwegian meningococcal outer membrane vesicle vaccine MenBvac. Infect Immun 2006;74:4557-65.

Finne, J., et al. Antigenic similarities between brain components and bacteria causing meningitidis. Implications for vaccine development and pathogenesis. Lancet. 1983, vol. 2, pp. 355-357.

Fisseha et al, Characterization of NOMV prepared from IpxL1 and IpxL2 mutants of Neisseria meningitidis with L3,7 and L8 lipooligosaccharide. Thirteen international Pathogenic Neisseria Conference Nordberg Aksidenstrykkeri, 2002.

Fisseha et al, Characterization of Native Outer Membrane Vesicles from IpxL Mutant Strains of Neisseria meningitidis for Use in Parenteral Vaccination. Infect Immun 2005;73(7):4070-80.

Fletcher et al, Vaccine potential of the Neisseria meningitidis 2086 lipoprotein. Infect Immun 2004;72(4):2088-100.

Frasch C.E. "Meningococcal Vaccines: Past, Present and Future," In: Cartwright K, ed. Meningococcal Disease. New York: John Wiley & Sons, 1995:245-83.

Frasch et al, Meningococcal vaccines: methods and protocols. Totowa, New Jersey: Humana Press, 2001:81-107.

Frasch, C. E. and Chapman, 1973, "Classification of *Neisseria meningitidis* Group B into Distinct Serotypes. III. Application of a New Bactericidal-Inhibition Technique to Distribution of Serotypes among Cases and Carriers" *Journal of Infectious Disease*, 127:149-154.

Fukasawa, L. O., et al. Immune response to native NadA from neisseria meningitidis and its expression in clinical isolates in Brazil. J. Med. Microbiol. 2003, vol. 52, pp. 121-125.

(56) References Cited

OTHER PUBLICATIONS

Fukasawa et al, Adjuvant can improve protection induced by OMV vaccine against Neisseria meningitidis serogroups B/C in neonatal mice. FEMS Immunol Med Microbiol 2004;41:205-10.
Fusco et al., 1997, "Preclinical Evaluation of a Novel Group B Meningococcal Conjugate Vaccine that Elicits Bactericidal Activity in both Mice and Nonhuman Primates", *Journal of Infectious Diseases*, 175: 364-372.
Giuliani et al, A universal vaccine for serogroup B Meningococcus. In: 15th International Pathogenic Neisseria Conference. Cairns, Australia, 2006.
Giuliani et al, The region comprising amino acids 100 to 255 of Neisseria meningitidis lipoprotein GNA 1870 elicits bactericidal antibodies. Infect Immun 2005;73:1151-60.
Gold et al., 1969-1970, "Meningococcal Infections" *Bull. WHO*, 45: 272-282.
Gold R, et al, "Meningococcal infections. 2. Field trial of group C meningococcal polysaccharide vaccine in 1969-70," Bull World Health Organ 1971;45:279-82.
Goldschneider et al, 1969, "Human Immunity to the Meningococcus: I. The Role of the Humoral Antibodies" *J. Exp. Med.* 129:1307-1326.
Goldschneider I, et al, "Human immunity to the meningococcus. II. Development of natural immunity," J Exp Med 1969;129:1327-48.
Gonzalez et al, Immunization with Neisseria meningitidis outer membrane vesicles prevents bacteremia in neonatal mice. Vaccine 2006;24:1633-43.
Gotschlich et al., 1969, "Human Immunity to the Meningococcus: III. Preparation and Immunochemical Properties of the Group A, Group B, and Group C Meningococcal Polysaccharides", *J. Exp. Med.* 129:134-136.
Granoff et al., 1998, "Bacterial Monoclonal Antibodies That Define Unique Meningococcal B Polysaccharide Epitopes That Do Not Cross-React with Human Polysialic Acid", *J. Immunol*; 160: 5028-5036.
Granoff et al., 1998, "Induction of Immunologic Refractoriness in Adults by Meningococcal C Polysaccharide Vaccination", *J. Infect. Dis.* 178(3): 870-4.
Granoff, et al. (2001) "A novel mimetic antigen eliciting protective antibody to Neisseria meningitidis" *J. Immunol.* 167(11):6487-6496.
Granoff, D., et al. Meningococcal Vaccines. In: Vaccines 4th ed., Plotkin, S.A. and Orenstein, W. A., eds. Philadelphia: W.B. Saunders Company, 2003:959-987.
Giuliani, et al. (2006) "A universal vaccine for serogroup B meningococcus" *PNAS USA* 103(29):10834-10839.
Greenspan & Di Cera (1999) "Defining epitopes: It's not as easy as it seems" *Nat. Biotechnol.* 17(10):936-937.
Hankins, 1982, Clinical and Serological Evaluation of a Meningococcal Polysaccharide Vaccine Groups A,C,Y, and W135 (41306), *Proc. Soc. Biol. Med.* 169: 54-57.
Haneberg et al. 1998, "Intranasal Administration of a Meningococcal Outer Membrane Vesicle Vaccine Induces Persistant Local Mucosal Antibodies and Serum Antibodies with Strong Bactericidal Activity in Humans", *Infection and Immunity*, vol. 66(4): 1334-1341.
Harris SL, et al, "Age-related disparity in functional activities of human group C serum anticapsular antibodies elicited by meningococcal polysaccharide vaccine," Infect Immun 2003;71:275-86.
Holst et al, The concept of "tailor-made", protein-based, outer membrane vesicle vaccines against meningococcal disease. Vaccine 2005;23:2202-5.
Holst, et al. (2003) "Serum bactericidal activity correlates with the vaccine efficacy of outer membrane vesicle vaccines against Neisseria meningitidis serogroup B disease" *Vaccine* 21(7-8):734-737.
Hong et al., 1981, "Inhibitory Effect of K-76 Monocarboxylic Acid, an Anticomplementary Agent, on the C3b Inactivator System" *J Immunol.* 127:104-108.
Hou, et al. "Protective antibody responses elicited by a meningococcal outer membrane vesicle vaccine with overexpressed genome-derived neisserial antigen 1870" J. Infect. Dis. 2005;192:580-90 (Epub Jul. 15, 2005).
Hou, et al. "Conformational epitopes recognized by protective anti-neisserial surface protein A antibodies" *Infect. Immun.* 71(12):6844-6849.
Humphries, H.E., et al. Recombinant meningococcal PorA protein, expressed using a vector system with potential for human vaccination, induces a bactericidal immune response. Vaccine. 2004, vol. 22, pp. 1564-1569.
Jacobsson et al, Sequence constancies and variations in genes encoding three new meningococcal vaccine candidate antigens. Vaccine 2006;24:2161-8.
Jansen, C., et al. Immunogenicity of in vitro folded outer membrane protein PorA of Neisseria meningitidis. FEMS Immunol Med Microbiol. 2000, vol. 27, pp. 227-233.
Jennings, H. J., et al. Immunochemistry of groups A, B, and C meningococcal polysaccharide-tetanus toxoid conjugates. J Immunol. 1981, vol. 127, pp. 1011-1018.
Jessouroun et al, Outer membrane vesicles (OMVs) and detoxified lipooligosaccharide (dLOS) obtained from Brazilian prevalent N. meningitidis serogroup B strains protect mice against homologous and heterologous meningococcal infection and septic shock. Vaccine 2004;22:2617-25.
Jodar, L., et al. Development of vaccines against meningococcal disease. Lancet. 2002, vol. 359, pp. 1499-1508.
Kahler et al, Genetic basis for biosynthesis, structure, and function of meningococcal lipooligosaccharide (endotoxin). Crit Rev Microbiol 1998;24:281-334.
Keiser et al. A phase 1 study of a meningococcal native outer membrane vesicle vaccine made from a group B strain with deleted IpxL1 and synX, over-expressed factor H binding protein, two PorAs and stabilized OpcA expression. Vaccine (2011) doi:10.1016/j.vaccine.2010.12.039, in press.
Koeberling, et al. "A Critical Threshold of Meningococcal Factor H Binding Protein Expression Is Required for Increased Breadth of Protective Antibodies Elicited by Native Outer Membrane Vesicle Vaccines", Clin Vaccine Immunol. May 2011; 18(5): 736-742.
Koeberling et al. Improved immunogenicity of a H44/76 group B outer membrane vesicle vaccine with over-expressed genome-derived Neisserial antigen 1870. Vaccine 2007;25:1912-20 (Epub Apr. 21, 2006).
Koeberling, et al. Bactericidal antibody responses elicited by a meningococcal outer membrane vesicle vaccine with overexpressed factor H-binding protein and genetically attenuated endotoxin. J Infect Dis. Jul. 15, 2008;198(2):262-70.
Koeberling, et al. Meningococcal outer membrane vesicle vaccines derived from mutant strains engineered to express factor H binding proteins from antigenic variant groups 1 and 2. Clin Vaccine Immunol. Feb. 2009;16(2):156-62.
Kijek, T., et al. Characterization of genetically detoxified native outer membrane vesicle (NOMV) vaccine prepared for human use. Thirteenth International Pathogenic Neisseria Conference. Norwegian Institute of Public Health, Oslo, Norway; Sep. 1-6, 2002. (Please see Abstracts of the Thirteenth International Pathogenic *Neisseria* Conference, p. 267).
Lehmann et al. 1999, "Human Opsonins Induced during Meningococcal Disease Recognize Outer Membrane Proteins PorA and PorB", *Infection and Immunity*, vol. 67(5):2552-2560.
Lingappa, J. R., et al. Surveillance for meningococcal disease and strategies for use of conjugate meningococcal vaccines in the United States. Vaccine. 2001, vol. 19, pp. 4566-4575.
Luijkx et al, Relative immunogenicity of PorA subtypes in a multivalent Neisseria meningitidis vaccine is not dependent on presentation form. Infect Immun 2003;71:6367-71.
MacDonald et al., 1998, "Induction of Immunologic Memory by Conjugated vs Plain Meningococcal C Polysaccharide Vaccine in Toddlers", *JAMA* 280:1685-1689.
MacDonald et al., 2000, "Can Meningococcal C Conjugate Vaccine Overcome Immune Hyporesponsiveness Induced by Previous Administration of Plain Polysaccharide Vaccine?" JAMA 283:1826-1827.

(56) References Cited

OTHER PUBLICATIONS

MacLennan et al., 2000, "Safety, Immunogenicity, and Induction of Immunologic memory by a Serogroup C Meningococcal Conjugate Vaccine in Infants" JAMA 283: 2795-2801.
Maiden et al., 1998, "Multilocus sequence typing: A portable approach to the identification of clones within populations of pathogenic microorganisms", *Proc. Natl. Acad. Sci.* USA 95:3140-3145.
Madico et al, The meningococcal vaccine candidate GNA1870 binds the complement regulatory protein factor H and enhances serum resistance. J Immunol 2006;177:501-10.
Martin et al, 2000, "Effect of sequence variation in meningococcal PorA outer membrane protein on the effectiveness of a hexavalent PorA outer membrane vesicle vaccine", *Vaccine*, 18:2476-2481.
Martin et al., 2000. "Candidate *Neisseria* meningitidis NspA vaccine", *J. Biotechnol.* 83:27-31.
Martin, D., et al. Recombinant NspA incorporated into liposomal vesicles induces functional antibodies. Thirteenth International Pathogenic Neisseria Conference. Norwegian Institute of Public Health, Oslo, Norway; Sep. 1-6, 2002. (Please see Abstracts of the Thirteenth International Pathogenic *Neisseria* Conference, p. 134).
Masignani et al, Vaccination against Neisseria meningitidis using three variants of the lipoprotein GNA1870. J Exp Med 2003;197(6):789-99.
Maslanka SE, et al. "Age-dependent *Neisseria meningitidis* serogroup C class-specific antibody concentrations and bactericidal titers in sera from young children from Montana immunized with a licensed polysaccharide vaccine," Infect Immun 1998;66:2453-9.
McGuinness, S., et al. Point mutation in meningococcal PorA gene associated with increased endemic disease. Lancet. 1991, vol. 337, pp. 514-517.
Milagres et al., 1994, "Immune Response of Brazilian Children to a *Neisseria meningitidis* Serogroup B Outer Membrane Protein Vaccine; Comparison with Efficacy" *Infection and Immunity*, 62: 4419-4424.
Mirlashari et al, Outer membrane vesicles from Neisseria meningitidis: effects on tissue factor and plasminogen activator inhibitor-2 production in human monocytes. Thromb Res 2001;102:375-80.
Mirlashari et al., Outer membrane vesicles from Neisseria meningitidis: effects on cytokine production in human whole blood. Cytokine 2001;13:91-7.
Moe et al. 1999, "Molecular Mimetics of Polysaccharide Epitopes as Vaccine Candidates for Prevention of *Neisseria Menignitidis* Serogroup B Disease", FEMS Immunology and Medical Microbiology 26, 209-226.
Moe et al. 1999,"Differences in Surface Expression of NspA among Neisseria meningitidis Group B Strains", *Infection and Immunity*, 67:5664-5675.
Moe et al. 2001, "Functional Activity of Anti-Neisserial Surface Protein A Monoclonal Antibodies against Strains of *Neisseria meningitidis* Serogroup B", *Infection and Immunity*, 69:3762-3771.
Moe, G. R., et al. Sequential Immunization with vesicles prepared from heterologous *Neisseria meningitidis* strains elicits broadly protective serum antibodies to group B strains. Infection and Immunity. 2002, vol. 70, pp. 6021-6031.
Morley et al. Vaccine prevention of meningococcal disease, coming soon? Vaccine 2001;20:666-87.
Mukhopadhyay et al, Rapid characterization of outer-membrane proteins in Neisseria lactam ica by SELDI-TOF-MS (surface-enhanced laser desorption ionization-time-of-flight MS) for use in a meningococcal vaccine. Biotechnol Appl Biochem 2005;41:175-82.
Muttilainen, S., et al. The Neisseria meningitidis outer membrane protein P1 produced in bacillus subtilis and reconstituted into phospholipid vesicles elicits antibodies to native P1 epitopes. Microb Pathog. 1995, vol. 18, pp. 423-436.
Næss, et al. 1998, "Human T-Cell Response after Vaccination with the Norwegian Group B Meningococcal Outer Membrane Vesicle Vaccine" *Infection and Immunity*, vol. 66(3): 959-965.
Newcombe et al, Infection with an avirulent phoP mutant of neisseria meningitidis confers broad cross-reactive immunity. Infect Immun 2004;72:338-44.
Nicholson A, Lepow IH. "Host defense against *Neisseria meningitidis* requires a complement-dependent bactericidal activity," Science 1979;205:298-9.
Nøokleby, et al. (2007) "Safety review: two outer membrane vesicle (OMV) vaccines against systemic Neisseria meningitidis serogroup B disease" *Vaccine* 25(16):3080-3084.
O'Dwyer, et al, Expression of heterologous antigens in commensal *Neisseria* spp.: preservation of conformational epitopes with vaccine potential. Infect Immun 2004;72(11):6511-8.
Oliver, K. J., et al. *Neisseria lactamica* protects against experimental meningococcal infection. Infection and Immunity. 2002, vol. 70, pp. 3621-3626.
Parmar et al, Incorporation of bacterial membrane proteins into liposomes: factors influencing protein reconstitution. Biochim Biophys Acta 1999;1421:77-90.
Perrett et al, Towards an improved serogroup B Neisseria meningitidis vaccine. Expert Opin Biol Ther 2005;5:1611-25.
Peeters et al, Immunogenicity of various presentation forms of PorA outer membrane protein of Neisseria meningititdis in mice. Vaccine 1999;17:2702-12.
Peeters et al, Phase I clinical trial with a hexavalent PorA containing meningococcal outer membrane vesicle vaccine. Vaccine 1996;14:1009-15.
Petrov et al, Toxicity and immunogenicity of Neisseria meningitidis lipopolysaccharide incorporated into liposomes. Infect Immun 1992;60:3897-903.
Pillai, et al. (2005) "Outer Membrane Protein (OMP) based Vaccine for *Neisseria meningitidis* Serogroup B" *Vaccine* 23(17-18):2206-2209.
Pizza et al. 2000 "Identification of Vaccine Candidates Against Serogroup B Meningococcus by Whole-Genome Sequencing" *Science* 287:1816-1820.
Pollard AJ, et al, "Development of natural immunity to *Neisseria meningitides*," Vaccine 2001;19:1327-46.
Post et al, Biochemical and functional characterization of membrane blebs purified from Neisseria meningitidis serogroup B. J Biol Chem 2005;280:38383-94.
Raghunathan, P. L., et al. Opportunities for control of meningococcal disease in the United States. Annu Rev Med. 2004, vol. 55, pp. 333-353.
Rouppe Van Der Voort et al., 1997, Human B- and T-cell responses after immunization with a hexavalent PorA meningococcal outer membrane vesicle vaccine. Infect Immun. Dec.;65(12):5184-90.
Rosenstein, N. E., et al. The changing epidemiology of meningococcal disease in the United States, 1992-1996. Journal of Infectious Disease. 1999, vol. 180, pp. 1894-1901.
Rosenqvist et al. "Human Antibody Responses to Meningococcal Outer Membrane Antigens after three Doses of the Norwegian Group B Meningococcal Vaccine", *Infection and Immunity*, vol. 63(12): 46-42-4652.
Rouppe Van Der Voort et al, Immunogenicity studies with a genetically engineered hexavalent PorA and a wild-type meningococcal group B outer membrane vesicle vaccine in infant cynomolgus monkeys. Vaccine 2000;18:1334-43.
Russell, J. E., et al. PorA variable regions of *Neisseria meningitidis*. Emerging Infectious Diseases. 2004, vol. 10, No. 4, pp. 674-678.
Sacchi et al., 1998, "Correlation between Serological and Sequencing Analyses of the Po. rB Outer Membrane Protein in the *Neisseria meningitidis* Serotyping System", *Clin. Dag. Lab. Immunol.* 5:348-354.
Sacchi et al., 2000, "Diversity and Prevalence of PorA Types in *Neisseria meningitidis* Serogroup B in the United States", *Journal of Infectious Diseases*, 182:1169-1176.
Sanchez, S., et al. Interspecific Neisserial high molecular weight proteins able to induce natural immunity responses are strongly correlated with no vitro bactericidal activity. Vaccine. 2002, vol. 20, pp. 2964-2971.
Sandbu, et al. (2007) "Immunogenicity and safety of a combination of two serogroup B meningococcal outer membrane vesicle vaccines" *Clin. Vaccine Immunol.* 14(9):1062-1069.

(56) References Cited

OTHER PUBLICATIONS

Saukkonen et al. 1988, "Monoclonal Antibodies to the Rough Lipopolysaccharide of *Neisseria meningitidis* Protect Infant Rats From Meningococcal Infection" *Journal of Infectious Diseases*, 158: 209-212.
Saunders et al, Immunogenicity of intranasally administered meningococcal native outer membrane vesicles in mice. Infect. and Immun. 1999;67:113-119.
Slaterus, K. W., 1961, Ant. V. Leeuwenhoek, "Types of Meningococcal Isolated from Carriers and Patients ina Non-Epidemic Period in the Netherlands", *J. Microbiol. Serol.* 29: 265-271.
Steeghs et al, Meningitis bacterium is viable without endotoxin. Nature 1998;392:449-50.
Steeghs et al, Teasing apart structural determinants of 'toxicity' and 'adjuvanticity': implications for meningococcal vaccine development. J Endotoxin Res 2004;10:113-9.
Steeghs, et al. (1999) "Immunogenicity of outer membrane proteins in a lipopolysaccharide-deficient mutant of Neisseria meningitidis: influence of adjuvants on the immune response" *Infect. Immun.* 67(10):4988-4993.
Steeghs et al, Outer membrane composition of a lipopolysaccharide-deficient Neisseria meningitidis mutant. EMBO J 2001;20:6937-45.
Steeghs et al. Differential activation of human and mouse Toll-like receptor 4 by the adjuvant candidate LpxL1 of Neisseria meningitidis. Infection and Immunity, Aug. 2008, p. 3801-3807.
Stephens et al. 1991, "Insertion of Tn916 in *Neisseria meningitidis* Resulting in Loss of Group B Capsular Polysaccharide", *Infection and Immunity*, 59: 4097-4107.
Taha et al, Use of available outer membrane vesicle vaccines to control serogroup B meningococcal outbreaks. Vaccine 2007;25:2537-8.
Tappero et al., 1999, "Immunogenicity of 2 Serogroup B Outer-Membrane Protein Meningococcal Vaccines", *JAMA* 281:1520-1572.
Thomas, M., et al. Prevention of group B meningococcal disease by vaccination: a difficult task. N Z Med J. 2004, vol. 117, p. U1016.
Troncoso, G., et al. Antigenic cross-reactivity between outer-membrane proteins of Neisseria meningitidis and commensal Neisseria species. FEMS Immunol Med Microbiol. 2000, vol. 27, pp. 103-109.
Trotter, C.L., et al. Effectiveness of meningococcal serogroup C conjugate vaccine 4 years after introduction. Lancet. 2004, vol. 364, pp. 365-367.
Tzeng et al, Endotoxin of Neisseria meningitidis composed only of intact lipid A: inactivation of the meningococcal 3-deoxy-D-manno-octulosonic acid transferase. J Bacteriol 2002;184:2379-88.
Unemo, et al. (2005) "The porA pseudogene of Neisseria gonorrhoeae—low level of genetic polymorphism and a few, mainly identical, inactivating mutations" *APMIS* 113(6):410-419.

Van Der Ley, et al. (2001) "Modification of lipid A biosynthesis in Neisseria meningitidis IpxL mutants: influence on lipopolysaccharide structure, toxicity, and adjuvant activity" *Infect. Immun.* 69(10):5981-5990.
Van Der Ley, et al. "Construction of *Neisseria meningitidis* strains carrying multiple chromosomal copies of the porA gene for use in the production of a multivalent outer membrane vesicle vaccine" Vaccine. 1995, vol. 13, No. 4, pp. 401-407.
Vandeputte-Rutten, L., et al. Crystal structure of Neisserial surface protein A (NspA), a conserved outer membrane protein with vaccine potential. Journal of Biological Chemistry. 2003, vol. 278, pp. 24825-24830.
Vipond et al, Proteomic analysis of a meningococcal outer membrane vesicle vaccine prepared from the group B strain NZ98/254. Proteomics 2006;6:3400-13.
Wedege, et al. "Functional and specific antibody responses in adult volunteers vaccinated with two different meningococcal serogroup B outer membrane vesicle vaccines in New Zealand" Clin Vaccine Immunol 2007;14(7):830-8.
Wedege et al. 1998, "Immune Response against Major Outer Membrane Antigens of *Neisseria meningitidis* in Vaccines and Controls Contracted Meningococcal Disease during the Norwegian Serogroup B Protection Trail", *Infection and Immunity*, vol. 66(7): 3223-3231.
Welsch, et al. (2008) "Complement-dependent synergistic bactericidal activity of antibodies against factor H-binding protein, a sparsely distributed meningococcal vaccine antigen" *J. Infect. Dis.* 197(7)1053-1061.
Welsch, et al. (2003) "Antibody to genome-derived neisserial antigen 2132, a Neisseria meningitidis candidate vaccine, confers protection against bacteremia in the absence of complement-mediated bactericidal activity" *J. Infect. Dis.* 188(11):1730-1740.
Welsch et al, Protective activity of monoclonal antibodies to genome-derived neisserial antigen 1870, a Neisseria meningitidis candidate vaccine. J Immunol 2004;172:5606-15.
Weynants, et al. " Additive and Synergistic Bactericidal Activity of Antibodies Directed against Minor Outer Membrane Proteins of Neisseria meningitidis", Infect Immun. Nov. 2007; 75(11): 5434-5442.
Wong et al, New Zealand epidemic strain meningococcal B outer membrane vesicle vaccine in children aged 16-24 months. Pediatr Infect Dis J 2007;26:345-50.
World Health Organization. Requirements for meningococcal polysaccharide vaccine (requirements for biological substances No. 23). WHO Tech Rep Ser 1976;594:72-73.
Wyle et al., 1972, "Immunologic Response of Man to Group B Meningococcal Polysaccharide Vaccines", *J Infect. Dis.* 126: 514-522.
Zollinger et al. Design and evaluation in mice of a broadly protective meningococcal group B native outer membrane vesicle vaccine. Vaccine 28, 2010, 5057-5067.
Zollinger, et al., 1979, "Complex of Meningococcal Group B Polysaccharide and Type 2 Outer Membrane Protein Immunogenic in Man", *J Clin. Invest.* 63: 836-848.

* cited by examiner

FIG. 2A
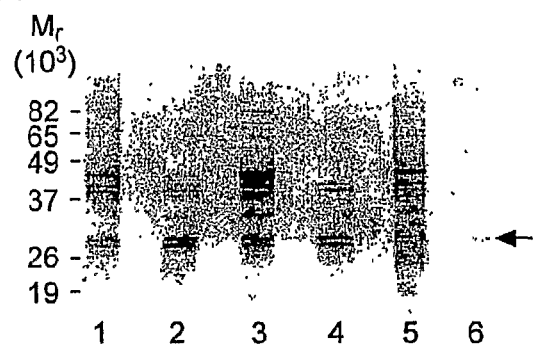
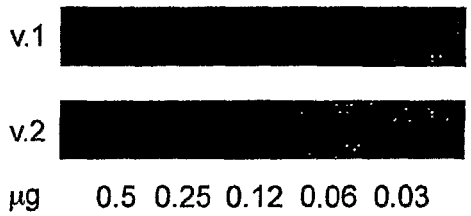
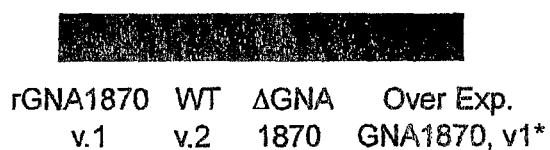

FIG. 7

```
            1
type 1  -19:VNRTAFCCLSLTTALILTACS.....SGGGGVAADIGAGLADALTAPLDH: 26
type 2  -19:VNRTAFCCLSLTAALILTACS.....SGGGGVAADIGAGLADALTAPLDH: 26
type 3  -19:VNRTAFCCLSLTTALILTACSSGGGSGGGGVAADIGTGLADALTAPLDH: 31 type 1  -27:KDKGLQSLTLDQSVRKNEKLKLAAQGAEKTYGND...SLNTGKLKNDKV: 73
type 2  -27:KDKSLQSLTLDQSVRKNEKLKLAAQGAEKTYGND...SLNTGKLKNDKV: 73
type 3   32:KDKSLKSLTLEDSIPQNGTLTLSAQGAEKTFKAGDKDNSLNTGKLKNDKI: 81 type 1   74:SRFDFIRQIEVDGQLITLESGEFQVYKQSHSALTAFQTEQIQDSEHSGKM:123
type 2   74:SRFDFIRQIEVDGQLITLESGEFQIYKQDHSAVVAEQTEKINNPDKIDSL:123
type 3   82:SRFDFVQKIEVDGQTITLASGEFQIYKQNHSAVVALQIEKINNPDKIDSL:131 type 1  124:VAKRQFRIGDIAGEHTSFDKLPEGGRATYRGTAFGSDDAGGKLTYTIDFA:173
type 2  124:INQRSFLVSGLGGEHTAFNQLP.DGKAEYHGKAFSSDDAGGKLTYTIDFA:172
type 3  132:INQRSFLVSGLGGEHTAFNQLP.GGKAEYHGKAFSSDDPNGRLHYSIDFT:180 type 1  174:AKQGNGKIEHLKSPELNVDLAAADIKPDGKRHAVISGSVLYNQAEKGSYS:223
type 2  173:AKQGHGKIEHLKTPEQNVELAAAELKADEKSHAVILGDTRYGSEEKGTYH:222
type 3  181:KKQGYGRIEHLKTLEQNVELAAAELKADEKSHAVILGDTRYGSEEKGTYH:230 type 1  224:LGIFGGKAQEVAGSAEVKTVGIRHIGLAAKQ:255   SEQ ID NO: 74
type 2  223:LALFGDRAQEIAGSATVKIGEKVHEIGIAGKQ:254   SEQ ID NO: 75
type 3  231:LALFGDRAQEIAGSATVKIGEKVHEIGIAGKQ:262   SEQ ID NO: 76
```

FIG. 8A

*SEQ ID NO: 1 – strain MC58 [WO99/57280]*
MNRTAFCCLSLTTALILTACSSGGGVAADIGAGLADALTAPLDHKDKGLQSLTLDQSVRKNEKLKLAAQGAEKTYGNGDSLNTGKLKNDKVSRFD
FIRQIEVDGQLITLESGEFQVYKQSHSALTAFQTEQIQDSEHSGKMVAKRQFRIGDIAGEHTSFDKLPEGGRATYRGTAFGSDDAGGKLTYTIDFA
AKQGNGKIEHLKSPELNVDLAAADIKPDGKRHAVISGSVLYNQAEKGSYSLGIFGGKAQEVAGSAEVRKTVNGIRHIGLAAKQ

*SEQ ID NO: 2 – strain gb185*
MNRTAFCCLSLTTALILTACSSGGGVAADIGAGLADALTAPLDHKDKGLQSLMLDQSVRKNEKLKLAAQGAEKTYGNGDSLNTGKLKNDKVSRFD
FIRQIEVDGKLITLESGEFQVYKQSHSALTALQTEQVQDSEDSGKMVAKRQFRIGDIAGEHTSFDKLPKGGSATYRGTAFGSDDAGGKLTYTIDFA
AKQGHGKIEHLKSPELNVELATAYIKPDEKHHAVISGSVLYNQDEKGSYSLGIFGGQAQEVAGSAEVETANGIHHIGLAAKQ

*SEQ ID NO: 3 – strain m4030*
MNRTAFCCFSLTAALILTACSSGGGVAADIGAGLADALTAPLDHKDKSLQSLTLDQSVRKNEKLKLAAQGAEKTYGNGDSLNTGKLKNDKVSRFD
FIRQIEVDGQLITLESGEFQVYKQSHSALTALQTEQVQDSEDSGKMVAKRQFRIGDIAGEHTSFDKLPKGGSATYRGTAFGSDDAGGKLTYTIDFA
AKQGHGKIEHLKSPELNVELATAYIKPDEKRHAVISGSVLYNQDEKGSYSLGIFGGQAQEVAGSAEVETANGIHHIGLAAKQ

*SEQ ID NO: 4 – strain iss1001*
MNRTAFCCFSLTAALILTACSSGGGVAADIGAGLADALTAPLDHKDKSLQSLTLDQSVRKNEKLKLAAQGAEKTYGNGDSLNTGKLKNDKVSRFD
FIRQIEVDGQLITLESGEFQVYKQSHSALTALQTEQEQDPEHSGKMVAKRRFKIGDIAGEHTSFDKLPKDVMATYRGTAFGSDDAGGKLTYTIDFA
AKQGHGKIEHLKSPELNVELATAYIKPDEKHHAVISGSVLYNQDEKGSYSLGIFGGQAQEVAGSAEVETANGIHHIGLAAKQ

*SEQ ID NO: 5 – strain lnp17592*
MNRTTFFCLSLTAALILTACSSGGGGSGGGGVAADIGAGLADALTAPLDHKDKGLQSLTLDQSVRKNEKLKLAAQGAEKTYGNGDSLNTGKLKNDK
VSRFDFIRQIEVDGQLITLESGEFQVYKQSHSALTALQTEQVQDSEDSGKMVAKRQFRIGDIAGEHTSFDKLPKGGSATYRGTAFGSDDAGGKLTY
TIDFAVKQGHGKIEHLKSPELNVDLAAAYIKPDKKRHAVISGSVLYNQDEKGSYSLGIFGGQAQEVAGSAEVETANGIHHIGLAAKQ

*SEQ ID NO: 6 – strain f6124*
MNRTAFCCLSLTAALILTACSSGGGVAADIGAVLADALTAPLDHKDKSLQSLTLDQSVRKNEKLKLAAQGAEKTYGNGDSLNTGKLKNDKVSRFD
FIRQIEVDGQLITLESGEFQVYKQSHSALTALQTEQVQDSEHSGKMVAKRQFRIGDIAGEHTSFDKLPEGGRATYRGTAFGSDDASGKLTYTIDFA
AKQGHGKIEHLKSPELNVDLAASDIKPDKKRHAVISGSVLYNQAEKGSYSLGIFGGQAQEVAGSAEVETANGIRHIGLAAKQ

*SEQ ID NO: 7 – strain m198172*
MNRTAFCCLSLTAALILTACSSGGGVAADIGAGLADALTAPLDHKDKSLQSLTLDQSVRKNEKLKLAAQGAEKTYGNGDSLNTGKLKNDKVSRFD
FIRQIEVDGQLITLESGEFQVYKQSHSALTALQTEQVQDSEHSGKMVAKRQFRIGDIAGEHTSFDKLPEGGRATYRGTAFGSDDASGKLTYTIDFA
AKQGHGKIEHLKSPELNVDLAASDIKPDKKRHAVISGSVLYNQAEKGSYSLGIFGGQAQEVAGSAEVETANGIRHIGLAAKQ

*SEQ ID NO: 8 – strain m2197*
MNRTAFCCLSLTTALILTACSSGGGVAADIGAGLADALTAPLDHKDKGLQSLMLDQSVRKNEKLKLAAQGAEKTYGNGDSLNTGKLKNDKVSRFD
FIRQIEVDGQLITLESGEFQVYKQSHSALTALQTEQVQDSEHSGKMVAKRQFRIGDIAGEHTSFDKLPEGGRATYRGTAFGSDDAGGKLIYTIDFA
AKQGHGKIEHLKSPELNVDLAAAYIKPDEKHHAVISGSVLYNQAEKGSYSLGIFGGKAQEVAGSAEVKTVNGIRHIGLAAKQ

*SEQ ID NO: 9 – strain m2937*
MNRTAFCCLSLTAALILTACSSGGGGVAADIGAGLADALTAPLDHKDKGLRSLTLDQSVRKNEKLKLAAQGAEKTYGNGDSLNTGKLKNDKVSRFD
FIRQIEVDGQLITLESGEFQVYKQSHSALTALQTEQEQDLEHSGKMVAKRRFRIGDIAGEHTSFDKLREGGRATYRGTAFGSDDAGGKLTYTIDFA
AKQGYGKIEHLKSPELNVDLAAADIKPDEKHHAVISGSVLYNQDEKGSYSLGIFGGEAQEVAGSAEVKTANGIHHIGLAAKQ

*SEQ ID NO: 10 – strain 961-5945*
MNRTAFCCLSLTAALILTACSSGGGGVAADIGAGLADALTAPLDHKDKSLQSLTLDQSVRKNEKLKLAAQGAEKTYGNGDSLNTGKLKNDKVSRFD
FIRQIEVDGQLITLESGEFQIYKQDHSAVVALQIEKINNPDKIDSLINQRSFLVSGLGGEHTAFNQLPDGKAEYHGKAFSDDAGGKLTYTIDFAA
KQGHGKIEHLKTPEQNVELAAAELKADEKSHAVILGDTRYGSEEKGTYHLALFGDRAQEIAGSATVKIGEKVHEIGIAGKQ

*SEQ ID NO: 11 – strain gb013*
MNRTAFCCLSLTAALILTACSSGGGGVAADIGAGLADALTAPLDHKDKSLQSLTLDQSVRKNEKLKLAAQGAEKTYGNGDSLNTGKLKNDKVSRFD
FIRQIEVDGQLITLESGEFQIYKQDHSAVVALQIEKINNPDKIDSLINQRSFLVSGLGGEHTAFNQLPSGKAEYHGKAFSSDDAGGKLTYTIDFAA
KQGHGKIEHLKTPEQNVELASAELKADEKSHAVILGDTRYGGEEKGTYHLALFGDRAQEIAGSATVKIREKVHEIGIAGKQ

FIG. 8B

*SEQ ID NO: 12 – strain 860800*
MNRTAFCCLSLTAALILTACSSGGGGVAADIGAGLADALTAPLDHKDKGLQSLTLDQSVRKNEKLKLAAQGAEKTYGNGDSLNTGKLKNDKVSRFD
FIRQIEVDGQLITLESGEFQIYKQDHSAVVALQIEKINNPDKIDSLINQRSFLVSGLGGEHTAFNQLPSGKAEYHGKAFSSDDPNGRLHYSIDFTK
KQGYGRIEHLKTPEQNVELASAELKADEKSHAVILGDTRYGGEEKGTYHLALFGDRAQEIAGSATVKIREKVHEIGIAGKQ

*SEQ ID NO: 13 – strain 95n477*
MNRTAFCCLSLTAALILTACSSGGGGVAADIGAGLADALTAPLDHKDKSLQSLTLDQSVRKNEKLKLAAQGAEKTYGNGDSLNTGKLKNDKVSRFD
FIRQIEVDGQLITLESGEFQIYKQDHSAVVALQIEKINNPDKIDSLINQRSFLVSGLGGEHTAFNQLPSGKAEYHGKAFSSDDPNGRLHYSIDFTK
KQGYGRIEHLKTPEQNVELASAELKADEKSHAVILGDTRYGGEEKGTYHLALFGDRAQEIAGSATVKIREKVHEIGIAGKQ

*SEQ ID NO: 14 – strain m2671*
MNRTAFCCLSLTAALILTACSSGGGGVAADIGAGLADALTAPLDHKDKSLQSLTLDQSVRKNEKLKLAAQGAEKTYGNGDSLNTGKLKNDKVSRFD
FIRQIEVDGQLITLESGEFQIYKQDHSAVVALQIEKINNPDKIDSLINQRSFLVSGLGGEHTAFNQLPGGKAEYHGKAFSSDDPNGRLHYSIDFTK
KQGYGRIEHLKTPEQNVELASAELKADEKSHAVILGDTRYGSEEKGTYHLALFGDRAQEIAGSATVKIREKVHEIGIAGKQ

*SEQ ID NO: 15 – strain 1000*
MNRTAFCCLSLTAALILTACSSGGGGVAADIGAGLADALTTPLDHKDKSLQSLTLDQSVRKNEKLKLAAQGAEKTYGNGDSLNTGKLKNDKVSRFD
FIRQIEVDGQTITLASGEFQIYKQNHSAVVALQIEKINNPDKIDSLINQRSFLVSGLGGEHTAFNQLPDGKAEYHGKAFSSDDPNGRLHYSIDFTK
KQGYGRIEHLKTPEQNVELASAELKADEKSHAVILGDTRYGGEEKGTYHLALFGDRAQEIAGSATVKIREKVHEIGIAGKQ

*SEQ ID NO: 16 – strain m3279*
MNRTAFCCLSLTAALILTACSSGGGGVAADIGAGLADALTAPLDHKDKSLQSLTLDQSVRKNEKLKLAAQGAEKTYGNGDSLNTGKLKNDKVSRFD
FIRQIEVDGQTITLASGEFQIYKQNHSAVVALQIEKINNPDKIDSLINQRSFLVSGLGGEHTAFNQLPDGKAEYHGKAFSSDDPNGRLHYSIDFTK
KQGYGRIEHLKTPEQNVELASAELKADEKSHAVILGDTRYGGEEKGTYHLALFGDRAQEIAGSATVKIREKVHEIGIAGKQ

*SEQ ID NO: 17 – strain 193-4286*
MNRTAFCCLSLTTALILTACSSGGGGVAADIGAGLADALTAPLDHKDKGLQSLMLDQSVRKNEKLKLAAQGAEKTYGNGDSLNTGKLKNDKVSRFD
FIRQIEVDGQTITLASGEFQIYKQNHSAVVALQIEKINNPDKIDSLINQRSFLVSGLGGEHTAFNQLPDGKAEYHGKAFSSDDPNGRLHYSIDFTK
KQGYGRIEHLKTPEQNVELASAELKADEKSHAVILGDTRYGGEEKGTYHLALFGDRAQEIAGSATVKIREKVHEIGIAGKQ

*SEQ ID NO: 18 – strain m1239*
MNRTAFCCLSLTTALILTACSSGGGGSGGGGVAADIGTGLADALTAPLDHKDKGLKSLTLEDSIPQNGTLTLSAQGAEKTFKAGDKDNSLNTGKLK
NDKISRFDFVQKIEVDGQTITLASGEFQIYKQNHSAVVALQIEKINNPDKTDSLINQRSFLVSGLGGEHTAFNQLPGGKAEYHGKAFSSDDPNGRL
HYSIDFTKKQGYGRIEHLKTLEQNVELAAAELKADEKSHAVILGDTRYGSEEKGTYHLALFGDRAQEIAGSATVKIGEKVHEIGIAGKQ

*SEQ ID NO: 19 – strain 16889*
MNRTAFCCLFLTTALILTACSGGGGSGGGGVAADIGTGLADALTAPLDHKDKGLKSLTLEDSIPQNGTLTLSAQGAEKTFKAGDKDNSLNTGKLK
NDKISRFDFVQKIEVDGQTITLASGEFQIYKQDHSAVVALQIEKINNPDKIDSLINQRSFLVSGLGGEHTAFNQLPGGKAEYHGKAFSSDDAGGKL
TYTIDFAAKQGHGKIEHLKTPEQNVELAAAELKADEKSHAVILGDTRYGSEEKGTYHLALFGDRAQEIAGSATVKIGEKVHEISIAGKQ

*SEQ ID NO: 20 – strain gb355*
MNRTAFCCLFLTTALILTACSGGGGSGSGGVAADIGTGLADALTTPLDHKDKGLKSLTLEDSIPQNGTLTLSAQGAEKTFKAGDKDNSLNTGKLK
NDKISRFDFVQKIEVDGQTITLASGEFQIYKQDHSAVVALQIEKINNPDKIDSLINQRSFLVSGLGGEHTAFNQLPGGKAEYHGKAFSSDDAGGKL
TYTIDFAAKQGHGKIEHLKTPEQNVELAAAELKADEKSHAVILGDTRYGSEEKGTYHLALFGDRAQEIAGSATVKIGEKVHEIGIAGKQ

*SEQ ID NO: 21 – strain m3813*
MNRTAFCCLFLTTALILTACSSGGGGSGGIAADIGTGLADALTAPLDHKDKGLKSLTLEDSIPQNGTLTLSAQGAEKTFKAGDKDNSLNTGKLKND
KISRFDFVQKIEVDGQTITLASGEFQIYKQDHSAVVALQIEKINNPDKIDSLINQRSFLVSGLGGEHTAFNQLPGGKAEYHGKAFSSDDAGGKLTY
TIDFAAKQGHGKIEHLKTPEQNVELAAAELKADEKSHAVILGDTRYGSEEKGTYHLALFGDRAQEIAGSATVKIGEKVHEIGIAGKQ

*SEQ ID NO: 22 – strain ngp165*
MNRTTFCCLSLTTALILTACSGGGGSGGGGVAADIGAGLADALTAPLDHKDKGLKSLTLEDSIPQNGTLTLSAQGAEKTFKAGGKDNSLNTGKLK
NDKISRFDFVQKIEVDGQTITLASGEFQIYKQDHSAVVALQIEKINNPDKTDSLINQRSFLVSGLGGEHTAFNQLPGGKAEYHGKAFSSDDPNGRL
HYTIDFTNKQGYGRIEHLKTPEQNVELASAELKADEKSHAVILGDTRYGSEEKGTYHLALFGDRAQEIAGSATVKIGEKVHEIGIAGKQ

*SEQ ID NO: 23 – strain fa1090*
MNRTTFCCLSLTAGPDSDRLQQRRGGGGGVAADIGTGLADALTAPLDHKDKGLKSLTLEASIPQNGTLTLSAQGAEKTFKAGGKDNSLNTGKLKND
KISRFDFVQKIEVDGQTITLASGEFQIYKQDHSAVVALRIEKINNPDKIDSLINQRSFLVSDLGGEHTAFNQLPDGKAEYHGKAFSSDDADGKLTY
TIDFAAKQGHGKIEHLKTPEQNVELASAELKADEKSHAVILGDTRYGGEEKGTYRLALFGDRAQEIAGSATVKIGEKVHEIGIADKQ

FIG. 8C

*SEQ ID NO: 24 – strain MC58*
CSSGGGGVAADIGAGLADALTAPLDHKDKGLQSLTLDQSVRKNEKLKLAAQGAEKTYGNGDSLNTGKLKNDKVSRFDFIRQIEVDGQLITLESGEF
QVYKQSHSALTAFQTEQIQDSEHSGKMVAKRQFRIGDIAGEHTSFDKLPEGGRATYRGTAFGSDDAGGKLTYTIDFAAKQGNGKIEHLKSPELNVD
LAAADIKPDGKRHAVISGSVLYNQAEKGSYSLGIFGGKAQEVAGSAEVKTVNGIRHIGLAAKQ

*SEQ ID NO: 25 – strain gb185*
CSSGGGGVAADIGAGLADALTAPLDHKDKGLQSLMLDQSVRKNEKLKLAAQGAEKTYGNGDSLNTGKLKNDKVSRFDFIRQIEVDGKLITLESGEF
QVYKQSHSALTALQTEQVQDSEDSGKMVAKRQFRIGDIAGEHTSFDKLPKGGSATYRGTAFGSDDAGGKLTYTIDFAAKQGHGKIEHLKSPELNVE
LATAYIKPDEKHHAVISGSVLYNQDEKGSYSLGIFGGQAQEVAGSAEVETANGIHHIGLAAKQ

*SEQ ID NO: 26 – strain m4030*
CSSGGGGVAADIGAGLADALTAPLDHKDKSLQSLTLDQSVRKNEKLKLAAQGAEKTYGNGDSLNTGKLKNDKVSRFDFIRQIEVDGQLITLESGEF
QVYKQSHSALTALQTEQVQDSEDSGKMVAKRQFRIGDIAGEHTSFDKLPKGGSATYRGTAFGSDDAGGKLTYTIDFAAKQGHGKIEHLKSPELNVE
LATAYIKPDEKRHAVISGSVLYNQDEKGSYSLGIFGGQAQEVAGSAEVETANGIHHIGLAAKQ

*SEQ ID NO: 27 – strain iss1001*
CSSGGGGVAADIGAGLADALTAPLDHKDKSLQSLTLDQSVRKNEKLKLAAQGAEKTYGNGDSLNTGKLKNDKVSRFDFIRQIEVDGQLITLESGEF
QVYKQSHSALTALQTEQEQDPEHSGKMVAKRRFKIGDIAGEHTSFDKLPKDVMATYRGTAFGSDDAGGKLTYTIDFAAKQGHGKIEHLKSPELNVE
LATAYIKPDEKHHAVISGSVLYNQDEKGSYSLGIFGGQAQEVAGSAEVETANGIHHIGLAAKQ

*SEQ ID NO: 28 – strain lnp17592*
CSSGGGGSGGGGVAADIGAGLADALTAPLDHKDKGLQSLTLDQSVRKNEKLKLAAQGAEKTYGNGDSLNTGKLKNDKVSRFDFIRQIEVDGQLITL
ESGEFQVYKQSHSALTALQTEQVQDSEDSGKMVAKRQFRIGDIAGEHTSFDKLPKGGSATYRGTAFGSDDAGGKLTYTIDFAVKQGHGKIEHLKSP
ELNVDLAAAYIKPDKKRHAVISGSVLYNQDEKGSYSLGIFGGQAQEVAGSAEVETANGIHHIGLAAKQ

*SEQ ID NO: 29 – strain f6124*
CSSGGGGVAADIGAVLADALTAPLDHKDKSLQSLTLDQSVRKNEKLKLAAQGAEKTYGNGDSLNTGKLKNDKVSRFDFIRQIEVDGQLITLESGEF
QVYKQSHSALTALQTEQVQDSEHSGKMVAKRQFRIGDIAGEHTSFDKLPEGGRATYRGTAFGSDDASGKLTYTIDFAAKQGHGKIEHLKSPELNVD
LAASDIKPDKKRHAVISGSVLYNQAEKGSYSLGIFGGQAQEVAGSAEVETANGIRHIGLAAKQ

*SEQ ID NO: 30 – strain m198172*
CSSGGGGVAADIGAGLADALTAPLDHKDKSLQSLTLDQSVRKNEKLKLAAQGAEKTYGNGDSLNTGKLKNDKVSRFDFIRQIEVDGQLITLESGEF
QVYKQSHSALTALQTEQVQDSEHSGKMVAKRQFRIGDIAGEHTSFDKLPEGGRATYRGTAFGSDDASGKLTYTIDFAAKQGHGKIEHLKSPELNVD
LAASDIKPDKKRHAVISGSVLYNQAEKGSYSLGIFGGQAQEVAGSAEVETANGIRHIGLAAKQ

*SEQ ID NO: 31 – strain m2197*
CSSGGGGVAADIGAGLADALTAPLDHKDKGLQSLMLDQSVRKNEKLKLAAQGAEKTYGNGDSLNTGKLKNDKVSRFDFIRQIEVDGQLITLESGEF
QVYKQSHSALTALQTEQVQDSEHSGKMVAKRQFRIGDIAGEHTSFDKLPEGGRATYRGTAFGSDDAGGKLIYTIDFAAKQGHGKIEHLKSPELNVD
LAAAYIKPDEKHHAVISGSVLYNQAEKGSYSLGIFGGKAQEVAGSAEVKTVNGIRHIGLAAKQ

*SEQ ID NO: 32 – strain m2937*
CSSGGGGVAADIGAGLADALTAPLDHKDKGLRSLTLDQSVRKNEKLKLAAQGAEKTYGNGDSLNTGKLKNDKVSRFDFIRQIEVDGQLITLESGEF
QVYKQSHSALTALQTEQEQDLEHSGKMVAKRRFRIGDIAGEHTSFDKLREGGRATYRGTAFGSDDAGGKLTYTIDFAAKQGYGKIEHLKSPELNVD
LAAADIKPDEKHHAVISGSVLYNQDEKGSYSLGIFGGEAQEVAGSAEVKTANGIHHIGLAAKQ

*SEQ ID NO: 33 – strain 961-5945*
CSSGGGGVAADIGAGLADALTAPLDHKDKSLQSLTLDQSVRKNEKLKLAAQGAEKTYGNGDSLNTGKLKNDKVSRFDFIRQIEVDGQLITLESGEF
QIYKQDHSAVVALQIEKINNPDKIDSLINQRSFLVSGLGGEHTAFNQLPDGKAEYHGKAFSSDDAGGKLTYTIDFAAKQGHGKIEHLKTPEQNVEL
AAAELKADEKSHAVILGDTRYGSEEKGTYHLALFGDRAQEIAGSATVKIGEKVHEIGIAGKQ

*SEQ ID NO: 34 – strain gb013*
CSSGGGGVAADIGAGLADALTAPLDHKDKSLQSLTLDQSVRKNEKLKLAAQGAEKTYGNGDSLNTGKLKNDKVSRFDFIRQIEVDGQLITLESGEF
QIYKQDHSAVVALQIEKINNPDKIDSLINQRSFLVSGLGGEHTAFNQLPSGKAEYHGKAFSSDDAGGKLTYTIDFAAKQGHGKIEHLKTPEQNVEL
ASAELKADEKSHAVILGDTRYGGEEKGTYHLALFGDRAQEIAGSATVKIREKVHEIGIAGKQ

*SEQ ID NO: 35 – strain 860800*
CSSGGGGVAADIGAGLADALTAPLDHKDKGLQSLTLDQSVRKNEKLKLAAQGAEKTYGNGDSLNTGKLKNDKVSRFDFIRQIEVDGQLITLESGEF
QIYKQDHSAVVALQIEKINNPDKIDSLINQRSFLVSGLGGEHTAFNQLPSGKAEYHGKAFSSDDPNGRLHYSIDFTKKQGYGRIEHLKTPEQNVEL
ASAELKADEKSHAVILGDTRYGGEEKGTYHLALFGDRAQEIAGSATVKIREKVHEIGIAGKQ

FIG. 8D

*SEQ ID NO: 36 – strain 95n477*
CSSGGGGVAADIGAGLADALTAPLDHKDKSLQSLTLDQSVRKNEKLKLAAQGAEKTYGNGDSLNTGKLKNDKVSRFDFIRQIEVDGQLITLESGEF
QIYKQDHSAVVALQIEKINNPDKIDSLINQRSFLVSGLGGEHTAFNQLPSGKAEYHGKAFSSDDPNGRLHYSIDFTKKQGYGRIEHLKTPEQNVEL
ASAELKADEKSHAVILGDTRYGEEKGTYHLALFGDRAQEIAGSATVKIREKVHEIGIAGKQ

*SEQ ID NO: 37 – strain m2671*
CSSGGGGVAADIGAGLADALTAPLDHKDKSLQSLTLDQSVRKNEKLKLAAQGAEKTYGNGDSLNTGKLKNDKVSRFDFIRQIEVDGQLITLESGEF
QIYKQDHSAVVALQIEKINNPDKIDSLINQRSFLVSGLGGEHTAFNQLPGGKAEYHGKAFSSDDPNGRLHYSIDFTKKQGYGRIEHLKTPEQNVEL
ASAELKADEKSHAVILGDTRYGSEEKGTYHLALFGDRAQEIAGSATVKIREKVHEIGIAGKQ

*SEQ ID NO: 38 – strain 1000*
CSSGGGGVAADIGAGLADALTTPLDHKDKSLQSLTLDQSVRKNEKLKLAAQGAEKTYGNGDSLNTGKLKNDKVSRFDFIRQIEVDGQTITLASGEF
QIYKQNHSAVVALQIEKINNPDKIDSLINQRSFLVSGLGGEHTAFNQLPDGKAEYHGKAFSSDDPNGRLHYSIDFTKKQGYGRIEHLKTPEQNVEL
ASAELKADEKSHAVILGDTRYGGEEKGTYHLALFGDRAQEIAGSATVKIREKVHEIGIAGKQ

*SEQ ID NO: 39 – strain m3279*
CSSGGGGVAADIGAGLADALTAPLDHKDKSLQSLTLDQSVRKNEKLKLAAQGAEKTYGNGDSLNTGKLKNDKVSRFDFIRQIEVDGQTITLASGEF
QIYKQNHSAVVALQIEKINNPDKIDSLINQRSFLVSGLGGEHTAFNQLPDGKAEYHGKAFSSDDPNGRLHYSIDFTKKQGYGRIEHLKTPEQNVEL
ASAELKADEKSHAVILGDTRYGGEEKGTYHLALFGDRAQEIAGSATVKIREKVHEIGIAGKQ

*SEQ ID NO: 40 – strain 193-4286*
CSSGGGGVAADIGAGLADALTAPLDHKDKGLQSLMLDQSVRKNEKLKLAAQGAEKTYGNGDSLNTGKLKNDKVSRFDFIRQIEVDGQTITLASGEF
QIYKQNHSAVVALQIEKINNPDKIDSLINQRSFLVSGLGGEHTAFNQLPDGKAEYHGKAFSSDDPNGRLHYSIDFTKKQGYGRIEHLKTPEQNVEL
ASAELKADEKSHAVILGDTRYGGEEKGTYHLALFGDRAQEIAGSATVKIREKVHEIGIAGKQ

*SEQ ID NO: 41 – strain m1239*
CSSGGGGSGGGGVAADIGTGLADALTAPLDHKDKGLKSLTLEDSIPQNGTLTLSAQGAEKTFKAGDKDNSLNTGKLKNDKISRFDFVQKIEVDGQT
ITLASGEFQIYKQNHSAVVALQIEKINNPDKTDSLINQRSFLVSGLGGEHTAFNQLPGGKAEYHGKAFSSDDPNGRLHYSIDFTKKQGYGRIEHLK
TLEQNVELAAAELKADEKSHAVILGDTRYGSEEKGTYHLALFGDRAQEIAGSATVKIGEKVHEIGIAGKQ

*SEQ ID NO: 42 – strain 16889*
CSSGGGGSGGGGVAADIGTGLADALTAPLDHKDKGLKSLTLEDSIPQNGTLTLSAQGAEKTFKAGDKDNSLNTGKLKNDKISRFDFVQKIEVDGQT
ITLASGEFQIYKQDHSAVVALQIEKINNPDKIDSLINQRSFLVSGLGGEHTAFNQLPGGKAEYHGKAFSSDDAGGKLTYTIDFAAKQGHGKIEHLK
TPEQNVELAAAELKADEKSHAVILGDTRYGSEEKGTYHLALFGDRAQEIAGSATVKIGEKVHEISIAGKQ

*SEQ ID NO: 43 – strain gb355*
CSSGGGGSGSGGVAADIGTGLADALTTPLDHKDKGLKSLTLEDSIPQNGTLTLSAQGAEKTFKAGDKDNSLNTGKLKNDKISRFDFVQKIEVDGQT
ITLASGEFQIYKQDHSAVVALQIEKINNPDKIDSLINQRSFLVSGLGGEHTAFNQLPGGKAEYHGKAFSSDDAGGKLTYTIDFAAKQGHGKIEHLK
TPEQNVELAAAELKADEKSHAVILGDTRYGSEEKGTYHLALFGDRAQEIAGSATVKIGEKVHEIGIAGKQ

*SEQ ID NO: 44 – strain m3813*
CSSGGGGSGGIAADIGTGLADALTAPLDHKDKGLKSLTLEDSIPQNGTLTLSAQGAEKTFKAGDKDNSLNTGKLKNDKISRFDFVQKIEVDGQTIT
LASGEFQIYKQDHSAVVALQIEKINNPDKIDSLINQRSFLVSGLGGEHTAFNQLPGGKAEYHGKAFSSDDAGGKLTYTIDFAAKQGHGKIEHLKTP
EQNVELAAAELKADEKSHAVILGDTRYGSEEKGTYHLALFGDRAQEIAGSATVKIGEKVHEIGIAGKQ

*SEQ ID NO: 45 – strain ngp165*
CSSGGGGSGGGGVAADIGAGLADALTAPLDHKDKGLKSLTLEDSIPQNGTLTLSAQGAEKTFKAGGKDNSLNTGKLKNDKISRFDFVQKIEVDGQT
ITLASGEFQIYKQDHSAVVALQIEKINNPDKTDSLINQRSFLVSGLGGEHTAFNQLPGGKAEYHGKAFSSDDPNGRLHYTIDFTNKQGYGRIEHLK
TPEQNVELASAELKADEKSHAVILGDTRYGSEEKGTYHLALFGDRAQEIAGSATVKIGEKVHEIGIAGKQ

*SEQ ID NO: 46 – N-terminal sequence for expression*
GPDSDRLQQRRG

*SEQ ID NO: 47 – PCR primer*
CGCGGATCCCATATGGTCGCCGCCGACATCG

*SEQ ID NO: 48 – PCR primer*
CCCGCTCGAGTTGCTTGGCGGCAAGGC

*SEQ ID NO: 49 – PCR primer*
CGCGGATCCCATATGGGCCCTGATTCTGACCGCCTGCAGCAGCGGAGGGTCGCCGCCGACATCGG

FIG. 8E

*SEQ ID NO: 50 - strain FN131217*
MNRTAFCCLSLTAALILTACSSGGGGVAADIGAGLADALTAPLDHKDKSLQSLTLDQSVRKNEKLKLAAQGAEKTYGNGDSLNTGKLKNDKVSRFD
FIRQIEVDGQLITLESGEFQVYKQSHSALTALQTEQVQDSEHSGKMVAKRQFRIGDIAGEHTSFDKLPEGGRATYRGTAFGSDDASGKLTYTIDFA
AKQGHGKIEHLKSLELNVDLAASDIKPDKKRHAVISGSVLYNQAEKGSYSLGIFGGQAQEVAGSAEVETANGIRHIGLAAKQ

*SEQ ID NO: 51 - strain ES14933*
MNRTAFCCFSLTAALILTACSSGGGGVAADIGAGLADALTAPLDHKDKSLQSLTLDQSVRKNEKLKLAAQGAEKTYGNGDSLNTGKLKNDKVSRFD
FIRQIEVDGQLITLESGEFQIYKQDHSALTALQTEQEQDPEHSGKMVAKRRFKIGDIAGEHTSFDKLPKDVMATYRGTAFGSDDAGGKLTYTIDFA
AKQGHGKIEHLKSPELNVELATAYIKPDEKHHAVISGSVLYNQDEKGSYSLGIFGGQAQEVAGSAEVETANGIHHIGLAAKQ

*SEQ ID NO: 52 - strain GB0993*
MNRTAFCCLSLTTALILTACSSGGGGVAADIGAGLADALTAPLDHKDKGLQSLMLDQSVRKNEKLKLAAQGAEKTYGNGDSLNTGKLKNDKVSRFD
FIRQIEVDGQLITLESGEFQVYKQSHSALTALQTEQVQDSEDSGKMVAKRQFRIGDIAGEHTSFDKLPKDVMATYRGTAFGSDDAGGKLTYTIDFA
AKQGHGKIEHLKSPELNVELAAAYIKPDEKHHAVISGSVLYNQDEKGSYSLGIFGGQAQEVAGSAEVETANGIQHIGLAAKQ

*SEQ ID NO: 53 - strain M6190*
MNRYTFCCLSLTAALILTACSSGGGGVAADIGAGLADALTAPLDHKDKGLQSLTLDQSVRKNEKLKLAAQGAEKTYGNGDSLNTGKLKNDKVSRFD
FIRQIEVNGQLITLESGEFQVYKQSHSALTALQTEQVQDSEHSRKMVAKRQFRIGDIAGEHTSFDKLPKGDSATYRGTAFGSDDAGGKLTYTIDFA
AKQGYGKIEHLKSPELNVDLAAAYIKPDEKHHAVISGSVLYNQDEKGSYSLGIFGGQAQEVAGSAEVKTANGIRHIGLAAKQ

FIG. 8F

SEQ ID NO: 54 - *strain F19324*
MNRTAFCCLSLTAALILTACSSGGGGVAADIGAGLADALTAPLDHKDKSLQSLTLDQSVRKNEKLKLAAQGAEKTYGNGDSLNTGKLKNDKVSRFD
FIRQIEVDGQLITLESGEFQVYKQSHSALTAFQTEQIQDSEHSGKMVAKRQFRIGDIAGEHTSFDKLPEGGRATYRGTAFGSDDAGGKLTYTIDFA
AKQGNGKIEHLKSPELNVDLAAADIKPDGKRHAVISGSVLYNQAEKGSYSLGIFGGKAQEVAGSAEVKTVNGIRHIGLAAKQ

SEQ ID NO: 55 - *strain ISS1113*
MNRTAFCCLSLTTALILTACSSGGGGVTADIGTGLADALTAPLDHKDKGLKSLTLEDSISQNGTLTLSACGAEKTYGNGDSLNTGKLKNDKVSRFD
FIRQIEVDGKLITLESGEFQVYKQSHSALTALQTEQVQDSEDSGKMVAKRQFRIGDIAGEHTSFDKLPKGGSATYRGTAFGSDDAGGKLTYTIDFA
AKQGHGKIEHLKSPELNVELATAYIKPDEKHHAVISGSVLYNQDEKGSYSLGIFGGQAQEVAGSAEVETANGIHHIGLAAKQ

SEQ ID NO: 56 - *strain gb0345*
MNRTAFCCFSLTAALILTACSSGGGGVAADIGAGLADALTAPLDHKDKGLQSLTLDQSVRKNEKLKLAAQGAEKTYGNGDSLNTGKLKNDKVSRFD
FIRQIEVDGKLITLESGEFQVYKQSHSALTALQTEQVQDSEDSGKMVAKRQFRIGDIAGEHTSFDKLPKGGSATYRGTAFGSDDAGGKLTYTIDFA
AKQGHGKIEHLKSPELNVELATAYIKPDEKRHAVISGSVLYNQDEKGSYSLGIFGGQAQEVAGSAEVETANGIHHIGLAAKQ

SEQ ID NO: 57 - *strain M0445*
MNRTAFCCLSLTAALILTACSSGGGGVAADIGAGLADALTAPLDHKDKGLQSLTLDQSVRKNEKLKLAAQGAEKTYGNGDSLNTGKLKNDKVSRFD
FIRQIEVDGQLITLESGEFQVYKQSHSALTALQTEQVQDSEDSGRMVAKRQFRIGDIAGEHTSFDKLPKGGSATYRGTAFSSDDAGGKLTYTIDFA
AKQGHGKIEHLKSPELNVELATAYIKPDEKRHAVISGSVLYNQDEKGSYSLGIFGGQAQEVAGSAEVETANGIQHIGLAAKQ

SEQ ID NO: 58 - *strain MK82*
MNRTAFCCLSLFAALILTACSSGGGGVAADIGAGLADALTAPLDHKDKSLQSLTLDQSVRKNEKLKLAAQGAEKTYGNGDSLNTGKLKNDKVSRFD
FIRQIEVDGQLITLESGEFQIYKQDHSAVVALQIEKINNPDKIDSLINQRSFLVSGLGGEHTAFNQLPVDKAEYHGKAFSSDDAGGKLTYTIDFAA
KQGHGKIEHLKTPEQNVELASAELKADEKSHAVILGDTRYGSEEKGTYHLALFGDRAQEIAGSATVKIGEKVHEIGIAGKQ

SEQ ID NO: 59 - *strain 8047*
MNRTAFCCLSLTAALILTACSSGGGGVAADIGARLADALTAPLDHKDKSLQSLTLDQSVRKNEKLKLAAQGAEKTYGNGDSLNTGKLKNDKVSRFD
FIRQIEVDGQLITLESGEFQIYKQDHSAVVALQIEKINNPDKIDSLINQRSFLVSGLGGEHTAFNQLPDGKAEYHGKAFSSDDAGGKLTYTIDFAA
KQGHGKIEHLKTPEQNVELAAAELKADEKSHAVILGDTRYGSEEKGTYHLALFGDRAQEIAGSATVKIGEKVHEIGIAGKQ

SEQ ID NO: 60 - *strain C4678*
MNRTAFCCLSLTTALILTACSSGGGGVAADIGAGLADALTAPLDHKDKSLQSLTLDQSVRKNEKLKLAAQGAEKTYGNGDSLNTGKLKNDKVSRFD
FIRQIEVDGQLITLESGEFQIYKQDHSAVVALQIEKINNPDKIDSLINQRSFLVSGLGGEHTAFNQLPGCKAEYHGKAFSSDDAGGKLTYTIDFAA
KQGHGKIEHLKTPEQNVELAAAELKADEKSHAVILGDTRYGSEEKGTYHLALFGDRAQEIAGSATVKIGEKVHEIGIAGKQ

SEQ ID NO: 61 - *strain ISS1133*
MNRTAFCCLSLTTALILTACSSGGGGVAADIGAGLADALTAPLDHKDKGLQSLTLDQSVRKNEKLKLAAQGAEKTYGNGDSLNTGKLKNDKVSRFD
FIRQIEVDGQLITLESGEFQIYKQDHSAVVALQIEKINNPDKIDSLINQRSFLVSGLGGEHTAFNQLPDGKAEYHGKAFSSDDAGGKLTYTIDFAA
KQGHGKIEHLKTPEQNVELAAAELKADEKSHAVILGDTRYGSEEKGTYHLALFGDRAQEIAGSATVKIGEKVHEIGIAGKQ

SEQ ID NO: 62 - *strain NG6/88*
MNRTAFCCLSLTTALILTACSSGGGGVAADIGTGLADALTAPLDHKDKGLQSLTLDQSVRKNEKLKLAAQGAEKTYGNGDSLNTGKLKNDKVSRFD
FIRQIEVDGQLITLESGEFQIYKQDHSAVVALQIEKINNPDKIDSLINQRSFLVSGLGGEHTAFNQLPSGKAEYHGKAFSSDDAGGKLTYTIDFAA
KQGHGKIEHLKTPEQNVELASAELKADEKSHAVILGDTRYGSEEKGTYHLALFGDRAQEIAGSATVKIREKVHEIGIAGKQ

SEQ ID NO: 63 - *strain M0579*
MNRTAFCCLSLTAALILTACSSGGGGVAADIGAGLADALTAPLDHKDKSLQSLTLDQSVRKNEKLKLAAQGAEKTYGNGDSLNTGKLKNDKVSRFD
FIRQIEVDGQLITLESGEFQIYKQDHSAVVALQIEKINNPDKIDSLINQRSFLVSGLGGEHTAFNQLPSGKAEYHGKAFSFDDAGGKLTYTIDFAA
KQGHGKIEHLKTPEQNVELASAELKADEKSHAVILGDTRYGSEEKGTYHLALFGDRAQEIAGSATVKIREKVHEIGIAGKQ

SEQ ID NO: 64 - *strain F16325*
MNRTAFCCFSLTAALILTACSSGGGGVAADIGAGLADALTAPLDHKDKGLQSLTLDQSVRKNEKLKLAAQGAEKTYGNGDSLNTGKLKNDKVSRFD
FIRQIEVDGQLITLESGEFQIYKQDHSAVVALQIEKINNPDKIDSLINQRSFLVSGLGGEHTAFNQLPSGKAEYHGKAFSSDDFNGRLHYSIDFTK
KQGYGRIEHLKTPEQNVELASAELKADEKSHAVILGDTRYGSEEKGTYHLALFGDRAQEIAGSATVKIREKVHEIGIAGKQ

SEQ ID NO: 65 - *strain gb988*
MNRTTFCCLSLTAALILTACSSGGGGSGGGGVAADIGTGLADALTAPLDHKDKGLKSLTLEDSIPQNGTLTLSAQGAEKTFKAGDKDNSLBTGKLK
NDKISRFDFVQKIEVDGQTITLASGEFQIYKQNHSAVVALQIEKINNPDKIDSLINQRSFLVSGLGGEHTAFNQLPGDKAEYHGKAFSSDDPNGRL
HYTIDFTNKQGYGRIEHLKTPRLNVDLASAELKADEKSHAVILGDTRYGSEEKGTYHLALFGDRAQEIAGSATVKIGEKVHEIGIAGKQ

FIG. 8G

*SEQ ID NO: 66 – strain 220173i*
MNRTAFCCLSLTTALILTACSSGGGGVAADIGAGLADALTAPLDHKDKGLQSLTLDQSVRKNEKLKLAAQGAEKTYGNGDSLNTGKLKNDKVSRFD
FIRQIEVDGQLITLESGEFQVYKQSHSALTAFQTEQIQDSEHSGKMVAKRQFRIGDIAGEHTSFDKLPEGGRATYRGTAFGSDDAGGKLTYTIDFA
AKQGNGKIEHLKSPELNVDLAAADIKPDGKRHAVISGSVLYNQAEKGSYSLGIFGGKA

*SEQ ID NO: 67 – strain gb101*
MNRTTFCCLSLTAALILTACSSGGGGSGGGGVAADIGAGLADALTAPLDHKDKGLKSLTLEDSISQNGTLTLSAQGAERTFKAGDKDNSLNTGKLK
NDKISRFDFIRQIEVDGQLITLESGEFQVYKQSHSALTALQTEQVQDSEHSGKMVAKRQFRIGDIVGEHTSFGKLPKDVMATYRGTAFGSDDAGGK
LTYTIDFAAKQGHGKIEHLKSPELNVDLAAADIKPDEKHHAVISGSVLYNQAEKGSYSLGIFGGQAQEVAGSAEVETANGIRHIGLAAKQ

*SEQ ID NO: 68 – strain nge31*
MNRTAFCCLSLTAALILTACSSGSGGGVAADIGTGLAYALTAPLDHKDKSLQSLTLDQSVRKNEKLKLAAQGAEKTYGNGDSLNTGKLKNDKVSR
FDFIRQIEVDGQLITLESGEFQIYKQDHSAVVALQIEKINNPDKIDSLINQRSFLVSGLGGEHTAFNQLPGGKAEYHGKAFSSDDPNGRLHYSIDF
TKKQGYGRIEHLKTPEQNVELASAELKADEKSHAVILGDTRYGCEEKGTYHLALFGDRAQEIAGSATVKIREKVHEIGIAGKQ

*SEQ ID NO:69 Triple NMB1870 tandem (MC58, 2996 and m1239)*
VAADIGAGLADALTAPLDHKDKGLQSLTLDQSVRKNEKLKLAAQGAEKTYGNGDSLNTGKLKNDKVSRFDFIRQIEVDGQLITLESGEFQVYKQSH
SALTAFQTEQIQDSEHSGKMVAKRQFRIGDIAGEHTSFDKLPEGGRATYRGTAFGSDDAGGKLTYTIDFAAKQGNGKIEHLKSPELNVDLAAADIK
PDGKRHAVISGSVLYNQAEKGSYSLGIFGGKAQEVAGSAEVKTVNGIRHIGLAAKQGSGGGGVAADIGAGLADALTAPLDHKDKSLQSLTLDQSVR
KNEKLKLAAQGAEKTYGNGDSLNTGKLKNDKVSRFDFIRQIEVDGQLITLESGEFQIYKQDHSAVVALQIEKINNPDKIDSLINQRSFLVSGLGGE
HTAFNQLPDGKAEYHGKAFSSDDAGGKLTYTIDFAAKQGHGKIEHLKTPEQNVELAAAELKADEKSHAVILGDTRYGSEEKGTYHLALFGDRAQEI
AGSATVKIGEKVHEIGIAGKQGSGGGGVAADIGTGLADALTAPLDHKDKGLKSLTLEDSIPQNGTLTLSAQGAEKTFKAGDKDNSLNTGKLKNDKI
SRFDFVQKIEVDGQTITLASGEFQIYKQNHSAVVALQIEKINNPDKTDSLINQRSFLVSGLGGEHTAFNQLPGGKAEYHGKAFSSDDPNGRLHYSI
DFTKKQGYGRIEHLKTLEQNVELAAAELKADEKSHAVILGDTRYGSEEKGTYHLALFGDRAQEIAGSATVKIGEKVHEIGIAGKQ

*SEQ ID NO:70 NadA from Hajj strains*
MKHFPSKVLTTAILATFCSGALAATNDDDVKKAATVAIAAAYNNGQEINGFKAGETIYDIDEDGTITKKDATAADVEADDFKGLGLKKVVTNLTKT
VNENKQNVDAKVKAAESEIEKLTTKLADTDAALADTDAALDATTNALNKLGENITTFAEETKTNIVKIDEKLEAVADTVDKHAEAFNDIADSLDET
NTKADEAVKTANEAKQTAEETKQNVDAKVKAAETAARGKAEAAAGTANTAADKAEAVAAKVTDIKADIATNKDNIAKKANSADVYTREESDSKFVRI
DGLNATTEKLDTRLASAEKSITEHGTRLNGLDRTVSDLRKETRQGLAEQAALSGLFQPYNVGRFNVTAAVGGYKSESAVAIGTGFRFTENFAAKAG
VAVGTSSGSSAAYHVGVNYEW

*SEQ ID NO: 71 – glycine linker*
GSGGGG

```
VR1 5      PLQ--NIQ-P ---------- ---QVTK R   SEQ ID NO: 85
VR1 7      AQAA-NGG-- -----ASGQV KVTKVTK A   SEQ ID NO: 86
VR1 12     KLSSTNAK-- --TGN----- KVE-VTK A   SEQ ID NO: 87
VR1 17     PPQK-NQSQP ---------- -V--VTK A   SEQ ID NO: 88
VR1 18     PPSK--G-Q- --TGN----- ---KVTK G   SEQ ID NO: 89
VR1 19     PPSK---SQP ---------- QV-KVTK A   SEQ ID NO: 90
VR1 20     QPQTANT--- -QQGG----- KV-KVTK A   SEQ ID NO: 91
VR1 21     QPQVTNG--- -VQGN----- QV-KVTK A   SEQ ID NO: 92
VR1 22     QPSKAQG-Q- --TNN----- QV-KVTK A   SEQ ID NO: 93
VR1 31     PPSSNQGKNQ AQTGNT---- ----VTK A   SEQ ID NO: 94
```

B

```
VR2 1      YV-AVENGV- ---------- AKKVA   SEQ ID NO: 95
VR2 2      HF-VQQTP-- -------KSQ PTLVP   SEQ ID NO: 96
VR2 3      TL-ANGANNT II-------- --RVP   SEQ ID NO: 97
VR2 4      HV-VVNNK-- ---------V ATHVP   SEQ ID NO: 98
VR2 9      YV-DEQ---- ---------- SKYHA   SEQ ID NO: 99
VR2 10     HF-VQNK--- ------QNQR PTLVP   SEQ ID NO: 100
VR2 13     YW-TTV-NTG SATTTTT--- --FVP   SEQ ID NO: 101
VR2 14     YV-DEKK--- ---------- -MVHA   SEQ ID NO: 102
VR2 15     HY-TRQNN-- ---------A DVFVP   SEQ ID NO: 103
VR2 16     YY-TKDT--- -------NNN LTLVP   SEQ ID NO: 104
VR2 23     HW-NTVYNTN GTTTT----- --FVP   SEQ ID NO: 105
VR2 25     TY-TVDSS-- --------GV VTPVP   SEQ ID NO: 106
VR2 26     HF-VADS--- -------QGK ITRVP   SEQ ID NO: 107
VR2 28     YYYTTATNSS TSTT------ --FVP   SEQ ID NO: 108
VR2 30     HY-TTVYN-- -ATTTTTT-- --FVP   SEQ ID NO: 109
VR2 34     YV-DDQGK-- ---------- -VKGP   SEQ ID NO: 110
VR2 35     TF-TLESN---------QMK --PVP   SEQ ID NO: 111
```

GNA1870-BASED VESICLE VACCINES FOR BROAD SPECTRUM PROTECTION AGAINST DISEASES CAUSED BY *NEISSERIA MENINGITIDIS*

CROSS-REFERENCE TO RELATED APPLICATIONS

This application is a continuation of U.S. application Ser. No. 14/688,594, filed Apr. 16, 2015, now U.S. Pat. No. 9,452,208, which is a continuation of U.S. application Ser. No. 11/795,739, filed Apr. 24, 2008, now U.S. Pat. No. 9,034,345 issued May 19, 2015, which claims the priority benefit of PCT/US2006/002523 filed on Jan. 23, 2006, which claims the priority benefit of U.S. provisional application Ser. No. 60/647,911, filed Jan. 27, 2005, all of which are hereby incorporated by reference in their entirety.

STATEMENT REGARDING FEDERALLY SPONSORED RESEARCH

This invention was made with government support under Public Health Service grant nos. RO1 AI46464, R21 AI1061533, awarded by the National Institute of Allergy and Infectious Diseases of the National Institutes of Health, and T32-HL007951, awarded by the National Heart, Lung and Blood Institute of the National Institutes of Health. The government has certain rights in the invention.

FIELD OF THE INVENTION

This invention relates to broad-spectrum vaccines for the prevention of diseases caused by *Neisseria meningitidis*.

BACKGROUND OF THE INVENTION

*Neisseria meningitidis* is a Gram-negative bacterium which colonizes the human upper respiratory tract and is responsible for worldwide sporadic and cyclical epidemic outbreaks of, most notably, meningitis and sepsis. The attack and morbidity rates are highest in children under 2 years of age. Like other Gram negative bacteria, *Neisseria meningitidis* typically possess a cytoplasmic membrane, a peptidoglycan layer, an outer membrane which together with the capsular polysaccharide constitute the bacterial wall, and pili which project into the outside environment. Encapsulated strains of *Neisseria meningitidis* are a major cause of bacterial meningitis and septicemia in children and young adults (Rosenstein et al. J Infect Dis 1999; 180:1894-901).

Humans are the only known reservoir for *Neisseria meningitidis* spp. Accordingly, *Neisserial* species have evolved a wide variety of highly effective strategies to evade the human immune system. These include expression of a polysaccharide capsule that is structurally identical with host polysialic acid (i.e. serogroup B) and high antigenic mutability for the immunodominant noncapsular epitopes, i.e. epitopes of antigens that are present at the surface in relatively large quantities, are accessible to antibodies, and elicit a strong antibody response.

The prevalence and economic importance of invasive *Neisseria meningitidis* infections have driven the search for effective vaccines that can confer immunity across serotypes, and particularly across group B serotypes or serosubtypes. However, many efforts to develop broad spectrum vaccines have been hampered by the wide variety of highly effective strategies used by *Neisserial* species to evade the human immune system.

Capsular-based vaccines are available for prevention of disease caused by group A, C, Y and W-135 strains (reviewed in Granoff et al. Meningococcal Vaccines. In: Plotkin S A, Orenstein W A, eds. Vaccines. 4th ed. Philadelphia: W. B. Saunders Company, 2003). However, there is no vaccine approved for use in the U.S. or Europe for prevention of disease caused by group B strains, which account for about 30% of disease in North America (Lingappa et al. Vaccine 2001; 19:4566-75; Raghunathan et al. Annu Rev Med 2004; 55:333-5) and more than two-thirds of cases in Europe (Cartwright et al. Vaccine 2001; 19:4347-56; Trotter et al. Lancet 2004; 364:365-7). One reason for the lack of a group B capsular-based vaccine is that the group B capsule can elicit an autoantibody response in humans (Finne et al. Lancet 1983; 2:355-7), and the polysaccharide is poorly immunogenic, even when conjugated to carrier proteins (Jennings et al. J Immunol 1981; 127:1011-8). There also are potential safety issues for a capsular-based group B vaccine that is capable of eliciting autoreactive group B anticapsular antibodies. Therefore, recent group B meningococcal vaccine research has focused on the use of non-capsular antigens.

Outer membrane vesicle (OMV) vaccines have been proven to elicit protective immunity against group B meningococcal disease in humans (reviewed in Jodar et al. Lancet 2002; 359:1499-1508). Recently an OMV vaccine was licensed and introduced in New Zealand in response to a public health intervention to halt a group B epidemic that has been ongoing for more than a decade (Thomas et al. N Z Med J 2004; 117:U1016; Desmond et al. Nurs N Z 2004; 10:2; Baker et al. J Paediatr Child Health 2001; 37:513-9). Other vesicle-based approaches to immunization have been described (see, e.g., Cartwright K et al, 1999, Vaccine; 17:2612-2619; de Kleinjn et al, 2000, Vaccine, 18:1456-1466; Rouupe van der Voort E R, 2000, Vaccine, 18:1334-1343; Tappero et al., 1999, *JAMA* 281:1520; Rouupe van der Voort E R, 2000, Vaccine, 18:1334-1343; US 2002/0110569; WO 02/09643).

Immunization of children and adults with meningococcal outer membrane vesicle (OMV) vaccines induces serum bactericidal antibodies, a serological correlate of protection against disease (Goldschneider et al, 1969, J. Exp. Med. 129:1307). The efficacy of OMV vaccines for prevention of meningococcal B disease also has been demonstrated directly in older children and adults in randomized, prospective clinical trials, and in retrospective case-control studies. Thus, the clinical effectiveness of outer membrane vesicle vaccines is not in dispute. Such vaccines are licensed for use in children in New Zealand, and close to licensure in Norway for use in older children and adults, and are in late-stage clinical development for licensure in other European countries. An OMV vaccine prepared by the Finley Institute in Cuba also is available commercially and has been given to millions of children in South America.

However, the serum bactericidal antibody response to OMV vaccines tends to be strain specific (Tappero et al., 1999, *JAMA* 281:1520; and Rouupe van der Voort E R, 2000, Vaccine, 18:1334-1343). Moreover, currently available OMV vaccines are also limited in that the bactericidal antibody responses are largely directed against surface-exposed loops of a major porin protein, PorA (Tappero et al. *JAMA* 1999; 281:1520-7), which is antigenically variable (Sacchi et al. J Infect Dis 2000; 182:1169-76). Because of the immunodominance of PorA, the immunity induced is predominantly specific to the strains from which the membrane vesicles were obtained (Tappero et al., 1999, *JAMA* 281:1520; Martin S L et al, 2000, Vaccine, 18:2476-2481).

Thus, OMV vaccines are useful for prevention of disease in epidemic situations caused by a predominant meningococcal strain with a single PorA serosubtype, such as the P1.4 epidemic strain in New Zealand (Baker et al. 2001, supra). However, there is considerable PorA diversity among strains causing endemic disease such as that found in the U.S (Sacchi et al. 2000, supra). Furthermore, even minor amino acid polymorphisms can decrease susceptibility of strains to the bactericidal activity of antibodies to PorA (Martin et al. Vaccine 2000; 18:2476-81).

The completion of genome sequencing projects for several Neisseria meningitidis strains provided a catalogue of all potential meningococcal protein antigens. Through a combination of bioinformatics, microarray technology, proteomics and immunologic screening, a large number of new meningococcal vaccine candidates have been identified (Pizza et al. Science 2000; 287:1816-20; De Groot et al. Expert Rev Vaccines 2004; 3:59-76). Among these numerous candidates is Genome derived Neisserial Antigen 1870 (GNA1870). GNA1870, which is also known as NMB 1870 (WO 2004/048404) or LP2086 (see, e.g., Fletcher et al. Infect Immun 2004 72:2088-2100), is an approximately 27 kDa lipoprotein expressed in all N. meningitidis strains tested (Masignani et al. J Exp Med 2003; 197:789-99; Giuliani et al. Infect. Immun 2005; 73:1151-60; Welsch et al J Immunol 2004; 172:5606-15).

N. meningitidis strains can be sub-divided into three GNA1870 variant groups (v.1, v.2, and v.3) based on amino acid sequence variability and immunologic cross-reactivity (Masignani et al. J Exp Med 2003; 197:789-99). Variant 1 strains account for about 60% of disease-producing group B isolates (Masignani et al. 2003, supra). Within each variant group, there is on the order of about 92% or greater conservation of amino acid sequence.

Mice immunized with recombinant GNA1870 developed high serum bactericidal antibody responses against strains expressing GNA1870 proteins of the homologous variant group (Masignani et al. 2003, supra; Welsch et al. 2004, supra). However, a number of strains that expressed subvariants of the respective GNA1870 protein were resistant to anti-GNA1870 complement-mediated bacteriolysis. Although the cause of this phenomenon is not known, conceivably this may be due to minor GNA1870 polymorphisms, or due to strain differences in the accessibility of critical GNA1870 epitopes on the surface of the bacteria that result in decreased binding and/or complement activation by the anti-GNA1870 antibodies. The recombinant GNA1870 protein vaccine used in the above immunogenicity studies was expressed in E. coli as a His-Tag protein devoid of the leader peptide. The recombinant protein also lacked the motif necessary for post-translational lipidation, which may decrease immunogenicity (Fletcher et al. Infect Immun 2004; 72:2088-100).

The vaccine potential of a combination of recombinant PorA and recombinant GNA1870 has been explored (Fletcher et al. Infect Immun 2004, 72:2088-1200). There was no apparent interference in the antibody responses to the two antigens when the combination vaccine was given to mice. However, the recombinant combination required restoration of conformation PorA epitopes, which are necessary for eliciting ant-PorA bactericidal antibodies (See, for example, Christodoulides et al, Microbiology, 1998; 144: 3027-37 and Muttilainen et al, Microb Pathog 1995; 18:423-36). Also, the combination recombinant vaccine was not shown to enhance anti-GNA1870 bactericidal antibodies against N. meningitidis strains expressing subvariants of the GNA1870 protein used in the vaccine.

O'Dwyer et al. (Infect Immun 2004; 72:6511-80) describes preparation of an outer membrane vesicle (OMV) vaccine from a commensal N. flavescens strain that was genetically engineered to express Neisserial surface protein A (NspA), a highly conserved meningococcal membrane protein vaccine candidate that is not naturally-expressed by N. flavescens. The immunized mice developed NspA-specific serum opsonophagocytic activity. Also, after absorption of antibodies to the OMV, the residual anti-NspA antibodies conferred passive protection to mice given a lethal challenge of an encapsulated N. meningitidis strain. However, the antibodies elicited by the modified N. flavescens OMV vaccine in this study were not shown to give superior protection to those elicited by the OMV from N. flavescens that did not express the heterologous antigen. Also, the modified N. flavescens OMV did not elicit serum bactericidal antibody responses whereas in previous studies, mice immunized with recombinant NspA expressed in E. coli vesicles (Moe et al. Infect Immun 1999; 67:5664-75; Moe et al. Infect Immun 2001; 69:3762-71), or reconstituted in liposomes (Martin et al. In: Thirteenth International Pathogenic Neisseria Conference. Oslo: Nordberg Aksidenstrykkeri A S, 2002), developed serum bactericidal antibody. PCT publication No. WO 02/09746 and US Publication No. US 20040126389 also describes OMV prepared from strains engineered to over-express a Neisserial antigen, with NspA, Omp85, pili (PilQ, PilC), PorA, PorB, Opa, Tbp2, TbpA, TbpB, Hsf, PldA, HasR, FrpA/C, FrpB, Hap, LbpA/LbpB, FhaB, lipo02, MltA, and ctrAi listed as specific examples of such antigens.

The present invention overcomes the disadvantages of prior art approaches to vaccination and elicits protective immunity against a broad spectrum of Neisseria meningitidis strains, notably (but not exclusively) including strains belonging to serogroup B.

LITERATURE

Bjune et al. NIPH Ann 1991; 14:125-30; discussion 130-2; Chen et al. In: Thirteenth International Pathogenic Neisseria Conference Nordberg Aksidenstrykkeri A S, 2002; Christodoulides et al. Microbiology 1998; 144 (Pt 11):3027-37; Claassen et al. Vaccine 1996; 14:1001-8; de Kleijn et al. Vaccine 2000; 18:1456-66; Frasch et al. Meningococcal vaccines: methods and protocols. Totowa, N.J.: Humana Press, 2001:81-107; Fukasawa et al. FEMS Immunol Med Microbiol 2004; 41:205-10; Holst et al. Vaccine 2003; 21:734-7; Humphries Vaccine 2004; 22:1564-9; Jansen et al. FEMS Immunol Med Microbiol 2000; 27:227-33; Kijet et al. In: Thirteen international Pathogenic Neisseria Conference Nordberg Aksidenstrykkeri, 2002; Martin et al. Vaccine 2000; 18:2476-81; McGuinness et al. Lancet 1991; 337:514-7; Morley et al. Vaccine 2001; 20:666-87; Muttilainen et al. Microb Pathog 1995; 18:423-36; Parmar et al. Biochim Biophys Acta 1999; 1421:77-90; Newcombe et al. Infect Immun 2004; 72:338-44; O'Dwyer et al. Infect Immun 2004; 72:6511-8; Oliver et al. Infect Immun 2002; 70:3621-6 Peeters et al. Vaccine 1996; 14:1009-15; Peeters et al. Vaccine 1999; 17:2702-12; Rouppe van der Voort et al. Vaccine 2000; 18:1334-43; Sanchez et al. Vaccine 2002; 20:2964-71; Steeghs et al. EMBO J 2001; 20:6937-45; Steeghs et al. J Endotoxin Res 2004; 10:113-9; Troncoso et al. 1-EMS Immunol Med Microbiol 2000; 27:103-9; Vandeputte et al. J Biol Chem 2003; van der Ley P et al. Vaccine 1995; 13:401-7; Claassen et al. Vaccine 1996;

SUMMARY OF THE INVENTION

The present invention generally provides methods and compositions for eliciting an immune response against *Neisseria* spp. bacteria in a subject, particularly against a *Neisseria meningitidis* serogroup B strain.

In one aspect, the invention features compositions comprising antigenic vesicles prepared from a first *Neisseria* species bacterium, wherein the *Neisseria* species bacterium produces a level of a GNA1870 polypeptide sufficient to provide for production of a vesicle that, when administered to a subject, elicits anti-GNA1870 antibodies; and a pharmaceutically acceptable carrier. The vesicle can be outer membrane vesicles (OMVs), microvesicles (MV), or a mixture of OMVs and MVs. The *Neisseria* species bacterium can be a naturally occurring bacterium, or genetically modified in GNA1870 polypeptide production (e.g., to provide for expression of a GNA1870 polypeptide from a heterologous promoter, to express an exogenous GNA1870 polypeptide, and the like). The GNA1870 polypeptide can be endogenous to the host cell. In some embodiments, the *Neisseria* species bacterium is genetically modified to disrupt production of an endogenous GNA1870 polypeptide, and is genetically modified to produce a GNA1870 polypeptide from a nucleic acid exogenous to the host cell. In other embodiments, the *Neisseria* species bacterium is genetically modified to produce at least two different GNA1870 polypeptides (e.g., GNA1870 polypeptides of different variant groups (v.1, v.2, and v.3). In further related embodiments, the *Neisseria* species bacterium is deficient in production of capsular polysaccharide.

In one embodiment, the composition further comprises an antigenic vesicle prepared from a second *Neisseria* species bacterium, wherein the second *Neisseria* species bacterium produces a level of a GNA1870 polypeptide sufficient to provide for production of vesicles that, when administered to a subject, elicit anti-GNA1870 antibodies, and wherein the second *Neisseria* species bacterium is genetically diverse to the first *Neisseria* species bacterium (e.g., the first and second bacteria differ in at least one of serogroup, serotype, or serosubtype). In further related embodiments, the GNA1870 polypeptide of the second *Neisseria* species bacterium is different from the GNA1870 polypeptide of the first *Neisseria* species bacterium.

In another embodiment, the composition further comprises an antigenic vesicle prepared from a third *Neisseria* species bacterium, wherein the second *Neisseria* species bacterium produces a level of a GNA1870 polypeptide sufficient to provide for production of vesicles that, when administered to a subject, elicit anti-GNA1870 antibodies, and wherein the third *Neisseria* species bacterium is genetically diverse to the first *Neisseria* species bacterium (e.g., differ in at least one of serogroup, serotype, or serosubtype). In related embodiments the GNA1870 polypeptides of the first, second and third *Neisseria* species bacterium are different.

In an embodiment of specific interest, the composition comprises a first antigenic vesicle prepared from a first *Neisseria meningitidis* bacterium genetically modified to overexpress a GNA1870 polypeptide; a second antigenic vesicle prepared from a second *Neisseria meningitidis* bacterium genetically modified to overexpress a GNA1870 polypeptide; and a pharmaceutically acceptable carrier; wherein the GNA1870 polypeptide of the first and second bacterium are different GNA1870 polypeptide variant groups, and the first and second bacteria produce different PorA polypeptides. In a related embodiment, the composition further comprises a third antigenic vesicle prepared from a third *Neisseria meningitidis* bacterium genetically modified to overexpress a GNA1870 polypeptide, wherein the GNA1870 polypeptide of the third bacterium is of a different GNA1870 polypeptide variant group than that of the first and second bacteria, and wherein the third bacterium produces a PorA polypeptide different from the PorA polypeptide of the first and second bacteria. In further related embodiments, the vesicles are prepared without use of a detergent.

In another aspect the invention features a method of producing an antigenic composition by culturing a *Neisseria* species bacterium producing a GNA1870 polypeptide, wherein the GNA1870 polypeptide is produced at a level sufficient to provide for production of vesicles that, when administered to a subject, elicit anti-GNA1870 antibodies; preparing vesicles from the cultured bacterium; and combining the vesicles with a pharmaceutically acceptable carrier to produce an antigenic composition suitable for administration to a subject. The first and second vesicles can be, independently, an outer membrane vesicle (OMV) or a microvesicle (MV). The *Neisseria* species bacterium can be a naturally occurring bacterium and thus express an endogenous GNA1870, or genetically modified in GNA1870 polypeptide production (e.g., to provide for expression of a GNA1870 polypeptide from a heterologous promoter, to express an exogenous GNA1870 polypeptide, and the like). The GNA1870 polypeptide can be endogenous to the host cell. In some embodiments, the *Neisseria* species bacterium is genetically modified to disrupt production of an endogenous GNA1870 polypeptide. In other embodiments, the *Neisseria* species bacterium is genetically modified to produce at least two different GNA1870 polypeptides (e.g., GNA1870 polypeptides of different variant groups (v.1, v.2, and v.3). In other embodiments, the *Neisseria* species bacterium is genetically modified to disrupt production of an endogenous full-length GNA1870 polypeptide, and produces a GNA1870 polypeptide from a nucleic acid exogenous to the host cell. In further related embodiments, the *Neisseria* species bacterium is deficient in production of capsular polysaccharide.

In another aspect the invention features a method of eliciting an immune response against *Neisseria* by administering to a mammal an immunologically effective amount of a composition comprising a first antigenic preparation comprising vesicles prepared from a first *Neisseria* species bacterium, wherein the *Neisseria* species bacterium produces a level of a GNA1870 polypeptide sufficient to provide for production of vesicles that, when administered to a subject, elicit anti-GNA1870 antibodies; wherein said administering is sufficient to elicit an immune response to a GNA1870 polypeptide present in the vesicles. The vesicles can be outer membrane vesicles (OMVs), microvesicles (MVs), or a mixture of OMVs and MVs. The *Neisseria* species bacterium can be a naturally occurring bacterium and thus express an endogenous GNA1870, or genetically modified in GNA1870 polypeptide production (e.g., to provide for expression of a GNA1870 polypeptide from a heterologous promoter, to express an exogenous GNA1870 polypeptide, and the like). The GNA1870 polypeptide can be endogenous to the host cell. In some embodiments, the *Neisseria* species bacterium is genetically modified to disrupt production of an endogenous GNA1870 polypeptide. In other embodiments, the *Neisseria* species bacterium has been engineered to over-express GNA1870. In still further embodiments, the GNA1870 polypeptide is a chimeric protein (a fusion protein), wherein the chimeric protein contains at least an antigenic portion of GNA1870 for presentation on vesicles (e.g., OMVs, MVs). In further related embodiments, the *Neisseria* species bacterium is deficient in production of capsular polysaccharide.

In other embodiments, the *Neisseria* species bacterium is genetically modified to produce at least two different GNA1870 polypeptides (e.g., GNA1870 polypeptides of different variant groups (v.1, v.2, and v.3). In other embodiments, the *Neisseria* species bacterium is genetically modified to disrupt production of an endogenous full-length GNA1870 polypeptide, and produces a GNA1870 polypeptide from a nucleic acid exogenous to the host cell.

In related embodiments, the composition administered in the method comprises an immunologically effective amount of a second antigenic preparation comprising vesicles prepared from a second *Neisseria* species bacterium, wherein the second *Neisseria* species bacterium produces a level of a GNA1870 polypeptide sufficient to provide for production of vesicles that, when administered to a subject, elicit anti-GNA1870 antibodies, and wherein the second *Neisseria* species bacterium is genetically diverse to the first *Neisseria* species bacterium (e.g., the first and second bacteria are of a different serogroup, serotype, or serosubtype). The GNA1870 polypeptide of the second *Neisseria* species bacterium can be different from the GNA1870 polypeptide of the first *Neisseria* species bacterium.

In further related embodiments, the composition further comprises a third isolated antigenic preparation comprising vesicles prepared from a third *Neisseria* species bacterium, wherein the second *Neisseria* species bacterium produces a level of a GNA1870 polypeptide sufficient to provide for production of vesicles that, when administered to a subject, elicit anti-GNA1870 antibodies, and wherein the third *Neisseria* species bacterium is genetically diverse to the first or second *Neisseria* species bacterium (e.g., the first, second and third *Neisseria* species bacteria are genetically diverse in that they differ in at least one of serogroup, serotype, or serosubtype). The GNA1870 polypeptides of the first, second and third *Neisseria* species bacteria can be different.

The method can provide for eliciting a protective immune response in the subject against more than one strain of *Neisseria*, particularly *N. meningitidis*, more particularly serogroup B *Neisseria meningitidis*.

The antigenic compositions described herein can elicit a combination of optimal anti-GNA1870, anti-PorA, and/or anti-OpC bactericidal antibody responses and, thereby, confer broad protection against meningococcal disease.

Vaccines prepared from GNA1870 over-expressing strains as described herein can elicit an antibody response that is bactericidal for *Neisserial* strains that share the GNA1870 variant and/or PorA of the strain from which the vesicles were prepared, as well as an antibody response that is bactericidal for *Neisserial* strains that have a GNA1870 subvariant and have a heterologous PorA relative to the vesicle production strain.

Vaccines prepared from GNA1870 over-expressing strains can also decrease the likelihood of selection and emergence of disease-causing *N. meningitidis* strains in the population with decreased expression of PorA. These mutants are of particular concern if conventional OMV vaccines are widely used in the population. Because expression of PorA is phase-variable (van der Ende et al, J. Bacteriology 1995:177:2475-2480), and mutants deficient in PorA expression are relatively common and can be readily selected by killing *N. meningitidis* with anti-PorA antibody and complement. PorA-deficient strains also are virulent and capable of causing disease.

The present disclosure also provides methods that can be advantageous with respect to the ease of preparation of an effective vaccine composition relative to preparation of a vaccine involving a recombinant polypeptide, or a combination vaccine formulation that incorporates multiple individual antigens, or a recombinant protein such as PorA that require renaturation of conformational epitopes to elicit bactericidal antibody.

Aspects, features, and advantages of the invention will be readily apparent to the ordinarily skilled artisan upon reading the present disclosure.

BRIEF DESCRIPTION OF THE DRAWINGS

FIG. 2A provides results of SDS PAGE and Western blot analysis of OMVs. Panel A is a photograph of a COOMASSIE dye-stained SDS PAGE. Lanes 1 to 5, OMV preparations (about 5 µg of protein in each lane except in lane 5 where 10 µg was loaded). Lane 1, wild-type (WT) strain RM1090; lane 2, WT strain transformed with shuttle vector pFP12 without the GNA1870 gene; lane 3. RM1090ΔGNA1870 knockout (KO); lane 4, RM1090ΔGNA1870 KO transformed with pFP12 without the GNA1870 gene; lane 5, RM1090ΔGNA1870 KO transformed with shuttle vector pFP12-GNA1870 containing the GNA1870 gene; lane 6, rGNA1870 (about 1 µg). Panels B and C are photographs of Western blots using polyclonal anti-GNA1870 antisera from mice immunized with variant 1, 2 and 3 rGNA1870 proteins. Panel B: The sensitivity of detection of this antiserum was slightly higher for the variant 2 (v.2) recombinant GNA1870 protein as compared with the variant 1 recombinant GNA1870 protein (v.1). Panel C: Lane 1, recombinant GNA1870 v.1; Lane 2, OMV from WT RM1090; Lane 3, OMV from RM1090ΔGNA1870; Lane 4, OMV from RM1090 transformed with the pFP12 shuttle vector containing the GNA1870 gene. The over-expression of GNA1870 v.1 in the RM1090ΔGNA 1870 strain transformed with the shuttle vector is greater than the native expression level of GNA1870 in the wild-type strain (lane 2).

FIG. 7 is an alignment of exemplary amino acid sequences of GNA1870 variants 1, 2 and 3 from *N. meningitidis* strains MC58, 951-5945, and M1239, respectively. "1" indicates that first amino acid of the mature protein, with amino acids indicated by negative numbers part of the leader sequence. Grey and black backgrounds indicate conserved and identical amino acid residues, respectively.

Figure 8H:
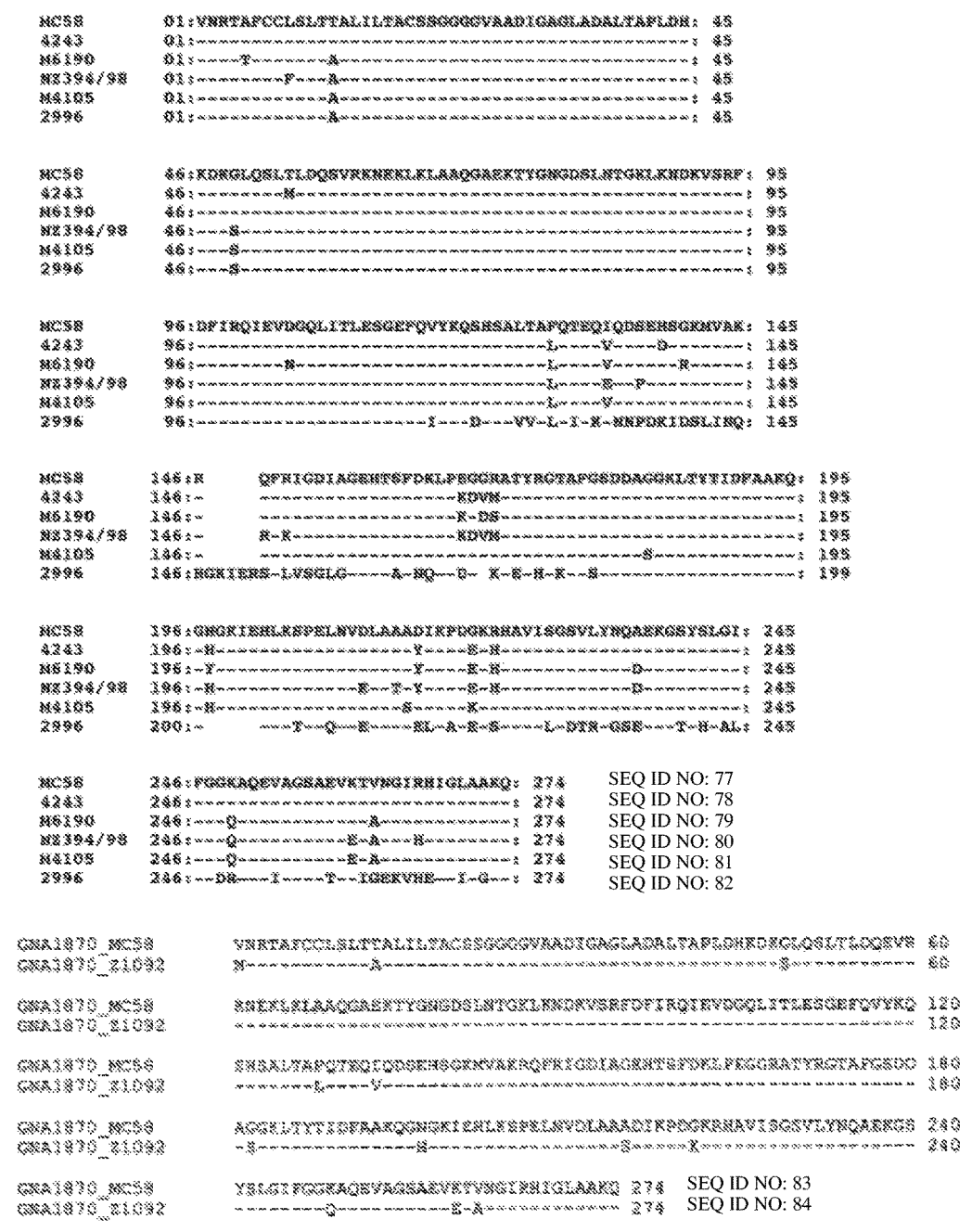

FIGS. 8A-8H provide amino acid sequences of exemplary GNA1870 polypeptides useful in the invention, including an amino acid sequence alignments of selected exemplary GNA1870 polypeptides (FIG. 8H).

FIG. 9 provides alignments of the amino acid sequences of exemplary PorA VR1 family prototype (Panel A) and the amino acid sequences of exemplary PorA VR2 family prototype (Panel B).

Figure 1A:
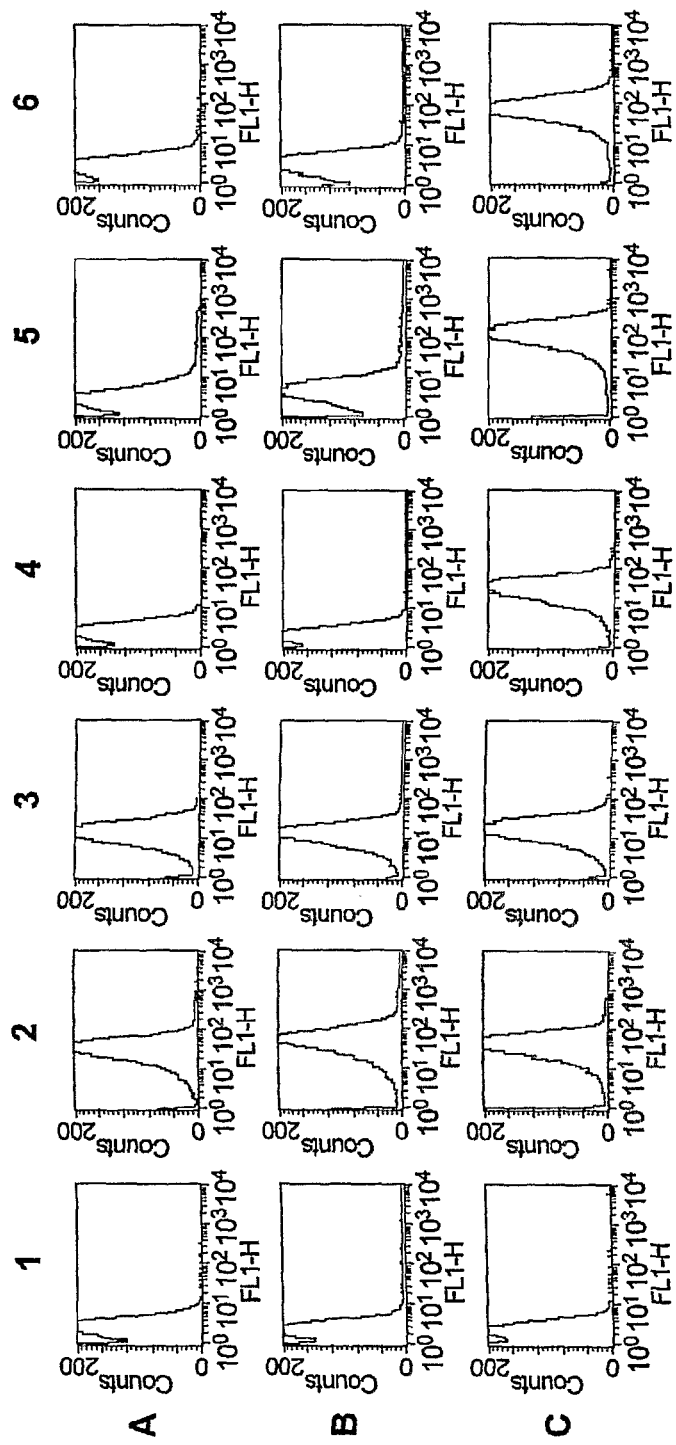
FIG. 1A shows the results of a flow cytometry experiment measuring binding of anti-GNA1870 antibodies on the surface of live encapsulated *N. meningitidis* cells of strain RM1090 and RM1090 mutants as determined by indirect fluorescence. Row A. RM1090ΔGNA1870 strain. Row B. RM1090 wild-type strain. Row C. RM1090 strain transformed with shuttle vector pFP12 containing the GNA1870 gene. Column 1 Negative control serum (1:10 dilution) from mice immunized with aluminum phosphate alone. Column 2 Positive control anti-group C polysaccharide mAb (10 µg/ml). Column 3. Positive control anti-PorA mAb (anti-P1.2, 1:500 dilution). Column 4. Anti-GNA1870 (v. 1) mAb (2 µg/ml). Column 5. Polyclonal anti-GNA1870 antisera prepared against v. 1, 2 and 3 recombinant proteins (1:10 dilution). Column 6. Same as column 5 but a 1:250 dilution of serum.

Before the present invention and specific exemplary embodiments of the invention are described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges may independently be included in the smaller ranges is also encompassed within the invention, subject to any specifically excluded limit in the stated range. Where the stated range includes one or both of the limits, ranges excluding either both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a", "and", and "the" include plural referents unless the context clearly dictates otherwise. Thus, for example, reference to "an antigen" includes a plurality of such antigens and reference to "the vesicle" includes reference to one or more vesicles and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DETAILED DESCRIPTION OF THE INVENTION

The present invention is based on the discovery that an OMV vaccine prepared from a mutant *N. meningitidis* strain engineered to over-express GNA1870 elicits broader bactericidal antibody responses in mice than a recombinant GNA1870 (rGNA1870) protein vaccine or an OMV prepared from a naturally-occurring strain, or a combination of a recombinant protein vaccine and an OMV vaccine.

OMV vaccines have been administered safely to millions of humans, and are proven to be efficacious against developing meningococcal disease. As noted in the introduction section, their principal limitation is that they elicit strain-specific bactericidal antibody responses. Also there is concern that if OMV vaccines are used widely in the population that the immune response may select for emergence of "escape mutants" of *N. meningitidis* strains (i.e., strains with mutations in PorA amino acid sequence of surface-accessible loops or with decreased expression of PorA). In short, the invention provides that, by selection of a prevalent PorA serosubtype and preparing a mutant that over-expresses GNA1870, it is possible to prepare a vesicle-based vaccine (e.g., OMV, MV) that elicits a combination of optimal anti-GNA1870 and anti-PorA bactericidal antibody responses and, thereby, confers broad protection against meningococcal disease. Use of such a vaccine also has a lower risk than a convention OMV vaccine for selection of disease-producing PorA-deficient mutant strains in the population.

In addition, vesicles prepared from a strain over-expressing GNA1870 have an altered protein profile compared with vesicles prepared from a strain that expresses a relatively lower level of GNA1870. As discussed in more detail in the Examples, OMV prepared from GNA1870 over-expressing strains showed decreased expression of a number of other cell envelope proteins as compared with OMV prepared from the wild-type vaccine RM1090 strain, or the RM1090 ΔGNA1870 knockout strain. While the ability of antisera from mice immunized with OMV over-expressing GNA1870 to elicit bactericidal antibody to strain Cu385 or activate C3b deposition on strain NZ98/294 was a result of antibodies elicited by GNA1870, the decrease in these other outer cell envelope proteins may serve to further enhance the immunogenicity and protective immune response elicited by vesicles prepared from GNA1870 over-expressing strains (e.g., due to "unmasking" of other antigens in the vesicle).

The examples provided herein illustrate the breadth of protection elicited by immunization with an OMV vaccine prepared from a *N. meningitidis* strain that over-expresses (e.g., is genetically engineered to over-express) GNA1870. Functional activities of the anti-GNA1870 antibodies elicited by the OMV vaccine that over-expressed GNA1870 were greater than that of the antibodies elicited by the recombinant GNA1870 vaccine, or a combination of recombinant GNA1870 and OMV prepared from the wildtype strain. For example, despite a lower magnitude of the anti-GNA1870 antibody response as measured by ELISA (Table 2), sera from mice immunized with the OMV vaccine prepared from the strain engineered to over-express GNA1870 showed higher bactericidal activity against strain Z1092 than that of sera from mice immunized with the recombinant protein GNA1870 vaccine, or with OMV vaccines prepared from the wild-type or GNA1870 knock-out RM1090 strains, or with OMV vaccine mixed with the recombinant GNA1870 protein vaccine (FIG. 3).

Figure 4A:
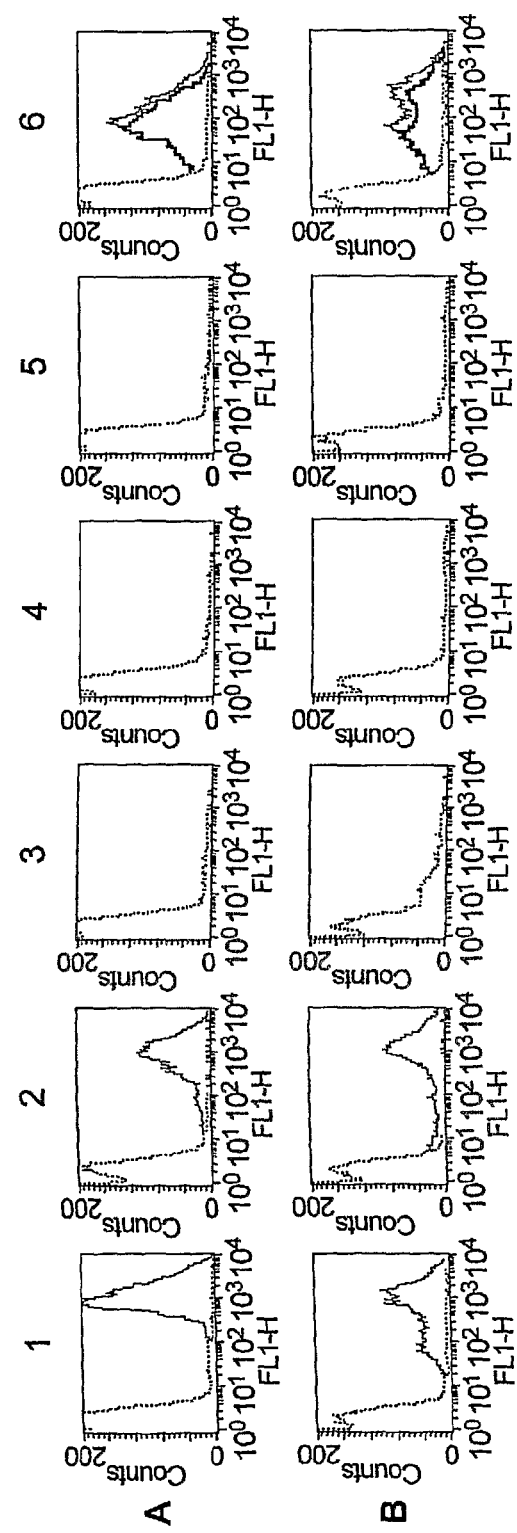
FIG. 4A is a series of graphs showing activation of human C3b and iC3b complement deposition on the surface of live encapsulated *N. meningitidis* cells as determined by indirect fluorescence flow cytometry. Row A. Strain NZ98/254. Row B. Strain M1390. Column 1, complement plus a positive control group B anticapsular MAb, 25 µg/ml (open area) or a 1:40 dilution of a serum pool from negative control mice immunized with aluminum phosphate alone (closed area). Column 2, complement plus anti-GNA1870 MAb JARS, 1 µg/ml (open) or heat-inactivated complement+the anti-GNA1870 MAb, 5 µg/ml (closed). Columns 3, 4 and 5, complement plus 1:100 dilution of serum pools from mice immunized with: column 3 (rGNA1870 vaccine); Column 4 (OMV vaccine from RM1090 WT strain); or column 5 (a mixture of rGNA1870 vaccine and OMV vaccine from strain RM1090ΔGNA1870). Column 6, complement plus dilutions of a serum pool from mice immunized with OMV vaccine from strain RM1090 over-expressing GNA1870 (open area, 1:100 dilution and gray area 1:400 dilution). For comparison, panels in column 6 also show data from complement plus a 1:100 dilution of a serum pool from mice immunized with OMV vaccine from strain RM1090ΔGNA1870 (closed area).
Figure 6:
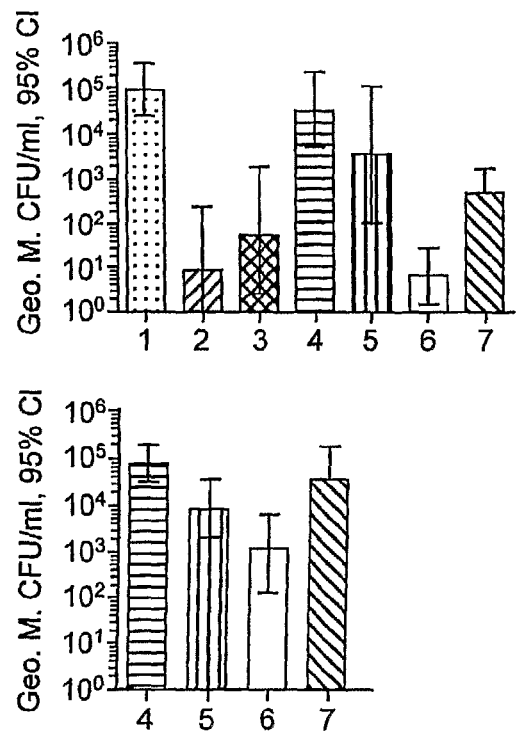
FIG. 6 provides graphs showing results of analysis of passive protection in the infant rat meningococcal bacteremia model. At time 0, infant rats were treated intraperitoneally (IP) with dilutions of serum pools from immunized mice (N=9 to 10 individual sera per pool) and challenged two hours later with group B strain NZ98/294 (about 60,000 CFU/rat given IP). Quantitative blood cultures were obtained 4 to 6 hours after the bacterial challenge. Panel A: 1:15 serum dilutions. Panel B: 1:60 serum dilutions. Bar 1: Serum from mice immunized with aluminum phosphate only; bar 2: Anticapsular mAb (10 µg/rat); bar 3: Anti-GNA1870 mAb (10 µg/rat); bar 4: Serum from mice immunized with OMV vaccine from RM1090 ΔGNA1870; bar 5: Serum from mice immunized with mixture of OMV vaccine from RM1090ΔGNA plus recombinant GNA1870 protein vaccine; bar 6: Serum from mice immunized with OMV vaccine from RM1090 over-expressing GNA1870; bar 7: Serum from mice immunized with recombinant GNA1870 protein vaccine.

Furthermore, even in the absence of strong bactericidal activity, the antibodies elicited by the OMV vaccine that over-expressed GNA1870 gave greater C3b deposition on the surface of strains NZ98/254 or M1390 (FIG. 4A, column 6) than antibodies raised to the other vaccines, and the former also conferred greater passive protection against bacteremia in infant rats challenged with strain NZ98/254 (FIG. 6, Panels A-B). The ability to activate C3b deposition on strain NZ98/254 was lost after absorption of anti-GNA1870 antibodies (Table 3). In short, the modified OMV vaccine conferred broader protective activity than the GNA1870 recombinant protein or the OMV vaccine from the wild-type vaccine strain as a result of the ability of the modified OMV vaccine to elicit both serosubtype-specific bactericidal activity against strains expressing a homologous PorA molecule to that of the vaccine strain, and anti-GNA1870 antibodies with greater functional activity against strains expressing sub-variants of the GNA1870 variant 1 protein than elicited by recombinant GNA1870 vaccine.

The modified OMV vaccine prepared from a GNA1870 over-expressing strain was advantageous over recombinant GNA1870 against strains expressing sub-variants of the variant 1 GNA1870 protein and/or expressing a homologous PorA serosubtype. Interestingly, mice immunized with a vesicle vaccine prepared from a *N. meningitidis* strain (RM1090) engineered to over-express NspA had more 10-fold higher ELISA anti-NspA antibody titers but lower serum bactericidal titers against some *N. meningitidis* strains such as Cu385 or Z1092 than control mice immunized with a control vesicle vaccine prepared from strain RM1090 in which the gene encoding NspA had been inactivated (Table 5). O'Dwyer et al. also observed lack of serum bactericidal activity in mice vaccinated with an OMV vaccine prepared from a *N. flavescens* strain engineered to over-express NspA (Infect. Innun. 2004; 72:6511-80). Thus, the present findings showing enhanced bactericidal and protective antibody responses to an OMV vaccine over-expressing GNA1870 are surprising.

Figure 5:
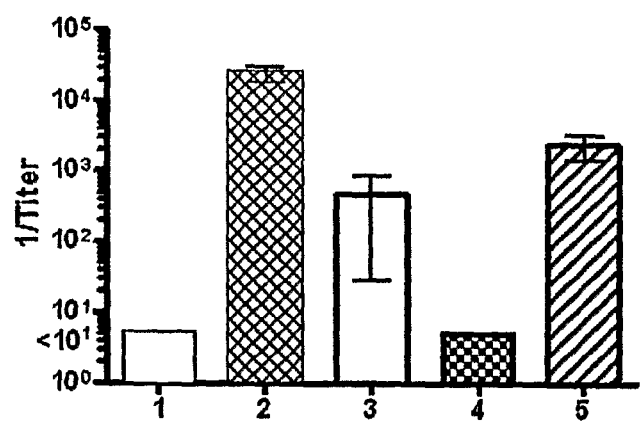
FIG. 5 is a bar graph showing serum anti-GNA1870 antibody responses as measured by ELISA (GMT±SD). The antigen on the plate was rGNA1870 variant 1. The secondary antibody was alkaline phosphatase-conjugated goat anti-mouse IgG+A+M. The bars represent the respective geometric mean titers of 2 antiserum pools (4-5 mice per pool) from groups of mice immunized with (1) Adjuvant; (2) rGNA1870; (3) H44/76 wildtype OMV; (4) H44/76 ΔGNA1870 OMV; (5) H44/76 OE GNA1870 OMV.

Over-expression of GNA1870 v.1 in strain H44/76 resulted in ~3-fold more GNA1870 in the OMV as compared with the naturally-higher amounts of GNA1870 in OMV prepared from the H44176 wildtype strain. In contrast with our previous study of mice immunized with OMV from wildtype strain RM1090, mice immunized with OMV prepared from wildtype H44/76 developed anti-GNA1870 antibody responses as measured by ELISA (FIG. 5). However, the group of mice given OMV from the strain with over-expressed GNA1870 had ~10-fold higher titers. The titers measured by ELISA did not correlate well with antibody functional activity. For example, the highest serum anti-GNA1870 titers were in mice immunized with the recombinant GNA1870 vaccine but the bactericidal and C3b deposition activity of serum from mice immunized with the recombinant protein were limited to strain H44/76. Susceptibility of this strain was expected because virtually all *N. meningitides* strains with genetic lineage of ET 5 are high expressers of the canonical GNA1870 v. 1 protein (identical amino acid sequence to that of MC58) and these strains are highly susceptible to complement-mediated bactericidal activity of anti-GNA1870 antibodies (Masignani et al. 2003, supra; Welsch et al. 2004, supra). The remaining five *N. meningitidis* test strains in our study express lower amounts of GNA1870 than strain H44/76, and the respective proteins are subvariants of GNA1870 v.1. The five strains also have heterologous PorA molecules to that of the H44/76 vaccine strain. These five strains were resistant to bactericidal activity and complement activation by antibodies elicited by the recombinant GNA1870 vaccine, or by the anti-PorA antibodies elicited by the OMV vaccines. In contrast, four of the five strains were susceptible to bactericidal activity and/or complement deposition activity of sera from mice immunized with H44/76 OMV vaccine with over-expressed GNA1870. Activation of C3b on the surface of live bacteria have led to predicted passive protection of infant rats against meningococcal bacteremia (Welsch et al. J Infect Dis 2003; 188:1730-40; Welsch et al J Immunol 2004; 172:5606-15; Hou et al. J Infect Dis 2005; 192:580-90; Moe et al. Infect Immun 2002; 70:6021-31). The OMV vaccine with over-expressed GNA 1870 consists of a complex mixture of antigens and would be expected to elicit antibody to a number of antigenic targets. However, in absorption experiments, the antibody functional activity against these strains was directed against GNA1870 (Table 3).

Remarkably, an OMV vaccine prepared from a mutant strain with only a modest increase in GNA1870 level elicited higher and broader GNA1870-specific bactericidal antibody responses and/or greater C3 deposition than an OMV vaccine prepared from a wildtype strain selected to have relatively high expression of GNA1870. Thus, even a slight change in the ratio of GNA1870 to total protein in the OMV vaccine preparation appears to determine whether or not there is an antibody response to GNA1870. Further, the quality of the antibodies elicited by the OMV vaccine with over-expressed GNA1870 is superior to that of antibodies elicited by the recombinant GNA1870 vaccine. For example the recombinant vaccine elicited higher ELISA antibody binding titers than those elicited by the OMV vaccine with over-expressed GNA1870, but the antibodies to the recombinant protein had lower bactericidal and complement activation activity. Defining the mechanisms by which the modified GNA1870-OMV vaccine elicits serum antibodies with broader functional activity than the recombinant protein or control OMV vaccine will require further study.

The present invention thus provides methods and compositions for eliciting an immune response that is broadly reactive with diverse disease-producing *N. meningitidis* strains. The invention circumvents the problem of immunodominance of antigenically variable domains of PorA in vesicle- or PorA-based vaccines by enhancing the antibody response to GNA1870 and, possibly, to other common antigens in the vaccine strains. Importantly, the methods of the invention elicit serum bactericidal antibody, the only proven serologic correlate of protection in humans (Goldschneider et al. 1969, supra), against strains of *Neisseria* expressing serosubtype epitopes that were not used in the vaccine preparations. Further, the method elicits serum bactericidal antibody against strains that are not killed by antibody to a conserved protein such as *Neisserial* surface protein A, a candidate meningococcal vaccine (Martin et al., 2000. J. Biotechnol. 83:27-31; Moe et al. (1999 Infect. Immun 67: 5664; Moe et al. Infect Immun 2001 69:3762). Without being held to theory, the vaccine and immunization regimen of the invention provides its unexpected advantages in broad spectrum protective immunity by eliciting antibodies that are specific for both conserved and non-conserved antigens.

Definitions

The term "protective immunity" means that a vaccine or immunization schedule that is administered to a mammal induces an immune response that prevents, retards the development of, or reduces the severity of a disease that is caused by *Neisseria meningitidis*, or diminishes or altogether eliminates the symptoms of the disease.

The phrase "a disease caused by a strain of serogroup B of *Neisseria meningitidis*" encompasses any clinical symptom or combination of clinical symptoms that are present in an infection with a member of serogroup B of *Neisseria meningitidis*. These symptoms include but are not limited to: colonization of the upper respiratory tract (e.g. mucosa of the nasopharynx and tonsils) by a pathogenic strain of serogroup B of *Neisseria meningitidis*, penetration of the bacteria into the mucosa and the submucosal vascular bed, septicemia, septic shock, inflammation, hemorrhagic skin lesions, activation of fibrinolysis and of blood coagulation, organ dysfunction such as kidney, lung, and cardiac failure, adrenal hemorrhaging and muscular infarction, capillary leakage, edema, peripheral limb ischaemia, respiratory distress syndrome, pericarditis and meningitis.

The phrase "broad spectrum protective immunity" means that a vaccine or immunization schedule elicits "protective immunity" against at least one or more (or against at least two, at least three, at least four, at least five, against at least eight, or at least against more than eight) strains of *Neisseria meningitidis*, wherein each of the strains belongs to a different serosubtype as the strains used to prepare the vaccine. The invention specifically contemplates and encompasses a vaccine or vaccination regimen that confers protection against a disease caused by a member of serogroup B of *Neisseria meningitidis* and also against other serogroups, particularly serogroups A, C, Y and W-135.

The phrase "specifically binds to an antibody" or "specifically immunoreactive with", when referring to an antigen such as a polysaccharide, phospholipid, protein or peptide, refers to a binding reaction which is based on and/or is probative of the presence of the antigen in a sample which may also include a heterogeneous population of other molecules. Thus, under designated immunoassay conditions, the specified antibody or antibodies bind(s) to a particular antigen or antigens in a sample and do not bind in a significant amount to other molecules present in the sample. Specific binding to an antibody under such conditions may require an antibody or antiserum that is selected for its specificity for a particular antigen or antigens.

The phrase "in a sufficient amount to elicit an immune response to epitopes present in said preparation" means that there is a detectable difference between an immune response indicator measured before and after administration of a particular antigen preparation. Immune response indicators include but are not limited to: antibody titer or specificity, as detected by an assay such as enzyme-linked immunoassay (ELISA), bactericidal assay, flow cytometry, immunoprecipitation, Ouchterlony immunodiffusion; binding detection assays of, for example, spot, Western blot or antigen arrays; cytotoxicity assays, etc.

A "surface antigen" is an antigen that is present in a surface structure of *Neisseria meningitidis* (e.g. the outer membrane, inner membrane, periplasmic space, capsule, pili, etc.).

The phrase "genetically diverse" as used in the context of genetically diverse strains of *Neisseria meningitidis*, refers to strains that differ from one another in the amino acid sequence of at least one, and usually at least two, more usually at least three polypeptides, particularly antigenic polypeptides. Genetic diversity of strains can be accomplished by selecting strains that differ in at least one or more, preferably at least two or more, of serogroup, serotype, or serosubtype (e.g., two strains that differ in at least one of the proteins selected from outer membrane, PorA and PorB proteins, are said to genetically diverse with respect to one another). Genetic diversity can also be defined by, for example, multi-locus sequence typing and/or multi-locus enzyme typing (see, e.g., Maiden et al., 1998, *Proc. Natl. Acad. Sci. USA* 95:3140; Pizza et al. 2000 Science 287: 1816), multi-locus enzyme electrophoresis, and other methods known in the art.

"Serogroup" as used herein refers to classification of *Neisseria meningitides* by virtue of immunologically detectable variations in the capsular polysaccharide. About 12 serogroups are known: A, B, C, X, Y, Z, 29-E, W-135, H, I, K and L. Any one serogroup can encompass multiple serotypes and multiple serosubtypes.

"Serotype" as used herein refers to classification of *Neisseria meningitides* strains based on monoclonal antibody defined antigenic differences in the outer membrane protein Porin B. A single serotype can be found in multiple serogroups and multiple serosubtypes.

"Serosubtype" as used herein refers classification of *Neisseria meningitides* strains based on antibody defined antigenic variations on an outer membrane protein called Porin A, or upon VR typing of amino acid sequences deduced from DNA sequencing (Sacchi et al., 2000, *J. Infect. Dis.* 182:1169; see also the Multi Locus Sequence Typing web site). Most variability between PorA proteins occurs in two (loops I and IV) of eight putative, surface exposed loops. The variable loops I and IV have been designated VR1 and VR2, respectively. A single serosubtype can be found in multiple serogroups and multiple serotypes.

"Enriched" means that an antigen in an antigen composition is manipulated by an experimentalist or a clinician so that it is present in at least a three-fold greater concentration by total weight, usually at least 5-fold greater concentration, more preferably at least 10-fold greater concentration, more usually at least 100-fold greater concentration than the concentration of that antigen in the strain from which the antigen composition was obtained. Thus, if the concentration of a particular antigen is 1 microgram per gram of total bacterial preparation (or of total bacterial protein), an enriched preparation would contain at least 3 micrograms per gram of total bacterial preparation (or of total bacterial protein).

The term "heterologous" refers to two biological components that are not found together in nature. The components may be host cells, genes, or regulatory regions, such as promoters. Although the heterologous components are not found together in nature, they can function together, as when a promoter heterologous to a gene is operably linked to the gene. Another example is where a *Neisserial* sequence is heterologous to a *Neisserial* host of a different strain. "Heterologous" as used herein in the context of proteins expressed in two different bacterial strains, e.g., "heterologous PorA" or "heterologous GNA1870", indicates that the proteins in question differ in amino acid sequence. For example, a first *Neisserial* strain expressing PorA 1.5-2,10 and a second *Neisserial* strain expressing PorA 7-2,4 are said to have "heterologous PorA proteins" or are "heterologous with respect to PorA".

The term "immunologically naïve with respect to *Neisseria meningitidis*" denotes an individual (e.g., a mammal such as a human patient) that has never been exposed (through infection or administration) to *Neisseria meningitidis* or to an antigen composition derived from *Neisseria meningitidis* in sufficient amounts to elicit protective immunity, or if exposed, failed to mount a protective immune response. (An example of the latter would be an individual exposed at a too young age when protective immune responses may not occur. Molages et al., 1994, Infect. Immun. 62: 4419-4424). It is further desirable (but not necessary) that the "immunologically naïve" individual has also not been exposed to a *Neisserial* species other than *Neisseria meningitidis* (or an antigen composition prepared from a *Neisserial* species), particularly not to a cross-reacting strain of *Neisserial* species (or antigen composition). Individuals that have been exposed (through infection or administration) to a *Neisserial* species or to an antigen composition derived from that *Neisserial* species in sufficient amounts to elicit an immune response to the epitopes exhibited by that species, are "primed" to immunologically respond to the epitopes exhibited by that species.

*Neisserial* Strains Expressing GNA1870 for Use in Vesicle Production

In general, the invention involves production of vesicles (microvesicles or outer membrane vesicles) from a naturally-occurring or genetically modified *Neisserial* strain that produces a level of GNA1870 protein sufficient to provide for vesicles that, when administered to a subject, evoke serum anti-GNA1870 antibodies. The anti-GNA1870 antibodies produced facilitate immunoprotection against 1, 2, 3, 4, 5, 6, 7, 8, 9, 10 or more *Neisserial* strains, which strains can be genetically diverse (or "heterologous") with respect to, for example, serogroup, serotype, serosubtype (e.g., as determined by PorA protein), Sequence type, electrophoretic type, GNA1870 variant, and/or GNA1870 subvariant.

Any of a variety of *Neisseria* spp. strains that produce or can be modified to produce GNA1870, and, optionally, which produce or can be modified to produce other antigens of interest, such as PorA, can be used in the methods of the invention. Characteristics of suitable strains with respect to GNA1870 production are discussed in more detail below.

Pathogenic *Neisseria* spp. or strains derived from pathogenic *Neisseria* spp., particularly strains pathogenic for humans or derived from strains pathogenic or commensal for humans, are of particular interest. Exemplary *Nessserial* spp. include *N. meningitidis*, *N. flavescens N. gonorrhoeae*, *N. lactamica*, *N. polysaccharea*, *N. cinerea*, *N. mucosa*, *N. subflava*, *N. sicca*, *N. elongata*, and the like. "Derived from" in the context of bacterial strains is meant to indicate that a strain was obtained through passage in vivo, or in in vitro culture, of a parental strain and/or is a recombinant cell obtained by modification of a parental strain.

*N. meningitidis* strains are of particular interest in the present invention. *N. meningitidis* strains can be divided into serologic groups, serotypes and subtypes on the basis of reactions with polyclonal (Frasch, C. E. and Chapman, 1973, *J. Infect. Dis.* 127: 149-154) or monoclonal antibodies that interact with different surface antigens. Serogrouping is based on immunologically detectable variations in the capsular polysaccharide. About 12 serogroups (A, B, C, X, Y, Z, 29-E, and W-135) are known. Strains of the serogroups A, B, C, Y and W-135 account for nearly all meningococcal disease.

Serotyping is based on monoclonal antibody defined antigenic differences in an outer membrane protein called Porin B (PorB). Antibodies defining about 21 serotypes are currently known (Sacchi et al., 1998, *Clin. Diag. Lab. Immunol.* 5:348). Serosubtyping is based on antibody defined antigenic variations on an outer membrane protein called Porin A (PorA). Antibodies defining about 18 serosubtypes are currently known. Serosubtyping is especially important in *Neisseria meningitidis* strains where immunity may be serosubtype specific. Most variability between PorA proteins occurs in two (loops I and IV) of eight putative, surface exposed loops. The variable loops I and IV have been designated VR1 and VR2, respectively. Since more PorA VR1 and VR2 sequence variants exist that have not been defined by specific antibodies, an alternative nomenclature based on VR typing of amino acid sequence deduced from DNA sequencing has been proposed (Sacchi et al., 2000, *J. Infect. Dis.* 182:1169; see also the Multi Locus Sequence Typing web site). Lipopolysaccharides can also be used as typing antigens, giving rise to so-called immunotypes: L1, L2, etc.

*N. meningitidis* also may be divided into clonal groups or subgroups, using various techniques that directly or indirectly characterize the bacterial genome. These techniques include multilocus enzyme electrophoresis (MLEE), based on electrophoretic mobility variation of an enzyme, which reflects the underlying polymorphisms at a particular genetic locus. By characterizing the variants of a number of such proteins, genetic "distance" between two strains can be inferred from the proportion of mismatches. Similarly, clonality between two isolates can be inferred if the two have identical patterns of electrophoretic variants at number of loci. More recently, multilocus sequence typing (MLST) has superseded MLEE as the method of choice for characterizing the microorganisms. Using MLST, the genetic distance between two isolates, or clonality is inferred from the proportion of mismatches in the DNA sequences of 11 housekeeping genes in *Neisseria meningitidis* strains (Maiden et al., 1998, *Proc. Natl. Acad. Sci. USA* 95:3140).

The strain used for vesicle production can be selected according to a number of different characteristics that may be desired. For example, in addition to selection according to a level of GNA1870 production, the strain may be selected according to: a desired PorA type (a "serosubtype", as described above), serogroup, serotype, and the like; decreased capsular polysaccharide production; and the like.

For example, the production strain can produce any desired PorA polypeptide, and may express one or more PorA polypeptides (either naturally or due to genetic engineering). Exemplary strains includes those that produce a PorA polypeptide which confers a serosubtype of P1.7,16; P1.19,15; P1.7,1; P1.5,2; P1.22a,14; P1.14; P1.5,10; P1.7,4; P1.12,13; as well as variants of such PorA polypeptides which may or may not retain reactivity with conventional serologic reagents used in serosubtyping.

Also of interest are PorA polypeptides characterized according to PorA variable region (VR) typing (see, e.g., Russell et al. Emerging Infect Dis 2004 10:674-678; Sacchi C T, et al, Clin Diagn Lab Immunol 1998; 5:845-55; Sacchi et al, J. Infect Dis 2000; 182:1169-1176). A substantial number of distinct VR types have been identified, which can be classified into VR1 and VR2 family "prototypes". A web-accessible database describing this nomenclature and its relationship to previous typing schemes is found at neisseria.org/nm/typing/pora. Alignments of exemplary PorA VR1 and VR2 types is provided in Russell et al. Emerging Infect Dis 2004 10:674-678, and provided in FIG. 9 for the convenience of the reader.

Exemplary PorA polypeptides as characterized by PorA serosubtypes include P1.5,2; P1.5a,2a; P1.5a,2c; P1.5a,2c; P1.5a,2c; P1.5b,10; P1.5b,10; P1.5b,C; P1.7,16; P1.7d,1; P1.7d,1; P1.7d,1; P1.7d,1; P1.7b,3; P1.7b,4; P1.7b,4; P1.12, 16; P1.12a,13a; P1.22,9; P1.23,14; P1.23,14; P1.19,15; P1.B,1; P1.C,1; P1.E,A; P1.E,A; P1.E,A; P1.5,2; P1.5,2; P1.5a,10a; P1.5b,10; P1.5b,10; P1.5b,10b; P1.7,16; P1.7,16; P1.7b,1; P1.7b,13e; P1.7b,4; P1.7b,4; P1.7d,1; P1.7d,1; P1.7b,13a; P1.23,3; P1.23,3; P1.23,3; P1.19,15; P1.19,1; P1.19,15; P1.19,15; P1.19,15; P1.19,15; P1.19,15; P1.19,15; P1.19,15; P1.E,A; P1.E,A; P1.E,16a; P1.E,4a; P1.E,4a; P1.Ea,3; P1.Eb,9; P1.Eb,9; P1.Eb,9; P1.Eb,9; P1.Eb,9; P1.F, 16; P1.7a,1; P1.7b,3; P1.7d,1; P1.Ea,3; P1.5b,10; P1.5b,10; P1.5b,10; P1.5b,10; P1.5b,10; P1.5b,10; P1.5b,10b; P1.5b, 10; P1.22,14a; P1.F,16; P1.D,2d; P1.D,2; P1.D,2d; P1.19c, 2c; P1.D,10f; P1.A,10e; P1.A,10g; P1.A,10; P1.19,15; P1.19,15; P1.19,15; P1.19,15; P1.7b,16; P1.7,16b; P1.7,16; P1.19,15; P1.Eb,9; P1.5,2e; P1.E,A; P1.7b,13d; P1.Ea,3; P1.7,16b; P1.Ec,1; P1.7b,4; P1.7b,4; P1.7,9; P1.19,15; P1.19,15; P1.19,15; P1.19,15a; P1.19a,15b; P1.19,15; P1.5b,16; P1.19b,13a; P1.5,16; P1.5,2; P1.5,2b; P1.7b,16; P1.7,16b; P1.7b,3; P1.Ea,3; P1.5a,2c; P1.F,16; P1.5a,9; P1.7c,10c; P1.7b,13a; P1.7,13a; P1.7a,10; P1.20,9; P1.22,B; P1.5b,del; P1.5b,10; P1.7,13a; P1.12a,13f; P1.12a,13; P1.12a,13a; P1.12a,13a; P1.12a,13; P1.12a,13; P1.E,13b; P1.7b,13a; P1.7b,13; P1.5,2; P1.5,2; P1.Ea,3; P1.22,9; P1.5, 2; P1.5,2; P1.19,15; P1.5,2; P1.12b,13a; P1.5c,10a; P1.7e, 16e; P1.B,16d; P1.F,16e; P1.F,16e; P1.7b,13e; P1.B,16d; P1.7e,16e; P1.7b,13g; P1.B,16f; P1.7,16c; P1.22,14b; P1.22,14c; P1.7,14; P1.7,14; and P1.23,14.

Amino acid sequences of exemplary PorA polypeptides are found at GenBank accession nos. X57182, X57180, U92941, U92944, U92927, U92931, U92917, U92922, X52995, X57184, U92938, U92920, U92921, U92929, U92925, U92916, X57178, AF051542, X57181, U92919, U92926, X57177, X57179, U92947, U92928, U92915, X57183, U92943, U92942, U92939, U92918, U92946, U92496, U97260, U97259, AF042541, U92923, AF051539, AF051538, U92934, AF029088, U92933, U97263, U97261, U97262, U92945, AF042540, U92935, U92936, U92924, AF029086, AF020983, U94958, U97258, U92940, AF029084, U92930, U94959, U92948, AF016863, AF029089, U92937, AF029087, U92932, AF029090, AF029085, AF051540, AF051536, AF052743, AF054269, U92495, U92497, U92498, U92499, U92500, U92501, U92502, U92503, AF051541, X12899, Z48493, Z48489, Z48485, Z48494, Z48487, Z48488, Z48495, Z48490, Z48486, Z48491, Z48492, X66478, X66479, X66477, X66480, X81110, X79056, X78467, X81111, X78802, Z14281/82, Z14273/74, Z14275/76, Z14261/62, Z14265/66, Z14277/78, Z14283/84, Z14271/72, Z14269/70, Z14263/64, Z14259/60, Z14257/58, Z14293/94, Z14291/92, Z14279/80, Z14289/90, Z14287/88, Z14267/68, Z14285/86, L02929, X77423, X77424, X77433, X77426, X77428, X77430, X77427, X77429, X77425, X77432, X77431, X77422, Z48024/25, Z48032/33, Z48020/21, Z48022/23, Z48028/29, Z48016/17, Z48012/13, Z48014/15, Z48018/19, Z48026/27, U31060, U31061, U31062, U31063, U31064, U31065, U31066, U31067, U93898, U93899, U93900, U93901, U93902, U93903, U93904, U93905, U93906, U93907, and U93908.

Alternatively or in addition, the production strain can be a capsule deficient strain. Capsule deficient strains can provide vesicle-based vaccines that provide for a reduced risk of eliciting a significant autoantibody response in a subject to whom the vaccine is administered (e.g., due to production of antibodies that cross-react with sialic acid on host cell surfaces). "Capsule deficient" or "deficient in capsular polysaccharide" as used herein refers to a level of capsular polysaccharide on the bacterial surface that is lower than that of a naturally-occurring strain or, where the strain is genetically modified, is lower than that of a parental strain from which the capsule deficient strain is derived. A capsule deficient strain includes strains that are decreased in surface capsular polysaccharide production by at least 10%, 20%, 25%, 30%, 40%, 50%, 60%, 75%, 80%, 85%, 90% or more, and includes strains in which capsular polysaccharide is not detectable on the bacterial surface (e.g., by whole cell ELISA using an anti-capsular polysaccharide antibody).

Capsule deficient strains include those that are capsule deficient due to a naturally-occurring or recombinantly-generated genetic modification. Naturally-occurring capsule deficient strains (see, e.g., Dolan-Livengood et al. J. Infect. Dis. (2003) 187(10):1616-28), as well as methods of identifying and/or generating capsule-deficient strains (see, e.g., Fisseha et al. (2005) Infect. Immun. 73(7):4070-4080; Stephens et al. (1991) Infect Immun 59(11):4097-102; Frosch et al. (1990) Mol Microbiol. 1990 4(7):1215-1218) are known in the art.

Modification of a *Neisserial* host cell to provide for decreased production of capsular polysaccharide may include modification of one or more genes involved in capsule synthesis, where the modification provides for, for example, decreased levels of capsular polysaccharide relative to a parent cell prior to modification. Such genetic modifications can include changes in nucleotide and/or amino acid sequences in one or more capsule biosynthesis genes rendering the strain capsule deficient (e.g., due to one or more insertions, deletions, substitutions, and the like in one or more capsule biosynthesis genes). Capsule deficient strains can lack or be non-functional for one or more capsule genes.

Of particular interest are strains that are deficient in sialic acid biosynthesis. Such strains can provide for production of vesicles that have reduced risk of eliciting anti-sialic acid antibodies that cross-react with human sialic acid antigens, and can further provide for improved manufacturing safety. Strains having a defect in sialic acid biosynthesis (due to either a naturally occurring modification or an engineered modification) can be defective in any of a number of different genes in the sialic acid biosynthetic pathway. Of particular interest are strains that are defective in a gene product encoded by the N-acetylglucosamine-6-phosphate 2-epimerase gene (known as synX AAF40537.1 or siaA AAA20475), with strains having this gene inactivated being of especial interest. For example, in one embodiment, a capsule deficient strain is generated by disrupting production of a functional synX gene product (see, e.g., Swartley et al. (1994) J Bacteriol. 176(5):1530-4).

Capsular deficient strains can also be generated from naturally-occurring strains using non-recombinant techniques, e.g., by use of bactericidal anti-capsular antibodies to select for strains that reduced in capsular polysaccharide.

Where the invention involves use of two or more strains (e.g., to produce antigenic compositions of vesicles from different strains, as discussed below in more detail), the strains can be selected so as to differ in on or more strain characteristics, e.g., to provide for vesicles that differ in PorA type and/or GNA1870 variant group.

GNA1870 Production in *Neisserial* Host Cells

In general as noted above, vesicles can be produced according to the invention using a naturally-occurring or modified non-naturally-occurring *Neisserial* strain that produces vesicles with sufficient GNA1870 protein that, when administered to a subject, provide for production of anti-GNA1870 antibodies.

In one embodiment, the *Neisserial* strain used to produce vesicles according to the invention can be naturally occurring strains that express a higher level of GNA1870 relative to strains that express no detectable or a low level of GNA1870. RM1090 is an example of a strain that produces a low level of GNA1870. Naturally occurring strains that produce GNA1870 at a level that is 1.5, 2, 2.5 3, 3.5, 4, 4.5, 5, 5.5, 6, 6.5, 7, 7.5, 8, 8.5, 9, 9.5, or 10-fold or greater over GNA1870 production in a low GNA1870-producing strain, such as RM1090, are of particular interest. Examples of naturally-occurring strains that express a high level of GNA1870 include ET-5 strains such as H44/76, Cu385 and MC58. For a discussion of strains that express low or undetectable levels of GNA1870, intermediate levels of GNA1870, or high levels of GNA1870 see Masignani et al. 2003, J Exp Med 197:789-199. In particular embodiments, the strain produces a level of GNA1870 that is greater than that produced in RM1090, and can be at least 1.5, 2, 2.5 3, 3.5, 4, 4.5, 5, 5.5, 6, 6.5, 7, 7.5, 8, 8.5, 9, 9.5, or 10-fold or greater than that in RM1090.

In another embodiment, the *Neisserial* strain is modified by recombinant or non-recombinant techniques to provide for a sufficiently high level of GNA1870 production. Such modified strains generally are produced so as to provide for an increase in GNA1870 production that is 1.5, 2, 2.5 3, 3.5, 4, 4.5, 5, 5.5, 6, 6.5, 7, 7.5, 8, 8.5, 9, 9.5, or 10-fold or greater over GNA1870 production in the unmodified parental cell or over GNA1870 production of the strain RM1090. Any suitable strain can be used in this embodiment, including strains that produce low or undetectable levels of GNA1870 prior to modification and strains that naturally produce high levels of GNA1870 relative to strains that express no detectable or a low level of GNA1870.

Modified strains can be generated by non-recombinant techniques such as, for example, exposure to chemicals, radiation, or other DNA modifying or damaging agent, and the like. Modified strains having a desired protein expression profile, particularly with respect to GNA1870 production, can be identified through screening for strains producing a desired level of GNA1870 (e.g., an increased level of GNA1870 as compared to the unmodified parental strain or a low GNA1870 producer (such as RM1090), or a level similar to that of a strain that produces GNA1870 at acceptably high levels).

Alternatively, and more usually, modified strains are produced using recombinant techniques, usually by introduction of nucleic acid encoding a GNA1870 polypeptide or manipulation of an endogenous GNA1870 gene to provide for increased expression of endogenous GNA1870.

Methods for determining GNA1870 production levels are known in the art. Such methods include, for example, Western blot (optionally with analysis assisted by densitometry scan), flow cytometric (e.g., FACS) analysis using anti-GNA1870 antibody, detection of GNA1870 RNA levels, and the like. Strains that have higher levels of GNA1870 production, either naturally or due to genetic modification, are sometimes referred to herein as GNA1870 "over-expressers" or are said to "overexpress" GNA1870.

Production of Genetically Modified *Neisserial* Strains

As noted above, by introduction of nucleic acid encoding a GNA1870 polypeptide or manipulation of an endogenous GNA1870 gene to provide for increased expression of endogenous GNA1870.

*Neisserial* Host Cells Genetically Modified to Provide for Increased Expression of an Endogenous GNA1870

Endogenous GNA1870 expression can be increased by altering in situ the regulatory region controlling the expression of GNA1870. Methods for providing for increased expression of an endogenous *Neisserial* gene are known in the art (see, e.g., WO 02/09746). Furthermore, the nucleic acid sequences of genes encoding genomic GNA1870 variants and subvariants are known, providing for ready adaptation of such methods in the upregulation of endogenous GNA1870 expression.

The endogenous GNA1870 may be of any desired variant group (e.g., v.1, v.2, v.3, and the like) or subvariant of GNA1870. A "canonical" v.1 GNA1870 polypeptide of strain MC58 is of particular interest. Also of interest is a subvariant GNA1870 polypeptide of strain NZ98/294, and v.2 GNA1870 polypeptide of strain 2996.

Modification of a *Neisserial* host cell to provide for increased production of endogenous GNA1870 may include partial or total replacement of all of a portion of the endogenous gene controlling GNA1870 expression, where the modification provides for, for example, enhanced transcriptional activity relative to the unmodified parental strain. Increased transcriptional activity may be conferred by variants (point mutations, deletions and/or insertions) of the endogenous control regions, by naturally occurring or modified heterologous promoters or by a combination of both. In general the genetic modification confers a transcriptional activity greater than that of the unmodified endogenous transcriptional activity (e.g., by introduction of a strong promoter), resulting in an enhanced expression of GNA1870.

Typical strong promoters that may be useful in increasing GNA1870 transcription production can include, for example, the promoters of porA, porB, lbpB, tbpB, p110, hpuAB, lgtF, Opa, p110, 1st, and hpuAB. PorA, RMp and PorB are of particular interest as constitutive, strong promoters. PorB promoter activity is contained in a fragment corresponding to nucleotides −1 to −250 upstream of the initation codon of porB.

Methods are available in the art to accomplish introduction of a promoter into a host cell genome so as to operably link the promoter to an endogenous GNA1870-encoding nucleic acid. For example, double cross-over homologous recombination technology to introduce a promoter in a region upstream of the coding sequence, e.g., about 1000 bp, from about 30-970 bp, about 200-600 bp, about 300-500 bp, or about 400 bp upstream (5') of the initiation ATG codon of the GNA1870-encoding nucleic acid sequence to provide for up-regulation. Optimal placement of the promoter can be determined through routine use of methods available in the art.

For example, a highly active promoter (e.g., PorA, PorB or Rmp promoters) upstream of the targeted gene. As an example, the PorA promoter can be optimized for expression as described by van der Ende et al. Infect Immun 2000; 68:6685-90. Insertion of the promoter can be accomplished by, for example, PCR amplification of the upstream segment of the targeted GNA1870 gene, cloning the upstream segment in a vector, and either inserting appropriate restriction sites during PCR amplification, or using naturally occurring restriction sites to insert the PorA promoter segment. For example, an about 700 bp upstream segment of the GNA1870 gene can be cloned. Using naturally occurring restriction enzyme sites located at an appropriate distance (e.g., about 400 bp) upstream of the GNA1870 promoter within this cloned segment a PorA promoter segment is inserted. An antibiotic (e.g., erythromycin) resistance cassette can be inserted within the segment further upstream of the PorA promoter and the construct was used to replace the wild-type upstream GNA1870 segment by homologous recombination.

Another approach involves introducing a GNA1870 polypeptide-encoding sequence downstream of an endogenous promoter that exhibits strong transcriptional activity in the host cell genome. For example, the coding region of the Rmp gene can be replaced with a coding sequence for a GNA1870 polypeptide. This approach takes advantage of the highly active constitutive Rmp promoter to drive expression.

*Neisserial* Host Cells Genetically Modified to Express an Exogenous GNA1870

*Neisserial* strains can be genetically modified to over-express GNA1870 bp introduction of a construct encoding a GNA1870 polypeptide into a *Neisserial* host cell. The GNA1870 introduced for expression is referred to herein as an "exogenous" GNA1870. The host cell produces an endogenous GNA1870, the exogenous GNA1870 may have the same or different amino acid sequence compared to the endogenous GNA1870.

The strain used as the host cell in this embodiment can produce any level of GNA1870 (e.g., high level, intermediate level, or low level GNA1870 production). Of particular interest is use of a strain that is selected for low level or no detectable GNA1870 production, or that is modified to exhibit no detectable, or a low level, of GNA1870 production. For example, the host cell may be genetically modified so that the endogenous GNA1870 gene is disrupted so that GNA1870 is not produced or is not present in the cell envelope (and thus is not present at detectable levels in a vesicle prepared from such a modified cell). In other embodiments, the host cell produces an intermediate or high level of GNA1870 (e.g., relative to a level of GNA1870 produced by, for example, RM1090).

GNA1870 Polypeptides

The host cell can be genetically modified to express any suitable GNA1870 polypeptide, including GNA1870 variants or subvariants. As described in more detail below, the amino acid sequences of many GNA1870 polypeptides are known; alignment of these sequences provides guidance as to residues that are conserved among the variants, thus providing guidance as to amino acid modifications (e.g., substitutions, insertions, deletions) that can be made.

Accordingly, "GNA1870 polypeptide" as used herein encompasses naturally-occurring and synthetic (non-naturally occurring) polypeptides which share at least about 60%, 65%, 70%, 75%, 80%, 85%, 90%, 95% or greater sequence identity at the nucleotide or amino acid level with a naturally-occurring GNA1870 polypeptide, and which are capable of eliciting antibodies that specifically bind a naturally-occurring GNA1870 polypeptide present on a whole cell Neisserial bacterium. "GNA1870 polypeptide" also encompasses fusion proteins, e.g., a GNA1870 polypeptide having a heterologous polypeptide at the N- and/or C-terminus.

The host cell can be genetically modified to express at least 1 GNA1870 polypeptide, and can be modified to express 2, 3, 4 or more GNA1870 polypeptides in the same host cell. For example, a single host cell can be genetically modified to express at least one variant 1 GNA1870 polypeptide, at least one variant 2 GNA1870 polypeptide, and at least one variant 3 GNA1870 polypeptide.

Where expression of multiple GNA1870 polypeptides meets with difficulty due to toxicity to the host cell, the different GNA1870 polypeptides may be expressed from different promoters so as to allow a range of expression. For example, varying both the base composition and number of bases between the −10 and −35 regions of the PorA promoter should result in a wide range of expression of the desired recombinant protein (van der Ende et al. Infect Immun 2000; 68:6685-90).

Nucleic acids encoding a GNA1870 polypeptide for use in the invention are known in the art. Suitable GNA1870 polypeptides are described in, for example, WO 2004/048404; Masignani et al. 2003 J Exp Med 197:789-799; Fletcher et al. Infect Immun 2004 2088-2100; Welsch et al. J Immunol 2004 172:5606-5615; and WO 99/57280. Nucleic acid (and amino acid sequences) for GNA1870 variants and subvariants are also provided in GenBank as accession nos.: NC_003112, GeneID: 904318 (NCBI Ref. NP_274866) (from N. meningitidis strain MC58); AY548371 (AAT01290.1) (from N. meningitidis strain CU385); AY548370 (AAT01289.1) (from N. meningitidis strain H44/76); AY548377 (AAS56920.1) (from N. meningitidis strain M4105); AY548376 (AAS56919.1) (from N. strain M1390); AY548375 (AAS56918.1) (from N. meningitidis strain N98/254); AY548374 (AAS56917.1) (from N. meningitidis strain M6190); AY548373 (AAS56916.1) (from N. meningitidis strain 4243); and AY548372 (AAS56915.1) (from N. meningitidis strain BZ83).

FIG. 7 is an alignment of exemplary amino acid sequences of GNA1870 variants 1, 2 and 3 from N. meningitidis strains MC58, 951-5945, and M1239, respectively (WO 2004/048404). The immature GNA1870 protein includes a leader sequence of about 19 residues, with each variant usually containing an N-terminal cysteine to which a lipid moiety can be covalently attached. This cysteine residue is usually lipidated in the naturally-occurring protein. "1" indicates that first amino acid of the mature protein, with amino acids indicated by negative numbers part of the leader sequence. Grey and black backgrounds indicate conserved and identical amino acid residues, respectively. Additional amino acid sequences of GNA1870 polypeptides, including non-naturally occurring variants, is provided in FIGS. 8A-8H and 9.

The GNA1870 can be lipidated or non-lipidated. It is generally preferred that the GNA1870 be lipidated, so as to provide for positioning of the polypeptide in the membrane. Lipidated GNA1870 can be prepared by expression of the GNA1870 polypeptide having the N-terminal signal peptide to direct lipidation by diacylglyceryl transferase, followed by cleavage by lipoprotein-specific (type II) signal peptidase.

The GNA1870 polypeptide useful in the invention includes non-naturally occurring (artificial or mutant) GNA1870 polypeptides that differ in amino acid sequence from a naturally-occurring GNA1870 polypeptide, but which are present in the membrane of a Neisserial host so that vesicles prepared from the host contain GNA1870 in a form that provides for presentation of epitopes of interest, preferably a bactericidal epitope, and provides for an anti-GNA1870 antibody response. In one embodiment, the GNA1870 polypeptide is a variant 1 (v.1) or variant 2 (v.2) or variant 3 (v.3) GNA1870 polypeptide, with subvariants of v.1 v.2 and v.3 being of interest, including subvariants of v.1 (see, e.g., Welsch et al. J Immunol 2004 172:5606-5615). In one embodiment, the GNA1870 polypeptide comprises an amino acid sequence of a GNA1870 polypeptide that is most prevalent among the strains endemic to the population to be vaccinated.

GNA1870 polypeptides useful in the invention also include fusion proteins, where the fusion protein comprises a GNA1870 polypeptide having a fusion partner at its N-terminus or C-terminus Fusion partners of interest include, for example, glutathione S transferase (GST), maltose binding protein (MBP), His-tag, and the like, as well as leader peptides from other proteins, particularly lipoproteins (e.g., the amino acid sequence prior to the N-terminal cysteine may be replaced with another leader peptide of interest).

Other GNA1870 polypeptide-encoding nucleic acids can be identified using techniques well known in the art, where GNA1870 polypeptides can be identified based on amino acid sequences similarity to a known GNA1870 polypeptide. Such GNA1870 polypeptides generally share at least about 60%, 65%, 70%, 75%, 80%, 85%, 90%, 95% or greater sequence identity at the nucleotide or amino acid level. Sequence identity can be determined using methods for alignment and comparison of nucleic acid or amino acid sequences, which methods are well known in the art. Comparison of longer sequences may require more sophisticated methods to achieve optimal alignment of two sequences. Optimal alignment of sequences for aligning a comparison window may be conducted by the local homology algorithm of Smith and Waterman (1981) Adv. Appl. Math. 2:482, by the homology alignment algorithm of Needleman and Wunsch (1970) J. Mol. Biol. 48:443, by the search for similarity method of Pearson and Lipman (1988) Proc. Natl. Acad. Sci. (USA) 85:2444, by computerized implementations of these algorithms (GAP, BESTFIT, FASTA, and TFASTA in the Wisconsin Genetics Software Package Release 7.0, Genetics Computer Group, 575 Science Dr., Madison, Wis.), or by inspection, and the best alignment (i.e. resulting in the highest percentage of sequence similarity over the comparison window) generated by the various methods is selected.

The terms "identical" or percent "identity," in the context of two or more nucleic acids or polypeptide sequences, refer to two or more sequences or subsequences that are the same or have a specified percentage of amino acid residues or nucleotides that are the same, when compared and aligned for maximum correspondence, as measured using one of the following sequence comparison algorithms or by visual inspection. Polypeptides of interest include those having at least 60%, 70%, 75%, 80%, 85%, 90%, 95% or more nucleotide or amino acid residue identity, when compared and aligned for maximum correspondence, as measured using one of the following sequence comparison algorithms or by visual inspection. Preferably, the region sharing sequence identity exists over a region of the sequences that is at least about 10, 20, 30, 40, 50, 60, 70, 80, or 100 contiguous residues in length. In a most preferred embodiment, identity of the sequences is determined by comparison of the sequences over the entire length of the coding region of a reference polypeptide.

For sequence comparison, typically one sequence acts as a reference sequence (e.g., a naturally-occurring GNA1870 polypeptide sequence), to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally, Current Protocols in Molecular Biology, F. M. Ausubel et al., eds., Current Protocols, a joint venture between Greene Publishing Associates, Inc. and John Wiley & Sons, Inc., (1995 Supplement) (Ausubel)).

Examples of algorithms that are suitable for determining percent sequence identity and sequence similarity are the BLAST and BLAST 2.0 algorithms, which are described in Altschul et al. (1990) J. Mol. Biol. 215: 403-410 and Altschuel et al. (1977) Nucleic Acids Res. 25: 3389-3402, respectively. Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al, supra).

These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4, and a comparison of both strands. For amino acid sequences, the BLASTP program uses as defaults a wordlength (W) of 3, an expectation (E) of 10, and the BLOSUM62 scoring matrix (see Henikoff & Henikoff, Proc. Natl. Acad. Sci. USA 89:10915 (1989)).

In addition to calculating percent sequence identity, the BLAST algorithm also performs a statistical analysis of the similarity between two sequences (see, e.g., Karlin & Altschul, Proc. Nat'l. Acad. Sci. USA 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.1, more preferably less than about 0.01, and most preferably less than about 0.001.

A further indication that two nucleic acid sequences or polypeptides share sequence identity is that the polypeptide encoded by the first nucleic acid is immunologically cross reactive with the polypeptide encoded by the second nucleic acid, as described below. Thus, a polypeptide typically share sequence identity with a second polypeptide, for example, where the two polypeptides differ only by conservative substitutions. Another indication that two nucleic acid sequences share sequence identity is that the two molecules hybridize to each other under stringent conditions. The selection of a particular set of hybridization conditions is selected following standard methods in the art (see, for example, Sambrook, et al., *Molecular Cloning: A Laboratory Manual*, Second Edition, (1989) Cold Spring Harbor, N.Y.). An example of stringent hybridization conditions is hybridization at 50° C. or higher and 0.1×SSC (15 mM sodium chloride/1.5 mM sodium citrate). Another example of stringent hybridization conditions is overnight incubation at 42° C. in a solution: 50% formamide, 5×SSC (150 mM NaCl, 15 mM trisodium citrate), 50 mM sodium phosphate (pH7.6), 5×Denhardt's solution, 10% dextran sulfate, and 20 mg/ml denatured, sheared salmon sperm DNA, followed by washing the filters in 0.1×SSC at about 65° C. Stringent hybridization conditions are hybridization conditions that are at least as stringent as the above representative conditions, where conditions are considered to be at least as stringent if they are at least about 80% as stringent, typically at least about 90% as stringent as the above specific stringent conditions. Other stringent hybridization conditions are known in the art and may also be employed to identify nucleic acids of this particular embodiment of the invention.

Preferably, residue positions which are not identical differ by conservative amino acid substitutions. Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine-valine, and asparagine-glutamine.

Vector and Methods for Introducing Genetic Material into *Neisserial* Host Cells Methods and compositions which can be readily adapted to provide for genetic modification of a *Neisserial* host cell to express an exogenous GNA1870 polypeptide are known in the art. Exemplary vectors and methods are provided in WO 02/09746 and O'Dwyer et al. Infect Immun 2004; 72:6511-80.

Methods for transfer of genetic material into a *Neisserial* host include, for example, conjugation, transformation, electroporation, calcium phosphate methods and the like. The method for transfer should provide for stable expression of the introduced GNA1870-encoding nucleic acid. The GNA1870-encoding nucleic acid can be provided as an inheritable episomal element (e.g., plasmid) or can be genomically integrated.

Suitable vectors will vary in composition depending what type of recombination event is to be performed. Integrative vectors can be conditionally replicative or suicide plasmids, bacteriophages, transposons or linear DNA fragments obtained by restriction hydrolysis or PCR amplification. Selection of the recombination event can be accomplished by means of selectable genetic marker such as genes conferring resistance to antibiotics (for instance kanamycin, erythromycin, chloramphenicol, or gentamycin), genes conferring resistance to heavy met als and/or toxic compounds or genes complementing auxotrophic mutations (for instance pur, leu, met, aro).

In one embodiment, the vector is an expression vector based on episomal plasmids containing selectable drug resistance markers that autonomously replicate in both *E. coli* and *N. meningitidis*. One example of such a "shuttle vector" is the plasmid pFP10 (Pagotto et al. Gene 2000 244:13-19).

Preparation of *Neisseria meningitidis* Vesicles

The antigenic compositions for use in the invention generally include vesicles prepared from *Neisserial* cells that express an acceptable level of GNA1870, either naturally or due to genetic modification (e.g., due to expression of a recombinant GNA1870). As referred to herein "vesicles" is meant to encompass outer membrane vesicles as well as microvesicles (which are also referred to as blebs).

In one embodiment, the antigenic composition comprises outer membrane vesicles (OMV) prepared from the outer membrane of a cultured strain of *Neisseria meningitidis* spp. OMVs may be obtained from a *Neisseria meningitidis* grown in broth or solid medium culture, preferably by separating the bacterial cells from the culture medium (e.g. by filtration or by a low-speed centrifugation that pellets the cells, or the like), lysing the cells (e.g. by addition of detergent, osmotic shock, sonication, cavitation, homogenization, or the like) and separating an outer membrane fraction from cytoplasmic molecules (e.g. by filtration; or by differential precipitation or aggregation of outer membranes and/or outer membrane vesicles, or by affinity separation methods using ligands that specifically recognize outer membrane molecules; or by a high-speed centrifugation that pellets outer membranes and/or outer membrane vesicles, or the like); outer membrane fractions may be used to produce OMVs.

In another embodiment, the antigenic composition comprises microvesicles (MV) or blebs that are released during culture of said *Neisseria meningitidis* spp. MVs may be obtained by culturing a strain of *Neisseria meningitidis* in broth culture medium, separating whole cells from the broth culture medium (e.g. by filtration, or by a low-speed centrifugation that pellets only the cells and not the smaller blebs, or the like), and then collecting the MVs that are present in the cell-free culture medium (e.g. by filtration, differential precipitation or aggregation of MVs, or by a high-speed centrifugation that pellets the blebs, or the like). Strains for use in production of MVs can generally be selected on the basis of the amount of blebs produced in culture (e.g., bacteria can be cultured in a reasonable number to provide for production of blebs suitable for isolation and administration in the methods described herein). An exemplary strain that produces high levels of blebs is described in PCT Publication No. WO 01/34642. In addition to bleb production, strains for use in MV production may also be selected on the basis of NspA production, where strains that produce higher levels of NspA may be preferable (for examples of *N. meningitides* strains having different NspA production levels, see, e.g., Moe et al. (1999 Infect. Immun 67: 5664).

In another embodiment, the antigenic composition comprises vesicles from one strain, or from 2, 3, 4, 5 or more strains, which strains may be homologous or heterologous, usually heterologous, to one another with respect to one or both of GNA1870 or PorA. In one embodiment, the vesicles are prepared from a strain that expresses 1, 2, 3, 4, 5, 6, 7, 8, 9 or 10 or more GNA1870 proteins, which may be different variants (v.1, v.2, v.3) or subvariants (e.g., a subvariant of v.1, v.2, or v.3). In another embodiment, the antigenic compositions comprises a mixture of OMVs and MVs, which may be from the same or different strains. In such embodiments, vesicles from different strains can be administered as a mixture. Further, OMVs and MVs from the same or different strains can be administered as a mixture. In addition to vesicles (OMVs and/or MVs), isolated antigens or particular combinations of antigens may be included in the antigenic compositions of the invention.

Reduction of Lipid Toxicity

Where desired (e.g., where the strains used to produce vesicles are associated with endotoxin or particular high levels of endotoxin), the vesicles are optionally treated to reduce endotoxin, e.g., to reduce toxicity following administration. Although less desirable as discussed below, reduction of endotoxin can be accomplished by extraction with a suitable detergent (for example, BRIJ-96, sodium deoxycholate, sodium lauoylsarcosinate, EMPIGEN BB detergent, TRITON X-100 detergent, TWEEN 20 (sorbitan monolaurate polyoxyethylene), TWEEN 80, at a concentration of 0.1-10%, preferably 0.5-2%, and SDS). Where detergent extraction is used, it is preferable to use a detergent other than deoxycholate. In some embodiment, vesicles are produced without use of detergent, e.g., without use of deoxycholate or other detergent.

In embodiments of particular interest, the vesicles of the antigenic compositions are prepared without detergent. Although detergent treatment is useful to remove endotoxin activity, it may deplete the native GNA1870 lipoprotein by extraction during vesicle production. Thus it may be particularly desirable to decrease endotoxin activity using technology that does not require a detergent. In one approach, strains that are relatively low producers of endotoxin (lipopolysaccharide, LPS) are used so as to avoid the need to remove endotoxin from the final preparation prior to use in humans. For example, the vesicles can be prepared from *Neisseria* mutants in which lipooligosaccharide or other antigens that may be undesirable in a vaccine (e.g. Rmp) is reduced or eliminated.

For example, vesicles can be prepared from *N. meningitidis* strains that contain genetic modifications that result in decreased or no detectable toxic activity of lipid A. For example, such strain can be genetically modified in lipid A biosynthesis (Steeghs et al. Infect Immun 1999; 67:4988-93; van der Ley et al. Infect Immun 2001; 69:5981-90; Steeghs et al. J Endotoxin Res 2004; 10:113-9). Mutations in genes responsible for the terminal modifications steps lead to temperature-sensitive (htrB) or permissive (msbB) phenotypes. Mutations resulting in a decreased (or no) expression of these genes (or decreased or no activity of the product of these genes) result in altered toxic activity of lipid A. Non-lauroylated (htrB mutant) or non-myristoylated (msbB mutant) lipid A are less toxic than the wild-type lipid A. Mutations in the lipid A 4'-kinase encoding gene (lpxK) also decreases the toxic activity of lipid A.

LPS toxic activity can also be altered by introducing mutations in genes/loci involved in polymyxin B resistance (such resistance has been correlated with addition of aminoarabinose on the 4' phosphate of lipid A). These genes/loci could be pmrE that encodes a UDP-glucose dehydrogenase, or a region of antimicrobial peptide-resistance genes common to many enterobacteriaciae which could be involved in aminoarabinose synthesis and transfer. The gene pmrF that is present in this region encodes a dolicol-phosphate manosyl transferase (Gunn J. S., Kheng, B. L., Krueger J., Kim K., Guo L., Hackett M., Miller S. I. 1998. Mol. Microbiol. 27: 1171-1182).

Mutations in the PhoP-PhoQ regulatory system, which is a phospho-relay two component regulatory system (e.g., PhoP constitutive phenotype, PhoP$^c$), or low $Mg^{++}$ environmental or culture conditions (that activate the PhoP-PhoQ regulatory system) lead to the addition of aminoarabinose on the 4'-phosphate and 2-hydroxymyristate replacing myristate (hydroxylation of myristate). This modified lipid A displays reduced ability to stimulate E-selectin expression by human endothelial cells and TNF-α secretion from human monocytes.

Polymyxin B resistant strains are also suitable for use in the invention, as such strains have been shown to have reduced LPS toxicity (see, e.g., van der Ley et al. 1994. In: Proceedings of the ninth international pathogenic *Neisseria* conference. The Guildhall, Winchester, England). Alternatively, synthetic peptides that mimic the binding activity of polymyxin B may be added to the antigenic compositions to reduce LPS toxic activity (see, e.g., Rustici et al. 1993, Science 259:361-365; Porro et al. Frog Clin Biol Res. 1998; 397:315-25).

Endotoxin can also be reduced through selection of culture conditions. For example, culturing the strain in a growth medium containing 0.1 mg-100 mg of aminoarabinose per liter medium provides for reduced lipid toxicity (see, e.g., WO 02/097646).

Formulations

Immunogenic compositions used as vaccines comprise an immunologically effective amount of antigen, particularly an immunologically effective amount of GNA1870, as well as any other compatible components, as needed. By "immunologically effective amount" is meant that the administration of that amount to an individual, either in a single dose or as part of a series, is effective to elicit for treatment or prevention. This amount varies depending upon the health and physical condition of the individual to be treated, age, the taxonomic group of the individual to be treated (e.g., non-human primate, primate, human, etc.), the capacity of the individual's immune system to synthesize antibodies, the degree of protection desired, the formulation of the vaccine, the treating clinician's assessment of the medical situation, and other relevant factors. It is expected that the amount will fall in a relatively broad range that can be determined through routine trials.

Dosage regimen may be a single dose schedule or a multiple dose schedule (e.g., including booster doses) with a unit dosage form of the antigenic composition administered at different times. The term "unit dosage form," as used herein, refers to physically discrete units suitable as unitary dosages for human and animal subjects, each unit containing a predetermined quantity of the antigenic compositions of the present invention in an amount sufficient to produce the desired effect, which compositions are provided in association with a pharmaceutically acceptable excipient (e.g., pharmaceutically acceptable diluent, carrier or vehicle). The vaccine may be administered in conjunction with other immunoregulatory agents.

The antigenic compositions to be administered are provided in a pharmaceutically acceptable diluent such as an aqueous solution, often a saline solution, a semi-solid form (e.g., gel), or in powder form. Such diluents can be inert, although the compositions of the invention may also include an adjuvant. Examples of known suitable adjuvants that can be used in humans include, but are not necessarily limited to, alum, aluminum phosphate, aluminum hydroxide, MF59 (4.3% w/v squalene, 0.5% w/v TWEEN 80 detergent, 0.5% w/v SPAN 85 emulsifier), CpG-containing nucleic acid (where the cytosine is unmethylated), QS21, MPL, 3DMPL, extracts from Aquilla, ISCOMS, LT/CT mutants, poly(D,L-lactide-co-glycolide) (PLG) microparticles, Quil A, interleukins, and the like. For experimental animals, one can use Freund's, N-acetyl-muramyl-L-threonyl-D-isoglutamine (thr-MDP), N-acetyl-nor-muramyl-L-alanyl-D-isoglutamine (CGP 11637, referred to as nor-MDP), N-acetylmuramyl-L-alanyl-D-isoglutaminyl-L-alanine-2-(1'-2'-dipalmitoyl-sn-glycero-3-hydroxyphosphoryloxy)-ethylamine (CGP 19835A, referred to as MTP-PE), and RIBI, which contains three components extracted from bacteria, monophosphoryl lipid A, trehalose dimycolate and cell wall skeleton (MPL+TDM+CWS) in a 2% squalene/Tween 80 emulsion. The effectiveness of an adjuvant may be determined by measuring the amount of antibodies directed against the immunogenic antigen.

Further exemplary adjuvants to enhance effectiveness of the composition include, but are not limited to: (1) oil-in-water emulsion formulations (with or without other specific immunostimulating agents such as muramyl peptides (see below) or bacterial cell wall components), such as for example (a) MF59™ (WO90/14837; Chapter 10 in *Vaccine design: the subunit and adjuvant approach*, eds. Powell & Newman, Plenum Press 1995), containing 5% Squalene, 0.5% TWEEN 80, and 0.5% SPAN 85 emulsifier (optionally containing MTP-PE) formulated into submicron particles using a microfluidizer, (b) SAF, containing 10% Squalane, 0.4% TWEEN 80 detergent, 5% PLURONIC-blocked polymer L121, and thr-MDP either microfluidized into a submicron emulsion or vortexed to generate a larger particle size emulsion, and (c) RIBI™ adjuvant system (RAS), (Ribi Immunochem, Hamilton, Mont.) containing 2% Squalene, 0.2% TWEEN 80 detergent, and one or more bacterial cell wall components such as monophosphorylipid A (MPL), trehalose dimycolate (TDM), and cell wall skeleton (CWS), preferably MPL+CWS (DETOX™); (2) saponin adjuvants, such as QS21 or STIMULON™ (Cambridge Bioscience, Worcester, Mass.) may be used or particles generated therefrom such as ISCOMs (immunostimulating complexes), which ISCOMS may be devoid of additional detergent e.g. WO00/07621; (3) Complete Freund's Adjuvant (CFA) and Incomplete Freund's Adjuvant (IFA); (4) cytokines, such as interleukins (e.g. IL-1, IL-2, IL-4, IL-5, IL-6, IL-7, IL-12 (WO99/44636), etc.), interferons (e.g. gamma interferon), macrophage colony stimulating factor (M-CSF), tumor necrosis factor (TNF), etc.; (5) monophosphoryl lipid A (MPL) or 3-O-deacylated MPL (3dMPL) e.g. GB-2220221, EP-A-0689454, optionally in the substantial absence of alum when used with pneumococcal saccharides e.g. WO00/56358; (6) combinations of 3dMPL with, for example, QS21 and/oroil-in-water emulsions e.g. EP-A-0835318, EP-A-0735898, EP-A-0761231; (7) oligonucleotides comprising CpG motifs [Krieg *Vaccine* 2000, 19, 618-622; Krieg *Curr opin Mol Ther* 2001 3:15-24; Roman et al., *Nat. Med.*, 1997, 3, 849-854; Weiner et al., *PNAS USA,* 1997, 94, 10833-10837; Davis et al, *J. Immunol,* 1998, 160, 870-876; Chu et al., *J. Exp. Med,* 1997, 186, 1623-1631; Lipford et al, *Ear. J. Immunol.,* 1997, 27, 2340-2344; Moldoveami et al., *Vaccine,* 1988, 16, 1216-1224, Krieg et al., *Nature,* 1995, 374, 546-549; Klinman et al., *PNAS USA,* 1996, 93, 2879-2883; Ballas et al, *J. Immunol,* 1996, 157, 1840-1845; Cowdery et al, *J. Immunol,* 1996, 156, 4570-4575; Halpern et al, *Cell Immunol,* 1996, 167, 72-78; Yamamoto et al, *Jpn. J. Cancer Res.,* 1988, 79, 866-873; Stacey et al, *J. Immunol.,* 1996, 157,2116-2122; Messina et al, *J. Immunol,* 1991, 147, 1759-1764; Yi et al, *J. Immunol,* 1996, 157,4918-4925; Yi et al, *J. Immunol,* 1996, 157, 5394-5402; Yi et al, *J. Immunol,* 1998, 160, 4755-4761; and Yi et al, *J. Immunol,* 1998, 160, 5898-5906; International patent applications WO96/02555, WO98/16247, WO98/18810, WO98/40100, WO98/55495, WO98/37919 and WO98/52581] i.e. containing at least one CG dinucleotide, where the cytosine is unmethylated; (8) a polyoxyethylene ether or a polyoxyethylene ester e.g. WO99/52549; (9) a polyoxyethylene sorbitan ester surfactant in combination with an octoxynol (WO01/21207) or a polyoxyethylene alkyl ether or ester surfactant in combination with at least one additional non-ionic surfactant such as an octoxynol (WO01/21152); (10) a saponin and an immunostimulatory oligonucleotide (e.g. a CpG oligonucleotide) (WO00/62800); (11) an immunostimulant and a particle of m et al salt e.g. WO00/23105; (12) a saponin and an oil-in-water emulsion e.g. WO99/11241; (13) a saponin (e.g. QS21)+3dMPL+IM2 (optionally+a sterol) e.g. WO98/57659; (14) other substances that act as immunostimulating agents to enhance the efficacy of the composition. Muramyl peptides include N-acetyl-muramyl-L-threonyl-D-isoglutamine (thr-MDP), N-25 acetyl-normuramyl-L-alanyl-D-isoglutamine (nor-MDP), N-acetylmuramyl-L-alanyl-D-isoglutarninyl-L-alanine-2-(1'-2'-dipalmitoyl-sn-glycero-3-hydroxyphosphoryloxy)-ethylamine MTP-PE), etc.

The antigenic compositions may be combined with a conventional pharmaceutically acceptable excipient, such as pharmaceutical grades of mannitol, lactose, starch, magnesium stearate, sodium saccharin, talcum, cellulose, glucose, sucrose, magnesium, carbonate, and the like. The compositions may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate and the like. The concentration of antigen in these formulations can vary widely, and will be selected primarily based on fluid volumes, viscosities, body weight and the like in accordance with the particular mode of administration selected and the patient's needs. The resulting compositions may be in the form of a solution, suspension, tablet, pill, capsule, powder, gel, cream, lotion, ointment, aerosol or the like.

The protein concentration of antigenic compositions of the invention in the pharmaceutical formulations can vary widely, i.e. from less than about 0.1%, usually at or at least about 2% to as much as 20% to 50% or more by weight, and will be selected primarily by fluid volumes, viscosities, etc., in accordance with the particular mode of administration selected.

Immunization

In general, the methods of the invention provide for administration of one or more antigenic compositions of the invention to a mammalian subject (e.g., a human) so as to elicit a protective immune response against more than one strain of *Neisseria* species bacteria, and thus protection against disease caused by such bacteria. In particular, the methods of the invention can provide for an immunoprotective immune response against a 1, 2, 3, 4, or more strains of *Neisseria meningitidis* species, where the strains differ in at least one of serogroup, serotype, serosubtype, or GNA1870 polypeptide (e.g., different GNA1870 variants and/or subvariants). Of particular interest is induction of a protective immune response against multiple strains of *Neisseria meningitidis* of serogroup B, particularly where the strains differ in serosubtype (e.g., have heterologous PorAs). Also of particular interest is induction of a protective immune response against strains that are heterologous to one other in terms of PorA and/or GNA1870.

The antigenic compositions of the invention can be administered orally, nasally, nasopharyngeally, parenterally, enterically, gastrically, topically, transdermally, subcutaneously, intramuscularly, in tablet, solid, powdered, liquid, aerosol form, locally or systemically, with or without added excipients. Actual methods for preparing parenterally administrable compositions will be known or apparent to those skilled in the art and are described in more detail in such publications as Remington's Pharmaceutical Science, 15th ed., Mack Publishing Company, Easton, Pa. (1980).

It is recognized that oral administration can require protection of the compositions from digestion. This is typically accomplished either by association of the composition with an agent that renders it resistant to acidic and enzymatic hydrolysis or by packaging the composition in an appropriately resistant carrier. Means of protecting from digestion are well known in the art.

The compositions are administered to an animal that is at risk from acquiring a *Neisserial* disease to prevent or at least partially arrest the development of disease and its complications. An amount adequate to accomplish this is defined as a "therapeutically effective dose." Amounts effective for therapeutic use will depend on, e.g., the antigenic composition, the manner of administration, the weight and general state of health of the patient, and the judgment of the prescribing physician. Single or multiple doses of the antigenic compositions may be administered depending on the dosage and frequency required and tolerated by the patient, and route of administration.

The antigenic compositions described herein can comprise a mixture of vesicles (e.g., OMV and MV), which vesicles can be from the same or different strains. In another embodiment, the antigenic compositions can comprise a mixture of vesicles from 2, 3, 4, 5 or more strains, where the vesicles can be OMV, MV or both.

The antigenic compositions are administered in an amount effective to elicit an immune response, particularly a humoral immune response, in the host. Amounts for the immunization of the mixture generally range from about 0.001 mg to about 1.0 mg per 70 kilogram patient, more commonly from about 0.001 mg to about 0.2 mg per 70 kilogram patient. Dosages from 0.001 up to about 10 mg per patient per day may be used, particularly when the antigen is administered to a secluded site and not into the blood stream, such as into a body cavity or into a lumen of an organ. Substantially higher dosages (e.g. 10 to 100 mg or more) are possible in oral, nasal, or topical administration. The initial administration of the mixture can be followed by booster immunization of the same of different mixture, with at least one booster, more usually two boosters, being preferred.

In one embodiment, the antigenic compositions used to prime and boost are prepared from strains of Neisseria that possess variant immunodominant antigens (the main antigens that are routinely detected by antisera from different host animals that have been infected with Neisseria; representative examples include Porin A, Porin B, pilin, NspA, phospholipids, polysaccharides, lipopolysaccharides, pilins, OmpA, Opa, Opc, etc.) and/or variant GNA1870 proteins. The strains also may vary with respect to the capsule molecule, as reflected by their serogroup.

Serotype and serosubtype classification is currently determined by detecting which of a panel of known monoclonals, which are known to recognize specific Porin molecules, bind to an unknown strain (Sacchi et al., 1998, Clin. Diag. Lab. Immunol. 5:348). It is probable that other such monoclonals will be identified. The use of any novel serotypes and serosubtypes which may be defined by any new monoclonals are specifically contemplated by the invention. In addition, serotypes and serosubtypes may be defined, not only by interaction with monoclonal antibodies, but also structurally by the absence and/or presence of defined peptide residues and peptide epitopes (Sacchi et al., 2000, J. Infect. Dis. 182:1169). Serotype and serosubtype classification schemes that are based on structural features of the Porins (known or that may be discovered at a later date) are specifically encompassed by the invention.

In another embodiment, the antigenic compositions administered are prepared from 2, 3, 4, 5 or more strains, which strains may be homologous or heterologous, usually heterologous, to one another with respect to one or both of GNA1870 or PorA. In one embodiment, the vesicles are prepared from strains express different GNA1870 proteins, which GNA1870 proteins may be different variants (v.1, v.2, v.3) or subvariants (e.g., a subvariant of v.1, v.2, or v.3). In another embodiment, the vesicles are prepared from strains that are heterologous to one another respect to PorA.

In embodiments of particular interest, vesicles are prepared from Neisserial strains that are genetically diverse to one another (e.g., the strains belong to different serotypes and/or serosubtypes; express different PorA proteins; express different GNA1870 variants or subvariants; and/or may also optionally belong to different capsular serogroups). The vesicles can be used to prepare an antigenic composition that is a mixture of vesicles prepared from at least 2, 3, 4, or more of such genetically diverse strains. For example, GNA1870 protein and/or PorA of the second Neisserial strain from which antigenic compositions are prepared and administered is/are different from that of the first strain used to produce vesicles.

The second, third, and further administered antigenic compositions can optionally be prepared from Neisserial strains are genetically diverse to the second strain (e.g., the strains belong to different serotypes and/or serosubtypes; express different GNA1870 proteins; express different PorA proteins; and/or belong to different capsular serogroups). For example, a third strain used for preparing a third antigenic composition may be genetically diverse to the first and second strains used to prepare the first and second antigenic compositions, but may, in some embodiments, not be genetically diverse with respect to the first strain.

The invention also contemplates that the antigenic compositions may be obtained from one or more strains of Neisseria, particular Neisseria meningitidis, that are genetically engineered by known methods (see, e.g. U.S. Pat. No. 6,013,267) to express one or more nucleic acids that encode GNA1870. The host cell may express an endogenous GNA1870 polypeptide or may modified or selected so as not to express any detectable endogenous GNA1870 polypeptide. The GNA1870 polypeptide expressed in the host cell by recombinant techniques (i.e., the exogenous GNA1870 polypeptide) can be of the same or different variant type as an endogenous GNA1870 polypeptide.

The host cells may be further modified to express additional antigens of interest, such as Porin A, Porin B, NspA, pilin, or other Neisserial proteins. In addition, the antigen compositions of the invention can comprise additional Neisserial antigens such as those exemplified in PCT Publication Nos. WO 99/24578, WO 99/36544; WO 99/57280, WO 00/22430, and WO 00/66791, as well as antigenic fragments of such proteins.

The antigen compositions are typically administered to a mammal that is immunologically naïve with respect to Neisseria, particularly with respect to Neisseria meningitidis. In a particular embodiment, the mammal is a human child about five years or younger, and preferably about two years old or younger, and the antigen compositions are administered at any one or more of the following times: two weeks, one month, 2, 3, 4, 5, 6, 7, 8, 9, 10, or 11 months, or one year or 15, 18, or 21 months after birth, or at 2, 3, 4, or 5 years of age.

In general, administration to any mammal is preferably initiated prior to the first sign of disease symptoms, or at the first sign of possible or actual exposure to Neisseria.

Passive Immunity

The invention also contemplates immunoprotective antibodies generated by immunization with an antigenic composition of the invention, and methods of use. Such antibodies can be administered to an individual (e.g., a human patient) to provide for passive immunity against a Neisserial disease, either to prevent infection or disease from occurring, or as a therapy to improve the clinical outcome in patients with established disease (e.g. decreased complication rate such as shock, decreased mortality rate, or decreased morbidity, such as deafness).

Antibodies administered to a subject that is of a species other than the species in which they are raised are often immunogenic. Thus, for example, murine or porcine antibodies administered to a human often induce an immunologic response against the antibody. The immunogenic properties of the antibody are reduced by altering portions, or all, of the antibody into characteristically human sequences thereby producing chimeric or human antibodies, respectively.

Chimeric antibodies are immunoglobulin molecules comprising a human and non-human portion. More specifically, the antigen combining region (or variable region) of a humanized chimeric antibody is derived from a non-human source (e.g. murine), and the constant region of the chimeric antibody (which confers biological effector function to the immunoglobulin) is derived from a human source. The chimeric antibody should have the antigen binding specificity of the non-human antibody molecule and the effector function conferred by the human antibody molecule. A large number of methods of generating chimeric antibodies are well known to those of skill in the art (see, e.g., U.S. Pat. Nos. 5,502,167, 5,500,362, 5,491,088, 5,482,856, 5,472, 693, 5,354,847, 5,292,867, 5,231,026, 5,204,244, 5,202,238, 5,169,939, 5,081,235, 5,075,431 and 4,975,369). An alternative approach is the generation of humanized antibodies by linking the CDR regions of non-human antibodies to human constant regions by recombinant DNA techniques. See Queen et al., *Proc. Natl. Acad. Sci. USA* 86: 10029-10033 (1989) and WO 90/07861.

In one embodiment, recombinant DNA vector is used to transfect a cell line that produces an antibody against a peptide of the invention. The novel recombinant DNA vector contains a "replacement gene" to replace all or a portion of the gene encoding the immunoglobulin constant region in the cell line (e.g. a replacement gene may encode all or a portion of a constant region of a human immunoglobulin, or a specific immunoglobulin class), and a "target sequence" which allows for targeted homologous recombination with immunoglobulin sequences within the antibody producing cell.

In another embodiment, a recombinant DNA vector is used to transfect a cell line that produces an antibody having a desired effector function (e.g. a constant region of a human immunoglobulin), in which case, the replacement gene contained in the recombinant vector may encode all or a portion of a region of an antibody and the target sequence contained in the recombinant vector allows for homologous recombination and targeted gene modification within the antibody producing cell. In either embodiment, when only a portion of the variable or constant region is replaced, the resulting chimeric antibody may define the same antigen and/or have the same effector function yet be altered or improved so that the chimeric antibody may demonstrate a greater antigen specificity, greater affinity binding constant, increased effector function, or increased secretion and production by the transfected antibody producing cell line, etc.

In another embodiment, this invention provides for fully human antibodies. Human antibodies consist entirely of characteristically human polypeptide sequences. The human antibodies of this invention can be produced by a wide variety of methods (see, e.g., Larrick et al., U.S. Pat. No. 5,001,065). In one embodiment, the human antibodies of the present invention are produced initially in trioma cells (descended from three cells, two human and one mouse). Genes encoding the antibodies are then cloned and expressed in other cells, particularly non-human mammalian cells. The general approach for producing human antibodies by trioma technology has been described by Ostberg et al. (1983), *Hybridoma* 2: 361-367, Ostberg, U.S. Pat. No. 4,634,664, and Engelman et al., U.S. Pat. No. 4,634,666. Triomas have been found to produce antibody more stably than ordinary hybridomas made from human cells.

Methods for producing and formulation antibodies suitable for administration to a subject (e.g., a human subject) are well known in the art. For example, antibodies can be provided in a pharmaceutical composition comprising an effective amount of an antibody and a pharmaceutical excipients (e.g., saline). The pharmaceutical composition may optionally include other additives (e.g., buffers, stabilizers, preservatives, and the like). An effective amount of antibody is generally an amount effective to provide for protection against *Neisserial* disease or symptoms for a desired period, e.g., a period of at least about 2 days to 10 days or 1 month to 2 months).

Diagnostic Assays

The antigenic compositions of the invention, or antibodies produced by administration of such compositions, can also be used for diagnostic purposes. For instance, the antigenic compositions can be used to screen pre-immune and immune sera to ensure that the vaccination has been effective. Antibodies can also be used in immunoassays to detect the presence of particular antigen molecules associated with *Neisserial* disease.

EXAMPLES

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

Materials and Methods

The following methods and materials were used in the Examples below.

Bacterial Strains.

The nine *N. meningitidis* strains used in this study (six capsular group B, and one capsular group A and two capsular group C) are listed in Table 1. Strains were collected over a period of 25 years from patients hospitalized in Cuba, The Netherlands, Germany, New Zealand, or the United States. Based on electrophoretic cluster analyses and/or sequencing typing, the strains are genetically diverse.

TABLE 1

Summary of *N. meningitidis* strains

| Strain | Country of Origin | Serologic Classification | PorA VR Sequence type[a] | Electrophoretic Type (ET) Cluster (Sequence Type, ST)[b] | GNA1870 Variant Group (% amino acid identity)[c] | Serum anti-rGNA1870 Bactericidal Titer[d] |
|---|---|---|---|---|---|---|
| Z1092 | Germany | A:4, 21:P1.10 | 1.5-2, 10 | ST-1 Complex/subgroup I/II | 1 (96) | 1:10 |
| BZ198 | Netherlands | B:NST:P1.4 | 7-2, 4 | ET154 | 1 (92) | <1:10 |
| CU385 | Cuba | B:4, 7:P1.19, 15 | 19, 15 | ET5 complex (33) | 1 (100) | 1:2500 |
| M1390 | U.S. | B:15:P1.7, 4 | ND | Lineage 3 (41) | 1 (92) | <1:10 |
| M6190 | U.S. | B:2a:P1.5, 2 | ND | ET37 complex (1988) | 1 (94) | <1:10 |
| NZ98/254 | NZ | B:4:P1.4 | 1.7-2, 4 | Lineage 3 (42) | 1 (92) | <1:10 |
| RM1090 | U.S. | C:2a:P1.5, 2 | 5-1, 2 | ND | 2 (70) | ND |
| 4243 | U.S. | C:2a:P1.5, 2 | ND | ET37 complex (11) | 1 (95) | <1:10 |
| H44/76 | Norway | B:15:P1.7, 16 | 1.7, 16 | ET5 complex (32) | 1 (100) | 1:900 |
| H44/76 | Norway | NT; P1.7, 16 | 1.7, 16 | ET5 complex (32) | 1 (100) | ND |

[a]Based on the proposed PorA VR type designation nomenclature of Russell et al Emerg Infect Dis 2004; 10: 674-8)
[b]ST typing was performed by multilocus sequencing as described (www. followed by mlst. followed by net); NT = not typable; no capsule detected by serology
[c] Percentage of amino acid identity as compared to that of strain MC58.
[d]Titer measured with human complement as reported in Welsch et al J Immunol 2004; 172: 5606-15, in Hou et al. J. Infect Dis. (2005 Aug. 15) 192(4): 580-90 (Epub 2005 Jul. 15);; see also FIGS. 3A and 3B.
ND, Not determined. Strains used as hosts for overexpression of GNA1870 and preparation of vaccines.

Group C strain RM1090 (C:2a:5-1,2) and mutants described below that were derived from this strain, and group B strain H44/76 and mutants described below that were derived from this strain, were used to prepare the outer membrane vesicle (OMV) vaccines. Strain RM1090 naturally expresses low levels of a GNA1870 variant 2 protein. The RM1090 strain in which the GNA1870 gene was inactivated (RM1090ΔGNA1870, described below) was used for over-expression of GNA1870 variant 1. Strain H44/76 is a relatively high expresser of GNA1870 variant 1. The remaining seven strains naturally express sub-variants of the GNA1870 variant 1 protein and were selected as test organisms to determine the breadth of vaccine-induced anti-GNA1870 variant 1 protective immunity. These strains are genetically diverse, as defined by electrophoretic type and/or multilocus sequencing type, and they also express several different PorA VR sequence types. Variant 1 strains were chosen because they account for about 60% of disease-producing group B isolates (Masignani et al. J Exp Med 2003; 197:789-99).

Strain Cu385 and strain H44/76 express GNA1870 variant 1 with an identical amino acid sequence to that of strain MC58 (Welsch et al. J Immunol 2004; 172:5606-15), the gene used to express the recombinant GNA1870 variant 1 protein in *E. coli*, and also used in the shuttle vector to over-express GNA1870 in the *N. meningitidis* vaccine strain RM1090 (see below). The remaining seven strains express subvariants of GNA1870 variant 1 with slight sequence variations from the variant of GNA1870 protein encoded by the gene from strain MC58 (Masignani et al. 2003, supra). In a previous study, strain Cu385 was highly susceptible to complement-mediated bactericidal activity of antibodies elicited in mice immunized with a recombinant GNA1870 protein vaccine (Table 1). In contrast, *N. meningitidis* strains BZ198, M1390, M6190 and NZ98/294 were selected because they were resistant to bactericidal activity of antisera prepared against the recombinant GNA1870 vaccine (bactericidal titers <1:10).

pFP12-GNA 1870 Shuttle Vector Construct.

Over-expression of GNA1870 in *N. meningitidis* was accomplished using the shuttle vector FP12, which has an origin of replication from a naturally-occurring plasmid in *N. gonorrhoeae* and has been shown to transform *E. coli* and *N. meningitidis* stably (Pagotto et al. Gene 2000; 244:13-9). The variant 1 GNA1870 gene, including the putative FUR box promoter from *N. meningitidis* strain MC58, was amplified from genomic DNA by PCR using the following primers: GNA1870FURSphIF 5',5"-ATCGGCATGCGCCGTTCGGACGACATTTG-3" (SEQ ID NO: 72) and GNA1870FURStuIR 3' 5"-AAGAAGGCCTTTATTGCTTGGCGGCAAGGC-3" (SEQ ID NO: 73). The PCR product was then digested with SphI and StuI restriction endonucleases and ligated into pFP12 plasmid digested with SphI and StuI, which removed the GFP gene. The resulting plasmid, pFP12-GNA1870, was transformed and propagated in *E. coli* strain TOP10 competent cells (Invitrogen), which was grown in Luria-Bertani medium at 37° C. under chloramphenicol selection (50 μg/ml).

Transformation of *N. meningitidis*.

The RM1090 strain in which the GNA1870 gene was inactivated (RM1090ΔGNA1870) was made by homologous recombination by transformation with plasmid pBSUDGNA1870ERM using erythromycin selection (5 μg/ml). For preparation of a mutant over-expressing GNA1870, 3-4 colonies of the RM1090ΔGNA1870 knockout strain were selected from a chocolate agar plate that had been grown overnight. The colonies of bacteria were mixed with 3 μg of the plasmid pFP12-GNA1870 in 20 μl EB buffer (Qiagen), plated onto a chocolate agar plate, and incubated for 5 hrs at 37° C. Serial dilutions of the bacteria were re-cultured onto chocolate agar plates containing chloramphenicol (5 μg/ml). The culture plates were incubated overnight at 37° C., and the colonies were screened for GNA1870 expression by a colony blot assay using mouse polyclonal anti-rGNA1870 antibody. Positive individual colonies were selected and re-cultured onto chocolate agar plates containing chloramphenicol. The meningococcal bacterial cells were frozen in 2% skim milk (wt/vol), and stored at −80° C.

An analogous procedure was used to transform strain H44/76 and a mutant thereof that over-expresses GNA1870. Chromosomal gna1870 in strain H44/76 was inactivated by transformation with pBSUDgna1870erm (Hou et al. Infect Immun 2003; 71:6844-49). The mutant (H44/76Δgna1870) was then transformed with plasmid pFP12-GNA1870 that encoded GNA1870 variant 1 from strain MC58. The transformants were selected on chocolate agar plates containing 5 μg/ml chloramphenicol.

Membrane Preparations.

*N. meningitidis* were subcultured from frozen stock onto chocolate agar plates (Remel, Laztakas, Kans.) After overnight incubation at 37° C. in 5% $CO_2$, several colonies were selected and inoculated into about 6 ml of Mueller-Hinton broth containing 0.25% glucose and 0.02 mM CMP-NANA in an atmosphere containing 5% $CO_2$ to an optical density at 620 nm ($OD_{620}$) of 0.1. All strains containing the introduced pFP12-GNA1870 shuttle vector were grown in the presence of 5 μg/mL of chloramphenicol. The inoculated broth was incubated at 37° C. and 5% $CO_2$ with rocking until $OD_{620}$ reached 0.6 to 0.7 (2 to 3 h). Six 6-ml starter cultures were used to inoculate 1 L of Mueller-Hinton broth. The larger culture was grown at 37° C. with vigorous shaking to an $OD_{620}$ of 0.8 to 1.0. Phenol was added (0.5% wt/vol), and the broth was left at 4° C. overnight to kill the bacteria. The bacterial cells were pelleted by centrifugation (10,000×g) for 30 min at 4° C., and frozen and stored at −20° C. until used for preparation of the outer membrane vesicle vaccines.

For the cultures containing strain H44/76 and the mutant thereof, six 7 ml starter cultures were used. The cells were transferred into 1 L of Mueller-Hinton broth without added chloramphenicol and were grown with vigorous shaking until $OD_{620}$ reached 0.8 to 1.0. Phenol was added (0.5% wt/vol), and the culture was left at 37° C. for two hours and incubated overnight at 4° C. to kill the bacteria. The cells were pelleted by centrifugation (11,000×g) for 30 min at 4° C.

*N. meningitidis* membrane fractions for OMVs were prepared as previously described without the use of detergents to avoid extraction of the GNA1870 lipoprotein (Moe et al. 2002, supra). In brief, the frozen bacterial cells were suspended in 40 ml of PBS and sonicated on ice with a sonifier fitted with a microtip (Branson, Danbury, Conn.) for four 15-s bursts, which was sufficient to release membrane blebs but not to cause complete lysis of the bacteria. The bacterial suspensions were cooled on ice between the bursts. Cell debris was removed by centrifugation at 5,000×g for 15 min, and the membrane fraction remaining in the supernatant was obtained by ultracentrifugation at 100,000×g for 1 h at 4° C., and re-suspended in 5 ml of PBS. These preparations were referred to as OMVs. Alternatively, MVs could be used, which are obtained from blebs released by the bacteria into the supernatant as described in (Moe et al. 2002, supra); see also WO 02/09643.

For H44/76 (and mutant thereof), the frozen bacterial cells were resuspended in 20 ml PBS buffer, and sonicated with four 15-s bursts. Cell debris was removed by centrifugation (16,000×g) for 30 min at 4° C., and the cell membranes, which were enriched with outer membrane proteins, were collected from the soluble fraction by centrifugation (100,000×g) for 2 hours.

Characterization of Vaccines.

The protein concentrations were determined by the DC protein assay (Bio-Rad, Richmond, Calif.) and the BCA Protein Assay Kit (Pierce, Rockford, Ill.). The OMV preparations were analyzed by 15% SDS-PAGE (12.5% SDS-PAGE for the H44/76 preparations) as described by Laemmli (Nature 1970; 227:680-5) employing a Mini-Protean II electrophoresis apparatus (Bio-Rad), and Western blot. Samples were suspended in sample buffer (0.06 M Tris.HCl, pH 6.8, 10% (v/v) glycerol, 2% (w/v) SDS, 5% (v/v) 2-mercaptoethanol, 10 µg/ml bromophenol blue) and heated to 100° C. for 5 min. before loading directly onto the gel.

For Western blots, the gel was equilibrated with buffer (48 mM Tris.HCl, 39 mM glycine [pH 9.0] 20% (v/v) methanol) and transferred to a nitrocellulose membrane (Bio-Rad) using a Trans-Blot™ (Bio-Rad) semi-dry electrophoretic transfer cell. The nitrocellulose membranes were blocked with 2% (w/v) non-fat milk in PBS, and reacted with a 1:20,000 dilution of anti-rGNA1870-antiserum in PBS containing 1% (w/v) BSA and 1% (w/v) TWEEN-20 detergent. Bound antibody was detected using rabbit anti-mouse IgG+A+M-horseradish peroxidase conjugated polyclonal antibody (Zymed, South San Francisco, Calif.) and WESTERN LIGHTNING chemiluminescence reagents (PerkinElmer Life Sciences, Inc., Boston, Mass.). The detecting anti-GNA1870 antiserum was from mice immunized sequentially with one injection each of 10 µg of recombinant GNA1870 v.1 (gene from *N. meningitidis* strain MC58), followed by a dose of recombinant v.3 protein (gene from strain M1239), followed by a dose of recombinant v.2 protein (gene from strain 2996). Each injection was separated by 3- to 4-weeks.

Immunization.

The recombinant protein vaccine was expressed in *E. coli* as previously described using a GNA1870 DNA sequence encoding six COOH-terminal histidines (His tag) and devoid of the N-terminal sequence coding for the putative leader peptide (Welsch et al. J Immunol 2004; 172:5606-15). This non-lipidated HisTag GNA1870 protein was used since it provides for greater ease of preparation than the recombinant lipoprotein, and data from earlier studies indicated that the non-lipidated antigen given with Freund's complete and incomplete adjuvants elicited strong bactericidal antibody responses in mice against the majority of strains tested.

The OMV preparations or recombinant GNA1870 protein were diluted in PBS and adsorbed with an equal volume of aluminum phosphate adjuvant (1% ALHYDROGEL final concentration [wt/vol; Superfos Biosector, Frederikssund, Denmark]) that had been incubated with PBS buffer). Groups of 4-6 week old female CD1 mice (Charles River Breeding Laboratories, Raleigh, N.C.) (N=10 per group) were immunized intraperitoneally (IP). Each mouse received a dose containing 5 µg of total protein (for the mixture group, 2.5 µg each of OMV and rGNA1870). A total of three injections were given, each separated by 3-week intervals. Two weeks after the third dose, mice were bled by cardiac puncture and sacrificed. The sera were separated and stored frozen at 20° C.

For the H44/76 preparations, each mouse received a dose of 1.25 µg of total protein present in OMV and 170 µg of aluminum phosphate. Three injections were given separated by three weeks. Blood was collected by cardiac puncture three weeks after the third dose. The sera were separated by centrifugation and stored frozen at −70° C. until use.

Absorption of Anti-GNA1870 Antibodies.

To test the contribution of anti-GNA1870 antibodies to antibody functional activity, we absorbed serum pools to remove anti-GNA1870 antibodies. In brief, 100 µl of serum pools diluted 1:2 in PBS buffer containing 10 mM imidazole was added to a column that contained 250 µl of Ni-NTA SEPHAROSE (Qiagen, Valencia, Calif.) that had been complexed with 200 µg of recombinant GNA1870-HisTag protein or, as a negative control, recombinant NadA-HisTag protein (Comanducci et al. J Exp Med 2002; 195:1445-54; Hou et al. 2005, supra). The columns were incubated overnight at 4° C., and washed with 500 µl of PBS buffer containing 10 mM imidazole. Five fractions (100 µl each) that passed through the column were combined and concentrated to the original 50 µl serum volumes by membrane filtration (MICROCON YM-10, 10,000 MWCO, Millipore Corp., Bedford, Mass.). Based on an ELISA, more than 98-99% of the anti-GNA1870 antibodies were removed by the GNA1870 column.

Anti-GNA1870 Antibody.

ELISA was used to measure serum antibody titers to GNA1870, which was performed as previously described (Welsch et al J Immunol 2004; 172:5606-1). The solid-phase antigen consisted of rGNA1870 v.1 or v.2 proteins. The secondary antibody was a 1:2000 dilution of alkaline phosphatase-conjugated rabbit anti-mouse IgM+G+A (Zymed). The serum titer was defined as the dilution giving an $OD_{405}$ of 0.5 after a 30-min incubation with substrate.

Complement-Mediated Bactericidal Antibody Activity.

The bactericidal assay was performed as previously described (Moe et al. 2002, supra) using mid-log phase bacteria grown in Mueller Hinton broth supplemented with 0.25% glucose. The final reaction mixture contained different dilutions of test sera, 20% (v/v) human complement, and Gey's buffer containing 1% BSA. The complement source was human serum from a healthy adult with no detectable intrinsic bactericidal activity (Granoff et al J Immunol 1998; 160:5028-36; Welsch et al. 2003, supra). Serum bactericidal titers were defined as the serum dilution resulting in a 50% decrease in CFU per ml after 60 min of incubation of bacteria in the reaction mixture, as compared with control CFU per ml at time 0. Typically, bacteria incubated with the negative control antibody and complement showed a 150 to 200% increase in CFU/mL during the 60 min of incubation.

Binding of Antibodies to the Surface of Live Encapsulated *N. meningitidis*.

The ability of anti-GNA1870 antibodies to bind to the surface of live *N. meningitidis* was determined by flow cytometric detection of indirect fluorescence assay, performed as described previously (Granoff et al. J Immunol 2001; 167:3487-3496). Positive controls included mouse monoclonal antibodies specific for the group C polysaccharide capsule (1076.1 (Garcia-Ojeda et al. Infect Immun 2000; 68:239-46)), PorA P1.2 (Granoff et al. J Immunol 2001; 167:3487-3496), and GNA1870 variant 1 (JARS) (Welsch et al J Immunol 2004; 172:5606-15) and a 1:300 dilution of FITC conjugated Goat anti-mouse (Fab')2 IgG (H+L) (Jackson Immuno Research Laboratories, West Grove, Pa.)_.

Activation of Human Complement Deposition on the Surface of Live Encapsulated Meningococci.

Anti-GNA1870 antibody-dependent deposition of C3b or iC3b on the bacterial surface of live *N. meningitidis* bacteria was determined by flow cytometry, performed as previously described (Welsch et al. J Infect Dis 2003; 188:1730-40). Washed, log-phase bacteria were incubated in a reaction mixture containing 5% (v/v) human complement and appropriate serum dilutions in veranol buffer. Complement deposition was detected with FITC-conjugated sheep anti-human complement C3c (BioDesign Intl., Saco, Me.), which reacts with both C3b and iC3b. The complement source was the same human serum described above for the bactericidal assay.

Passive Protection in Infant Rats.

The ability of antiserum to confer passive protection against *N. meningitidis* group B bacteremia was tested in infant rats challenged IP with group B strain NZ98/254 Welsch et al. 2003, supra; Moe et al. Infect Immun 1999; 67:5664-75; Moe et al. Infect Immun 2001; 69:3762-71). In brief, 4-day old infant pups from litters of outbred Wistar rats (Charles River, Hollister, Calif.) were randomly redistributed to the nursing mothers. At time 0, groups of eight animals were administered antisera or antibodies IP that had been diluted in PBS containing 1% BSA. Two hours later, the animals were challenged IP with approximately $6 \times 10^4$ CFU of washed log-phase bacteria grown in Mueller-Hinton supplemented with 0.25% glucose and 10 μM CMP-NANA (Sigma, St. Louis, Mo.). Four to six hours after the bacterial challenge, blood specimens were obtained by cardiac puncture and aliquots of 1, 10 and 100 μl of blood were plated onto chocolate agar to ascertain CFU/ml.

Example 1: Surface-Accessibility of GNA1870 on *N. meningitidis* Strain RM1090

To determine whether the GNA180 protein expressed by the RM1090 strain transformed with pFP12-GNA1870 is an integral part of the outer membrane and exposed on the cell surface, and to determine whether overexpressed GNA1870 in strain H44/76 is anchored and surface-accessible in the outer membrane, binding of anti-GNA1870 and control antibodies to live encapsulated bacterial cells was measured by flow cytometry (FIG. 1).

As shown in FIG. 1A, positive control mAbs specific for group C capsular polysaccharide (column 2) or PorA (anti-P1.2, column 3) showed strong binding to the parent RM1090 strain (row B) and to the two RM1090 mutant strains: a GNA1870 knockout transformed with the shuttle vector without the GNA1870 gene (row A), and the knockout transformed with the shuttle vector encoding the GNA1870 variant 1 protein (row C). With all three strains there was no significant binding with a 1:10 dilution of a negative control serum pool from mice immunized with aluminum phosphate alone (column 1). There also was no significant binding of anti-GNA1870 monoclonal or polyclonal antibodies with the GNA1870 knockout strain (Row A, columns 5 and 6, respectively). The wild-type RM1090 strain, which naturally expresses low levels of a GNA1870 v. 2 protein, had no detectable binding with an anti-GNA1870 mAb specific for a v. 1 protein (Row B, column 4), and showed minimal binding above background with a polyclonal mouse antiserum (columns 5 and 6) prepared against recombinant v. 1, 2 and 3 GNA1870 proteins (see below). In contrast, the strain transformed with the shuttle vector encoding GNA1870 (variant 1) showed strong binding with both the polyclonal and monoclonal anti-GNA1870 antibodies. Thus, GNA1870 is exposed on the surface of the RM1090 strain transformed with the pFP12-GNA1870 shuttle vector.

Figure 1B:
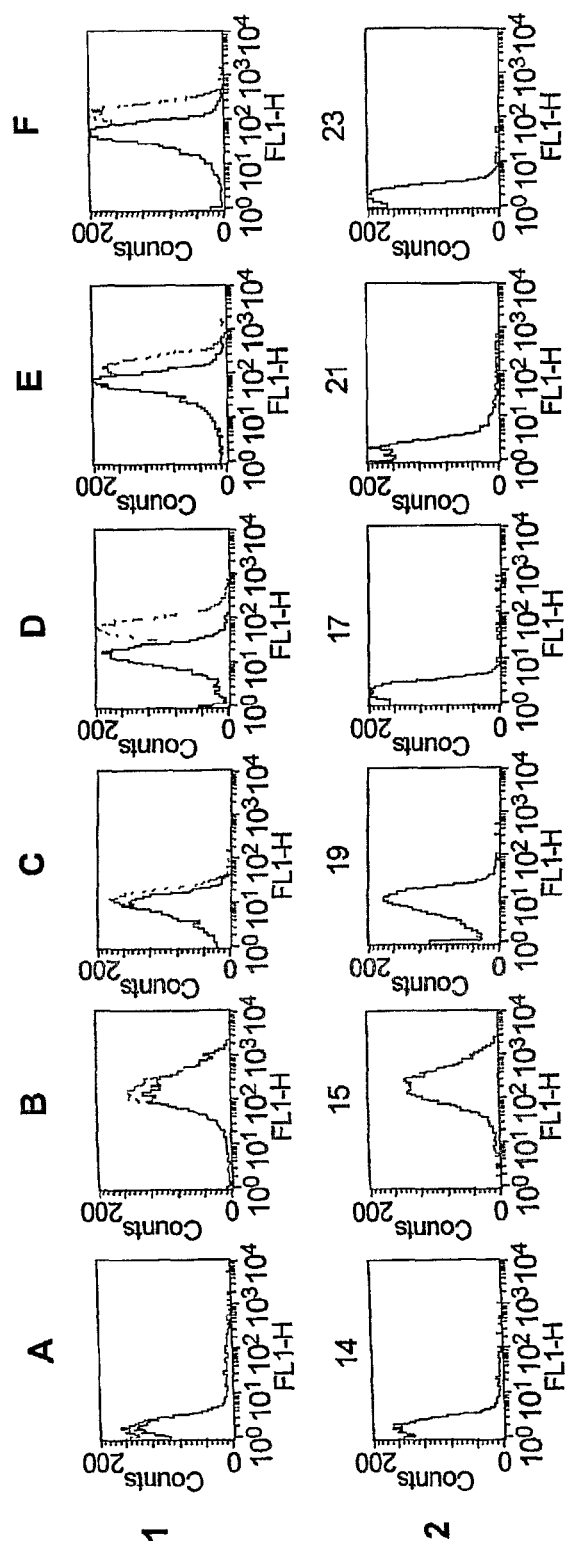
FIG. 1B shows the binding of antibodies to the surface of live Group B *N. meningitidis* cells as determined by indirect fluorescence cytometry. Row 1: wildtype H44/76 strain (grey area); H44/76 mutant over-expressing GNA1870 (black area). Row 2. H44/76ΔGNA1870. Panel A, anti-adjuvant negative control antiserum 1:10 dilution; Panel B, anti-PorA mAb (P1.16) 1:500 dilution; Panel C, anticapsular mAb 10 µg/ml; Panel D, anti-rGNA1870 mAb JARS 10 µg/ml; Panel E, anti-rGNA1870 polyclonal antiserum 1:10 dilution; Panel F, same as Panel E with a 1:250 dilution.

As shown in FIG. 1B, the positive control anticapsular and anti-PorA (P1.16) monoclonal antibodies bound to H44/76 wildtype strain and to a mutant of strain H44/76 that over-expresses GNA1870 (both shown in row 1). The positive control antibodies also bound to H44/76 ΔGNA1870 (shown in row 2). As expected, there was no binding of the anti-GNA1870 monoclonal or polyclonal antibodies to the mutant strain H44/76 in which the gene encoding GNA1870 had been inactivated (columns D to F). Incubation of the wildtype strain with the anti-GNA1870 antibodies showed good binding, a result that reflected the relatively high level of natural GNA1870 expression in strain H4476. There was a modest increase in binding to the mutant strain that had been engineered to over-express GNA1870, as evidenced by a small shift to the right of immune fluorescence. Thus, over-expression of GNA1870 resulted in a small increase in the amount of the protein in the outer membrane, and the protein is surface-exposed.

Example 2: Analysis of OMV Vaccine

The major proteins in the OMV preparations from strain RM1090 and the respective mutants were separated by SDS-PAGE and visualized by staining with Coomasie Blue (FIG. 2A, Panel A). As is typical of OMV prepared from *N. meningitidis*, there were a limited number of major proteins resolving with apparent masses between 29 kDa (Opa/Opc) and 43 kDa (PorA). The OMV prepared from the wild-type strain (lane 1) and GNA1870 knockout strain (lane 3) expressed similar respective amounts of each of these proteins. In contrast, OMV from the strains transformed with the pFP12 shuttle vector that did not contain the gene encoding GNA1870 (lanes 2 and 4, respectively) showed decreased relative expression of three proteins migrating with apparent masses between 38 and 43 kDa. This result likely reflects in part decreased expression of the porin proteins by antibiotic selection from the presence of 5 μg/ml of chloramphenicol in the growth media (Tommassen et al. Infect Immun 1990; 58:1355-9). Lane 5 shows OMV prepared from strain RM1090 transformed with the shuttle vector encoding GNA1870. To better visualize the proteins, this lane was loaded with 2-fold more protein (about 10 μg) than in lanes 1 to 4. As compared with the other OMV preparations, the OMV prepared from the strain transformed with the shuttle vector containing the GNA1870 gene showed decreased expression of proteins resolving between 29 and 32 kDa. By SDS PAGE, GNA1870 is not readily apparent in any of the OMV preparations including the OMV prepared from the mutant strain over-expressing GNA1870 (lane 5). (For comparison, 1 μg of the recombinant GNA1870 variant protein is shown in Lane 6).

In FIG. 2A, Western blot with a polyclonal mouse antiserum raised against v. 1, 2 and 3 GNA1870 recombinant proteins was used to evaluate expression of GNA1870 in the different vaccine preparations. As shown in Panel B, the antiserum was slightly more reactive with the rGNA1870 v.2 protein than the v.1 recombinant protein. Even with this bias, the OMV prepared from RM1090 transformed with pFP12-GNA1870 showed increased reactivity by Western blot as compared with the OMV prepared from the wild-type RM1090 strain that naturally expresses a v. 2 protein (FIG. 2A, Panel C). In contrast, the negative control OMV from the GNA1870 knockout mutant (RM1090ΔGNA1870) had no detectable reactivity. The results of densitometry measurements indicated that expression of the v. 1 GNA1870 protein in the strain transformed with the shuttle vector was approximately 10-fold higher than that of the v. 2 protein expressed naturally by the wild-type parent RM1090 strain.

Figure 2B:
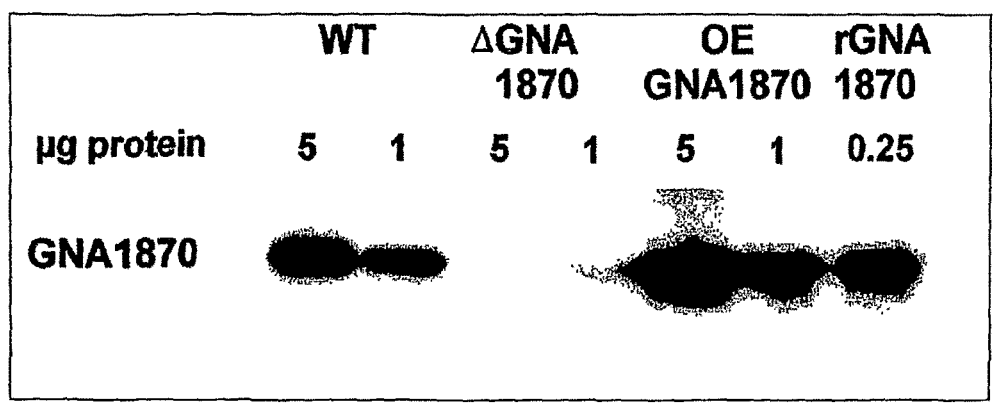
FIG. 2B provides results of Western-Blot analysis of OMV vaccines probed with anti-rGNA1870 polyclonal antibody. Wildtype, OMV prepared from wildtype H44/76 strain; ΔGNA1870, OMV prepared from a mutant of H44/76 in which the gene encoding GNA1870 had been inactivated; OE GNA1870, OMV from a mutant of H44/76 engineered to over-express GNA1870; rGNA1870, purified His-Tag GNA1870 expressed in *E. coli*.

The H44/76 OMV preparations were analyzed by Western blot using polyclonal antiserum to GNA1870 (FIG. 2B). The amount of OMV loaded onto the gel was standardized based on total protein content of the preparations. As expected, GNA1870 was expressed in the membrane preparations from the wildtype strain and was increased in the corresponding preparation from the mutant engineered to over-express this protein. However, the increase in GNA1870 was modest (approximately 3-fold)

Example 3: Analysis of Serum Antibody Responses

Table 2 and FIG. 5 summarize the serum anti-GNA1870 antibody responses of the different groups of mice as measured by ELISA. The highest antibody responses to the variant 1 protein in Table 2 were in mice immunized with the recombinant GNA1870 v.1 vaccine only, or with the recombinant GNA1870 v.1 vaccine given as a mixture with an OMV vaccine (titers against the variant 1 protein of 1:120,000 and 1:300,000, respectively). The mice immunized with OMV prepared from strain RM1090 over-expressing variant 1 GNA1870 had a 4- to 10-fold lower anti-GNA 1870 titer (1:32,000). Of interest, mice immunized with OMV prepared from the wild-type RM1090 strain had undetectable or negligible anti-GNA1870 antibody responses as measured against either the variant 1 or 2 proteins. This result suggests that in the absence of over-expression, GNA1870 in OMV from the wild-type strain is poorly immunogenic.

Groups of mice were immunized with H44/76 OMV (1.25 µg of total protein) or 5 µg of rGNA1870 given with aluminum phosphate. Serum samples were obtained 3 weeks after the third dose and pooled (2 pools per vaccine group, each pool prepared from 4 to 5 mice). As shown in FIG. 5, control mice immunized with the aluminum adjuvant alone had no detectable anti-GNA1870 antibody (GMT <1:10, bar 1), whereas mice immunized with rGNA1870 showed the highest responses (GMT 1:23,500, bar 2). Mice immunized with OMV prepared from H44/76 that over-expressed GNA1870 had ~10-fold higher anti-GNA1870 antibody responses than the respective group immunized with OMV from the wildtype strain (compare bars 5 and 3). Mice immunized with OMV prepared from H44/76 ΔGNA1870 had negligible antibody responses (GMT <1:10, bar 4).

TABLE 2

Anti-GNA1870 antibody responses of mice as measured by ELISA

| | 1/Antibody Titer[b] | |
| --- | --- | --- |
| | rGNA1870 Variant 1 | rGNA1870 Variant 2 |
| Vaccine[a] | | |
| Al$_2$(PO4)$_3$ alone | <50 | <50 |
| rGNA1870 (v. 1) | 120,000 | 3200 |
| rGNA1870 (v. 2) | ND | 1,600,000 |
| RM1090 OMV | | |
| Wild-type | 55 | <50 |
| ΔGNA1870 | <50 | <50 |
| Over-express GNA1870 | 32,000 | 1200 |
| ΔGNA1870 + rGNA1870 v. 1 | 300,000 | 4000 |

[a]The vaccines consisted of 5 µg of total protein absorbed with Al$_2$(PO4)$_3$. The OMV + rGNA1870 vaccine consisted of a mixture of 2.5 µg of OMV and 2.5 µg of rGNA1870 (v. 1).
[b]Serum dilution in an ELISA giving an OD of 0.5 after 30 mins incubation with substrate. Data shown are the respective geometric means of titers measured in 2 serum pools from each vaccine group. Each pool contained equal volumes of sera from 4 to 5 immunized mice.

Figure 3A:
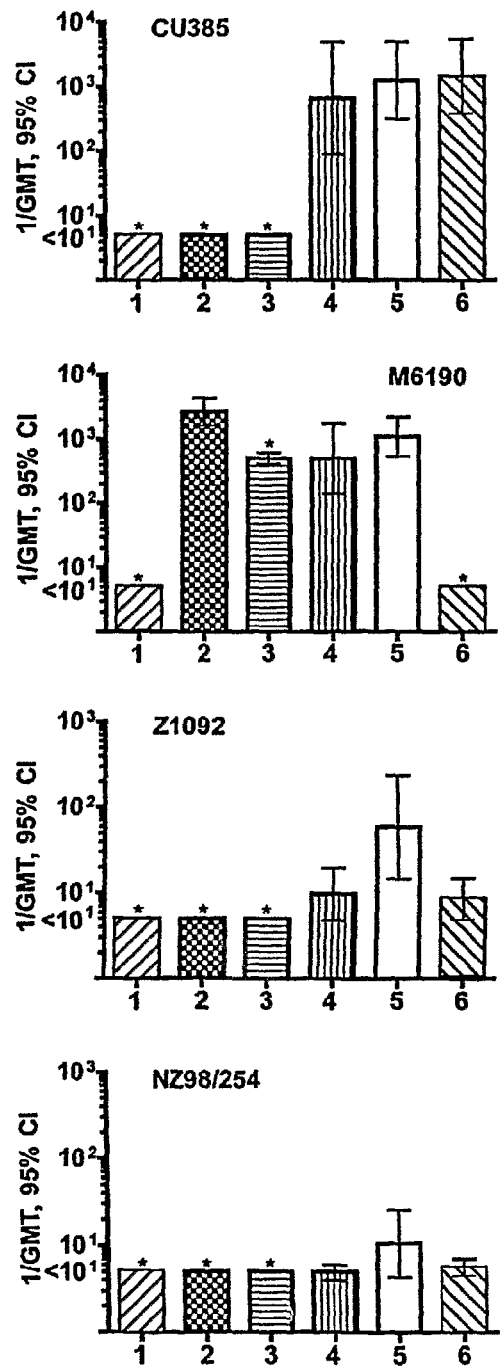
FIG. 3A shows graphs of the serum bactericidal titers of mice as measured against four representative encapsulated *N. meningitidis* strains: Cu385, M6190, Z1092 and NZ98/254. The vaccine groups were: bar 1, aluminum phosphate adjuvant alone; bar 2, OMV vaccine from RM1090 wildtype; bar 3, OMV vaccine from RM1090ΔGNA1870; bar 4, mixture of OMV vaccine from RM1090ΔGNA1870+recombinant GNA1870 protein; bar 5, OMV vaccine from RM1090 over-expressed GNA1870; bar 6, recombinant GNA1870 protein. Bars that show the 95% confidence intervals about the geometric means represent vaccine groups where sera were assayed from 9 to 10 individual animals. Bars with asterisks (*) represent geometric means of results from assaying two serum pools from each vaccine group (each pool from sera of 4- to 5 different mice).

FIG. 3A summarizes the serum bactericidal antibody responses of the different groups of mice as measured against four of the test strains. Mice immunized with the recombinant GNA1870 protein vaccine alone, or with the recombinant GNA1870 vaccine in combination with an OMV vaccine, or with the OMV over-expressing GNA1870, developed high bactericidal titers against strain Cu385 that were not significantly different from each other (compare bars 4, 5 and 6 of upper panel). In contrast, there was no detectable bactericidal activity against strain Cu385 in sera from control mice immunized with OMV vaccines prepared from the wild-type RM1090 or the GNA1870 knockout strains (bars 2 and 3, respectively; titers <1:10). Note that strain Cu385 expresses the canonical GNA1870 v. 1 protein (identical amino acid sequence as that of strain MC58, the gene used to express the recombinant GNA1870 protein), and was known from our previous study to be highly susceptible to bactericidal activity of antibody elicited in mice by the recombinant GNA1870 vaccine (Table 1). Also, Cu385 has a heterologous PorA serosubtype (P1.19,15) to that of the vaccine strain RM1090 (P1.5,2), and, therefore, strain Cu385 was expected to be resistant to bactericidal activity of antibodies raised against the control OMV vaccine that did not over-express GNA1870 variant 1 (Tappero et al. JAMA 1999; 281:1520-7; Moe et al. 2002, supra).

FIG. 3A, also shows the corresponding serum bactericidal titers measured against strain M6190 (second panel from the top) that expresses a sub-variant of v. 1 GNA1870 protein as compared with that of the engineered vaccine strain. There was no detectable bactericidal activity in sera from mice immunized with the recombinant GNA1870 variant 1 protein (bar 6, geometric mean titer <1:10), a result identical to that of our previous study (Table 1). However, because the PorA serosubtype (P1.5,2) of strain M6190 is homologous with that of the RM1090 vaccine strain, sera from mice immunized with any of the OMV-containing vaccines were highly bactericidal (bars 2, 3, 4 or 5).

FIG. 3A, (third and fourth panels from top), show the corresponding bactericidal responses against strains Z1092 and NZ98/254, respectively. Both strains express PorA molecules that are heterologous with that of the RM1090 vaccine strain (Table 1), and were not killed by sera from mice immunized with OMV vaccines prepared from the RM1090 wild-type or GNA1870 knockout strains (bars 2 and 3, geometric mean titers <1:10). However, mice immunized with OMV vaccine prepared from strain RM1090 that over-expressed GNA1870 (bar 5) had a significantly higher geometric mean serum bactericidal antibody titer against strain Z1092 than that of mice immunized with recombinant GNA1870 (bar 6, P<0.02), or with a mixture of the recombinant GNA1870 protein and OMV vaccine (bar 4, P<0.04). Similar trends were observed for the respective serum bactericidal responses measured against strain NZ98/254 (bottom panel), or against strains BZ198 and M1390 (data not shown). However, for these latter three strains, the magnitude of serum bactericidal responses of mice immunized with the OMV vaccine with over-expressed GNA1870 were lower than those measured against strain Z1092. Also, the geometric mean serum bactericidal titers against strains NZ98/294, BZ198 and M1390 of mice immunized with OMV that over-expressed GNA1870 were not statistically significant different as compared with the respective geometric mean titers of the mice in the other vaccine groups (P>0.10).

Figure 3B:
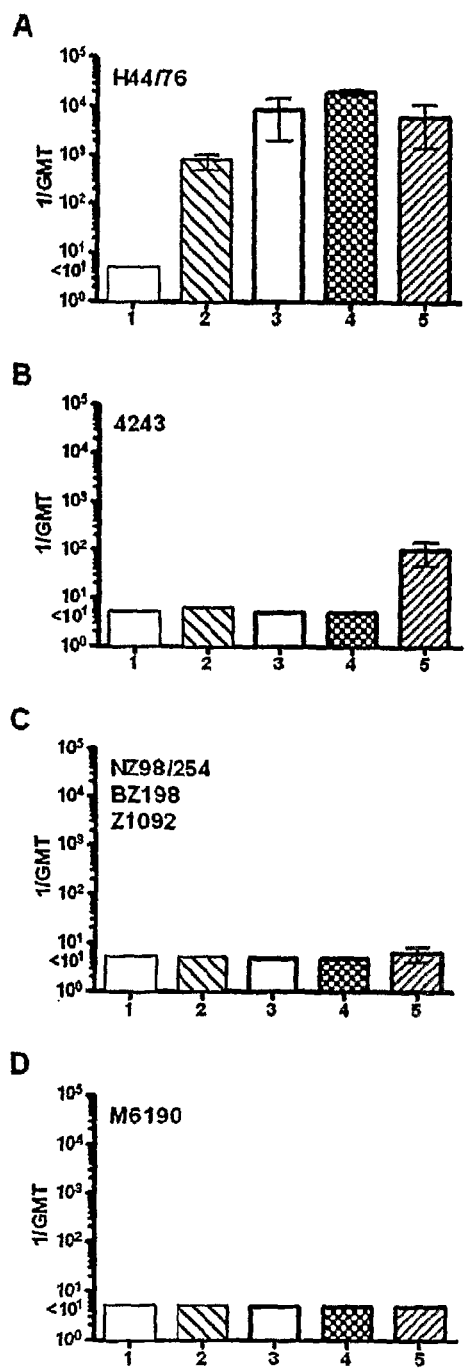
FIG. 3B shows graphs of the serum bactericidal activity (1/GMT±SD) of sera from mice immunized with H44/76 OMV vaccines. Serum pools were prepared as described in legend to FIG. 3A. Groups of mice immunized with (1) Adjuvant, (2) rGNA1870, (3) H44/76 wildtype (4) H44/76 ΔGNA1870 (5) H44/76 OE GNA1870. Although not shown on panels, all strains were killed by complement plus positive control anticapsular and/or anti-PorA monoclonal antibodies.

FIG. 3B summarizes the serum bactericidal antibody responses against six strains, including H44/76, which were used to prepare the OMV vaccine. Five of the six strains have PorA serosubtypes heterologous to that of H44/76. Strain H44/76 also expresses a GNA1870 variant 1 protein sequence identical to that of strain MC58, which contains the gene used to clone and express the recombinant GNA1870 protein vaccine. All of the vaccine preparations except the negative control aluminum adjuvant elicited high serum bactericidal antibody responses when measured against the H44/76 vaccine strain (FIG. 3B, Panel A). In contrast, when measured against heterologous strains 4243 (Panel B), Z1092, NZ98/254, and BZ198 (Panel C), or M6190 (Panel D), sera from mice immunized with the rGNA1870 vaccine, or the OMV vaccines prepared from the H44/76 wildtype or H44764GNA1870 strains, had low or undetectable bactericidal titers (bars 2, 3, and 4, respectively). Mice immunized with the OMV vaccine with over-expressed GNA1870 (bar 5) had high bactericidal antibody responses against strain 4243, low but detectable bactericidal responses against strains NZ98/254, BZ198, and Z1092, and no detectable bactericidal activity against M6190 (titer <1:10). Although not shown on FIG. 3B, all strains were readily killed by complement together with positive control antibodies to the respective PorA and/or polysaccharide capsules.

Example 4: Activation of C3B Complement Deposition on the Surface of Live Encapsulated *N. meningitidis* Cells In previous studies we found that certain mouse antimeningococcal antibodies that lacked bactericidal activity con TABLE 3-continued Activity of sera from mice immunized with OMV with over-expressed GNA1870 after absorption of anti-GNA1870 antibodies

| Assay, Strain | 1/antibody titer | | |
|---|---|---|---|
| | Serum not absorbed | Serum absorbed with negative control column | Serum absorbed with rGNA1870 column |
| C3 complement deposition | | | |
| NZ98/294 | ≥100 | ≥100 | <25 |
| BZ198 | ≥100 | ≥100 | <25 |
| Z1092 | ≥100 | ≥100 | <25 |

A pool prepared from sera from mice immunized with H44/76 OMV with overexpressed GNA1870 was adsorbed on a column containing a Ni-NTA matrix (Qiagen) that had been incubated over night with 50 µg/ml recombinant His-tagged GNA1870. The flow through was collected and concentrated to the original volume. The control column contained Ni-NTA matrix without the His-tagged protein.

Example 6: Role of Anti-GNA1870 Antibody in Functional Activity

The OMV vaccine prepared from the RM1090 *N. meningitis* strain that is engineered to over-expresses GNA1870 showed decreased expression of several other cell envelope proteins as compared with the respective proteins in OMV prepared from the wild-type vaccine RM1090 strain, or the RM1090 ΔGNA1870 knockout strain (FIG. 2A, Panel A). Therefore, it was possible that the higher functional activity of the antisera from mice immunized with OMV that over-expressed GNA1870 resulted from antibodies elicited by antigens other than GNA1870. To investigate this possibility, a serum pool from mice immunized with RM1090 OMV over-expressing GNA1870 was absorbed using an anti-GNA1870 affinity column. By ELISA, 99% of the anti-GNA1870 antibodies were removed. The resulting absorbed antiserum also lost all the ability to activate human C3b deposition on *N. meningitidis* strain NZ98/294 (Table 4). In contrast, there was no effect on C3b deposition by absorbing the serum pool on an anti-NadA affinity column, which served as a negative control (Table 4).

TABLE 4

Functional activity of antiserum from mice immunized with OMV that over-expresses GNA1870 after depletion of anti-GNA1870 antibodies[a]

| Assay | 1/Antibody Titer | | |
|---|---|---|---|
| | Serum Not Absorbed | Serum Absorbed with GNA1870 | Serum Absorbed with NadA |
| Anti-GNA187 ELISA | 40,000 | 400 | 30,000 |
| C3b complement deposition (flow cytometry)[b] | ≥400 | <25 | ≥400 |
| Bactericidal activity | | | |
| Strain Cu385 | 2500 | <10 | 3000 |
| Strain M6190 | 1000 | 600 | 600 |

Figure 4B:
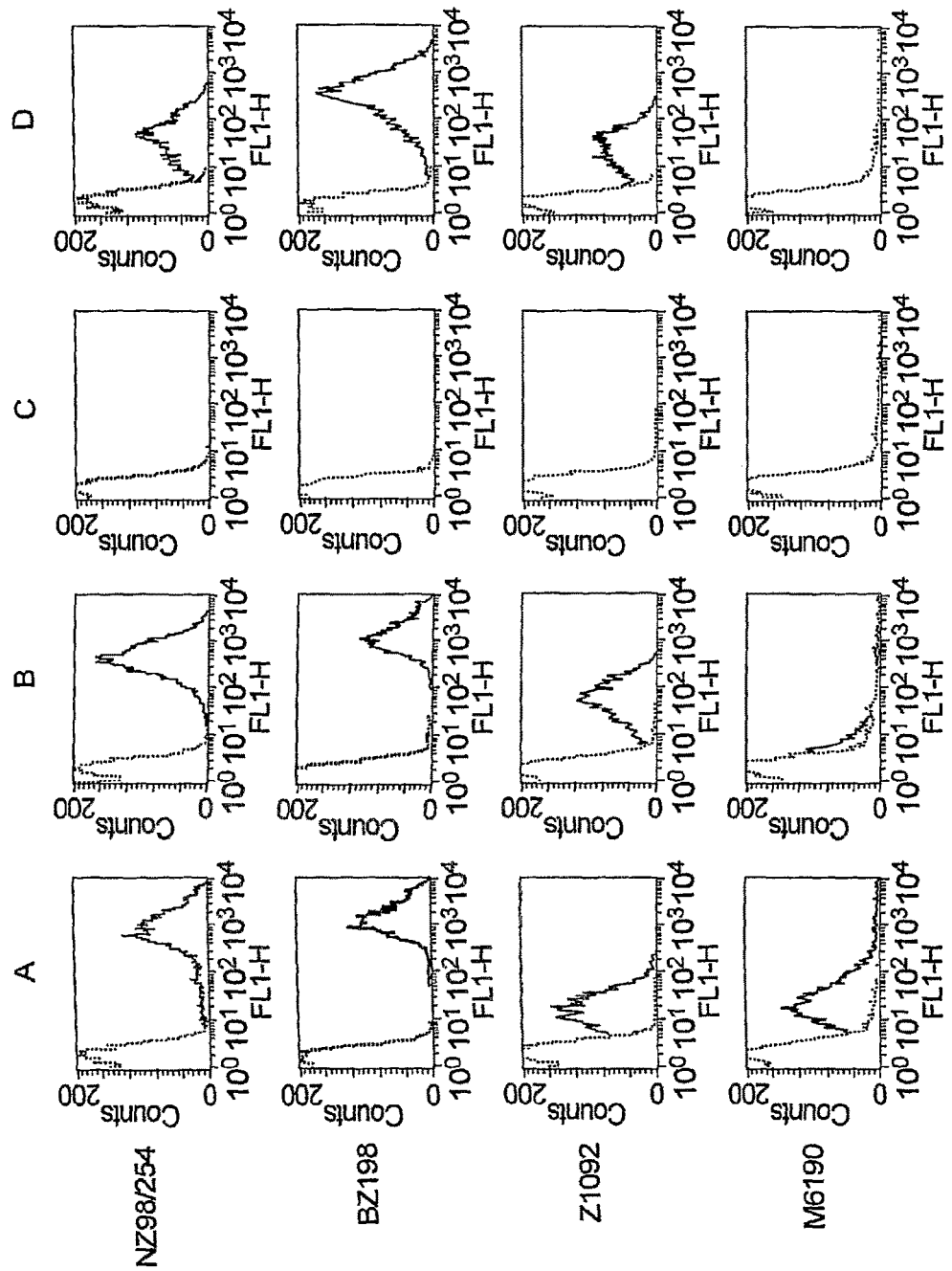
FIG. 4B is a series of graphs showing activation of human C3b and iC3b complement deposition on the surface of live encapsulated *N. meningitidis* cells as determined by indirect fluorescence flow cytometry. Strains NZ 98/254, BZ198, Z1092 and M6190. Panel A, open area: complement plus anticapsular mAb (25 µg/ml for Group B strains NZ98/254, BZ198, and M61903, and 1 µg/ml for Group A strain Z1092); filled area: complement plus 1:100 dilution of anti-adjuvant antisera. Panel B, open area: complement plus anti-rGNA1870 mAb JARS 25 µg/ml; filled area: complement plus 1:100 dilution of polyclonal anti-rGNA1870 antisera. Panel C, complement plus 1:100 dilution of antisera against OMV from wildtype H44/76; Panel D, open area: complement plus 1:100 dilution of antisera prepared against OMV with over-expressed GNA1870 that had been absorbed with a negative control column (Ni-NTA only); filled area: complement plus 1:25 dilution of antisera prepared against OMV with over-expressed GNA1870 after absorption with a solid phase GNA1870 column.

[a]A serum pool was prepared from five mice immunized with the OMV vaccine from strain RM1090 engineered to over-express GNA1870. The antiserum was absorbed on a recombinant GNA1870 affinity column or, as a negative control, an affinity column containing recombinant NadA (See methods). The pass-through fractions were combined and concentrated to their original serum volume by membrane filtration (see methods).
[b]Serum dilution in the flow cytometric complement activation assay that elicited a 10-fold increase in immunofluorescence as compared with negative control serum (See FIG. 4).

Table 4 also summarizes the bactericidal titers of the absorbed serum pools as measured against strains Cu385 and M6190. Absorption of the anti-GNA1870 antibodies completely removed the bactericidal activity against strain Cu385 but had no significant effect on the titer against strain M6190. This latter result was expected since strain M6190 expresses a PorA with has a homologous serosubtype to PorA expressed by the RM1090 vaccine strain and the bactericidal anti-PorA antibodies would not be removed by the GNA1870 or NadA affinity columns.

Example 8: Passive Protection in the Infant Rat Meningococcal Bacteremia Model Infant rats were pretreated with serum pools from the different groups of mice, and challenged 2 hours later with *N. meningitidis* strain NZ98/254. FIG. 6 shows the geometric means of the CFU/ml in blood obtained 4- to 6-hours after the challenge. All 10 rats treated with a 1:15 dilution of the serum pool from negative control mice immunized with aluminum phosphate alone had bacteremia with a geometric mean CFU/ml of ~$10^5$ (Panel A, bar 1). In contrast, pre-treatment with 10 µg/rat of a positive control group B anticapsular antibody (bar 2) or an anti-GNA1870 monoclonal antibody (bar 3) resulted in a 3- to 4-log lower geometric mean CFU/ml ($P<0.0001$). Compared with animals treated with the negative control serum, there was no significant passive protective activity by serum pools from mice immunized with the OMV vaccine prepared from the RM1090ΔGNA1870 knockout strain (bar 4), or the OMV vaccine mixed with recombinant GNA1870 (bar 5). In contrast, the serum pool from mice immunized with the OMV vaccine that over-expressed GNA1870 (bar 6) conferred protection (4 log decrease in geometric mean CFU/ml, $P<0.0001$). The serum pool from mice immunized with the recombinant GNA1870 vaccine alone (bar 7) conferred modest protection (~2 log decrease, $P<0.0001$) but the protective activity was less than that of the serum pool from the mice immunized with OMV that over-expressed GNA1870 ($P<0.0001$, comparing the respective geometric means of the CFU/ml).

FIG. 6, Panel B shows the corresponding geometric means of the CFU/ml of rats pre-treated with 1:60 dilutions of the serum pools. At this higher dilution, the serum pool from the mice immunized with the OMV vaccine that over-expressed GNA1870 (bar 6) conferred protection ($P<0.0002$ compared with the geometric mean of rats treated with a 1:15 dilution of the negative control serum) but there was no significant protective activity by the higher dilution of the serum pools from the mice immunized with any of the other 3 vaccine groups tested, including the serum from mice given the recombinant GNA1870 vaccine (bar 7, $P>0.10$).

Example 9: Immunization of Mice with a Vesicle Vaccine Prepared from Strain RM1090 that Over-Expresses *Neisserial* Surface Protein A (NspA) is not Associated with Enhanced Serum Bactericidal Antibody Responses It was of interest to determine whether the enhanced protection induced by the vesicle vaccine prepared from the RM1090 strain engineered to over-express GNA1870 was specific for GNA1870, or also would occur with a vesicle vaccines prepared from a strains engineered to over-express another vaccine target. Therefore, a microvesicle vaccine was prepared from strain RM1090 in which the gene for NspA in the wildtype strain had been inactivated. A second vesicle vaccine was prepared from the RM1090 NspA-knockout strain transformed with the shuttle vector pFP12 containing the NspA gene from strain 8047. By SDS PAGE, the resulting vesicles from the strain transformed with the shuttle vector contained 10-fold increased expression of the NspA protein as compared with the RM1090 wildtype strain (data not shown).

Groups of mice were immunized with 3 doses of the vesicle vaccines given with aluminum phosphate, and serum was collected 3 weeks after the last immunization. The vaccine over-expressing NspA elicited high anti-NspA antibody titers as measured by ELISA (1:19,000 as compared with a titer of 1:700 in mice immunized with the vesicle vaccine prepared from the NspA knockout strain, and a titer of <1:50 from mice immunized with aluminum phosphate alone). Table 5 summarizes the serum bactericidal antibody responses as measured against four test strains, BZ198, NZ98/254, Cu385 and Z1090.

TABLE 5

Immunization of mice with vesicle vaccines prepared from a mutant strain RM1090 genetically engineered to over-express Neisserial Surface Protein A (NspA

| N. meningitidis strain | VR sequence type (PorA) | Anti-capsular MAb (BC$_{50}$)$^b$ μg/ml | Negative Control Mice immunized with aluminum phosphate (1/Titer)$^c$ | Mice immunized with vesicles from N. meningitidis strain RM1090$^a$ | |
|---|---|---|---|---|---|
| | | | | Over-express NspA$^d$ (1/Titer)$^c$ | NspA Knockout (1/Titer)$^c$ |
| BZ198 | (7, 4) | <6 | <1:10 | 1:16 | <1:4 |
| NZ98/254 | (7-2, 4) | 8 | <1:10 | <1:4 | <1:4 |
| Cu385 | (19, 15) | 10 | <1:10 | <1:4 | 1:12 |
| Z1092 | (5-2, 10) | <1 | <1:10 | 1:12 | 1:250 |

$^a$Microvesicles were prepared as described by Moe et al (Infection Immunity 2002: 70: 6021-6031) from a NspA-knockout the knockout strain transformed with shuttle vector pFP12 containing the NspA gene from strain 8047. Mice were immunized with three injections and bled ~3 weeks after the last injection. The titers shown are from pooled serum from 9 to 10 mice in each vaccine group. The respective anti-NspA antibody titers as measured by ELISA were <1:50 (aluminum phosphate group), 1:700 (vesicles from RM1090 NspA knockout strain) and 1:19,000 (vesicles from RM1090 strain over-expressing NspA).
$^b$Lowest concentration giving 50% killing of bacteria after 1 hr. incubation with human complement
$^c$Highest dilution of serum giving 50% killing of bacteria after 1 hr. incubation with human complement
$^d$Expressed in the NspA knockout background All four strains expressed a heterologous PorA as compared with that of the vaccine strain RM1090. With strain BZ198, which was selected for testing bactericidal activity in this experiment based on previous data showing high susceptibility to bactericidal activity of anti-NspA antisera prepared against recombinant NspA expressed in E. coli vesicles (Moe et al., Infection and Immunity 1999; 67:5664-5675), there was evidence of increased bactericidal activity in the antiserum from mice immunized with the vesicle vaccine derived from the strain over-expressing NspA. However, against strain NZ98/254 there was no increase in bactericidal activity, and for strains Cu385 and Z1090 there was evidence that immunizing with a vesicle vaccine that over-expressed NspA induced 3- to 10-fold lower serum bactericidal antibody responses than those induced by a control vesicle vaccine prepared from the corresponding NspA-knockout strain. Thus, in contrast with vesicle vaccines that over-express GNA1870, a vesicle vaccine that over-expresses NspA did not consistently provide for enhanced bactericidal antibody responses, and appears to have suppressed bactericidal antibody responses to some strains.

What is claimed is:

1. A composition comprising:

isolated antigenic vesicles prepared from a *Neisseria meningitidis* (*N. meningitidis*), wherein the *N. meningitidis* is genetically modified to disrupt production of the endogenous GNA1870 polypeptide so that the endogenous GNA1870 is not present at detectable levels in a vesicle prepared from the *N. meningitidis* and overexpress at least one full length meningococcal GNA1870 polypeptide so as to produce a level of the overexpressed GNA1870 polypeptide sufficient to provide for production of the isolated antigenic vesicles that, when administered to a mammalian subject, elicit anti-meningococcal GNA1870 polypeptide antibodies, wherein the overexpressed GNA1870 polypeptide is a variant 1 or a variant 2 meningococcal GNA1870 polypeptide heterologous to the *N. meningitidis*, wherein the isolated antigenic vesicles are outer membrane vesicles (OMVs), microvesicles (MVs), or a mixture of the OMVs and the MVs, and wherein the *N. meningitidis* is genetically modified to provide for decreased toxic activity of its lipid A relative to its parental unmodified *N. meningitidis*; and a pharmaceutically acceptable carrier.

2. The composition of claim 1, wherein the *N. meningitidis* is genetically modified to provide for expression of the overexpressed meningococcal GNA1870 polypeptide from a heterologous promoter.

3. The composition of claim 1, wherein the *N. meningitidis* is deficient in its capsular polysaccharide.

4. The composition of claim 1, wherein the *N. meningitidis* comprises a mutation in a gene involved in biosynthesis or modification of lipid A of its lipopolysaccharide.

5. The composition of claim 1, wherein the isolated antigenic vesicles are prepared without using a detergent.

6. The composition of claim 1, wherein the *N. meningitidis* is genetically modified to produce at least two different full length meningococcal GNA1870 polypeptides.

7. The composition of claim 1, wherein the *N. meningitidis* is H44/76 or NZ98/254.

8. A *Neisseria meningitidis* (*N. meningitidis*) that is genetically modified to disrupt production of the endogenous GNA1870 polypeptide so that the endogenous GNA1870 is not present at detectable levels in antigenic vesicles isolated from the *N. meningitidis* and to overexpress at least one full length meningococcal GNA1870 polypeptide so as to produce a level of the overexpressed GNA1870 polypeptide sufficient to provide for production of the isolated antigenic vesicles that, when administered to a mammalian subject, elicit anti-meningococcal GNA1870 polypeptide antibodies, wherein the overexpressed GNA1870 polypeptide is a variant 1 or a variant 2 meningococcal GNA1870 polypeptide heterologous to the *N. meningitidis*, and wherein the antigenic vesicles are outer membrane vesicles (OMVs), microvesicles (MVs), or a mixture of the OMVs and the MVs.

9. The *N. meningitidis* of claim 8, wherein the *N. meningitidis* is H44/76 or NZ98/254.

10. The *N. meningitidis* of claim 8, wherein the *N. meningitidis* is genetically modified to provide for no detectable toxic activity of lipid A.

11. The *N. meningitidis* of claim 8, wherein the overexpressed GNA1870 polypeptide is a variant 1 meningococcal GNA1870 polypeptide.

12. The *N. meningitidis* of claim 8, wherein the overexpressed GNA1870 polypeptide is a variant 2 meningococcal GNA1870 polypeptide.

* * * * *

UNITED STATES PATENT AND TRADEMARK OFFICE
CERTIFICATE OF CORRECTION

| | | |
|---|---|---|
| PATENT NO. | : 10,046,043 B2 | Page 1 of 1 |
| APPLICATION NO. | : 15/237495 | |
| DATED | : August 14, 2018 | |
| INVENTOR(S) | : Dan M. Granoff et al. | |

It is certified that error appears in the above-identified patent and that said Letters Patent is hereby corrected as shown below:

In the Specification

In Column 1, Lines 22-28, please replace the STATEMENT REGARDING FEDERALLY SPONSORED RESEARCH section with the following:
-- This invention was made with government support under grants AI046464, AI061533, and HL007951 awarded by the National Institutes of Health. The government has certain rights in the invention. --

Signed and Sealed this
Eleventh Day of June, 2024

Katherine Kelly Vidal
*Director of the United States Patent and Trademark Office*

SEQUENCE LISTING

<160> NUMBER OF SEQ ID NOS: 111

<210> SEQ ID NO 1
<211> LENGTH: 274
<212> TYPE: PRT
<213> ORGANISM: Neisseria meningitidis

<400> SEQUENCE: 1

Met Asn Arg Thr Ala Phe Cys Cys Leu Ser Leu Thr Thr Ala Leu Ile
1               5                   10                  15

Leu Thr Ala Cys Ser Ser Gly Gly Gly Val Ala Ala Asp Ile Gly
            20                  25                  30

Ala Gly Leu Ala Asp Ala Leu Thr Ala Pro Leu Asp His Lys Asp Lys
            35                  40                  45

Gly Leu Gln Ser Leu Thr Leu Asp Gln Ser Val Arg Lys Asn Glu Lys
 50                  55                  60

Leu Lys Leu Ala Ala Gln Gly Ala Glu Lys Thr Tyr Gly Asn Gly Asp
 65                  70                  75                  80

Ser Leu Asn Thr Gly Lys Leu Lys Asn Asp Lys Val Ser Arg Phe Asp
                 85                  90                  95

Phe Ile Arg Gln Ile Glu Val Asp Gly Gln Leu Ile Thr Leu Glu Ser
                100                 105                 110

Gly Glu Phe Gln Val Tyr Lys Gln Ser His Ser Ala Leu Thr Ala Phe
            115                 120                 125

Gln Thr Glu Gln Ile Gln Asp Ser Glu His Ser Gly Lys Met Val Ala
130                 135                 140

Lys Arg Gln Phe Arg Ile Gly Asp Ile Ala Gly Glu His Thr Ser Phe
145                 150                 155                 160

Asp Lys Leu Pro Glu Gly Gly Arg Ala Thr Tyr Arg Gly Thr Ala Phe
                165                 170                 175

Gly Ser Asp Asp Ala Gly Gly Lys Leu Thr Tyr Thr Ile Asp Phe Ala
            180                 185                 190

Ala Lys Gln Gly Asn Gly Lys Ile Glu His Leu Lys Ser Pro Glu Leu
            195                 200                 205

Asn Val Asp Leu Ala Ala Ala Asp Ile Lys Pro Asp Gly Lys Arg His
            210                 215                 220

Ala Val Ile Ser Gly Ser Val Leu Tyr Asn Gln Ala Glu Lys Gly Ser
225                 230                 235                 240

Tyr Ser Leu Gly Ile Phe Gly Gly Lys Ala Gln Glu Val Ala Gly Ser
                245                 250                 255

Ala Glu Val Lys Thr Val Asn Gly Ile Arg His Ile Gly Leu Ala Ala
                260                 265                 270

Lys Gln

<210> SEQ ID NO 2
<211> LENGTH: 274
<212> TYPE: PRT
<213> ORGANISM: Neisseria meningitidis

<400> SEQUENCE: 2

Met Asn Arg Thr Ala Phe Cys Cys Leu Ser Leu Thr Thr Ala Leu Ile
 1               5                  10                  15

Leu Thr Ala Cys Ser Ser Gly Gly Gly Val Ala Ala Asp Ile Gly
            20                  25                  30

Ala Gly Leu Ala Asp Ala Leu Thr Ala Pro Leu Asp His Lys Asp Lys
            35                  40                  45

Gly Leu Gln Ser Leu Met Leu Asp Gln Ser Val Arg Lys Asn Glu Lys
 50                  55                  60

Leu Lys Leu Ala Ala Gln Gly Ala Glu Lys Thr Tyr Gly Asn Gly Asp
 65                  70                  75                  80

Ser Leu Asn Thr Gly Lys Leu Lys Asn Asp Lys Val Ser Arg Phe Asp
                 85                  90                  95

Phe Ile Arg Gln Ile Glu Val Asp Gly Lys Leu Ile Thr Leu Glu Ser
                100                 105                 110

Gly Glu Phe Gln Val Tyr Lys Gln Ser His Ser Ala Leu Thr Ala Leu
            115                 120                 125

-continued

```
Gln Thr Glu Gln Val Gln Asp Ser Glu Asp Ser Gly Lys Met Val Ala
    130                 135                 140

Lys Arg Gln Phe Arg Ile Gly Asp Ile Ala Gly Glu His Thr Ser Phe
145                 150                 155                 160

Asp Lys Leu Pro Lys Gly Gly Ser Ala Thr Tyr Arg Gly Thr Ala Phe
                165                 170                 175

Gly Ser Asp Asp Ala Gly Gly Lys Leu Thr Tyr Thr Ile Asp Phe Ala
                180                 185                 190

Ala Lys Gln Gly His Gly Lys Ile Glu His Leu Lys Ser Pro Glu Leu
            195                 200                 205

Asn Val Glu Leu Ala Thr Ala Tyr Ile Lys Pro Asp Glu Lys His His
210                 215                 220

Ala Val Ile Ser Gly Ser Val Leu Tyr Asn Gln Asp Glu Lys Gly Ser
225                 230                 235                 240

Tyr Ser Leu Gly Ile Phe Gly Gly Gln Ala Gln Glu Val Ala Gly Ser
                245                 250                 255

Ala Glu Val Glu Thr Ala Asn Gly Ile His His Ile Gly Leu Ala Ala
            260                 265                 270

Lys Gln

<210> SEQ ID NO 3
<211> LENGTH: 274
<212> TYPE: PRT
<213> ORGANISM: Neisseria meningitidis

<400> SEQUENCE: 3

Met Asn Arg Thr Ala Phe Cys Cys Phe Ser Leu Thr Ala Ala Leu Ile
1               5                   10                  15

Leu Thr Ala Cys Ser Ser Gly Gly Gly Val Ala Ala Asp Ile Gly
            20                  25                  30

Ala Gly Leu Ala Asp Ala Leu Thr Ala Pro Leu Asp His Lys Asp Lys
            35                  40                  45

Ser Leu Gln Ser Leu Thr Leu Asp Gln Ser Val Arg Lys Asn Glu Lys
    50                  55                  60

Leu Lys Leu Ala Ala Gln Gly Ala Glu Lys Thr Tyr Gly Asn Gly Asp
65                  70                  75                  80

Ser Leu Asn Thr Gly Lys Leu Lys Asn Asp Lys Val Ser Arg Phe Asp
                85                  90                  95

Phe Ile Arg Gln Ile Glu Val Asp Gly Gln Leu Ile Thr Leu Glu Ser
            100                 105                 110

Gly Glu Phe Gln Val Tyr Lys Gln Ser His Ser Ala Leu Thr Ala Leu
            115                 120                 125

Gln Thr Glu Gln Val Gln Asp Ser Glu Asp Ser Gly Lys Met Val Ala
    130                 135                 140

Lys Arg Gln Phe Arg Ile Gly Asp Ile Ala Gly Glu His Thr Ser Phe
145                 150                 155                 160

Asp Lys Leu Pro Lys Gly Gly Ser Ala Thr Tyr Arg Gly Thr Ala Phe
                165                 170                 175

Gly Ser Asp Asp Ala Gly Gly Lys Leu Thr Tyr Thr Ile Asp Phe Ala
                180                 185                 190

Ala Lys Gln Gly His Gly Lys Ile Glu His Leu Lys Ser Pro Glu Leu
            195                 200                 205

Asn Val Glu Leu Ala Thr Ala Tyr Ile Lys Pro Asp Glu Lys Arg His
210                 215                 220
```

```
Ala Val Ile Ser Gly Ser Val Leu Tyr Asn Gln Asp Glu Lys Gly Ser
225                 230                 235                 240

Tyr Ser Leu Gly Ile Phe Gly Gly Gln Ala Gln Glu Val Ala Gly Ser
                245                 250                 255

Ala Glu Val Glu Thr Ala Asn Gly Ile His His Ile Gly Leu Ala Ala
            260                 265                 270

Lys Gln

<210> SEQ ID NO 4
<211> LENGTH: 274
<212> TYPE: PRT
<213> ORGANISM: Neisseria meningitidis

<400> SEQUENCE: 4

Met Asn Arg Thr Ala Phe Cys Cys Phe Ser Leu Thr Ala Ala Leu Ile
1               5                   10                  15

Leu Thr Ala Cys Ser Ser Gly Gly Gly Val Ala Ala Asp Ile Gly
            20                  25                  30

Ala Gly Leu Ala Asp Ala Leu Thr Ala Pro Leu Asp His Lys Asp Lys
            35                  40                  45

Ser Leu Gln Ser Leu Thr Leu Asp Gln Ser Val Arg Lys Asn Glu Lys
50                  55                  60

Leu Lys Leu Ala Ala Gln Gly Ala Glu Lys Thr Tyr Gly Asn Gly Asp
65                  70                  75                  80

Ser Leu Asn Thr Gly Lys Leu Lys Asn Asp Lys Val Ser Arg Phe Asp
                85                  90                  95

Phe Ile Arg Gln Ile Glu Val Asp Gly Gln Leu Ile Thr Leu Glu Ser
                100                 105                 110

Gly Glu Phe Gln Val Tyr Lys Gln Ser His Ser Ala Leu Thr Ala Leu
            115                 120                 125

Gln Thr Glu Gln Glu Gln Asp Pro Glu His Ser Gly Lys Met Val Ala
130                 135                 140

Lys Arg Arg Phe Lys Ile Gly Asp Ile Ala Gly Glu His Thr Ser Phe
145                 150                 155                 160

Asp Lys Leu Pro Lys Asp Val Met Ala Thr Tyr Arg Gly Thr Ala Phe
                165                 170                 175

Gly Ser Asp Asp Ala Gly Gly Lys Leu Thr Tyr Thr Ile Asp Phe Ala
            180                 185                 190

Ala Lys Gln Gly His Gly Lys Ile Glu His Leu Lys Ser Pro Glu Leu
            195                 200                 205

Asn Val Glu Leu Ala Thr Ala Tyr Ile Lys Pro Asp Glu Lys His His
210                 215                 220

Ala Val Ile Ser Gly Ser Val Leu Tyr Asn Gln Asp Glu Lys Gly Ser
225                 230                 235                 240

Tyr Ser Leu Gly Ile Phe Gly Gly Gln Ala Gln Glu Val Ala Gly Ser
                245                 250                 255

Ala Glu Val Glu Thr Ala Asn Gly Ile His His Ile Gly Leu Ala Ala
            260                 265                 270

Lys Gln

<210> SEQ ID NO 5
<211> LENGTH: 279
<212> TYPE: PRT
<213> ORGANISM: Neisseria meningitidis
```

<400> SEQUENCE: 5

```
Met Asn Arg Thr Thr Phe Phe Cys Leu Ser Leu Thr Ala Ala Leu Ile
1               5                   10                  15

Leu Thr Ala Cys Ser Ser Gly Gly Gly Ser Gly Gly Gly Gly Gly Val
            20                  25                  30

Ala Ala Asp Ile Gly Ala Gly Leu Ala Asp Ala Leu Thr Ala Pro Leu
            35                  40                  45

Asp His Lys Asp Lys Gly Leu Gln Ser Leu Thr Leu Asp Gln Ser Val
        50                  55                  60

Arg Lys Asn Glu Lys Leu Lys Leu Ala Ala Gln Gly Ala Glu Lys Thr
65                  70                  75                  80

Tyr Gly Asn Gly Asp Ser Leu Asn Thr Gly Lys Leu Lys Asn Asp Lys
                85                  90                  95

Val Ser Arg Phe Asp Phe Ile Arg Gln Ile Glu Val Asp Gly Gln Leu
            100                 105                 110

Ile Thr Leu Glu Ser Gly Glu Phe Gln Val Tyr Lys Gln Ser His Ser
        115                 120                 125

Ala Leu Thr Ala Leu Gln Thr Glu Gln Val Gln Asp Ser Glu Asp Ser
    130                 135                 140

Gly Lys Met Val Ala Lys Arg Gln Phe Arg Ile Gly Asp Ile Ala Gly
145                 150                 155                 160

Glu His Thr Ser Phe Asp Lys Leu Pro Lys Gly Gly Ser Ala Thr Tyr
                165                 170                 175

Arg Gly Thr Ala Phe Gly Ser Asp Asp Ala Gly Gly Lys Leu Thr Tyr
            180                 185                 190

Thr Ile Asp Phe Ala Val Lys Gln Gly His Gly Lys Ile Glu His Leu
        195                 200                 205

Lys Ser Pro Glu Leu Asn Val Asp Leu Ala Ala Tyr Ile Lys Pro
    210                 215                 220

Asp Lys Lys Arg His Ala Val Ile Ser Gly Ser Val Leu Tyr Asn Gln
225                 230                 235                 240

Asp Glu Lys Gly Ser Tyr Ser Leu Gly Ile Phe Gly Gly Gln Ala Gln
                245                 250                 255

Glu Val Ala Gly Ser Ala Glu Val Glu Thr Ala Asn Gly Ile His His
            260                 265                 270

Ile Gly Leu Ala Ala Lys Gln
        275
```

<210> SEQ ID NO 6
<211> LENGTH: 274
<212> TYPE: PRT
<213> ORGANISM: Neisseria meningitidis

<400> SEQUENCE: 6

```
Met Asn Arg Thr Ala Phe Cys Cys Leu Ser Leu Thr Ala Ala Leu Ile
1               5                   10                  15

Leu Thr Ala Cys Ser Ser Gly Gly Gly Gly Val Ala Ala Asp Ile Gly
            20                  25                  30

Ala Val Leu Ala Asp Ala Leu Thr Ala Pro Leu Asp His Lys Asp Lys
            35                  40                  45

Ser Leu Gln Ser Leu Thr Leu Asp Gln Ser Val Arg Lys Asn Glu Lys
        50                  55                  60

Leu Lys Leu Ala Ala Gln Gly Ala Glu Lys Thr Tyr Gly Asn Gly Asp
65                  70                  75                  80
```

```
Ser Leu Asn Thr Gly Lys Leu Lys Asn Asp Lys Val Ser Arg Phe Asp
                85                  90                  95

Phe Ile Arg Gln Ile Glu Val Asp Gly Gln Leu Ile Thr Leu Glu Ser
        100                 105                 110

Gly Glu Phe Gln Val Tyr Lys Gln Ser His Ser Ala Leu Thr Ala Leu
            115                 120                 125

Gln Thr Glu Gln Val Gln Asp Ser Glu His Ser Gly Lys Met Val Ala
130                 135                 140

Lys Arg Gln Phe Arg Ile Gly Asp Ile Ala Gly Glu His Thr Ser Phe
145                 150                 155                 160

Asp Lys Leu Pro Glu Gly Gly Arg Ala Thr Tyr Arg Gly Thr Ala Phe
                165                 170                 175

Gly Ser Asp Asp Ala Ser Gly Lys Leu Thr Tyr Thr Ile Asp Phe Ala
            180                 185                 190

Ala Lys Gln Gly His Gly Lys Ile Glu His Leu Lys Ser Pro Glu Leu
        195                 200                 205

Asn Val Asp Leu Ala Ala Ser Asp Ile Lys Pro Asp Lys Lys Arg His
    210                 215                 220

Ala Val Ile Ser Gly Ser Val Leu Tyr Asn Gln Ala Glu Lys Gly Ser
225                 230                 235                 240

Tyr Ser Leu Gly Ile Phe Gly Gly Gln Ala Gln Glu Val Ala Gly Ser
                245                 250                 255

Ala Glu Val Glu Thr Ala Asn Gly Ile Arg His Ile Gly Leu Ala Ala
            260                 265                 270

Lys Gln

<210> SEQ ID NO 7
<211> LENGTH: 274
<212> TYPE: PRT
<213> ORGANISM: Neisseria meningitidis

<400> SEQUENCE: 7

Met Asn Arg Thr Ala Phe Cys Cys Leu Ser Leu Thr Ala Ala Leu Ile
1               5                   10                  15

Leu Thr Ala Cys Ser Ser Gly Gly Gly Val Ala Ala Asp Ile Gly
            20                  25                  30

Ala Gly Leu Ala Asp Ala Leu Thr Ala Pro Leu Asp His Lys Asp Lys
        35                  40                  45

Ser Leu Gln Ser Leu Thr Leu Asp Gln Ser Val Arg Lys Asn Glu Lys
    50                  55                  60

Leu Lys Leu Ala Ala Gln Gly Ala Glu Lys Thr Tyr Gly Asn Gly Asp
65                  70                  75                  80

Ser Leu Asn Thr Gly Lys Leu Lys Asn Asp Lys Val Ser Arg Phe Asp
                85                  90                  95

Phe Ile Arg Gln Ile Glu Val Asp Gly Gln Leu Ile Thr Leu Glu Ser
        100                 105                 110

Gly Glu Phe Gln Val Tyr Lys Gln Ser His Ser Ala Leu Thr Ala Leu
            115                 120                 125

Gln Thr Glu Gln Val Gln Asp Ser Glu His Ser Gly Lys Met Val Ala
130                 135                 140

Lys Arg Gln Phe Arg Ile Gly Asp Ile Ala Gly Glu His Thr Ser Phe
145                 150                 155                 160

Asp Lys Leu Pro Glu Gly Gly Arg Ala Thr Tyr Arg Gly Thr Ala Phe
                165                 170                 175
```

Gly Ser Asp Asp Ala Ser Gly Lys Leu Thr Tyr Thr Ile Asp Phe Ala
            180                 185                 190

Ala Lys Gln Gly His Gly Lys Ile Glu His Leu Lys Ser Pro Glu Leu
            195                 200                 205

Asn Val Asp Leu Ala Ala Ser Asp Ile Lys Pro Asp Lys Lys Arg His
            210                 215                 220

Ala Val Ile Ser Gly Ser Val Leu Tyr Asn Gln Ala Glu Lys Gly Ser
225                 230                 235                 240

Tyr Ser Leu Gly Ile Phe Gly Gly Gln Ala Gln Glu Val Ala Gly Ser
                245                 250                 255

Ala Glu Val Glu Thr Ala Asn Gly Ile Arg His Ile Gly Leu Ala Ala
            260                 265                 270

Lys Gln

<210> SEQ ID NO 8
<211> LENGTH: 274
<212> TYPE: PRT
<213> ORGANISM: Neisseria meningitidis

<400> SEQUENCE: 8

Met Asn Arg Thr Ala Phe Cys Cys Leu Ser Leu Thr Thr Ala Leu Ile
1               5                   10                  15

Leu Thr Ala Cys Ser Ser Gly Gly Gly Val Ala Ala Asp Ile Gly
            20                  25                  30

Ala Gly Leu Ala Asp Ala Leu Thr Ala Pro Leu Asp His Lys Asp Lys
            35                  40                  45

Gly Leu Gln Ser Leu Met Leu Asp Gln Ser Val Arg Lys Asn Glu Lys
        50                  55                  60

Leu Lys Leu Ala Ala Gln Gly Ala Glu Lys Thr Tyr Gly Asn Gly Asp
65                  70                  75                  80

Ser Leu Asn Thr Gly Lys Leu Lys Asn Asp Lys Val Ser Arg Phe Asp
                85                  90                  95

Phe Ile Arg Gln Ile Glu Val Asp Gly Gln Leu Ile Thr Leu Glu Ser
            100                 105                 110

Gly Glu Phe Gln Val Tyr Lys Gln Ser His Ser Ala Leu Thr Ala Leu
            115                 120                 125

Gln Thr Glu Gln Val Gln Asp Ser Glu His Ser Gly Lys Met Val Ala
        130                 135                 140

Lys Arg Gln Phe Arg Ile Gly Asp Ile Ala Gly Glu His Thr Ser Phe
145                 150                 155                 160

Asp Lys Leu Pro Glu Gly Gly Arg Ala Thr Tyr Arg Gly Thr Ala Phe
                165                 170                 175

Gly Ser Asp Asp Ala Gly Gly Lys Leu Ile Tyr Thr Ile Asp Phe Ala
            180                 185                 190

Ala Lys Gln Gly His Gly Lys Ile Glu His Leu Lys Ser Pro Glu Leu
            195                 200                 205

Asn Val Asp Leu Ala Ala Ala Tyr Ile Lys Pro Asp Glu Lys His His
            210                 215                 220

Ala Val Ile Ser Gly Ser Val Leu Tyr Asn Gln Ala Glu Lys Gly Ser
225                 230                 235                 240

Tyr Ser Leu Gly Ile Phe Gly Gly Lys Ala Gln Glu Val Ala Gly Ser
                245                 250                 255

Ala Glu Val Lys Thr Val Asn Gly Ile Arg His Ile Gly Leu Ala Ala
            260                 265                 270

Lys Gln

<210> SEQ ID NO 9
<211> LENGTH: 274
<212> TYPE: PRT
<213> ORGANISM: Neisseria meningitidis

<400> SEQUENCE: 9

```
Met Asn Arg Thr Ala Phe Cys Cys Leu Ser Leu Thr Ala Ala Leu Ile
1               5                   10                  15

Leu Thr Ala Cys Ser Ser Gly Gly Gly Val Ala Ala Asp Ile Gly
            20                  25                  30

Ala Gly Leu Ala Asp Ala Leu Thr Ala Pro Leu Asp His Lys Asp Lys
        35                  40                  45

Gly Leu Arg Ser Leu Thr Leu Asp Gln Ser Val Arg Lys Asn Glu Lys
    50                  55                  60

Leu Lys Leu Ala Ala Gln Gly Ala Glu Lys Thr Tyr Gly Asn Gly Asp
65                  70                  75                  80

Ser Leu Asn Thr Gly Lys Leu Lys Asn Asp Lys Val Ser Arg Phe Asp
                85                  90                  95

Phe Ile Arg Gln Ile Glu Val Asp Gly Gln Leu Ile Thr Leu Glu Ser
            100                 105                 110

Gly Glu Phe Gln Val Tyr Lys Gln Ser His Ser Ala Leu Thr Ala Leu
        115                 120                 125

Gln Thr Glu Gln Glu Gln Asp Leu Glu His Ser Gly Lys Met Val Ala
    130                 135                 140

Lys Arg Arg Phe Arg Ile Gly Asp Ile Ala Gly Glu His Thr Ser Phe
145                 150                 155                 160

Asp Lys Leu Arg Glu Gly Gly Arg Ala Thr Tyr Arg Gly Thr Ala Phe
                165                 170                 175

Gly Ser Asp Asp Ala Gly Gly Lys Leu Thr Tyr Thr Ile Asp Phe Ala
            180                 185                 190

Ala Lys Gln Gly Tyr Gly Lys Ile Glu His Leu Lys Ser Pro Glu Leu
        195                 200                 205

Asn Val Asp Leu Ala Ala Ala Asp Ile Lys Pro Asp Glu Lys His His
    210                 215                 220

Ala Val Ile Ser Gly Ser Val Leu Tyr Asn Gln Asp Glu Lys Gly Ser
225                 230                 235                 240

Tyr Ser Leu Gly Ile Phe Gly Gly Glu Ala Gln Glu Val Ala Gly Ser
                245                 250                 255

Ala Glu Val Lys Thr Ala Asn Gly Ile His His Ile Gly Leu Ala Ala
            260                 265                 270

Lys Gln
```

<210> SEQ ID NO 10
<211> LENGTH: 273
<212> TYPE: PRT
<213> ORGANISM: Neisseria meningitidis

<400> SEQUENCE: 10

```
Met Asn Arg Thr Ala Phe Cys Cys Leu Ser Leu Thr Ala Ala Leu Ile
1               5                   10                  15

Leu Thr Ala Cys Ser Ser Gly Gly Gly Val Ala Ala Asp Ile Gly
            20                  25                  30

Ala Gly Leu Ala Asp Ala Leu Thr Ala Pro Leu Asp His Lys Asp Lys
        35                  40                  45
```

Ser Leu Gln Ser Leu Thr Leu Asp Gln Ser Val Arg Lys Asn Glu Lys
            50                  55                  60

Leu Lys Leu Ala Ala Gln Gly Ala Glu Lys Thr Tyr Gly Asn Gly Asp
 65                  70                  75                  80

Ser Leu Asn Thr Gly Lys Leu Lys Asn Asp Lys Val Ser Arg Phe Asp
                 85                  90                  95

Phe Ile Arg Gln Ile Glu Val Asp Gly Gln Leu Ile Thr Leu Glu Ser
            100                 105                 110

Gly Glu Phe Gln Ile Tyr Lys Gln Asp His Ser Ala Val Val Ala Leu
        115                 120                 125

Gln Ile Glu Lys Ile Asn Asn Pro Asp Lys Ile Asp Ser Leu Ile Asn
    130                 135                 140

Gln Arg Ser Phe Leu Val Ser Gly Leu Gly Gly Glu His Thr Ala Phe
145                 150                 155                 160

Asn Gln Leu Pro Asp Gly Lys Ala Glu Tyr His Gly Lys Ala Phe Ser
                165                 170                 175

Ser Asp Asp Ala Gly Gly Lys Leu Thr Tyr Thr Ile Asp Phe Ala Ala
            180                 185                 190

Lys Gln Gly His Gly Lys Ile Glu His Leu Lys Thr Pro Glu Gln Asn
        195                 200                 205

Val Glu Leu Ala Ala Ala Glu Leu Lys Ala Asp Glu Lys Ser His Ala
    210                 215                 220

Val Ile Leu Gly Asp Thr Arg Tyr Gly Ser Glu Lys Gly Thr Tyr
225                 230                 235                 240

His Leu Ala Leu Phe Gly Asp Arg Ala Gln Glu Ile Ala Gly Ser Ala
                245                 250                 255

Thr Val Lys Ile Gly Glu Lys Val His Glu Ile Gly Ile Ala Gly Lys
            260                 265                 270

Gln

<210> SEQ ID NO 11
<211> LENGTH: 273
<212> TYPE: PRT
<213> ORGANISM: Neisseria meningitidis

<400> SEQUENCE: 11

Met Asn Arg Thr Ala Phe Cys Cys Leu Ser Leu Thr Ala Ala Leu Ile
 1               5                  10                  15

Leu Thr Ala Cys Ser Ser Gly Gly Gly Val Ala Ala Asp Ile Gly
             20                  25                  30

Ala Gly Leu Ala Asp Ala Leu Thr Ala Pro Leu Asp His Lys Asp Lys
         35                  40                  45

Ser Leu Gln Ser Leu Thr Leu Asp Gln Ser Val Arg Lys Asn Glu Lys
     50                  55                  60

Leu Lys Leu Ala Ala Gln Gly Ala Glu Lys Thr Tyr Gly Asn Gly Asp
 65                  70                  75                  80

Ser Leu Asn Thr Gly Lys Leu Lys Asn Asp Lys Val Ser Arg Phe Asp
                 85                  90                  95

Phe Ile Arg Gln Ile Glu Val Asp Gly Gln Leu Ile Thr Leu Glu Ser
            100                 105                 110

Gly Glu Phe Gln Ile Tyr Lys Gln Asp His Ser Ala Val Val Ala Leu
        115                 120                 125

Gln Ile Glu Lys Ile Asn Asn Pro Asp Lys Ile Asp Ser Leu Ile Asn
    130                 135                 140

```
Gln Arg Ser Phe Leu Val Ser Gly Leu Gly Gly Glu His Thr Ala Phe
145                 150                 155                 160

Asn Gln Leu Pro Ser Gly Lys Ala Glu Tyr His Gly Lys Ala Phe Ser
                165                 170                 175

Ser Asp Asp Ala Gly Gly Lys Leu Thr Tyr Thr Ile Asp Phe Ala Ala
            180                 185                 190

Lys Gln Gly His Gly Lys Ile Glu His Leu Lys Thr Pro Glu Gln Asn
            195                 200                 205

Val Glu Leu Ala Ser Ala Glu Leu Lys Ala Asp Glu Lys Ser His Ala
        210                 215                 220

Val Ile Leu Gly Asp Thr Arg Tyr Gly Gly Glu Lys Gly Thr Tyr
225                 230                 235                 240

His Leu Ala Leu Phe Gly Asp Arg Ala Gln Glu Ile Ala Gly Ser Ala
                245                 250                 255

Thr Val Lys Ile Arg Glu Lys Val His Glu Ile Gly Ile Ala Gly Lys
                260                 265                 270

Gln

<210> SEQ ID NO 12
<211> LENGTH: 273
<212> TYPE: PRT
<213> ORGANISM: Neisseria meningitidis

<400> SEQUENCE: 12

Met Asn Arg Thr Ala Phe Cys Cys Leu Ser Leu Thr Ala Ala Leu Ile
1               5                   10                  15

Leu Thr Ala Cys Ser Ser Gly Gly Gly Val Ala Ala Asp Ile Gly
            20                  25                  30

Ala Gly Leu Ala Asp Ala Leu Thr Ala Pro Leu Asp His Lys Asp Lys
        35                  40                  45

Gly Leu Gln Ser Leu Thr Leu Asp Gln Ser Val Arg Lys Asn Glu Lys
50                  55                  60

Leu Lys Leu Ala Ala Gln Gly Ala Glu Lys Thr Tyr Gly Asn Gly Asp
65                  70                  75                  80

Ser Leu Asn Thr Gly Lys Leu Lys Asn Asp Lys Val Ser Arg Phe Asp
                85                  90                  95

Phe Ile Arg Gln Ile Glu Val Asp Gly Gln Leu Ile Thr Leu Glu Ser
            100                 105                 110

Gly Glu Phe Gln Ile Tyr Lys Gln Asp His Ser Ala Val Val Ala Leu
        115                 120                 125

Gln Ile Glu Lys Ile Asn Asn Pro Asp Lys Ile Asp Ser Leu Ile Asn
130                 135                 140

Gln Arg Ser Phe Leu Val Ser Gly Leu Gly Gly Glu His Thr Ala Phe
145                 150                 155                 160

Asn Gln Leu Pro Ser Gly Lys Ala Glu Tyr His Gly Lys Ala Phe Ser
                165                 170                 175

Ser Asp Asp Pro Asn Gly Arg Leu His Tyr Ser Ile Asp Phe Thr Lys
            180                 185                 190

Lys Gln Gly Tyr Gly Arg Ile Glu His Leu Lys Thr Pro Glu Gln Asn
            195                 200                 205

Val Glu Leu Ala Ser Ala Glu Leu Lys Ala Asp Glu Lys Ser His Ala
        210                 215                 220

Val Ile Leu Gly Asp Thr Arg Tyr Gly Gly Glu Lys Gly Thr Tyr
225                 230                 235                 240
```

His Leu Ala Leu Phe Gly Asp Arg Ala Gln Glu Ile Ala Gly Ser Ala
                245                 250                 255

Thr Val Lys Ile Arg Glu Lys Val His Glu Ile Gly Ile Ala Gly Lys
            260                 265                 270

Gln

<210> SEQ ID NO 13
<211> LENGTH: 273
<212> TYPE: PRT
<213> ORGANISM: Neisseria meningitidis

<400> SEQUENCE: 13

Met Asn Arg Thr Ala Phe Cys Cys Leu Ser Leu Thr Ala Ala Leu Ile
1               5                   10                  15

Leu Thr Ala Cys Ser Ser Gly Gly Gly Val Ala Ala Asp Ile Gly
            20                  25                  30

Ala Gly Leu Ala Asp Ala Leu Thr Ala Pro Leu Asp His Lys Asp Lys
        35                  40                  45

Ser Leu Gln Ser Leu Thr Leu Asp Gln Ser Val Arg Lys Asn Glu Lys
    50                  55                  60

Leu Lys Leu Ala Ala Gln Gly Ala Glu Lys Thr Tyr Gly Asn Gly Asp
65                  70                  75                  80

Ser Leu Asn Thr Gly Lys Leu Lys Asn Asp Lys Val Ser Arg Phe Asp
                85                  90                  95

Phe Ile Arg Gln Ile Glu Val Asp Gly Gln Leu Ile Thr Leu Glu Ser
            100                 105                 110

Gly Glu Phe Gln Ile Tyr Lys Gln Asp His Ser Ala Val Val Ala Leu
        115                 120                 125

Gln Ile Glu Lys Ile Asn Asn Pro Asp Lys Ile Asp Ser Leu Ile Asn
    130                 135                 140

Gln Arg Ser Phe Leu Val Ser Gly Leu Gly Gly Glu His Thr Ala Phe
145                 150                 155                 160

Asn Gln Leu Pro Ser Gly Lys Ala Glu Tyr His Gly Lys Ala Phe Ser
                165                 170                 175

Ser Asp Asp Pro Asn Gly Arg Leu His Tyr Ser Ile Asp Phe Thr Lys
            180                 185                 190

Lys Gln Gly Tyr Gly Arg Ile Glu His Leu Lys Thr Pro Glu Gln Asn
        195                 200                 205

Val Glu Leu Ala Ser Ala Glu Leu Lys Ala Asp Glu Lys Ser His Ala
    210                 215                 220

Val Ile Leu Gly Asp Thr Arg Tyr Gly Gly Glu Glu Lys Gly Thr Tyr
225                 230                 235                 240

His Leu Ala Leu Phe Gly Asp Arg Ala Gln Glu Ile Ala Gly Ser Ala
                245                 250                 255

Thr Val Lys Ile Arg Glu Lys Val His Glu Ile Gly Ile Ala Gly Lys
            260                 265                 270

Gln

<210> SEQ ID NO 14
<211> LENGTH: 273
<212> TYPE: PRT
<213> ORGANISM: Neisseria meningitidis

<400> SEQUENCE: 14

Met Asn Arg Thr Ala Phe Cys Cys Leu Ser Leu Thr Ala Ala Leu Ile

```
          1               5                  10                 15
        Leu Thr Ala Cys Ser Ser Gly Gly Gly Val Ala Ala Asp Ile Gly
                        20                 25                 30

Ala Gly Leu Ala Asp Ala Leu Thr Ala Pro Leu Asp His Lys Asp Lys
                    35                 40                 45

Ser Leu Gln Ser Leu Thr Leu Asp Gln Ser Val Arg Lys Asn Glu Lys
            50                 55                 60

Leu Lys Leu Ala Ala Gln Gly Ala Glu Lys Thr Tyr Gly Asn Gly Asp
        65                 70                 75                 80

Ser Leu Asn Thr Gly Lys Leu Lys Asn Asp Lys Val Ser Arg Phe Asp
                        85                 90                 95

Phe Ile Arg Gln Ile Glu Val Asp Gly Gln Leu Ile Thr Leu Glu Ser
                        100                105                110

Gly Glu Phe Gln Ile Tyr Lys Gln Asp His Ser Ala Val Val Ala Leu
                    115                120                125

Gln Ile Glu Lys Ile Asn Asn Pro Asp Lys Ile Asp Ser Leu Ile Asn
        130                135                140

Gln Arg Ser Phe Leu Val Ser Gly Leu Gly Gly Glu His Thr Ala Phe
        145                150                155                160

Asn Gln Leu Pro Gly Gly Lys Ala Glu Tyr His Gly Lys Ala Phe Ser
                        165                170                175

Ser Asp Asp Pro Asn Gly Arg Leu His Tyr Ser Ile Asp Phe Thr Lys
                    180                185                190

Lys Gln Gly Tyr Gly Arg Ile Glu His Leu Lys Thr Pro Glu Gln Asn
                    195                200                205

Val Glu Leu Ala Ser Ala Glu Leu Lys Ala Asp Glu Lys Ser His Ala
            210                215                220

Val Ile Leu Gly Asp Thr Arg Tyr Gly Ser Glu Lys Gly Thr Tyr
        225                230                235                240

His Leu Ala Leu Phe Gly Asp Arg Ala Gln Glu Ile Ala Gly Ser Ala
                        245                250                255

Thr Val Lys Ile Arg Glu Lys Val His Glu Ile Gly Ile Ala Gly Lys
                    260                265                270

Gln

<210> SEQ ID NO 15
<211> LENGTH: 273
<212> TYPE: PRT
<213> ORGANISM: Neisseria meningitidis

<400> SEQUENCE: 15

Met Asn Arg Thr Ala Phe Cys Cys Leu Ser Leu Thr Ala Ala Leu Ile
        1               5                  10                 15

Leu Thr Ala Cys Ser Ser Gly Gly Gly Val Ala Ala Asp Ile Gly
                        20                 25                 30

Ala Gly Leu Ala Asp Ala Leu Thr Thr Pro Leu Asp His Lys Asp Lys
                    35                 40                 45

Ser Leu Gln Ser Leu Thr Leu Asp Gln Ser Val Arg Lys Asn Glu Lys
            50                 55                 60

Leu Lys Leu Ala Ala Gln Gly Ala Glu Lys Thr Tyr Gly Asn Gly Asp
        65                 70                 75                 80

Ser Leu Asn Thr Gly Lys Leu Lys Asn Asp Lys Val Ser Arg Phe Asp
                        85                 90                 95

Phe Ile Arg Gln Ile Glu Val Asp Gly Gln Thr Ile Thr Leu Ala Ser
```

```
            100                 105                 110
Gly Glu Phe Gln Ile Tyr Lys Gln Asn His Ser Ala Val Val Ala Leu
        115                 120                 125

Gln Ile Glu Lys Ile Asn Asn Pro Asp Lys Ile Asp Ser Leu Ile Asn
    130                 135                 140

Gln Arg Ser Phe Leu Val Ser Gly Leu Gly Gly Glu His Thr Ala Phe
145                 150                 155                 160

Asn Gln Leu Pro Asp Gly Lys Ala Glu Tyr His Gly Lys Ala Phe Ser
                165                 170                 175

Ser Asp Asp Pro Asn Gly Arg Leu His Tyr Ser Ile Asp Phe Thr Lys
            180                 185                 190

Lys Gln Gly Tyr Gly Arg Ile Glu His Leu Lys Thr Pro Glu Gln Asn
        195                 200                 205

Val Glu Leu Ala Ser Ala Glu Leu Lys Ala Asp Glu Lys Ser His Ala
    210                 215                 220

Val Ile Leu Gly Asp Thr Arg Tyr Gly Gly Glu Lys Gly Thr Tyr
225                 230                 235                 240

His Leu Ala Leu Phe Gly Asp Arg Ala Gln Glu Ile Ala Gly Ser Ala
                245                 250                 255

Thr Val Lys Ile Arg Glu Lys Val His Glu Ile Gly Ile Ala Gly Lys
            260                 265                 270

Gln

<210> SEQ ID NO 16
<211> LENGTH: 273
<212> TYPE: PRT
<213> ORGANISM: Neisseria meningitidis

<400> SEQUENCE: 16

Met Asn Arg Thr Ala Phe Cys Cys Leu Ser Leu Thr Ala Ala Leu Ile
1               5                   10                  15

Leu Thr Ala Cys Ser Ser Gly Gly Gly Val Ala Ala Asp Ile Gly
            20                  25                  30

Ala Gly Leu Ala Asp Ala Leu Thr Ala Pro Leu Asp His Lys Asp Lys
        35                  40                  45

Ser Leu Gln Ser Leu Thr Leu Asp Gln Ser Val Arg Lys Asn Glu Lys
    50                  55                  60

Leu Lys Leu Ala Ala Gln Gly Ala Glu Lys Thr Tyr Gly Asn Gly Asp
65                  70                  75                  80

Ser Leu Asn Thr Gly Lys Leu Lys Asn Asp Lys Val Ser Arg Phe Asp
                85                  90                  95

Phe Ile Arg Gln Ile Glu Val Asp Gly Gln Thr Ile Thr Leu Ala Ser
            100                 105                 110

Gly Glu Phe Gln Ile Tyr Lys Gln Asn His Ser Ala Val Val Ala Leu
        115                 120                 125

Gln Ile Glu Lys Ile Asn Asn Pro Asp Lys Ile Asp Ser Leu Ile Asn
    130                 135                 140

Gln Arg Ser Phe Leu Val Ser Gly Leu Gly Gly Glu His Thr Ala Phe
145                 150                 155                 160

Asn Gln Leu Pro Asp Gly Lys Ala Glu Tyr His Gly Lys Ala Phe Ser
                165                 170                 175

Ser Asp Asp Pro Asn Gly Arg Leu His Tyr Ser Ile Asp Phe Thr Lys
            180                 185                 190

Lys Gln Gly Tyr Gly Arg Ile Glu His Leu Lys Thr Pro Glu Gln Asn
```

```
            195                 200                 205
Val Glu Leu Ala Ser Ala Glu Leu Lys Ala Asp Glu Lys Ser His Ala
    210                 215                 220

Val Ile Leu Gly Asp Thr Arg Tyr Gly Gly Glu Lys Gly Thr Tyr
225                 230                 235                 240

His Leu Ala Leu Phe Gly Asp Arg Ala Gln Glu Ile Ala Gly Ser Ala
                245                 250                 255

Thr Val Lys Ile Arg Glu Lys Val His Glu Ile Gly Ile Ala Gly Lys
            260                 265                 270

Gln

<210> SEQ ID NO 17
<211> LENGTH: 273
<212> TYPE: PRT
<213> ORGANISM: Neisseria meningitidis

<400> SEQUENCE: 17

Met Asn Arg Thr Ala Phe Cys Cys Leu Ser Leu Thr Thr Ala Leu Ile
1               5                   10                  15

Leu Thr Ala Cys Ser Ser Gly Gly Gly Val Ala Ala Asp Ile Gly
            20                  25                  30

Ala Gly Leu Ala Asp Ala Leu Thr Ala Pro Leu Asp His Lys Asp Lys
        35                  40                  45

Gly Leu Gln Ser Leu Met Leu Asp Gln Ser Val Arg Lys Asn Glu Lys
    50                  55                  60

Leu Lys Leu Ala Ala Gln Gly Ala Glu Lys Thr Tyr Gly Asn Gly Asp
65                  70                  75                  80

Ser Leu Asn Thr Gly Lys Leu Lys Asn Asp Lys Val Ser Arg Phe Asp
                85                  90                  95

Phe Ile Arg Gln Ile Glu Val Asp Gly Gln Thr Ile Thr Leu Ala Ser
            100                 105                 110

Gly Glu Phe Gln Ile Tyr Lys Gln Asn His Ser Ala Val Val Ala Leu
        115                 120                 125

Gln Ile Glu Lys Ile Asn Asn Pro Asp Lys Ile Asp Ser Leu Ile Asn
    130                 135                 140

Gln Arg Ser Phe Leu Val Ser Gly Leu Gly Gly Glu His Thr Ala Phe
145                 150                 155                 160

Asn Gln Leu Pro Asp Gly Lys Ala Glu Tyr His Gly Lys Ala Phe Ser
                165                 170                 175

Ser Asp Asp Pro Asn Gly Arg Leu His Tyr Ser Ile Asp Phe Thr Lys
            180                 185                 190

Lys Gln Gly Tyr Gly Arg Ile Glu His Leu Lys Thr Pro Glu Gln Asn
        195                 200                 205

Val Glu Leu Ala Ser Ala Glu Leu Lys Ala Asp Glu Lys Ser His Ala
    210                 215                 220

Val Ile Leu Gly Asp Thr Arg Tyr Gly Gly Glu Lys Gly Thr Tyr
225                 230                 235                 240

His Leu Ala Leu Phe Gly Asp Arg Ala Gln Glu Ile Ala Gly Ser Ala
                245                 250                 255

Thr Val Lys Ile Arg Glu Lys Val His Glu Ile Gly Ile Ala Gly Lys
            260                 265                 270

Gln

<210> SEQ ID NO 18
```

<211> LENGTH: 281
<212> TYPE: PRT
<213> ORGANISM: Neisseria meningitidis

<400> SEQUENCE: 18

Met Asn Arg Thr Ala Phe Cys Cys Leu Ser Leu Thr Thr Ala Leu Ile
1               5                   10                  15

Leu Thr Ala Cys Ser Ser Gly Gly Gly Ser Gly Gly Gly Gly Gly Val
            20                  25                  30

Ala Ala Asp Ile Gly Thr Gly Leu Ala Asp Ala Leu Thr Ala Pro Leu
        35                  40                  45

Asp His Lys Asp Lys Gly Leu Lys Ser Leu Thr Leu Glu Asp Ser Ile
    50                  55                  60

Pro Gln Asn Gly Thr Leu Thr Leu Ser Ala Gln Gly Ala Glu Lys Thr
65                  70                  75                  80

Phe Lys Ala Gly Asp Lys Asp Asn Ser Leu Asn Thr Gly Lys Leu Lys
                85                  90                  95

Asn Asp Lys Ile Ser Arg Phe Asp Phe Val Gln Lys Ile Glu Val Asp
            100                 105                 110

Gly Gln Thr Ile Thr Leu Ala Ser Gly Glu Phe Gln Ile Tyr Lys Gln
        115                 120                 125

Asn His Ser Ala Val Val Ala Leu Gln Ile Glu Lys Ile Asn Asn Pro
    130                 135                 140

Asp Lys Thr Asp Ser Leu Ile Asn Gln Arg Ser Phe Leu Val Ser Gly
145                 150                 155                 160

Leu Gly Gly Glu His Thr Ala Phe Asn Gln Leu Pro Gly Gly Lys Ala
                165                 170                 175

Glu Tyr His Gly Lys Ala Phe Ser Ser Asp Pro Asn Gly Arg Leu
            180                 185                 190

His Tyr Ser Ile Asp Phe Thr Lys Lys Gln Gly Tyr Gly Arg Ile Glu
        195                 200                 205

His Leu Lys Thr Leu Glu Gln Asn Val Glu Leu Ala Ala Ala Glu Leu
    210                 215                 220

Lys Ala Asp Glu Lys Ser His Ala Val Ile Leu Gly Asp Thr Arg Tyr
225                 230                 235                 240

Gly Ser Glu Glu Lys Gly Thr Tyr His Leu Ala Leu Phe Gly Asp Arg
                245                 250                 255

Ala Gln Glu Ile Ala Gly Ser Ala Thr Val Lys Ile Gly Glu Lys Val
            260                 265                 270

His Glu Ile Gly Ile Ala Gly Lys Gln
        275                 280

<210> SEQ ID NO 19
<211> LENGTH: 281
<212> TYPE: PRT
<213> ORGANISM: Neisseria meningitidis

<400> SEQUENCE: 19

Met Asn Arg Thr Ala Phe Cys Cys Leu Phe Leu Thr Thr Ala Leu Ile
1               5                   10                  15

Leu Thr Ala Cys Ser Ser Gly Gly Gly Ser Gly Gly Gly Gly Gly Val
            20                  25                  30

Ala Ala Asp Ile Gly Thr Gly Leu Ala Asp Ala Leu Thr Ala Pro Leu
        35                  40                  45

Asp His Lys Asp Lys Gly Leu Lys Ser Leu Thr Leu Glu Asp Ser Ile
    50                  55                  60

```
Pro Gln Asn Gly Thr Leu Thr Leu Ser Ala Gln Gly Ala Glu Lys Thr
 65                  70                  75                  80

Phe Lys Ala Gly Asp Lys Asp Asn Ser Leu Asn Thr Gly Lys Leu Lys
                 85                  90                  95

Asn Asp Lys Ile Ser Arg Phe Asp Phe Val Gln Lys Ile Glu Val Asp
            100                 105                 110

Gly Gln Thr Ile Thr Leu Ala Ser Gly Glu Phe Gln Ile Tyr Lys Gln
            115                 120                 125

Asp His Ser Ala Val Val Ala Leu Gln Ile Glu Lys Ile Asn Asn Pro
130                 135                 140

Asp Lys Ile Asp Ser Leu Ile Asn Gln Arg Ser Phe Leu Val Ser Gly
145                 150                 155                 160

Leu Gly Gly Glu His Thr Ala Phe Asn Gln Leu Pro Gly Gly Lys Ala
                165                 170                 175

Glu Tyr His Gly Lys Ala Phe Ser Ser Asp Ala Gly Gly Lys Leu
                180                 185                 190

Thr Tyr Thr Ile Asp Phe Ala Ala Lys Gln Gly His Gly Lys Ile Glu
            195                 200                 205

His Leu Lys Thr Pro Glu Gln Asn Val Glu Leu Ala Ala Ala Glu Leu
210                 215                 220

Lys Ala Asp Glu Lys Ser His Ala Val Ile Leu Gly Asp Thr Arg Tyr
225                 230                 235                 240

Gly Ser Glu Glu Lys Gly Thr Tyr His Leu Ala Leu Phe Gly Asp Arg
                245                 250                 255

Ala Gln Glu Ile Ala Gly Ser Ala Thr Val Lys Ile Gly Glu Lys Val
            260                 265                 270

His Glu Ile Ser Ile Ala Gly Lys Gln
            275                 280
```

<210> SEQ ID NO 20
<211> LENGTH: 281
<212> TYPE: PRT
<213> ORGANISM: Neisseria meningitidis

<400> SEQUENCE: 20

```
Met Asn Arg Thr Ala Phe Cys Cys Leu Phe Leu Thr Thr Ala Leu Ile
 1               5                  10                  15

Leu Thr Ala Cys Ser Ser Gly Gly Gly Ser Gly Ser Gly Gly Val
             20                  25                  30

Ala Ala Asp Ile Gly Thr Gly Leu Ala Asp Ala Leu Thr Thr Pro Leu
             35                  40                  45

Asp His Lys Asp Lys Gly Leu Lys Ser Leu Thr Leu Glu Asp Ser Ile
 50                  55                  60

Pro Gln Asn Gly Thr Leu Thr Leu Ser Ala Gln Gly Ala Glu Lys Thr
 65                  70                  75                  80

Phe Lys Ala Gly Asp Lys Asp Asn Ser Leu Asn Thr Gly Lys Leu Lys
                 85                  90                  95

Asn Asp Lys Ile Ser Arg Phe Asp Phe Val Gln Lys Ile Glu Val Asp
            100                 105                 110

Gly Gln Thr Ile Thr Leu Ala Ser Gly Glu Phe Gln Ile Tyr Lys Gln
            115                 120                 125

Asp His Ser Ala Val Val Ala Leu Gln Ile Glu Lys Ile Asn Asn Pro
130                 135                 140

Asp Lys Ile Asp Ser Leu Ile Asn Gln Arg Ser Phe Leu Val Ser Gly
```

```
145                 150                 155                 160
Leu Gly Gly Glu His Thr Ala Phe Asn Gln Leu Pro Gly Gly Lys Ala
                    165                 170                 175
Glu Tyr His Gly Lys Ala Phe Ser Ser Asp Ala Gly Gly Lys Leu
                180                 185                 190
Thr Tyr Thr Ile Asp Phe Ala Ala Lys Gln Gly His Gly Lys Ile Glu
            195                 200                 205
His Leu Lys Thr Pro Glu Gln Asn Val Glu Leu Ala Ala Ala Glu Leu
        210                 215                 220
Lys Ala Asp Glu Lys Ser His Ala Val Ile Leu Gly Asp Thr Arg Tyr
225                 230                 235                 240
Gly Ser Glu Glu Lys Gly Thr Tyr His Leu Ala Leu Phe Gly Asp Arg
                    245                 250                 255
Ala Gln Glu Ile Ala Gly Ser Ala Thr Val Lys Ile Gly Glu Lys Val
                260                 265                 270
His Glu Ile Gly Ile Ala Gly Lys Gln
            275                 280

<210> SEQ ID NO 21
<211> LENGTH: 279
<212> TYPE: PRT
<213> ORGANISM: Neisseria meningitidis

<400> SEQUENCE: 21

Met Asn Arg Thr Ala Phe Cys Cys Leu Phe Leu Thr Thr Ala Leu Ile
1               5                   10                  15
Leu Thr Ala Cys Ser Ser Gly Gly Gly Ser Gly Gly Ile Ala Ala
            20                  25                  30
Asp Ile Gly Thr Gly Leu Ala Asp Ala Leu Thr Ala Pro Leu Asp His
        35                  40                  45
Lys Asp Lys Gly Leu Lys Ser Leu Thr Leu Glu Asp Ser Ile Pro Gln
    50                  55                  60
Asn Gly Thr Leu Thr Leu Ser Ala Gln Gly Ala Glu Lys Thr Phe Lys
65                  70                  75                  80
Ala Gly Asp Lys Asp Asn Ser Leu Asn Thr Gly Lys Leu Lys Asn Asp
                85                  90                  95
Lys Ile Ser Arg Phe Asp Phe Val Gln Lys Ile Glu Val Asp Gly Gln
            100                 105                 110
Thr Ile Thr Leu Ala Ser Gly Glu Phe Gln Ile Tyr Lys Gln Asp His
        115                 120                 125
Ser Ala Val Val Ala Leu Gln Ile Glu Lys Ile Asn Asn Pro Asp Lys
    130                 135                 140
Ile Asp Ser Leu Ile Asn Gln Arg Ser Phe Leu Val Ser Gly Leu Gly
145                 150                 155                 160
Gly Glu His Thr Ala Phe Asn Gln Leu Pro Gly Gly Lys Ala Glu Tyr
                    165                 170                 175
His Gly Lys Ala Phe Ser Ser Asp Ala Gly Gly Lys Leu Thr Tyr
                180                 185                 190
Thr Ile Asp Phe Ala Ala Lys Gln Gly His Gly Lys Ile Glu His Leu
            195                 200                 205
Lys Thr Pro Glu Gln Asn Val Glu Leu Ala Ala Ala Glu Leu Lys Ala
        210                 215                 220
Asp Glu Lys Ser His Ala Val Ile Leu Gly Asp Thr Arg Tyr Gly Ser
225                 230                 235                 240
```

```
Glu Glu Lys Gly Thr Tyr His Leu Ala Leu Phe Gly Asp Arg Ala Gln
            245                 250                 255

Glu Ile Ala Gly Ser Ala Thr Val Lys Ile Gly Glu Lys Val His Glu
        260                 265                 270

Ile Gly Ile Ala Gly Lys Gln
        275
```

<210> SEQ ID NO 22
<211> LENGTH: 281
<212> TYPE: PRT
<213> ORGANISM: Neisseria meningitidis

<400> SEQUENCE: 22

```
Met Asn Arg Thr Thr Phe Cys Cys Leu Ser Leu Thr Ala Leu Ile
1               5                   10                  15

Leu Thr Ala Cys Ser Ser Gly Gly Gly Ser Gly Gly Gly Val
            20                  25                  30

Ala Ala Asp Ile Gly Ala Gly Leu Ala Asp Ala Leu Thr Ala Pro Leu
        35                  40                  45

Asp His Lys Asp Lys Gly Leu Lys Ser Leu Thr Leu Glu Asp Ser Ile
    50                  55                  60

Pro Gln Asn Gly Thr Leu Thr Leu Ser Ala Gln Gly Ala Glu Lys Thr
65                  70                  75                  80

Phe Lys Ala Gly Gly Lys Asp Asn Ser Leu Asn Thr Gly Lys Leu Lys
                85                  90                  95

Asn Asp Lys Ile Ser Arg Phe Asp Phe Val Gln Lys Ile Glu Val Asp
            100                 105                 110

Gly Gln Thr Ile Thr Leu Ala Ser Gly Glu Phe Gln Ile Tyr Lys Gln
        115                 120                 125

Asp His Ser Ala Val Val Ala Leu Gln Ile Glu Lys Ile Asn Asn Pro
    130                 135                 140

Asp Lys Thr Asp Ser Leu Ile Asn Gln Arg Ser Phe Leu Val Ser Gly
145                 150                 155                 160

Leu Gly Gly Glu His Thr Ala Phe Asn Gln Leu Pro Gly Gly Lys Ala
                165                 170                 175

Glu Tyr His Gly Lys Ala Phe Ser Ser Asp Asp Pro Asn Gly Arg Leu
            180                 185                 190

His Tyr Thr Ile Asp Phe Thr Asn Lys Gln Gly Tyr Gly Arg Ile Glu
        195                 200                 205

His Leu Lys Thr Pro Glu Gln Asn Val Glu Leu Ala Ser Ala Glu Leu
    210                 215                 220

Lys Ala Asp Glu Lys Ser His Ala Val Ile Leu Gly Asp Thr Arg Tyr
225                 230                 235                 240

Gly Ser Glu Glu Lys Gly Thr Tyr His Leu Ala Leu Phe Gly Asp Arg
                245                 250                 255

Ala Gln Glu Ile Ala Gly Ser Ala Thr Val Lys Ile Gly Glu Lys Val
            260                 265                 270

His Glu Ile Gly Ile Ala Gly Lys Gln
        275                 280
```

<210> SEQ ID NO 23
<211> LENGTH: 279
<212> TYPE: PRT
<213> ORGANISM: Neisseria meningitidis

<400> SEQUENCE: 23

Met Asn Arg Thr Thr Phe Cys Cys Leu Ser Leu Thr Ala Gly Pro Asp
1               5                   10                  15

Ser Asp Arg Leu Gln Gln Arg Gly Gly Gly Gly Val Ala Ala
            20                  25                  30

Asp Ile Gly Thr Gly Leu Ala Asp Ala Leu Thr Ala Pro Leu Asp His
            35                  40                  45

Lys Asp Lys Gly Leu Lys Ser Leu Thr Leu Glu Ala Ser Ile Pro Gln
50                  55                  60

Asn Gly Thr Leu Thr Leu Ser Ala Gln Gly Ala Glu Lys Thr Phe Lys
65                  70                  75                  80

Ala Gly Gly Lys Asp Asn Ser Leu Asn Thr Gly Lys Leu Lys Asn Asp
                85                  90                  95

Lys Ile Ser Arg Phe Asp Phe Val Gln Lys Ile Glu Val Asp Gly Gln
            100                 105                 110

Thr Ile Thr Leu Ala Ser Gly Glu Phe Gln Ile Tyr Lys Gln Asp His
            115                 120                 125

Ser Ala Val Val Ala Leu Arg Ile Glu Lys Ile Asn Asn Pro Asp Lys
            130                 135                 140

Ile Asp Ser Leu Ile Asn Gln Arg Ser Phe Leu Val Ser Asp Leu Gly
145                 150                 155                 160

Gly Glu His Thr Ala Phe Asn Gln Leu Pro Asp Gly Lys Ala Glu Tyr
                165                 170                 175

His Gly Lys Ala Phe Ser Ser Asp Ala Asp Gly Lys Leu Thr Tyr
                180                 185                 190

Thr Ile Asp Phe Ala Ala Lys Gln Gly His Gly Lys Ile Glu His Leu
            195                 200                 205

Lys Thr Pro Glu Gln Asn Val Glu Leu Ala Ser Ala Glu Leu Lys Ala
210                 215                 220

Asp Glu Lys Ser His Ala Val Ile Leu Gly Asp Thr Arg Tyr Gly Gly
225                 230                 235                 240

Glu Glu Lys Gly Thr Tyr Arg Leu Ala Leu Phe Gly Asp Arg Ala Gln
                245                 250                 255

Glu Ile Ala Gly Ser Ala Thr Val Lys Ile Gly Glu Lys Val His Glu
            260                 265                 270

Ile Gly Ile Ala Asp Lys Gln
            275

<210> SEQ ID NO 24
<211> LENGTH: 255
<212> TYPE: PRT
<213> ORGANISM: Neisseria meningitidis

<400> SEQUENCE: 24

Cys Ser Ser Gly Gly Gly Val Ala Ala Asp Ile Gly Ala Gly Leu
1               5                   10                  15

Ala Asp Ala Leu Thr Ala Pro Leu Asp His Lys Asp Lys Gly Leu Gln
            20                  25                  30

Ser Leu Thr Leu Asp Gln Ser Val Arg Lys Asn Glu Lys Leu Lys Leu
            35                  40                  45

Ala Ala Gln Gly Ala Glu Lys Thr Tyr Gly Asn Gly Asp Ser Leu Asn
50                  55                  60

Thr Gly Lys Leu Lys Asn Asp Lys Val Ser Arg Phe Asp Phe Ile Arg
65                  70                  75                  80

Gln Ile Glu Val Asp Gly Gln Leu Ile Thr Leu Glu Ser Gly Glu Phe
            85                  90                  95

```
Gln Val Tyr Lys Gln Ser His Ser Ala Leu Thr Ala Phe Gln Thr Glu
                100                 105                 110

Gln Ile Gln Asp Ser Glu His Ser Gly Lys Met Val Ala Lys Arg Gln
            115                 120                 125

Phe Arg Ile Gly Asp Ile Ala Gly Glu His Thr Ser Phe Asp Lys Leu
130                 135                 140

Pro Glu Gly Gly Arg Ala Thr Tyr Arg Gly Thr Ala Phe Gly Ser Asp
145                 150                 155                 160

Asp Ala Gly Gly Lys Leu Thr Tyr Thr Ile Asp Phe Ala Ala Lys Gln
                165                 170                 175

Gly Asn Gly Lys Ile Glu His Leu Lys Ser Pro Glu Leu Asn Val Asp
            180                 185                 190

Leu Ala Ala Ala Asp Ile Lys Pro Asp Gly Lys Arg His Ala Val Ile
        195                 200                 205

Ser Gly Ser Val Leu Tyr Asn Gln Ala Glu Lys Gly Ser Tyr Ser Leu
    210                 215                 220

Gly Ile Phe Gly Gly Lys Ala Gln Glu Val Ala Gly Ser Ala Glu Val
225                 230                 235                 240

Lys Thr Val Asn Gly Ile Arg His Ile Gly Leu Ala Ala Lys Gln
                245                 250                 255

<210> SEQ ID NO 25
<211> LENGTH: 255
<212> TYPE: PRT
<213> ORGANISM: Neisseria meningitidis

<400> SEQUENCE: 25

Cys Ser Ser Gly Gly Gly Gly Val Ala Ala Asp Ile Gly Ala Gly Leu
1               5                   10                  15

Ala Asp Ala Leu Thr Ala Pro Leu Asp His Lys Asp Lys Gly Leu Gln
                20                  25                  30

Ser Leu Met Leu Asp Gln Ser Val Arg Lys Asn Glu Lys Leu Lys Leu
            35                  40                  45

Ala Ala Gln Gly Ala Glu Lys Thr Tyr Gly Asn Gly Asp Ser Leu Asn
        50                  55                  60

Thr Gly Lys Leu Lys Asn Asp Lys Val Ser Arg Phe Asp Phe Ile Arg
65                  70                  75                  80

Gln Ile Glu Val Asp Gly Lys Leu Ile Thr Leu Glu Ser Gly Glu Phe
                85                  90                  95

Gln Val Tyr Lys Gln Ser His Ser Ala Leu Thr Ala Leu Gln Thr Glu
            100                 105                 110

Gln Val Gln Asp Ser Glu Asp Ser Gly Lys Met Val Ala Lys Arg Gln
        115                 120                 125

Phe Arg Ile Gly Asp Ile Ala Gly Glu His Thr Ser Phe Asp Lys Leu
130                 135                 140

Pro Lys Gly Gly Ser Ala Thr Tyr Arg Gly Thr Ala Phe Gly Ser Asp
145                 150                 155                 160

Asp Ala Gly Gly Lys Leu Thr Tyr Thr Ile Asp Phe Ala Ala Lys Gln
                165                 170                 175

Gly His Gly Lys Ile Glu His Leu Lys Ser Pro Glu Leu Asn Val Glu
            180                 185                 190

Leu Ala Thr Ala Tyr Ile Lys Pro Asp Glu Lys His His Ala Val Ile
        195                 200                 205

Ser Gly Ser Val Leu Tyr Asn Gln Asp Glu Lys Gly Ser Tyr Ser Leu
```

Gly Ile Phe Gly Gly Gln Ala Gln Glu Val Ala Gly Ser Ala Glu Val
225                 230                 235                 240

Glu Thr Ala Asn Gly Ile His His Ile Gly Leu Ala Ala Lys Gln
                245                 250                 255

<210> SEQ ID NO 26
<211> LENGTH: 255
<212> TYPE: PRT
<213> ORGANISM: Neisseria meningitidis

<400> SEQUENCE: 26

Cys Ser Ser Gly Gly Gly Val Ala Ala Asp Ile Gly Ala Gly Leu
1               5                   10                  15

Ala Asp Ala Leu Thr Ala Pro Leu Asp His Lys Asp Lys Ser Leu Gln
                20                  25                  30

Ser Leu Thr Leu Asp Gln Ser Val Arg Lys Asn Glu Lys Leu Lys Leu
            35                  40                  45

Ala Ala Gln Gly Ala Glu Lys Thr Tyr Gly Asn Gly Asp Ser Leu Asn
        50                  55                  60

Thr Gly Lys Leu Lys Asn Asp Lys Val Ser Arg Phe Asp Phe Ile Arg
65                  70                  75                  80

Gln Ile Glu Val Asp Gly Gln Leu Ile Thr Leu Glu Ser Gly Glu Phe
                85                  90                  95

Gln Val Tyr Lys Gln Ser His Ser Ala Leu Thr Ala Leu Gln Thr Glu
                100                 105                 110

Gln Val Gln Asp Ser Glu Asp Ser Gly Lys Met Val Ala Lys Arg Gln
            115                 120                 125

Phe Arg Ile Gly Asp Ile Ala Gly Glu His Thr Ser Phe Asp Lys Leu
130                 135                 140

Pro Lys Gly Gly Ser Ala Thr Tyr Arg Gly Thr Ala Phe Gly Ser Asp
145                 150                 155                 160

Asp Ala Gly Gly Lys Leu Thr Tyr Thr Ile Asp Phe Ala Ala Lys Gln
                165                 170                 175

Gly His Gly Lys Ile Glu His Leu Lys Ser Pro Glu Leu Asn Val Glu
            180                 185                 190

Leu Ala Thr Ala Tyr Ile Lys Pro Asp Glu Lys Arg His Ala Val Ile
        195                 200                 205

Ser Gly Ser Val Leu Tyr Asn Gln Asp Glu Lys Gly Ser Tyr Ser Leu
    210                 215                 220

Gly Ile Phe Gly Gly Gln Ala Gln Glu Val Ala Gly Ser Ala Glu Val
225                 230                 235                 240

Glu Thr Ala Asn Gly Ile His His Ile Gly Leu Ala Ala Lys Gln
                245                 250                 255

<210> SEQ ID NO 27
<211> LENGTH: 255
<212> TYPE: PRT
<213> ORGANISM: Neisseria meningitidis

<400> SEQUENCE: 27

Cys Ser Ser Gly Gly Gly Val Ala Ala Asp Ile Gly Ala Gly Leu
1               5                   10                  15

Ala Asp Ala Leu Thr Ala Pro Leu Asp His Lys Asp Lys Ser Leu Gln
                20                  25                  30

Ser Leu Thr Leu Asp Gln Ser Val Arg Lys Asn Glu Lys Leu Lys Leu

```
            35                  40                  45
Ala Ala Gln Gly Ala Glu Lys Thr Tyr Gly Asn Gly Asp Ser Leu Asn
 50                  55                  60

Thr Gly Lys Leu Lys Asn Asp Lys Val Ser Arg Phe Asp Phe Ile Arg
 65                  70                  75                  80

Gln Ile Glu Val Asp Gly Gln Leu Ile Thr Leu Glu Ser Gly Glu Phe
                 85                  90                  95

Gln Val Tyr Lys Gln Ser His Ser Ala Leu Thr Ala Leu Gln Thr Glu
             100                 105                 110

Gln Glu Gln Asp Pro Glu His Ser Gly Lys Met Val Ala Lys Arg Arg
         115                 120                 125

Phe Lys Ile Gly Asp Ile Ala Gly Glu His Thr Ser Phe Asp Lys Leu
     130                 135                 140

Pro Lys Asp Val Met Ala Thr Tyr Arg Gly Thr Ala Phe Gly Ser Asp
145                 150                 155                 160

Asp Ala Gly Gly Lys Leu Thr Tyr Thr Ile Asp Phe Ala Ala Lys Gln
                 165                 170                 175

Gly His Gly Lys Ile Glu His Leu Lys Ser Pro Glu Leu Asn Val Glu
             180                 185                 190

Leu Ala Thr Ala Tyr Ile Lys Pro Asp Glu Lys His His Ala Val Ile
         195                 200                 205

Ser Gly Ser Val Leu Tyr Asn Gln Asp Glu Lys Gly Tyr Ser Leu
    210                 215                 220

Gly Ile Phe Gly Gly Gln Ala Gln Glu Val Ala Gly Ser Ala Glu Val
225                 230                 235                 240

Glu Thr Ala Asn Gly Ile His His Ile Gly Leu Ala Ala Lys Gln
                 245                 250                 255

<210> SEQ ID NO 28
<211> LENGTH: 260
<212> TYPE: PRT
<213> ORGANISM: Neisseria meningitidis

<400> SEQUENCE: 28

Cys Ser Ser Gly Gly Gly Gly Ser Gly Gly Gly Gly Val Ala Ala Asp
 1               5                  10                  15

Ile Gly Ala Gly Leu Ala Asp Ala Leu Thr Ala Pro Leu Asp His Lys
                 20                  25                  30

Asp Lys Gly Leu Gln Ser Leu Thr Leu Asp Gln Ser Val Arg Lys Asn
             35                  40                  45

Glu Lys Leu Lys Leu Ala Ala Gln Gly Ala Glu Lys Thr Tyr Gly Asn
 50                  55                  60

Gly Asp Ser Leu Asn Thr Gly Lys Leu Lys Asn Asp Lys Val Ser Arg
 65                  70                  75                  80

Phe Asp Phe Ile Arg Gln Ile Glu Val Asp Gly Gln Leu Ile Thr Leu
                 85                  90                  95

Glu Ser Gly Glu Phe Gln Val Tyr Lys Gln Ser His Ser Ala Leu Thr
             100                 105                 110

Ala Leu Gln Thr Glu Gln Val Gln Asp Ser Glu Asp Ser Gly Lys Met
         115                 120                 125

Val Ala Lys Arg Gln Phe Arg Ile Gly Asp Ile Ala Gly Glu His Thr
     130                 135                 140

Ser Phe Asp Lys Leu Pro Lys Gly Gly Ser Ala Thr Tyr Arg Gly Thr
145                 150                 155                 160
```

```
Ala Phe Gly Ser Asp Asp Ala Gly Gly Lys Leu Thr Tyr Thr Ile Asp
                165                 170                 175

Phe Ala Val Lys Gln Gly His Gly Lys Ile Glu His Leu Lys Ser Pro
            180                 185                 190

Glu Leu Asn Val Asp Leu Ala Ala Tyr Ile Lys Pro Asp Lys Lys
        195                 200                 205

Arg His Ala Val Ile Ser Gly Ser Val Leu Tyr Asn Gln Asp Glu Lys
    210                 215                 220

Gly Ser Tyr Ser Leu Gly Ile Phe Gly Gly Gln Ala Gln Glu Val Ala
225                 230                 235                 240

Gly Ser Ala Glu Val Glu Thr Ala Asn Gly Ile His His Ile Gly Leu
                245                 250                 255

Ala Ala Lys Gln
        260

<210> SEQ ID NO 29
<211> LENGTH: 255
<212> TYPE: PRT
<213> ORGANISM: Neisseria meningitidis

<400> SEQUENCE: 29

Cys Ser Ser Gly Gly Gly Val Ala Ala Asp Ile Gly Ala Val Leu
1               5                   10                  15

Ala Asp Ala Leu Thr Ala Pro Leu Asp His Lys Asp Lys Ser Leu Gln
            20                  25                  30

Ser Leu Thr Leu Asp Gln Ser Val Arg Lys Asn Glu Lys Leu Lys Leu
        35                  40                  45

Ala Ala Gln Gly Ala Glu Lys Thr Tyr Gly Asn Gly Asp Ser Leu Asn
    50                  55                  60

Thr Gly Lys Leu Lys Asn Asp Lys Val Ser Arg Phe Asp Phe Ile Arg
65                  70                  75                  80

Gln Ile Glu Val Asp Gly Gln Leu Ile Thr Leu Glu Ser Gly Glu Phe
                85                  90                  95

Gln Val Tyr Lys Gln Ser His Ser Ala Leu Thr Ala Leu Gln Thr Glu
            100                 105                 110

Gln Val Gln Asp Ser Glu His Ser Gly Lys Met Val Ala Lys Arg Gln
        115                 120                 125

Phe Arg Ile Gly Asp Ile Ala Gly Glu His Thr Ser Phe Asp Lys Leu
    130                 135                 140

Pro Glu Gly Gly Arg Ala Thr Tyr Arg Gly Thr Ala Phe Gly Ser Asp
145                 150                 155                 160

Asp Ala Ser Gly Lys Leu Thr Tyr Thr Ile Asp Phe Ala Ala Lys Gln
                165                 170                 175

Gly His Gly Lys Ile Glu His Leu Lys Ser Pro Glu Leu Asn Val Asp
            180                 185                 190

Leu Ala Ala Ser Asp Ile Lys Pro Asp Lys Lys Arg His Ala Val Ile
        195                 200                 205

Ser Gly Ser Val Leu Tyr Asn Gln Ala Glu Lys Gly Ser Tyr Ser Leu
    210                 215                 220

Gly Ile Phe Gly Gly Gln Ala Gln Glu Val Ala Gly Ser Ala Glu Val
225                 230                 235                 240

Glu Thr Ala Asn Gly Ile Arg His Ile Gly Leu Ala Ala Lys Gln
                245                 250                 255

<210> SEQ ID NO 30
```

```
<211> LENGTH: 255
<212> TYPE: PRT
<213> ORGANISM: Neisseria meningitidis

<400> SEQUENCE: 30

Cys Ser Ser Gly Gly Gly Gly Val Ala Ala Asp Ile Gly Ala Gly Leu
1               5                   10                  15

Ala Asp Ala Leu Thr Ala Pro Leu Asp His Lys Asp Lys Ser Leu Gln
            20                  25                  30

Ser Leu Thr Leu Asp Gln Ser Val Arg Lys Asn Glu Lys Leu Lys Leu
        35                  40                  45

Ala Ala Gln Gly Ala Glu Lys Thr Tyr Gly Asn Gly Asp Ser Leu Asn
    50                  55                  60

Thr Gly Lys Leu Lys Asn Asp Lys Val Ser Arg Phe Asp Phe Ile Arg
65                  70                  75                  80

Gln Ile Glu Val Asp Gly Gln Leu Ile Thr Leu Glu Ser Gly Glu Phe
                85                  90                  95

Gln Val Tyr Lys Gln Ser His Ser Ala Leu Thr Ala Leu Gln Thr Glu
            100                 105                 110

Gln Val Gln Asp Ser Glu His Ser Gly Lys Met Val Ala Lys Arg Gln
        115                 120                 125

Phe Arg Ile Gly Asp Ile Ala Gly Glu His Thr Ser Phe Asp Lys Leu
    130                 135                 140

Pro Glu Gly Gly Arg Ala Thr Tyr Arg Gly Thr Ala Phe Gly Ser Asp
145                 150                 155                 160

Asp Ala Ser Gly Lys Leu Thr Tyr Thr Ile Asp Phe Ala Ala Lys Gln
                165                 170                 175

Gly His Gly Lys Ile Glu His Leu Lys Ser Pro Glu Leu Asn Val Asp
            180                 185                 190

Leu Ala Ala Ser Asp Ile Lys Pro Asp Lys Lys Arg His Ala Val Ile
        195                 200                 205

Ser Gly Ser Val Leu Tyr Asn Gln Ala Glu Lys Gly Ser Tyr Ser Leu
    210                 215                 220

Gly Ile Phe Gly Gly Gln Ala Gln Glu Val Ala Gly Ser Ala Glu Val
225                 230                 235                 240

Glu Thr Ala Asn Gly Ile Arg His Ile Gly Leu Ala Ala Lys Gln
                245                 250                 255

<210> SEQ ID NO 31
<211> LENGTH: 255
<212> TYPE: PRT
<213> ORGANISM: Neisseria meningitidis

<400> SEQUENCE: 31

Cys Ser Ser Gly Gly Gly Gly Val Ala Ala Asp Ile Gly Ala Gly Leu
1               5                   10                  15

Ala Asp Ala Leu Thr Ala Pro Leu Asp His Lys Asp Lys Gly Leu Gln
            20                  25                  30

Ser Leu Met Leu Asp Gln Ser Val Arg Lys Asn Glu Lys Leu Lys Leu
        35                  40                  45

Ala Ala Gln Gly Ala Glu Lys Thr Tyr Gly Asn Gly Asp Ser Leu Asn
    50                  55                  60

Thr Gly Lys Leu Lys Asn Asp Lys Val Ser Arg Phe Asp Phe Ile Arg
65                  70                  75                  80

Gln Ile Glu Val Asp Gly Gln Leu Ile Thr Leu Glu Ser Gly Glu Phe
                85                  90                  95
```

Gln Val Tyr Lys Gln Ser His Ser Ala Leu Thr Ala Leu Gln Thr Glu
                100                 105                 110

Gln Val Gln Asp Ser Glu His Ser Gly Lys Met Val Ala Lys Arg Gln
            115                 120                 125

Phe Arg Ile Gly Asp Ile Ala Gly Glu His Thr Ser Phe Asp Lys Leu
        130                 135                 140

Pro Glu Gly Gly Arg Ala Thr Tyr Arg Gly Thr Ala Phe Gly Ser Asp
145                 150                 155                 160

Asp Ala Gly Gly Lys Leu Ile Tyr Thr Ile Asp Phe Ala Ala Lys Gln
                165                 170                 175

Gly His Gly Lys Ile Glu His Leu Lys Ser Pro Glu Leu Asn Val Asp
            180                 185                 190

Leu Ala Ala Ala Tyr Ile Lys Pro Asp Glu Lys His His Ala Val Ile
        195                 200                 205

Ser Gly Ser Val Leu Tyr Asn Gln Ala Glu Lys Gly Ser Tyr Ser Leu
    210                 215                 220

Gly Ile Phe Gly Gly Lys Ala Gln Glu Val Ala Gly Ser Ala Glu Val
225                 230                 235                 240

Lys Thr Val Asn Gly Ile Arg His Ile Gly Leu Ala Ala Lys Gln
                245                 250                 255

<210> SEQ ID NO 32
<211> LENGTH: 255
<212> TYPE: PRT
<213> ORGANISM: Neisseria meningitidis

<400> SEQUENCE: 32

Cys Ser Ser Gly Gly Gly Gly Val Ala Ala Asp Ile Gly Ala Gly Leu
1               5                   10                  15

Ala Asp Ala Leu Thr Ala Pro Leu Asp His Lys Asp Lys Gly Leu Arg
                20                  25                  30

Ser Leu Thr Leu Asp Gln Ser Val Arg Lys Asn Glu Lys Leu Lys Leu
            35                  40                  45

Ala Ala Gln Gly Ala Glu Lys Thr Tyr Gly Asn Gly Asp Ser Leu Asn
        50                  55                  60

Thr Gly Lys Leu Lys Asn Asp Lys Val Ser Arg Phe Asp Phe Ile Arg
65                  70                  75                  80

Gln Ile Glu Val Asp Gly Gln Leu Ile Thr Leu Glu Ser Gly Glu Phe
                85                  90                  95

Gln Val Tyr Lys Gln Ser His Ser Ala Leu Thr Ala Leu Gln Thr Glu
                100                 105                 110

Gln Glu Gln Asp Leu Glu His Ser Gly Lys Met Val Ala Lys Arg Arg
            115                 120                 125

Phe Arg Ile Gly Asp Ile Ala Gly Glu His Thr Ser Phe Asp Lys Leu
        130                 135                 140

Arg Glu Gly Gly Arg Ala Thr Tyr Arg Gly Thr Ala Phe Gly Ser Asp
145                 150                 155                 160

Asp Ala Gly Gly Lys Leu Thr Tyr Thr Ile Asp Phe Ala Ala Lys Gln
                165                 170                 175

Gly Tyr Gly Lys Ile Glu His Leu Lys Ser Pro Glu Leu Asn Val Asp
            180                 185                 190

Leu Ala Ala Ala Asp Ile Lys Pro Asp Glu Lys His His Ala Val Ile
        195                 200                 205

Ser Gly Ser Val Leu Tyr Asn Gln Asp Glu Lys Gly Ser Tyr Ser Leu

```
            210                 215                 220
Gly Ile Phe Gly Gly Glu Ala Gln Glu Val Ala Gly Ser Ala Glu Val
225                 230                 235                 240

Lys Thr Ala Asn Gly Ile His His Ile Gly Leu Ala Ala Lys Gln
                245                 250                 255

<210> SEQ ID NO 33
<211> LENGTH: 254
<212> TYPE: PRT
<213> ORGANISM: Neisseria meningitidis

<400> SEQUENCE: 33

Cys Ser Ser Gly Gly Gly Val Ala Ala Asp Ile Gly Ala Gly Leu
1               5                   10                  15

Ala Asp Ala Leu Thr Ala Pro Leu Asp His Lys Asp Lys Ser Leu Gln
                20                  25                  30

Ser Leu Thr Leu Asp Gln Ser Val Arg Lys Asn Glu Lys Leu Lys Leu
            35                  40                  45

Ala Ala Gln Gly Ala Glu Lys Thr Tyr Gly Asn Gly Asp Ser Leu Asn
        50                  55                  60

Thr Gly Lys Leu Lys Asn Asp Lys Val Ser Arg Phe Asp Phe Ile Arg
65                  70                  75                  80

Gln Ile Glu Val Asp Gly Gln Leu Ile Thr Leu Glu Ser Gly Glu Phe
                85                  90                  95

Gln Ile Tyr Lys Gln Asp His Ser Ala Val Val Ala Leu Gln Ile Glu
            100                 105                 110

Lys Ile Asn Asn Pro Asp Lys Ile Asp Ser Leu Ile Asn Gln Arg Ser
        115                 120                 125

Phe Leu Val Ser Gly Leu Gly Gly Glu His Thr Ala Phe Asn Gln Leu
130                 135                 140

Pro Asp Gly Lys Ala Glu Tyr His Gly Lys Ala Phe Ser Ser Asp Asp
145                 150                 155                 160

Ala Gly Gly Lys Leu Thr Tyr Thr Ile Asp Phe Ala Ala Lys Gln Gly
                165                 170                 175

His Gly Lys Ile Glu His Leu Lys Thr Pro Glu Gln Asn Val Glu Leu
            180                 185                 190

Ala Ala Ala Glu Leu Lys Ala Asp Glu Lys Ser His Ala Val Ile Leu
        195                 200                 205

Gly Asp Thr Arg Tyr Gly Ser Glu Glu Lys Gly Thr Tyr His Leu Ala
210                 215                 220

Leu Phe Gly Asp Arg Ala Gln Glu Ile Ala Gly Ser Ala Thr Val Lys
225                 230                 235                 240

Ile Gly Glu Lys Val His Glu Ile Gly Ile Ala Gly Lys Gln
                245                 250

<210> SEQ ID NO 34
<211> LENGTH: 254
<212> TYPE: PRT
<213> ORGANISM: Neisseria meningitidis

<400> SEQUENCE: 34

Cys Ser Ser Gly Gly Gly Val Ala Ala Asp Ile Gly Ala Gly Leu
1               5                   10                  15

Ala Asp Ala Leu Thr Ala Pro Leu Asp His Lys Asp Lys Ser Leu Gln
                20                  25                  30

Ser Leu Thr Leu Asp Gln Ser Val Arg Lys Asn Glu Lys Leu Lys Leu
```

```
            35                  40                  45
Ala Ala Gln Gly Ala Glu Lys Thr Tyr Gly Asn Gly Asp Ser Leu Asn
         50                  55                  60
Thr Gly Lys Leu Lys Asn Asp Lys Val Ser Arg Phe Asp Phe Ile Arg
 65                  70                  75                  80
Gln Ile Glu Val Asp Gly Gln Leu Ile Thr Leu Glu Ser Gly Glu Phe
                 85                  90                  95
Gln Ile Tyr Lys Gln Asp His Ser Ala Val Val Ala Leu Gln Ile Glu
            100                 105                 110
Lys Ile Asn Asn Pro Asp Lys Ile Asp Ser Leu Ile Asn Gln Arg Ser
        115                 120                 125
Phe Leu Val Ser Gly Leu Gly Gly Glu His Thr Ala Phe Asn Gln Leu
    130                 135                 140
Pro Ser Gly Lys Ala Glu Tyr His Gly Lys Ala Phe Ser Asp Asp
145                 150                 155                 160
Ala Gly Gly Lys Leu Thr Tyr Thr Ile Asp Phe Ala Ala Lys Gln Gly
                165                 170                 175
His Gly Lys Ile Glu His Leu Lys Thr Pro Glu Gln Asn Val Glu Leu
            180                 185                 190
Ala Ser Ala Glu Leu Lys Ala Asp Glu Lys Ser His Ala Val Ile Leu
        195                 200                 205
Gly Asp Thr Arg Tyr Gly Gly Glu Glu Lys Gly Thr Tyr His Leu Ala
    210                 215                 220
Leu Phe Gly Asp Arg Ala Gln Glu Ile Ala Gly Ser Ala Thr Val Lys
225                 230                 235                 240
Ile Arg Glu Lys Val His Glu Ile Gly Ile Ala Gly Lys Gln
                245                 250
```

<210> SEQ ID NO 35
<211> LENGTH: 254
<212> TYPE: PRT
<213> ORGANISM: Neisseria meningitidis

<400> SEQUENCE: 35

```
Cys Ser Ser Gly Gly Gly Val Ala Ala Asp Ile Gly Ala Gly Leu
 1               5                  10                  15
Ala Asp Ala Leu Thr Ala Pro Leu Asp His Lys Asp Lys Gly Leu Gln
             20                  25                  30
Ser Leu Thr Leu Asp Gln Ser Val Arg Lys Asn Glu Lys Leu Lys Leu
         35                  40                  45
Ala Ala Gln Gly Ala Glu Lys Thr Tyr Gly Asn Gly Asp Ser Leu Asn
     50                  55                  60
Thr Gly Lys Leu Lys Asn Asp Lys Val Ser Arg Phe Asp Phe Ile Arg
 65                  70                  75                  80
Gln Ile Glu Val Asp Gly Gln Leu Ile Thr Leu Glu Ser Gly Glu Phe
                 85                  90                  95
Gln Ile Tyr Lys Gln Asp His Ser Ala Val Val Ala Leu Gln Ile Glu
            100                 105                 110
Lys Ile Asn Asn Pro Asp Lys Ile Asp Ser Leu Ile Asn Gln Arg Ser
        115                 120                 125
Phe Leu Val Ser Gly Leu Gly Gly Glu His Thr Ala Phe Asn Gln Leu
    130                 135                 140
Pro Ser Gly Lys Ala Glu Tyr His Gly Lys Ala Phe Ser Asp Asp
145                 150                 155                 160
```

-continued

Pro Asn Gly Arg Leu His Tyr Ser Ile Asp Phe Thr Lys Lys Gln Gly
                165                 170                 175

Tyr Gly Arg Ile Glu His Leu Lys Thr Pro Glu Gln Asn Val Glu Leu
            180                 185                 190

Ala Ser Ala Glu Leu Lys Ala Asp Glu Lys Ser His Ala Val Ile Leu
        195                 200                 205

Gly Asp Thr Arg Tyr Gly Glu Glu Lys Gly Thr Tyr His Leu Ala
    210                 215                 220

Leu Phe Gly Asp Arg Ala Gln Glu Ile Ala Gly Ser Ala Thr Val Lys
225                 230                 235                 240

Ile Arg Glu Lys Val His Glu Ile Gly Ile Ala Gly Lys Gln
                245                 250

<210> SEQ ID NO 36
<211> LENGTH: 254
<212> TYPE: PRT
<213> ORGANISM: Neisseria meningitidis

<400> SEQUENCE: 36

Cys Ser Ser Gly Gly Gly Gly Val Ala Ala Asp Ile Gly Ala Gly Leu
1               5                   10                  15

Ala Asp Ala Leu Thr Ala Pro Leu Asp His Lys Asp Lys Ser Leu Gln
            20                  25                  30

Ser Leu Thr Leu Asp Gln Ser Val Arg Lys Asn Glu Lys Leu Lys Leu
        35                  40                  45

Ala Ala Gln Gly Ala Glu Lys Thr Tyr Gly Asn Gly Asp Ser Leu Asn
    50                  55                  60

Thr Gly Lys Leu Lys Asn Asp Lys Val Ser Arg Phe Asp Phe Ile Arg
65                  70                  75                  80

Gln Ile Glu Val Asp Gly Gln Leu Ile Thr Leu Glu Ser Gly Glu Phe
                85                  90                  95

Gln Ile Tyr Lys Gln Asp His Ser Ala Val Val Ala Leu Gln Ile Glu
            100                 105                 110

Lys Ile Asn Asn Pro Asp Lys Ile Asp Ser Leu Ile Asn Gln Arg Ser
        115                 120                 125

Phe Leu Val Ser Gly Leu Gly Gly Glu His Thr Ala Phe Asn Gln Leu
    130                 135                 140

Pro Ser Gly Lys Ala Glu Tyr His Gly Lys Ala Phe Ser Ser Asp Asp
145                 150                 155                 160

Pro Asn Gly Arg Leu His Tyr Ser Ile Asp Phe Thr Lys Lys Gln Gly
                165                 170                 175

Tyr Gly Arg Ile Glu His Leu Lys Thr Pro Glu Gln Asn Val Glu Leu
            180                 185                 190

Ala Ser Ala Glu Leu Lys Ala Asp Glu Lys Ser His Ala Val Ile Leu
        195                 200                 205

Gly Asp Thr Arg Tyr Gly Glu Glu Lys Gly Thr Tyr His Leu Ala
    210                 215                 220

Leu Phe Gly Asp Arg Ala Gln Glu Ile Ala Gly Ser Ala Thr Val Lys
225                 230                 235                 240

Ile Arg Glu Lys Val His Glu Ile Gly Ile Ala Gly Lys Gln
                245                 250

<210> SEQ ID NO 37
<211> LENGTH: 254
<212> TYPE: PRT
<213> ORGANISM: Neisseria meningitidis

<400> SEQUENCE: 37

```
Cys Ser Ser Gly Gly Gly Val Ala Ala Asp Ile Gly Ala Gly Leu
1               5                   10                  15

Ala Asp Ala Leu Thr Ala Pro Leu Asp His Lys Asp Lys Ser Leu Gln
            20                  25                  30

Ser Leu Thr Leu Asp Gln Ser Val Arg Lys Asn Glu Lys Leu Lys Leu
        35                  40                  45

Ala Ala Gln Gly Ala Glu Lys Thr Tyr Gly Asn Gly Asp Ser Leu Asn
    50                  55                  60

Thr Gly Lys Leu Lys Asn Asp Lys Val Ser Arg Phe Asp Phe Ile Arg
65                  70                  75                  80

Gln Ile Glu Val Asp Gly Gln Leu Ile Thr Leu Glu Ser Gly Glu Phe
                85                  90                  95

Gln Ile Tyr Lys Gln Asp His Ser Ala Val Val Ala Leu Gln Ile Glu
            100                 105                 110

Lys Ile Asn Asn Pro Asp Lys Ile Asp Ser Leu Ile Asn Gln Arg Ser
        115                 120                 125

Phe Leu Val Ser Gly Leu Gly Gly Glu His Thr Ala Phe Asn Gln Leu
    130                 135                 140

Pro Gly Gly Lys Ala Glu Tyr His Gly Lys Ala Phe Ser Ser Asp Asp
145                 150                 155                 160

Pro Asn Gly Arg Leu His Tyr Ser Ile Asp Phe Thr Lys Lys Gln Gly
                165                 170                 175

Tyr Gly Arg Ile Glu His Leu Lys Thr Pro Glu Gln Asn Val Glu Leu
            180                 185                 190

Ala Ser Ala Glu Leu Lys Ala Asp Glu Lys Ser His Ala Val Ile Leu
        195                 200                 205

Gly Asp Thr Arg Tyr Gly Ser Glu Glu Lys Gly Thr Tyr His Leu Ala
    210                 215                 220

Leu Phe Gly Asp Arg Ala Gln Glu Ile Ala Gly Ser Ala Thr Val Lys
225                 230                 235                 240

Ile Arg Glu Lys Val His Glu Ile Gly Ile Ala Gly Lys Gln
                245                 250
```

<210> SEQ ID NO 38
<211> LENGTH: 254
<212> TYPE: PRT
<213> ORGANISM: Neisseria meningitidis

<400> SEQUENCE: 38

```
Cys Ser Ser Gly Gly Gly Val Ala Ala Asp Ile Gly Ala Gly Leu
1               5                   10                  15

Ala Asp Ala Leu Thr Thr Pro Leu Asp His Lys Asp Lys Ser Leu Gln
            20                  25                  30

Ser Leu Thr Leu Asp Gln Ser Val Arg Lys Asn Glu Lys Leu Lys Leu
        35                  40                  45

Ala Ala Gln Gly Ala Glu Lys Thr Tyr Gly Asn Gly Asp Ser Leu Asn
    50                  55                  60

Thr Gly Lys Leu Lys Asn Asp Lys Val Ser Arg Phe Asp Phe Ile Arg
65                  70                  75                  80

Gln Ile Glu Val Asp Gly Gln Thr Ile Thr Leu Ala Ser Gly Glu Phe
                85                  90                  95

Gln Ile Tyr Lys Gln Asn His Ser Ala Val Val Ala Leu Gln Ile Glu
            100                 105                 110
```

```
Lys Ile Asn Asn Pro Asp Lys Ile Asp Ser Leu Ile Asn Gln Arg Ser
            115                 120                 125

Phe Leu Val Ser Gly Leu Gly Gly Glu His Thr Ala Phe Asn Gln Leu
        130                 135                 140

Pro Asp Gly Lys Ala Glu Tyr His Gly Lys Ala Phe Ser Ser Asp Asp
145                 150                 155                 160

Pro Asn Gly Arg Leu His Tyr Ser Ile Asp Phe Thr Lys Lys Gln Gly
                165                 170                 175

Tyr Gly Arg Ile Glu His Leu Lys Thr Pro Glu Gln Asn Val Glu Leu
            180                 185                 190

Ala Ser Ala Glu Leu Lys Ala Asp Glu Lys Ser His Ala Val Ile Leu
        195                 200                 205

Gly Asp Thr Arg Tyr Gly Gly Glu Lys Gly Thr Tyr His Leu Ala
210                 215                 220

Leu Phe Gly Asp Arg Ala Gln Glu Ile Ala Gly Ser Ala Thr Val Lys
225                 230                 235                 240

Ile Arg Glu Lys Val His Glu Ile Gly Ile Ala Gly Lys Gln
            245                 250
```

<210> SEQ ID NO 39
<211> LENGTH: 254
<212> TYPE: PRT
<213> ORGANISM: Neisseria meningitidis

<400> SEQUENCE: 39

```
Cys Ser Ser Gly Gly Gly Gly Val Ala Ala Asp Ile Gly Ala Gly Leu
1               5                   10                  15

Ala Asp Ala Leu Thr Ala Pro Leu Asp His Lys Asp Lys Ser Leu Gln
            20                  25                  30

Ser Leu Thr Leu Asp Gln Ser Val Arg Lys Asn Glu Lys Leu Lys Leu
        35                  40                  45

Ala Ala Gln Gly Ala Glu Lys Thr Tyr Gly Asn Gly Asp Ser Leu Asn
    50                  55                  60

Thr Gly Lys Leu Lys Asn Asp Lys Val Ser Arg Phe Asp Phe Ile Arg
65                  70                  75                  80

Gln Ile Glu Val Asp Gly Gln Thr Ile Thr Leu Ala Ser Gly Glu Phe
                85                  90                  95

Gln Ile Tyr Lys Gln Asn His Ser Ala Val Val Ala Leu Gln Ile Glu
            100                 105                 110

Lys Ile Asn Asn Pro Asp Lys Ile Asp Ser Leu Ile Asn Gln Arg Ser
        115                 120                 125

Phe Leu Val Ser Gly Leu Gly Gly Glu His Thr Ala Phe Asn Gln Leu
    130                 135                 140

Pro Asp Gly Lys Ala Glu Tyr His Gly Lys Ala Phe Ser Ser Asp Asp
145                 150                 155                 160

Pro Asn Gly Arg Leu His Tyr Ser Ile Asp Phe Thr Lys Lys Gln Gly
                165                 170                 175

Tyr Gly Arg Ile Glu His Leu Lys Thr Pro Glu Gln Asn Val Glu Leu
            180                 185                 190

Ala Ser Ala Glu Leu Lys Ala Asp Glu Lys Ser His Ala Val Ile Leu
        195                 200                 205

Gly Asp Thr Arg Tyr Gly Gly Glu Lys Gly Thr Tyr His Leu Ala
210                 215                 220

Leu Phe Gly Asp Arg Ala Gln Glu Ile Ala Gly Ser Ala Thr Val Lys
```

```
                225                 230                 235                 240
Ile Arg Glu Lys Val His Glu Ile Gly Ile Ala Gly Lys Gln
                245                 250

<210> SEQ ID NO 40
<211> LENGTH: 254
<212> TYPE: PRT
<213> ORGANISM: Neisseria meningitidis

<400> SEQUENCE: 40

Cys Ser Ser Gly Gly Gly Val Ala Ala Asp Ile Gly Ala Gly Leu
1               5                   10                  15

Ala Asp Ala Leu Thr Ala Pro Leu Asp His Lys Asp Lys Gly Leu Gln
                20                  25                  30

Ser Leu Met Leu Asp Gln Ser Val Arg Lys Asn Glu Lys Leu Lys Leu
            35                  40                  45

Ala Ala Gln Gly Ala Glu Lys Thr Tyr Gly Asn Gly Asp Ser Leu Asn
    50                  55                  60

Thr Gly Lys Leu Lys Asn Asp Lys Val Ser Arg Phe Asp Phe Ile Arg
65                  70                  75                  80

Gln Ile Glu Val Asp Gly Gln Thr Ile Thr Leu Ala Ser Gly Glu Phe
                85                  90                  95

Gln Ile Tyr Lys Gln Asn His Ser Ala Val Val Ala Leu Gln Ile Glu
            100                 105                 110

Lys Ile Asn Asn Pro Asp Lys Ile Asp Ser Leu Ile Asn Gln Arg Ser
        115                 120                 125

Phe Leu Val Ser Gly Leu Gly Gly Glu His Thr Ala Phe Asn Gln Leu
    130                 135                 140

Pro Asp Gly Lys Ala Glu Tyr His Gly Lys Ala Phe Ser Ser Asp Asp
145                 150                 155                 160

Pro Asn Gly Arg Leu His Tyr Ser Ile Asp Phe Thr Lys Lys Gln Gly
                165                 170                 175

Tyr Gly Arg Ile Glu His Leu Lys Thr Pro Glu Gln Asn Val Glu Leu
            180                 185                 190

Ala Ser Ala Glu Leu Lys Ala Asp Glu Lys Ser His Ala Val Ile Leu
        195                 200                 205

Gly Asp Thr Arg Tyr Gly Gly Glu Glu Lys Gly Thr Tyr His Leu Ala
    210                 215                 220

Leu Phe Gly Asp Arg Ala Gln Glu Ile Ala Gly Ser Ala Thr Val Lys
225                 230                 235                 240

Ile Arg Glu Lys Val His Glu Ile Gly Ile Ala Gly Lys Gln
                245                 250

<210> SEQ ID NO 41
<211> LENGTH: 262
<212> TYPE: PRT
<213> ORGANISM: Neisseria meningitidis

<400> SEQUENCE: 41

Cys Ser Ser Gly Gly Gly Gly Ser Gly Gly Gly Gly Val Ala Ala Asp
1               5                   10                  15

Ile Gly Thr Gly Leu Ala Asp Ala Leu Thr Ala Pro Leu Asp His Lys
                20                  25                  30

Asp Lys Gly Leu Lys Ser Leu Thr Leu Glu Asp Ser Ile Pro Gln Asn
            35                  40                  45

Gly Thr Leu Thr Leu Ser Ala Gln Gly Ala Glu Lys Thr Phe Lys Ala
```

-continued

```
                50                  55                  60
Gly Asp Lys Asp Asn Ser Leu Asn Thr Gly Lys Leu Lys Asn Asp Lys
 65                  70                  75                  80

Ile Ser Arg Phe Asp Phe Val Gln Lys Ile Glu Val Asp Gly Gln Thr
                 85                  90                  95

Ile Thr Leu Ala Ser Gly Glu Phe Gln Ile Tyr Lys Gln Asn His Ser
            100                 105                 110

Ala Val Val Ala Leu Gln Ile Glu Lys Ile Asn Asn Pro Asp Lys Thr
        115                 120                 125

Asp Ser Leu Ile Asn Gln Arg Ser Phe Leu Val Ser Gly Leu Gly Gly
    130                 135                 140

Glu His Thr Ala Phe Asn Gln Leu Pro Gly Gly Lys Ala Glu Tyr His
145                 150                 155                 160

Gly Lys Ala Phe Ser Ser Asp Asp Pro Asn Gly Arg Leu His Tyr Ser
                165                 170                 175

Ile Asp Phe Thr Lys Lys Gln Gly Tyr Gly Arg Ile Glu His Leu Lys
            180                 185                 190

Thr Leu Glu Gln Asn Val Glu Leu Ala Ala Ala Glu Leu Lys Ala Asp
        195                 200                 205

Glu Lys Ser His Ala Val Ile Leu Gly Asp Thr Arg Tyr Gly Ser Glu
    210                 215                 220

Glu Lys Gly Thr Tyr His Leu Ala Leu Phe Gly Asp Arg Ala Gln Glu
225                 230                 235                 240

Ile Ala Gly Ser Ala Thr Val Lys Ile Gly Glu Lys Val His Glu Ile
                245                 250                 255

Gly Ile Ala Gly Lys Gln
                260
```

<210> SEQ ID NO 42
<211> LENGTH: 262
<212> TYPE: PRT
<213> ORGANISM: Neisseria meningitidis

<400> SEQUENCE: 42

```
Cys Ser Ser Gly Gly Gly Gly Ser Gly Gly Gly Gly Val Ala Ala Asp
  1               5                  10                  15

Ile Gly Thr Gly Leu Ala Asp Ala Leu Thr Ala Pro Leu Asp His Lys
             20                  25                  30

Asp Lys Gly Leu Lys Ser Leu Thr Leu Glu Asp Ser Ile Pro Gln Asn
         35                  40                  45

Gly Thr Leu Thr Leu Ser Ala Gln Gly Ala Glu Lys Thr Phe Lys Ala
      50                  55                  60

Gly Asp Lys Asp Asn Ser Leu Asn Thr Gly Lys Leu Lys Asn Asp Lys
 65                  70                  75                  80

Ile Ser Arg Phe Asp Phe Val Gln Lys Ile Glu Val Asp Gly Gln Thr
                 85                  90                  95

Ile Thr Leu Ala Ser Gly Glu Phe Gln Ile Tyr Lys Gln Asp His Ser
            100                 105                 110

Ala Val Val Ala Leu Gln Ile Glu Lys Ile Asn Asn Pro Asp Lys Ile
        115                 120                 125

Asp Ser Leu Ile Asn Gln Arg Ser Phe Leu Val Ser Gly Leu Gly Gly
    130                 135                 140

Glu His Thr Ala Phe Asn Gln Leu Pro Gly Gly Lys Ala Glu Tyr His
145                 150                 155                 160
```

Gly Lys Ala Phe Ser Ser Asp Asp Ala Gly Lys Leu Thr Tyr Thr
            165                 170                 175

Ile Asp Phe Ala Ala Lys Gln Gly His Gly Lys Ile Glu His Leu Lys
            180                 185                 190

Thr Pro Glu Gln Asn Val Glu Leu Ala Ala Glu Leu Lys Ala Asp
        195                 200                 205

Glu Lys Ser His Ala Val Ile Leu Gly Asp Thr Arg Tyr Gly Ser Glu
    210                 215                 220

Glu Lys Gly Thr Tyr His Leu Ala Leu Phe Gly Asp Arg Ala Gln Glu
225                 230                 235                 240

Ile Ala Gly Ser Ala Thr Val Lys Ile Gly Glu Lys Val His Glu Ile
            245                 250                 255

Ser Ile Ala Gly Lys Gln
            260

<210> SEQ ID NO 43
<211> LENGTH: 262
<212> TYPE: PRT
<213> ORGANISM: Neisseria meningitidis

<400> SEQUENCE: 43

Cys Ser Ser Gly Gly Gly Gly Ser Gly Ser Gly Gly Val Ala Ala Asp
1               5                   10                  15

Ile Gly Thr Gly Leu Ala Asp Ala Leu Thr Thr Pro Leu Asp His Lys
            20                  25                  30

Asp Lys Gly Leu Lys Ser Leu Thr Leu Glu Asp Ser Ile Pro Gln Asn
        35                  40                  45

Gly Thr Leu Thr Leu Ser Ala Gln Gly Ala Glu Lys Thr Phe Lys Ala
    50                  55                  60

Gly Asp Lys Asp Asn Ser Leu Asn Thr Gly Lys Leu Lys Asn Asp Lys
65                  70                  75                  80

Ile Ser Arg Phe Asp Phe Val Gln Lys Ile Glu Val Asp Gly Gln Thr
            85                  90                  95

Ile Thr Leu Ala Ser Gly Glu Phe Gln Ile Tyr Lys Gln Asp His Ser
            100                 105                 110

Ala Val Val Ala Leu Gln Ile Glu Lys Ile Asn Asn Pro Asp Lys Ile
        115                 120                 125

Asp Ser Leu Ile Asn Gln Arg Ser Phe Leu Val Ser Gly Leu Gly Gly
    130                 135                 140

Glu His Thr Ala Phe Asn Gln Leu Pro Gly Gly Lys Ala Glu Tyr His
145                 150                 155                 160

Gly Lys Ala Phe Ser Ser Asp Asp Ala Gly Lys Leu Thr Tyr Thr
            165                 170                 175

Ile Asp Phe Ala Ala Lys Gln Gly His Gly Lys Ile Glu His Leu Lys
            180                 185                 190

Thr Pro Glu Gln Asn Val Glu Leu Ala Ala Glu Leu Lys Ala Asp
        195                 200                 205

Glu Lys Ser His Ala Val Ile Leu Gly Asp Thr Arg Tyr Gly Ser Glu
    210                 215                 220

Glu Lys Gly Thr Tyr His Leu Ala Leu Phe Gly Asp Arg Ala Gln Glu
225                 230                 235                 240

Ile Ala Gly Ser Ala Thr Val Lys Ile Gly Glu Lys Val His Glu Ile
            245                 250                 255

Gly Ile Ala Gly Lys Gln
            260

<210> SEQ ID NO 44
<211> LENGTH: 260
<212> TYPE: PRT
<213> ORGANISM: Neisseria meningitidis

<400> SEQUENCE: 44

Cys Ser Ser Gly Gly Gly Ser Gly Gly Ile Ala Ala Asp Ile Gly
1               5                   10                  15

Thr Gly Leu Ala Asp Ala Leu Thr Ala Pro Leu Asp His Lys Asp Lys
            20                  25                  30

Gly Leu Lys Ser Leu Thr Leu Glu Asp Ser Ile Pro Gln Asn Gly Thr
        35                  40                  45

Leu Thr Leu Ser Ala Gln Gly Ala Glu Lys Thr Phe Lys Ala Gly Asp
    50                  55                  60

Lys Asp Asn Ser Leu Asn Thr Gly Lys Leu Lys Asn Asp Lys Ile Ser
65                  70                  75                  80

Arg Phe Asp Phe Val Gln Lys Ile Glu Val Asp Gly Gln Thr Ile Thr
                85                  90                  95

Leu Ala Ser Gly Glu Phe Gln Ile Tyr Lys Gln Asp His Ser Ala Val
            100                 105                 110

Val Ala Leu Gln Ile Glu Lys Ile Asn Asn Pro Asp Lys Ile Asp Ser
        115                 120                 125

Leu Ile Asn Gln Arg Ser Phe Leu Val Ser Gly Leu Gly Gly Glu His
    130                 135                 140

Thr Ala Phe Asn Gln Leu Pro Gly Gly Lys Ala Glu Tyr His Gly Lys
145                 150                 155                 160

Ala Phe Ser Ser Asp Ala Gly Gly Lys Leu Thr Tyr Thr Ile Asp
                165                 170                 175

Phe Ala Ala Lys Gln Gly His Gly Lys Ile Glu His Leu Lys Thr Pro
            180                 185                 190

Glu Gln Asn Val Glu Leu Ala Ala Ala Glu Leu Lys Ala Asp Glu Lys
        195                 200                 205

Ser His Ala Val Ile Leu Gly Asp Thr Arg Tyr Gly Ser Glu Glu Lys
    210                 215                 220

Gly Thr Tyr His Leu Ala Leu Phe Gly Asp Arg Ala Gln Glu Ile Ala
225                 230                 235                 240

Gly Ser Ala Thr Val Lys Ile Gly Glu Lys Val His Glu Ile Gly Ile
                245                 250                 255

Ala Gly Lys Gln
            260

<210> SEQ ID NO 45
<211> LENGTH: 262
<212> TYPE: PRT
<213> ORGANISM: Neisseria meningitidis

<400> SEQUENCE: 45

Cys Ser Ser Gly Gly Gly Ser Gly Gly Gly Val Ala Asp
1               5                   10                  15

Ile Gly Ala Gly Leu Ala Asp Ala Leu Thr Ala Pro Leu Asp His Lys
            20                  25                  30

Asp Lys Gly Leu Lys Ser Leu Thr Leu Glu Asp Ser Ile Pro Gln Asn
        35                  40                  45

Gly Thr Leu Thr Leu Ser Ala Gln Gly Ala Glu Lys Thr Phe Lys Ala
    50                  55                  60

```
Gly Gly Lys Asp Asn Ser Leu Asn Thr Gly Lys Leu Lys Asn Asp Lys
65                  70                  75                  80

Ile Ser Arg Phe Asp Phe Val Gln Lys Ile Glu Val Asp Gly Gln Thr
            85                  90                  95

Ile Thr Leu Ala Ser Gly Glu Phe Gln Ile Tyr Lys Gln Asp His Ser
        100                 105                 110

Ala Val Val Ala Leu Gln Ile Glu Lys Ile Asn Asn Pro Asp Lys Thr
    115                 120                 125

Asp Ser Leu Ile Asn Gln Arg Ser Phe Leu Val Ser Gly Leu Gly Gly
130                 135                 140

Glu His Thr Ala Phe Asn Gln Leu Pro Gly Gly Lys Ala Glu Tyr His
145                 150                 155                 160

Gly Lys Ala Phe Ser Ser Asp Asp Pro Asn Gly Arg Leu His Tyr Thr
                165                 170                 175

Ile Asp Phe Thr Asn Lys Gln Gly Tyr Gly Arg Ile Glu His Leu Lys
            180                 185                 190

Thr Pro Glu Gln Asn Val Glu Leu Ala Ser Ala Glu Leu Lys Ala Asp
        195                 200                 205

Glu Lys Ser His Ala Val Ile Leu Gly Asp Thr Arg Tyr Gly Ser Glu
210                 215                 220

Glu Lys Gly Thr Tyr His Leu Ala Leu Phe Gly Asp Arg Ala Gln Glu
225                 230                 235                 240

Ile Ala Gly Ser Ala Thr Val Lys Ile Gly Glu Lys Val His Glu Ile
                245                 250                 255

Gly Ile Ala Gly Lys Gln
            260

<210> SEQ ID NO 46
<211> LENGTH: 12
<212> TYPE: PRT
<213> ORGANISM: Neisseria gonorrhoeae

<400> SEQUENCE: 46

Gly Pro Asp Ser Asp Arg Leu Gln Gln Arg Arg Gly
1               5                   10

<210> SEQ ID NO 47
<211> LENGTH: 31
<212> TYPE: DNA
<213> ORGANISM: Artificial sequence
<220> FEATURE:
<223> OTHER INFORMATION: Synthetic nucleic acid sequence

<400> SEQUENCE: 47
cgcggatccc atatggtcgc cgccgacatc g                              31

<210> SEQ ID NO 48
<211> LENGTH: 27
<212> TYPE: DNA
<213> ORGANISM: Artificial sequence
<220> FEATURE:
<223> OTHER INFORMATION: Synthetic nucleic acid sequence

<400> SEQUENCE: 48
cccgctcgag ttgcttggcg gcaaggc                                   27

<210> SEQ ID NO 49
<211> LENGTH: 65
<212> TYPE: DNA
```

<213> ORGANISM: Artificial sequence
<220> FEATURE:
<223> OTHER INFORMATION: Synthetic nucleic acid sequence

<400> SEQUENCE: 49

```
cgcggatccc atatgggccc tgattctgac cgcctgcagc agcggagggt cgccgccgac    60
atcgg                                                                65
```

<210> SEQ ID NO 50
<211> LENGTH: 274
<212> TYPE: PRT
<213> ORGANISM: Neisseria meningitidis

<400> SEQUENCE: 50

```
Met Asn Arg Thr Ala Phe Cys Cys Leu Ser Leu Thr Ala Ala Leu Ile
1               5                   10                  15

Leu Thr Ala Cys Ser Ser Gly Gly Gly Gly Val Ala Ala Asp Ile Gly
            20                  25                  30

Ala Gly Leu Ala Asp Ala Leu Thr Ala Pro Leu Asp His Lys Asp Lys
        35                  40                  45

Ser Leu Gln Ser Leu Thr Leu Asp Gln Ser Val Arg Lys Asn Glu Lys
    50                  55                  60

Leu Lys Leu Ala Ala Gln Gly Ala Glu Lys Thr Tyr Gly Asn Gly Asp
65                  70                  75                  80

Ser Leu Asn Thr Gly Lys Leu Lys Asn Asp Lys Val Ser Arg Phe Asp
                85                  90                  95

Phe Ile Arg Gln Ile Glu Val Asp Gly Gln Leu Ile Thr Leu Glu Ser
            100                 105                 110

Gly Glu Phe Gln Val Tyr Lys Gln Ser His Ser Ala Leu Thr Ala Leu
        115                 120                 125

Gln Thr Glu Gln Val Gln Asp Ser Glu His Ser Gly Lys Met Val Ala
    130                 135                 140

Lys Arg Gln Phe Arg Ile Gly Asp Ile Ala Gly Glu His Thr Ser Phe
145                 150                 155                 160

Asp Lys Leu Pro Glu Gly Gly Arg Ala Thr Tyr Arg Gly Thr Ala Phe
                165                 170                 175

Gly Ser Asp Asp Ala Ser Gly Lys Leu Thr Tyr Thr Ile Asp Phe Ala
            180                 185                 190

Ala Lys Gln Gly His Gly Lys Ile Glu His Leu Lys Ser Leu Glu Leu
        195                 200                 205

Asn Val Asp Leu Ala Ala Ser Asp Ile Lys Pro Asp Lys Lys Arg His
    210                 215                 220

Ala Val Ile Ser Gly Ser Val Leu Tyr Asn Gln Ala Glu Lys Gly Ser
225                 230                 235                 240

Tyr Ser Leu Gly Ile Phe Gly Gly Gln Ala Gln Glu Val Ala Gly Ser
                245                 250                 255

Ala Glu Val Glu Thr Ala Asn Gly Ile Arg His Ile Gly Leu Ala Ala
            260                 265                 270

Lys Gln
```

<210> SEQ ID NO 51
<211> LENGTH: 274
<212> TYPE: PRT
<213> ORGANISM: Neisseria meningitidis

<400> SEQUENCE: 51

```
Met Asn Arg Thr Ala Phe Cys Cys Phe Ser Leu Thr Ala Ala Leu Ile
1               5                   10                  15

Leu Thr Ala Cys Ser Ser Gly Gly Gly Val Ala Ala Asp Ile Gly
            20                  25                  30

Ala Gly Leu Ala Asp Ala Leu Thr Ala Pro Leu Asp His Lys Asp Lys
        35                  40                  45

Ser Leu Gln Ser Leu Thr Leu Asp Gln Ser Val Arg Lys Asn Glu Lys
50                  55                  60

Leu Lys Leu Ala Ala Gln Gly Ala Glu Lys Thr Tyr Gly Asn Gly Asp
65                  70                  75                  80

Ser Leu Asn Thr Gly Lys Leu Lys Asn Asp Lys Val Ser Arg Phe Asp
                85                  90                  95

Phe Ile Arg Gln Ile Glu Val Asp Gly Gln Leu Ile Thr Leu Glu Ser
            100                 105                 110

Gly Glu Phe Gln Ile Tyr Lys Gln Asp His Ser Ala Leu Thr Ala Leu
                115                 120                 125

Gln Thr Glu Gln Glu Gln Asp Pro Glu His Ser Gly Lys Met Val Ala
        130                 135                 140

Lys Arg Arg Phe Lys Ile Gly Asp Ile Ala Gly Glu His Thr Ser Phe
145                 150                 155                 160

Asp Lys Leu Pro Lys Asp Val Met Ala Thr Tyr Arg Gly Thr Ala Phe
                165                 170                 175

Gly Ser Asp Asp Ala Gly Gly Lys Leu Thr Tyr Thr Ile Asp Phe Ala
            180                 185                 190

Ala Lys Gln Gly His Gly Lys Ile Glu His Leu Lys Ser Pro Glu Leu
        195                 200                 205

Asn Val Glu Leu Ala Thr Ala Tyr Ile Lys Pro Asp Glu Lys His His
    210                 215                 220

Ala Val Ile Ser Gly Ser Val Leu Tyr Asn Gln Asp Glu Lys Gly Ser
225                 230                 235                 240

Tyr Ser Leu Gly Ile Phe Gly Gly Gln Ala Gln Glu Val Ala Gly Ser
                245                 250                 255

Ala Glu Val Glu Thr Ala Asn Gly Ile His His Ile Gly Leu Ala Ala
        260                 265                 270

Lys Gln
```

<210> SEQ ID NO 52
<211> LENGTH: 274
<212> TYPE: PRT
<213> ORGANISM: Neisseria meningitidis

<400> SEQUENCE: 52

```
Met Asn Arg Thr Ala Phe Cys Cys Leu Ser Leu Thr Thr Ala Leu Ile
1               5                   10                  15

Leu Thr Ala Cys Ser Ser Gly Gly Gly Val Ala Ala Asp Ile Gly
            20                  25                  30

Ala Gly Leu Ala Asp Ala Leu Thr Ala Pro Leu Asp His Lys Asp Lys
        35                  40                  45

Gly Leu Gln Ser Leu Met Leu Asp Gln Ser Val Arg Lys Asn Glu Lys
50                  55                  60

Leu Lys Leu Ala Ala Gln Gly Ala Glu Lys Thr Tyr Gly Asn Gly Asp
65                  70                  75                  80

Ser Leu Asn Thr Gly Lys Leu Lys Asn Asp Lys Val Ser Arg Phe Asp
                85                  90                  95
```

```
Phe Ile Arg Gln Ile Glu Val Asp Gly Gln Leu Ile Thr Leu Glu Ser
            100                 105                 110

Gly Glu Phe Gln Val Tyr Lys Gln Ser His Ser Ala Leu Thr Ala Leu
        115                 120                 125

Gln Thr Glu Gln Val Gln Asp Ser Glu Asp Ser Gly Lys Met Val Ala
    130                 135                 140

Lys Arg Gln Phe Arg Ile Gly Asp Ile Ala Gly Glu His Thr Ser Phe
145                 150                 155                 160

Asp Lys Leu Pro Lys Asp Val Met Ala Thr Tyr Arg Gly Thr Ala Phe
                165                 170                 175

Gly Ser Asp Asp Ala Gly Gly Lys Leu Thr Tyr Thr Ile Asp Phe Ala
            180                 185                 190

Ala Lys Gln Gly His Gly Lys Ile Glu His Leu Lys Ser Pro Glu Leu
        195                 200                 205

Asn Val Glu Leu Ala Ala Ala Tyr Ile Lys Pro Asp Glu Lys His His
    210                 215                 220

Ala Val Ile Ser Gly Ser Val Leu Tyr Asn Gln Asp Glu Lys Gly Ser
225                 230                 235                 240

Tyr Ser Leu Gly Ile Phe Gly Gly Gln Ala Gln Glu Val Ala Gly Ser
                245                 250                 255

Ala Glu Val Glu Thr Ala Asn Gly Ile Gln His Ile Gly Leu Ala Ala
            260                 265                 270

Lys Gln

<210> SEQ ID NO 53
<211> LENGTH: 274
<212> TYPE: PRT
<213> ORGANISM: Neisseria meningitidis

<400> SEQUENCE: 53

Met Asn Arg Thr Thr Phe Cys Cys Leu Ser Leu Thr Ala Ala Leu Ile
1               5                   10                  15

Leu Thr Ala Cys Ser Ser Gly Gly Gly Val Ala Ala Asp Ile Gly
            20                  25                  30

Ala Gly Leu Ala Asp Ala Leu Thr Ala Pro Leu Asp His Lys Asp Lys
        35                  40                  45

Gly Leu Gln Ser Leu Thr Leu Asp Gln Ser Val Arg Lys Asn Glu Lys
    50                  55                  60

Leu Lys Leu Ala Ala Gln Gly Ala Glu Lys Thr Tyr Gly Asn Gly Asp
65                  70                  75                  80

Ser Leu Asn Thr Gly Lys Leu Lys Asn Asp Lys Val Ser Arg Phe Asp
                85                  90                  95

Phe Ile Arg Gln Ile Glu Val Asn Gly Gln Leu Ile Thr Leu Glu Ser
            100                 105                 110

Gly Glu Phe Gln Val Tyr Lys Gln Ser His Ser Ala Leu Thr Ala Leu
        115                 120                 125

Gln Thr Glu Gln Val Gln Asp Ser Glu His Ser Arg Lys Met Val Ala
    130                 135                 140

Lys Arg Gln Phe Arg Ile Gly Asp Ile Ala Gly Glu His Thr Ser Phe
145                 150                 155                 160

Asp Lys Leu Pro Lys Gly Asp Ser Ala Thr Tyr Arg Gly Thr Ala Phe
                165                 170                 175

Gly Ser Asp Asp Ala Gly Gly Lys Leu Thr Tyr Thr Ile Asp Phe Ala
            180                 185                 190
```

```
Ala Lys Gln Gly Tyr Gly Lys Ile Glu His Leu Lys Ser Pro Glu Leu
            195                 200                 205

Asn Val Asp Leu Ala Ala Ala Tyr Ile Lys Pro Asp Glu Lys His His
210                 215                 220

Ala Val Ile Ser Gly Ser Val Leu Tyr Asn Gln Asp Glu Lys Gly Ser
225                 230                 235                 240

Tyr Ser Leu Gly Ile Phe Gly Gly Gln Ala Gln Glu Val Ala Gly Ser
            245                 250                 255

Ala Glu Val Lys Thr Ala Asn Gly Ile Arg His Ile Gly Leu Ala Ala
            260                 265                 270

Lys Gln

<210> SEQ ID NO 54
<211> LENGTH: 274
<212> TYPE: PRT
<213> ORGANISM: Neisseria meningitidis

<400> SEQUENCE: 54

Met Asn Arg Thr Ala Phe Cys Cys Leu Ser Leu Thr Ala Ala Leu Ile
1               5                   10                  15

Leu Thr Ala Cys Ser Ser Gly Gly Gly Val Ala Ala Asp Ile Gly
            20                  25                  30

Ala Gly Leu Ala Asp Ala Leu Thr Ala Pro Leu Asp His Lys Asp Lys
            35                  40                  45

Ser Leu Gln Ser Leu Thr Leu Asp Gln Ser Val Arg Lys Asn Glu Lys
        50                  55                  60

Leu Lys Leu Ala Ala Gln Gly Ala Glu Lys Thr Tyr Gly Asn Gly Asp
65                  70                  75                  80

Ser Leu Asn Thr Gly Lys Leu Lys Asn Asp Lys Val Ser Arg Phe Asp
                85                  90                  95

Phe Ile Arg Gln Ile Glu Val Asp Gly Gln Leu Ile Thr Leu Glu Ser
            100                 105                 110

Gly Glu Phe Gln Val Tyr Lys Gln Ser His Ser Ala Leu Thr Ala Phe
        115                 120                 125

Gln Thr Glu Gln Ile Gln Asp Ser Glu His Ser Gly Lys Met Val Ala
    130                 135                 140

Lys Arg Gln Phe Arg Ile Gly Asp Ile Ala Gly Glu His Thr Ser Phe
145                 150                 155                 160

Asp Lys Leu Pro Glu Gly Gly Arg Ala Thr Tyr Arg Gly Thr Ala Phe
                165                 170                 175

Gly Ser Asp Asp Ala Gly Gly Lys Leu Thr Tyr Thr Ile Asp Phe Ala
            180                 185                 190

Ala Lys Gln Gly Asn Gly Lys Ile Glu His Leu Lys Ser Pro Glu Leu
            195                 200                 205

Asn Val Asp Leu Ala Ala Ala Asp Ile Lys Pro Asp Gly Lys Arg His
210                 215                 220

Ala Val Ile Ser Gly Ser Val Leu Tyr Asn Gln Ala Glu Lys Gly Ser
225                 230                 235                 240

Tyr Ser Leu Gly Ile Phe Gly Gly Lys Ala Gln Glu Val Ala Gly Ser
            245                 250                 255

Ala Glu Val Lys Thr Val Asn Gly Ile Arg His Ile Gly Leu Ala Ala
            260                 265                 270

Lys Gln
```

<210> SEQ ID NO 55
<211> LENGTH: 274
<212> TYPE: PRT
<213> ORGANISM: Neisseria meningitidis

<400> SEQUENCE: 55

Met Asn Arg Thr Ala Phe Cys Cys Leu Ser Leu Thr Thr Ala Leu Ile
1               5                   10                  15

Leu Thr Ala Cys Ser Ser Gly Gly Gly Val Thr Ala Asp Ile Gly
            20                  25                  30

Thr Gly Leu Ala Asp Ala Leu Thr Ala Pro Leu Asp His Lys Asp Lys
        35                  40                  45

Gly Leu Lys Ser Leu Thr Leu Glu Asp Ser Ile Ser Gln Asn Gly Thr
    50                  55                  60

Leu Thr Leu Ser Ala Gln Gly Ala Glu Lys Thr Tyr Gly Asn Gly Asp
65                  70                  75                  80

Ser Leu Asn Thr Gly Lys Leu Lys Asn Asp Lys Val Ser Arg Phe Asp
                85                  90                  95

Phe Ile Arg Gln Ile Glu Val Asp Gly Lys Leu Ile Thr Leu Glu Ser
            100                 105                 110

Gly Glu Phe Gln Val Tyr Lys Gln Ser His Ser Ala Leu Thr Ala Leu
        115                 120                 125

Gln Thr Glu Gln Val Gln Asp Ser Glu Asp Ser Gly Lys Met Val Ala
    130                 135                 140

Lys Arg Gln Phe Arg Ile Gly Asp Ile Ala Gly Glu His Thr Ser Phe
145                 150                 155                 160

Asp Lys Leu Pro Lys Gly Gly Ser Ala Thr Tyr Arg Gly Thr Ala Phe
                165                 170                 175

Gly Ser Asp Asp Ala Gly Gly Lys Leu Thr Tyr Thr Ile Asp Phe Ala
            180                 185                 190

Ala Lys Gln Gly His Gly Lys Ile Glu His Leu Lys Ser Pro Glu Leu
        195                 200                 205

Asn Val Glu Leu Ala Thr Ala Tyr Ile Lys Pro Asp Glu Lys His His
    210                 215                 220

Ala Val Ile Ser Gly Ser Val Leu Tyr Asn Gln Asp Glu Lys Gly Ser
225                 230                 235                 240

Tyr Ser Leu Gly Ile Phe Gly Gly Gln Ala Gln Glu Val Ala Gly Ser
                245                 250                 255

Ala Glu Val Glu Thr Ala Asn Gly Ile His His Ile Gly Leu Ala Ala
            260                 265                 270

Lys Gln

<210> SEQ ID NO 56
<211> LENGTH: 274
<212> TYPE: PRT
<213> ORGANISM: Neisseria meningitidis

<400> SEQUENCE: 56

Met Asn Arg Thr Ala Phe Cys Cys Phe Ser Leu Thr Ala Ala Leu Ile
1               5                   10                  15

Leu Thr Ala Cys Ser Ser Gly Gly Gly Val Ala Ala Asp Ile Gly
            20                  25                  30

Ala Gly Leu Ala Asp Ala Leu Thr Ala Pro Leu Asp His Lys Asp Lys
        35                  40                  45

Gly Leu Gln Ser Leu Thr Leu Asp Gln Ser Val Arg Lys Asn Glu Lys
    50                  55                  60

```
Leu Lys Leu Ala Ala Gln Gly Ala Glu Lys Thr Tyr Gly Asn Gly Asp
 65                  70                  75                  80

Ser Leu Asn Thr Gly Lys Leu Lys Asn Asp Lys Val Ser Arg Phe Asp
                 85                  90                  95

Phe Ile Arg Gln Ile Glu Val Asp Gly Lys Leu Ile Thr Leu Glu Ser
            100                 105                 110

Gly Glu Phe Gln Val Tyr Lys Gln Ser His Ser Ala Leu Thr Ala Leu
            115                 120                 125

Gln Thr Glu Gln Val Gln Asp Ser Glu Asp Ser Gly Lys Met Val Ala
130                 135                 140

Lys Arg Gln Phe Arg Ile Gly Asp Ile Ala Gly Glu His Thr Ser Phe
145                 150                 155                 160

Asp Lys Leu Pro Lys Gly Gly Ser Ala Thr Tyr Arg Gly Thr Ala Phe
                165                 170                 175

Gly Ser Asp Asp Ala Gly Gly Lys Leu Thr Tyr Thr Ile Asp Phe Ala
                180                 185                 190

Ala Lys Gln Gly His Gly Lys Ile Glu His Leu Lys Ser Pro Glu Leu
            195                 200                 205

Asn Val Glu Leu Ala Thr Ala Tyr Ile Lys Pro Asp Glu Lys Arg His
            210                 215                 220

Ala Val Ile Ser Gly Ser Val Leu Tyr Asn Gln Asp Glu Lys Gly Ser
225                 230                 235                 240

Tyr Ser Leu Gly Ile Phe Gly Gly Gln Ala Gln Glu Val Ala Gly Ser
                245                 250                 255

Ala Glu Val Glu Thr Ala Asn Gly Ile His His Ile Gly Leu Ala Ala
            260                 265                 270

Lys Gln

<210> SEQ ID NO 57
<211> LENGTH: 274
<212> TYPE: PRT
<213> ORGANISM: Neisseria meningitidis

<400> SEQUENCE: 57

Met Asn Arg Thr Ala Phe Cys Cys Leu Ser Leu Thr Ala Ala Leu Ile
 1               5                  10                  15

Leu Thr Ala Cys Ser Ser Gly Gly Gly Val Ala Ala Asp Ile Gly
                20                  25                  30

Ala Gly Leu Ala Asp Ala Leu Thr Ala Pro Leu Asp His Lys Asp Lys
             35                  40                  45

Gly Leu Gln Ser Leu Thr Leu Asp Gln Ser Val Arg Lys Asn Glu Lys
 50                  55                  60

Leu Lys Leu Ala Ala Gln Gly Ala Glu Lys Thr Tyr Gly Asn Gly Asp
 65                  70                  75                  80

Ser Leu Asn Thr Gly Lys Leu Lys Asn Asp Lys Val Ser Arg Phe Asp
                 85                  90                  95

Phe Ile Arg Gln Ile Glu Val Asp Gly Gln Leu Ile Thr Leu Glu Ser
            100                 105                 110

Gly Glu Phe Gln Val Tyr Lys Gln Ser His Ser Ala Leu Thr Ala Leu
            115                 120                 125

Gln Thr Glu Gln Val Gln Asp Ser Glu Asp Ser Gly Lys Met Val Ala
130                 135                 140

Lys Arg Gln Phe Arg Ile Gly Asp Ile Ala Gly Glu His Thr Ser Phe
145                 150                 155                 160
```

```
Asp Lys Leu Pro Lys Gly Gly Ser Ala Thr Tyr Arg Gly Thr Ala Phe
            165                 170                 175

Ser Ser Asp Asp Ala Gly Gly Lys Leu Thr Tyr Thr Ile Asp Phe Ala
        180                 185                 190

Ala Lys Gln Gly His Gly Lys Ile Glu His Leu Lys Ser Pro Glu Leu
            195                 200                 205

Asn Val Glu Leu Ala Thr Ala Tyr Ile Lys Pro Asp Glu Lys Arg His
    210                 215                 220

Ala Val Ile Ser Gly Ser Val Leu Tyr Asn Gln Asp Glu Lys Gly Ser
225                 230                 235                 240

Tyr Ser Leu Gly Ile Phe Gly Gly Gln Ala Gln Glu Val Ala Gly Ser
                245                 250                 255

Ala Glu Val Glu Thr Ala Asn Gly Ile Gln His Ile Gly Leu Ala Ala
            260                 265                 270

Lys Gln
```

<210> SEQ ID NO 58
<211> LENGTH: 273
<212> TYPE: PRT
<213> ORGANISM: Neisseria meningitidis

<400> SEQUENCE: 58

```
Met Asn Arg Thr Ala Phe Cys Cys Leu Ser Leu Thr Ala Ala Leu Ile
1               5                   10                  15

Leu Thr Ala Cys Ser Ser Gly Gly Gly Val Ala Ala Asp Ile Gly
            20                  25                  30

Ala Gly Leu Ala Asp Ala Leu Thr Ala Pro Leu Asp His Lys Asp Lys
        35                  40                  45

Ser Leu Gln Ser Leu Thr Leu Asp Gln Ser Val Arg Lys Asn Glu Lys
    50                  55                  60

Leu Lys Leu Ala Ala Gln Gly Ala Glu Lys Thr Tyr Gly Asn Gly Asp
65                  70                  75                  80

Ser Leu Asn Thr Gly Lys Leu Lys Asn Asp Lys Val Ser Arg Phe Asp
                85                  90                  95

Phe Ile Arg Gln Ile Glu Val Asp Gly Gln Leu Ile Thr Leu Glu Ser
            100                 105                 110

Gly Glu Phe Gln Ile Tyr Lys Gln Asp His Ser Ala Val Val Ala Leu
        115                 120                 125

Gln Ile Glu Lys Ile Asn Asn Pro Asp Lys Ile Asp Ser Leu Ile Asn
    130                 135                 140

Gln Arg Ser Phe Leu Val Ser Gly Leu Gly Gly Glu His Thr Ala Phe
145                 150                 155                 160

Asn Gln Leu Pro Val Asp Lys Ala Glu Tyr His Gly Lys Ala Phe Ser
                165                 170                 175

Ser Asp Asp Ala Gly Gly Lys Leu Thr Tyr Thr Ile Asp Phe Ala Ala
            180                 185                 190

Lys Gln Gly His Gly Lys Ile Glu His Leu Lys Thr Pro Glu Gln Asn
        195                 200                 205

Val Glu Leu Ala Ser Ala Glu Leu Lys Ala Asp Glu Lys Ser His Ala
    210                 215                 220

Val Ile Leu Gly Asp Thr Arg Tyr Gly Ser Glu Glu Lys Gly Thr Tyr
225                 230                 235                 240

His Leu Ala Leu Phe Gly Asp Arg Ala Gln Glu Ile Ala Gly Ser Ala
                245                 250                 255
```

```
Thr Val Lys Ile Gly Glu Lys Val His Glu Ile Gly Ile Ala Gly Lys
            260                 265                 270
Gln

<210> SEQ ID NO 59
<211> LENGTH: 273
<212> TYPE: PRT
<213> ORGANISM: Neisseria meningitidis

<400> SEQUENCE: 59

Met Asn Arg Thr Ala Phe Cys Cys Leu Ser Leu Thr Ala Ala Leu Ile
1               5                   10                  15

Leu Thr Ala Cys Ser Ser Gly Gly Gly Gly Val Ala Ala Asp Ile Gly
            20                  25                  30

Ala Arg Leu Ala Asp Ala Leu Thr Ala Pro Leu Asp His Lys Asp Lys
        35                  40                  45

Ser Leu Gln Ser Leu Thr Leu Asp Gln Ser Val Arg Lys Asn Glu Lys
    50                  55                  60

Leu Lys Leu Ala Ala Gln Gly Ala Glu Lys Thr Tyr Gly Asn Gly Asp
65                  70                  75                  80

Ser Leu Asn Thr Gly Lys Leu Lys Asn Asp Lys Val Ser Arg Phe Asp
                85                  90                  95

Phe Ile Arg Gln Ile Glu Val Asp Gly Gln Leu Ile Thr Leu Glu Ser
            100                 105                 110

Gly Glu Phe Gln Ile Tyr Lys Gln Asp His Ser Ala Val Val Ala Leu
        115                 120                 125

Gln Ile Glu Lys Ile Asn Asn Pro Asp Lys Ile Asp Ser Leu Ile Asn
    130                 135                 140

Gln Arg Ser Phe Leu Val Ser Gly Leu Gly Gly Glu His Thr Ala Phe
145                 150                 155                 160

Asn Gln Leu Pro Asp Gly Lys Ala Glu Tyr His Gly Lys Ala Phe Ser
                165                 170                 175

Ser Asp Asp Ala Gly Gly Lys Leu Thr Tyr Thr Ile Asp Phe Ala Ala
            180                 185                 190

Lys Gln Gly His Gly Lys Ile Glu His Leu Lys Thr Pro Glu Gln Asn
        195                 200                 205

Val Glu Leu Ala Ala Ala Glu Leu Lys Ala Asp Glu Lys Ser His Ala
    210                 215                 220

Val Ile Leu Gly Asp Thr Arg Tyr Gly Ser Glu Glu Lys Gly Thr Tyr
225                 230                 235                 240

His Leu Ala Leu Phe Gly Asp Arg Ala Gln Glu Ile Ala Gly Ser Ala
                245                 250                 255

Thr Val Lys Ile Gly Glu Lys Val His Glu Ile Gly Ile Ala Gly Lys
            260                 265                 270

Gln

<210> SEQ ID NO 60
<211> LENGTH: 273
<212> TYPE: PRT
<213> ORGANISM: Neisseria meningitidis

<400> SEQUENCE: 60

Met Asn Arg Thr Ala Phe Cys Cys Leu Ser Leu Thr Thr Ala Leu Ile
1               5                   10                  15

Leu Thr Ala Cys Ser Ser Gly Gly Gly Gly Val Ala Ala Asp Ile Gly
```

```
            20                  25                  30
Ala Gly Leu Ala Asp Ala Leu Thr Ala Pro Leu Asp His Lys Asp Lys
        35                  40                  45

Ser Leu Gln Ser Leu Thr Leu Asp Gln Ser Val Arg Lys Asn Glu Lys
 50                  55                  60

Leu Lys Leu Ala Ala Gln Gly Ala Glu Lys Thr Tyr Gly Asn Gly Asp
 65                  70                  75                  80

Ser Leu Asn Thr Gly Lys Leu Lys Asn Asp Lys Val Ser Arg Phe Asp
                 85                  90                  95

Phe Ile Arg Gln Ile Glu Val Asp Gly Gln Leu Ile Thr Leu Glu Ser
            100                 105                 110

Gly Glu Phe Gln Ile Tyr Lys Gln Asp His Ser Ala Val Val Ala Leu
        115                 120                 125

Gln Ile Glu Lys Ile Asn Asn Pro Asp Lys Ile Asp Ser Leu Ile Asn
    130                 135                 140

Gln Arg Ser Phe Leu Val Ser Gly Leu Gly Gly Glu His Thr Ala Phe
145                 150                 155                 160

Asn Gln Leu Pro Gly Gly Lys Ala Glu Tyr His Gly Lys Ala Phe Ser
                165                 170                 175

Ser Asp Asp Ala Gly Gly Lys Leu Thr Tyr Thr Ile Asp Phe Ala Ala
            180                 185                 190

Lys Gln Gly His Gly Lys Ile Glu His Leu Lys Thr Pro Glu Gln Asn
        195                 200                 205

Val Glu Leu Ala Ala Ala Glu Leu Lys Ala Asp Glu Lys Ser His Ala
    210                 215                 220

Val Ile Leu Gly Asp Thr Arg Tyr Gly Ser Glu Lys Gly Thr Tyr
225                 230                 235                 240

His Leu Ala Leu Phe Gly Asp Arg Ala Gln Glu Ile Ala Gly Ser Ala
                245                 250                 255

Thr Val Lys Ile Gly Glu Lys Val His Glu Ile Gly Ile Ala Gly Lys
            260                 265                 270

Gln

<210> SEQ ID NO 61
<211> LENGTH: 273
<212> TYPE: PRT
<213> ORGANISM: Neisseria meningitidis

<400> SEQUENCE: 61

Met Asn Arg Thr Ala Phe Cys Cys Leu Ser Leu Thr Thr Ala Leu Ile
 1               5                  10                  15

Leu Thr Ala Cys Ser Ser Gly Gly Gly Val Ala Ala Asp Ile Gly
                 20                  25                  30

Ala Gly Leu Ala Asp Ala Leu Thr Ala Pro Leu Asp His Lys Asp Lys
        35                  40                  45

Gly Leu Gln Ser Leu Thr Leu Asp Gln Ser Val Arg Lys Asn Glu Lys
 50                  55                  60

Leu Lys Leu Ala Ala Gln Gly Ala Glu Lys Thr Tyr Gly Asn Gly Asp
 65                  70                  75                  80

Ser Leu Asn Thr Gly Lys Leu Lys Asn Asp Lys Val Ser Arg Phe Asp
                 85                  90                  95

Phe Ile Arg Gln Ile Glu Val Asp Gly Gln Leu Ile Thr Leu Glu Ser
            100                 105                 110

Gly Glu Phe Gln Ile Tyr Lys Gln Asp His Ser Ala Val Val Ala Leu
```

```
            115                 120                 125
Gln Ile Glu Lys Ile Asn Asn Pro Asp Lys Ile Asp Ser Leu Ile Asn
        130                 135                 140

Gln Arg Ser Phe Leu Val Ser Gly Leu Gly Gly Glu His Thr Ala Phe
145                 150                 155                 160

Asn Gln Leu Pro Asp Gly Lys Ala Glu Tyr His Gly Lys Ala Phe Ser
                165                 170                 175

Ser Asp Asp Ala Gly Gly Lys Leu Thr Tyr Thr Ile Asp Phe Ala Ala
            180                 185                 190

Lys Gln Gly His Gly Lys Ile Glu His Leu Lys Thr Pro Glu Gln Asn
        195                 200                 205

Val Glu Leu Ala Ala Ala Glu Leu Lys Ala Asp Glu Lys Ser His Ala
    210                 215                 220

Val Ile Leu Gly Asp Thr Arg Tyr Gly Ser Glu Glu Lys Gly Thr Tyr
225                 230                 235                 240

His Leu Ala Leu Phe Gly Asp Arg Ala Gln Glu Ile Ala Gly Ser Ala
                245                 250                 255

Thr Val Lys Ile Gly Glu Lys Val His Glu Ile Gly Ile Ala Gly Lys
            260                 265                 270

Gln

<210> SEQ ID NO 62
<211> LENGTH: 273
<212> TYPE: PRT
<213> ORGANISM: Neisseria meningitidis

<400> SEQUENCE: 62

Met Asn Arg Thr Ala Phe Cys Cys Leu Ser Leu Thr Thr Ala Leu Ile
1               5                   10                  15

Leu Thr Ala Cys Ser Ser Gly Gly Gly Gly Val Ala Ala Asp Ile Gly
            20                  25                  30

Thr Gly Leu Ala Asp Ala Leu Thr Ala Pro Leu Asp His Lys Asp Lys
        35                  40                  45

Gly Leu Gln Ser Leu Thr Leu Asp Gln Ser Val Arg Lys Asn Glu Lys
    50                  55                  60

Leu Lys Leu Ala Ala Gln Gly Ala Glu Lys Thr Tyr Gly Asn Gly Asp
65                  70                  75                  80

Ser Leu Asn Thr Gly Lys Leu Lys Asn Asp Lys Val Ser Arg Phe Asp
                85                  90                  95

Phe Ile Arg Gln Ile Glu Val Asp Gly Gln Leu Ile Thr Leu Glu Ser
            100                 105                 110

Gly Glu Phe Gln Ile Tyr Lys Gln Asp His Ser Ala Val Val Ala Leu
        115                 120                 125

Gln Ile Glu Lys Ile Asn Asn Pro Asp Lys Ile Asp Ser Leu Ile Asn
    130                 135                 140

Gln Arg Ser Phe Leu Val Ser Gly Leu Gly Gly Glu His Thr Ala Phe
145                 150                 155                 160

Asn Gln Leu Pro Ser Gly Lys Ala Glu Tyr His Gly Lys Ala Phe Ser
                165                 170                 175

Ser Asp Asp Ala Gly Gly Lys Leu Thr Tyr Thr Ile Asp Phe Ala Ala
            180                 185                 190

Lys Gln Gly His Gly Lys Ile Glu His Leu Lys Thr Pro Glu Gln Asn
        195                 200                 205

Val Glu Leu Ala Ser Ala Glu Leu Lys Ala Asp Glu Lys Ser His Ala
```

```
                    210                 215                 220
Val Ile Leu Gly Asp Thr Arg Tyr Gly Gly Glu Lys Gly Thr Tyr
225                 230                 235                 240

His Leu Ala Leu Phe Gly Asp Arg Ala Gln Glu Ile Ala Gly Ser Ala
                245                 250                 255

Thr Val Lys Ile Arg Glu Lys Val His Glu Ile Gly Ile Ala Gly Lys
                260                 265                 270
Gln
```

<210> SEQ ID NO 63
<211> LENGTH: 273
<212> TYPE: PRT
<213> ORGANISM: Neisseria meningitidis

<400> SEQUENCE: 63

```
Met Asn Arg Thr Ala Phe Cys Cys Leu Ser Leu Thr Ala Ala Leu Ile
1               5                   10                  15

Leu Thr Ala Cys Ser Ser Gly Gly Gly Val Ala Ala Asp Ile Gly
                20                  25                  30

Ala Gly Leu Ala Asp Ala Leu Thr Ala Pro Leu Asp His Lys Asp Lys
                35                  40                  45

Ser Leu Gln Ser Leu Thr Leu Asp Gln Ser Val Arg Lys Asn Glu Lys
50                  55                  60

Leu Lys Leu Ala Ala Gln Gly Ala Glu Lys Thr Tyr Gly Asn Gly Asp
65                  70                  75                  80

Ser Leu Asn Thr Gly Lys Leu Lys Asn Asp Lys Val Ser Arg Phe Asp
                85                  90                  95

Phe Ile Arg Gln Ile Glu Val Asp Gly Gln Leu Ile Thr Leu Glu Ser
                100                 105                 110

Gly Glu Phe Gln Ile Tyr Lys Gln Asp His Ser Ala Val Val Ala Leu
                115                 120                 125

Gln Ile Glu Lys Ile Asn Asn Pro Asp Lys Ile Asp Ser Leu Ile Asn
                130                 135                 140

Gln Arg Ser Phe Leu Val Ser Gly Leu Gly Gly Glu His Thr Ala Phe
145                 150                 155                 160

Asn Gln Leu Pro Ser Gly Lys Ala Glu Tyr His Gly Lys Ala Phe Ser
                165                 170                 175

Phe Asp Asp Ala Gly Gly Lys Leu Thr Tyr Thr Ile Asp Phe Ala Ala
                180                 185                 190

Lys Gln Gly His Gly Lys Ile Glu His Leu Lys Thr Pro Glu Gln Asn
                195                 200                 205

Val Glu Leu Ala Ser Ala Glu Leu Lys Ala Asp Glu Lys Ser His Ala
                210                 215                 220

Val Ile Leu Gly Asp Thr Arg Tyr Gly Gly Glu Lys Gly Thr Tyr
225                 230                 235                 240

His Leu Ala Leu Phe Gly Asp Arg Ala Gln Glu Ile Ala Gly Ser Ala
                245                 250                 255

Thr Val Lys Ile Arg Glu Lys Val His Glu Ile Gly Ile Ala Gly Lys
                260                 265                 270
Gln
```

<210> SEQ ID NO 64
<211> LENGTH: 273
<212> TYPE: PRT
<213> ORGANISM: Neisseria meningitidis

<400> SEQUENCE: 64

```
Met Asn Arg Thr Ala Phe Cys Cys Phe Ser Leu Thr Ala Ala Leu Ile
1               5                   10                  15

Leu Thr Ala Cys Ser Ser Gly Gly Gly Val Ala Ala Asp Ile Gly
            20                  25                  30

Ala Gly Leu Ala Asp Ala Leu Thr Ala Pro Leu Asp His Lys Asp Lys
            35                  40                  45

Gly Leu Gln Ser Leu Thr Leu Asp Gln Ser Val Arg Lys Asn Glu Lys
50                  55                  60

Leu Lys Leu Ala Ala Gln Gly Ala Glu Lys Thr Tyr Gly Asn Gly Asp
65                  70                  75                  80

Ser Leu Asn Thr Gly Lys Leu Lys Asn Asp Lys Val Ser Arg Phe Asp
                85                  90                  95

Phe Ile Arg Gln Ile Glu Val Asp Gly Gln Leu Ile Thr Leu Glu Ser
            100                 105                 110

Gly Glu Phe Gln Ile Tyr Lys Gln Asp His Ser Ala Val Val Ala Leu
            115                 120                 125

Gln Ile Glu Lys Ile Asn Asn Pro Asp Lys Ile Asp Ser Leu Ile Asn
130                 135                 140

Gln Arg Ser Phe Leu Val Ser Gly Leu Gly Gly Glu His Thr Ala Phe
145                 150                 155                 160

Asn Gln Leu Pro Ser Gly Lys Ala Glu Tyr His Gly Lys Ala Phe Ser
                165                 170                 175

Ser Asp Asp Pro Asn Gly Arg Leu His Tyr Ser Ile Asp Phe Thr Lys
            180                 185                 190

Lys Gln Gly Tyr Gly Arg Ile Glu His Leu Lys Thr Pro Glu Gln Asn
            195                 200                 205

Val Glu Leu Ala Ser Ala Glu Leu Lys Ala Asp Glu Lys Ser His Ala
210                 215                 220

Val Ile Leu Gly Asp Thr Arg Tyr Gly Gly Glu Glu Lys Gly Thr Tyr
225                 230                 235                 240

His Leu Ala Leu Phe Gly Asp Arg Ala Gln Glu Ile Ala Gly Ser Ala
                245                 250                 255

Thr Val Lys Ile Arg Glu Lys Val His Glu Ile Gly Ile Ala Gly Lys
            260                 265                 270

Gln
```

<210> SEQ ID NO 65
<211> LENGTH: 281
<212> TYPE: PRT
<213> ORGANISM: Neisseria meningitidis

<400> SEQUENCE: 65

```
Met Asn Arg Thr Thr Phe Cys Cys Leu Ser Leu Thr Ala Ala Leu Ile
1               5                   10                  15

Leu Thr Ala Cys Ser Ser Gly Gly Gly Ser Gly Gly Gly Val
            20                  25                  30

Ala Ala Asp Ile Gly Thr Gly Leu Ala Asp Ala Leu Thr Ala Pro Leu
            35                  40                  45

Asp His Lys Asp Lys Gly Leu Lys Ser Leu Thr Leu Glu Asp Ser Ile
50                  55                  60

Pro Gln Asn Gly Thr Leu Thr Leu Ser Ala Gln Gly Ala Glu Lys Thr
65                  70                  75                  80
```

```
Phe Lys Ala Gly Asp Lys Asp Asn Ser Leu Asn Thr Gly Lys Leu Lys
                85                  90                  95

Asn Asp Lys Ile Ser Arg Phe Asp Phe Val Gln Lys Ile Glu Val Asp
            100                 105                 110

Gly Gln Thr Ile Thr Leu Ala Ser Gly Glu Phe Gln Ile Tyr Lys Gln
            115                 120                 125

Asn His Ser Ala Val Val Ala Leu Gln Ile Glu Lys Ile Asn Asn Pro
        130                 135                 140

Asp Lys Ile Asp Ser Leu Ile Asn Gln Arg Ser Phe Leu Val Ser Gly
145                 150                 155                 160

Leu Gly Gly Glu His Thr Ala Phe Asn Gln Leu Pro Gly Asp Lys Ala
                165                 170                 175

Glu Tyr His Gly Lys Ala Phe Ser Ser Asp Pro Asn Gly Arg Leu
                180                 185                 190

His Tyr Thr Ile Asp Phe Thr Asn Lys Gln Gly Tyr Gly Arg Ile Glu
            195                 200                 205

His Leu Lys Thr Pro Glu Leu Asn Val Asp Leu Ala Ser Ala Glu Leu
        210                 215                 220

Lys Ala Asp Glu Lys Ser His Ala Val Ile Leu Gly Asp Thr Arg Tyr
225                 230                 235                 240

Gly Ser Glu Glu Lys Gly Thr Tyr His Leu Ala Leu Phe Gly Asp Arg
                245                 250                 255

Ala Gln Glu Ile Ala Gly Ser Ala Thr Val Lys Ile Gly Glu Lys Val
                260                 265                 270

His Glu Ile Gly Ile Ala Gly Lys Gln
            275                 280

<210> SEQ ID NO 66
<211> LENGTH: 250
<212> TYPE: PRT
<213> ORGANISM: Neisseria meningitidis

<400> SEQUENCE: 66

Met Asn Arg Thr Ala Phe Cys Cys Leu Ser Leu Thr Thr Ala Leu Ile
1               5                   10                  15

Leu Thr Ala Cys Ser Ser Gly Gly Gly Val Ala Ala Asp Ile Gly
            20                  25                  30

Ala Gly Leu Ala Asp Ala Leu Thr Ala Pro Leu Asp His Lys Asp Lys
        35                  40                  45

Gly Leu Gln Ser Leu Thr Leu Asp Gln Ser Val Arg Lys Asn Glu Lys
    50                  55                  60

Leu Lys Leu Ala Ala Gln Gly Ala Glu Lys Thr Tyr Gly Asn Gly Asp
65                  70                  75                  80

Ser Leu Asn Thr Gly Lys Leu Lys Asn Asp Lys Val Ser Arg Phe Asp
                85                  90                  95

Phe Ile Arg Gln Ile Glu Val Asp Gly Gln Leu Ile Thr Leu Glu Ser
            100                 105                 110

Gly Glu Phe Gln Val Tyr Lys Gln Ser His Ser Ala Leu Thr Ala Phe
            115                 120                 125

Gln Thr Glu Gln Ile Gln Asp Ser Glu His Ser Gly Lys Met Val Ala
        130                 135                 140

Lys Arg Gln Phe Arg Ile Gly Asp Ile Ala Gly Glu His Thr Ser Phe
145                 150                 155                 160

Asp Lys Leu Pro Glu Gly Gly Arg Ala Thr Tyr Arg Gly Thr Ala Phe
                165                 170                 175
```

```
Gly Ser Asp Asp Ala Gly Gly Lys Leu Thr Tyr Thr Ile Asp Phe Ala
            180                 185                 190

Ala Lys Gln Gly Asn Gly Lys Ile Glu His Leu Lys Ser Pro Glu Leu
            195                 200                 205

Asn Val Asp Leu Ala Ala Ala Asp Ile Lys Pro Asp Gly Lys Arg His
    210                 215                 220

Ala Val Ile Ser Gly Ser Val Leu Tyr Asn Gln Ala Glu Lys Gly Ser
225                 230                 235                 240

Tyr Ser Leu Gly Ile Phe Gly Gly Lys Ala
                245                 250

<210> SEQ ID NO 67
<211> LENGTH: 282
<212> TYPE: PRT
<213> ORGANISM: Neisseria meningitidis

<400> SEQUENCE: 67

Met Asn Arg Thr Thr Phe Cys Cys Leu Ser Leu Thr Ala Ala Leu Ile
1               5                   10                  15

Leu Thr Ala Cys Ser Ser Gly Gly Gly Ser Gly Gly Gly Gly Gly Val
            20                  25                  30

Ala Ala Asp Ile Gly Ala Gly Leu Ala Asp Ala Leu Thr Ala Pro Leu
            35                  40                  45

Asp His Lys Asp Lys Gly Leu Lys Ser Leu Thr Leu Glu Asp Ser Ile
    50                  55                  60

Ser Gln Asn Gly Thr Leu Thr Leu Ser Ala Gln Gly Ala Glu Arg Thr
65                  70                  75                  80

Phe Lys Ala Gly Asp Lys Asp Asn Ser Leu Asn Thr Gly Lys Leu Lys
                85                  90                  95

Asn Asp Lys Ile Ser Arg Phe Asp Phe Ile Arg Gln Ile Glu Val Asp
            100                 105                 110

Gly Gln Leu Ile Thr Leu Glu Ser Gly Glu Phe Gln Val Tyr Lys Gln
            115                 120                 125

Ser His Ser Ala Leu Thr Ala Leu Gln Thr Glu Gln Val Gln Asp Ser
    130                 135                 140

Glu His Ser Gly Lys Met Val Ala Lys Arg Gln Phe Arg Ile Gly Asp
145                 150                 155                 160

Ile Val Gly Glu His Thr Ser Phe Gly Lys Leu Pro Lys Asp Val Met
                165                 170                 175

Ala Thr Tyr Arg Gly Thr Ala Phe Gly Ser Asp Asp Ala Gly Gly Lys
            180                 185                 190

Leu Thr Tyr Thr Ile Asp Phe Ala Ala Lys Gln Gly His Gly Lys Ile
            195                 200                 205

Glu His Leu Lys Ser Pro Glu Leu Asn Val Asp Leu Ala Ala Ala Asp
    210                 215                 220

Ile Lys Pro Asp Glu Lys His His Ala Val Ile Ser Gly Ser Val Leu
225                 230                 235                 240

Tyr Asn Gln Ala Glu Lys Gly Ser Tyr Ser Leu Gly Ile Phe Gly Gly
                245                 250                 255

Gln Ala Gln Glu Val Ala Gly Ser Ala Glu Val Glu Thr Ala Asn Gly
            260                 265                 270

Ile Arg His Ile Gly Leu Ala Ala Lys Gln
            275                 280
```

```
<210> SEQ ID NO 68
<211> LENGTH: 275
<212> TYPE: PRT
<213> ORGANISM: Neisseria meningitidis

<400> SEQUENCE: 68

Met Asn Arg Thr Ala Phe Cys Cys Leu Ser Leu Thr Ala Ala Leu Ile
1               5                   10                  15

Leu Thr Ala Cys Ser Ser Gly Ser Gly Gly Gly Val Ala Ala Asp
            20                  25                  30

Ile Gly Thr Gly Leu Ala Tyr Ala Leu Thr Ala Pro Leu Asp His Lys
        35                  40                  45

Asp Lys Ser Leu Gln Ser Leu Thr Leu Asp Gln Ser Val Arg Lys Asn
    50                  55                  60

Glu Lys Leu Lys Leu Ala Ala Gln Gly Ala Glu Lys Thr Tyr Gly Asn
65                  70                  75                  80

Gly Asp Ser Leu Asn Thr Gly Lys Leu Lys Asn Asp Lys Val Ser Arg
                85                  90                  95

Phe Asp Phe Ile Arg Gln Ile Glu Val Asp Gly Gln Leu Ile Thr Leu
            100                 105                 110

Glu Ser Gly Glu Phe Gln Ile Tyr Lys Gln Asp His Ser Ala Val Val
        115                 120                 125

Ala Leu Gln Ile Glu Lys Ile Asn Asn Pro Asp Lys Ile Asp Ser Leu
    130                 135                 140

Ile Asn Gln Arg Ser Phe Leu Val Ser Gly Leu Gly Gly Glu His Thr
145                 150                 155                 160

Ala Phe Asn Gln Leu Pro Gly Gly Lys Ala Glu Tyr His Gly Lys Ala
                165                 170                 175

Phe Ser Ser Asp Asp Pro Asn Gly Arg Leu His Tyr Ser Ile Asp Phe
            180                 185                 190

Thr Lys Lys Gln Gly Tyr Gly Arg Ile Glu His Leu Lys Thr Pro Glu
        195                 200                 205

Gln Asn Val Glu Leu Ala Ser Ala Glu Leu Lys Ala Asp Glu Lys Ser
    210                 215                 220

His Ala Val Ile Leu Gly Asp Thr Arg Tyr Gly Gly Glu Glu Lys Gly
225                 230                 235                 240

Thr Tyr His Leu Ala Leu Phe Gly Asp Arg Ala Gln Glu Ile Ala Gly
                245                 250                 255

Ser Ala Thr Val Lys Ile Arg Glu Lys Val His Glu Ile Gly Ile Ala
            260                 265                 270

Gly Lys Gln
        275

<210> SEQ ID NO 69
<211> LENGTH: 757
<212> TYPE: PRT
<213> ORGANISM: Artificial sequence
<220> FEATURE:
<223> OTHER INFORMATION: Synthetic polypeptide sequence

<400> SEQUENCE: 69

Val Ala Ala Asp Ile Gly Ala Gly Leu Ala Asp Ala Leu Thr Ala Pro
1               5                   10                  15

Leu Asp His Lys Asp Lys Gly Leu Gln Ser Leu Thr Leu Asp Gln Ser
            20                  25                  30

Val Arg Lys Asn Glu Lys Leu Lys Leu Ala Ala Gln Gly Ala Glu Lys
        35                  40                  45
```

-continued

Thr Tyr Gly Asn Gly Asp Ser Leu Asn Thr Gly Lys Leu Lys Asn Asp
 50                  55                  60

Lys Val Ser Arg Phe Asp Phe Ile Arg Gln Ile Glu Val Asp Gly Gln
 65                  70                  75                  80

Leu Ile Thr Leu Glu Ser Gly Glu Phe Gln Val Tyr Lys Gln Ser His
                     85                  90                  95

Ser Ala Leu Thr Ala Phe Gln Thr Glu Gln Ile Gln Asp Ser Glu His
                100                 105                 110

Ser Gly Lys Met Val Ala Lys Arg Gln Phe Arg Ile Gly Asp Ile Ala
                115                 120                 125

Gly Glu His Thr Ser Phe Asp Lys Leu Pro Glu Gly Gly Arg Ala Thr
            130                 135                 140

Tyr Arg Gly Thr Ala Phe Gly Ser Asp Asp Ala Gly Gly Lys Leu Thr
145                 150                 155                 160

Tyr Thr Ile Asp Phe Ala Ala Lys Gln Gly Asn Gly Lys Ile Glu His
                165                 170                 175

Leu Lys Ser Pro Glu Leu Asn Val Asp Leu Ala Ala Ala Asp Ile Lys
            180                 185                 190

Pro Asp Gly Lys Arg His Ala Val Ile Ser Gly Ser Val Leu Tyr Asn
        195                 200                 205

Gln Ala Glu Lys Gly Ser Tyr Ser Leu Gly Ile Phe Gly Gly Lys Ala
    210                 215                 220

Gln Glu Val Ala Gly Ser Ala Glu Val Lys Thr Val Asn Gly Ile Arg
225                 230                 235                 240

His Ile Gly Leu Ala Ala Lys Gln Gly Ser Gly Gly Gly Val Ala
                245                 250                 255

Ala Asp Ile Gly Ala Gly Leu Ala Asp Ala Leu Thr Ala Pro Leu Asp
            260                 265                 270

His Lys Asp Lys Ser Leu Gln Ser Leu Thr Leu Asp Gln Ser Val Arg
        275                 280                 285

Lys Asn Glu Lys Leu Lys Leu Ala Ala Gln Gly Ala Glu Lys Thr Tyr
    290                 295                 300

Gly Asn Gly Asp Ser Leu Asn Thr Gly Lys Leu Lys Asn Asp Lys Val
305                 310                 315                 320

Ser Arg Phe Asp Phe Ile Arg Gln Ile Glu Val Asp Gly Gln Leu Ile
                325                 330                 335

Thr Leu Glu Ser Gly Glu Phe Gln Ile Tyr Lys Gln Asp His Ser Ala
            340                 345                 350

Val Val Ala Leu Gln Ile Glu Lys Ile Asn Asn Pro Asp Lys Ile Asp
        355                 360                 365

Ser Leu Ile Asn Gln Arg Ser Phe Leu Val Ser Gly Leu Gly Gly Glu
    370                 375                 380

His Thr Ala Phe Asn Gln Leu Pro Asp Gly Lys Ala Glu Tyr His Gly
385                 390                 395                 400

Lys Ala Phe Ser Ser Asp Asp Ala Gly Gly Lys Leu Thr Tyr Thr Ile
                405                 410                 415

Asp Phe Ala Ala Lys Gln Gly His Gly Lys Ile Glu His Leu Lys Thr
            420                 425                 430

Pro Glu Gln Asn Val Glu Leu Ala Ala Ala Glu Leu Lys Ala Asp Glu
        435                 440                 445

Lys Ser His Ala Val Ile Leu Gly Asp Thr Arg Tyr Gly Ser Glu Glu
    450                 455                 460

```
Lys Gly Thr Tyr His Leu Ala Leu Phe Gly Asp Arg Ala Gln Glu Ile
465                 470                 475                 480

Ala Gly Ser Ala Thr Val Lys Ile Gly Glu Lys Val His Glu Ile Gly
                485                 490                 495

Ile Ala Gly Lys Gln Gly Ser Gly Gly Gly Val Ala Ala Asp Ile
            500                 505                 510

Gly Thr Gly Leu Ala Asp Ala Leu Thr Ala Pro Leu Asp His Lys Asp
            515                 520                 525

Lys Gly Leu Lys Ser Leu Thr Leu Glu Asp Ser Ile Pro Gln Asn Gly
            530                 535                 540

Thr Leu Thr Leu Ser Ala Gln Gly Ala Glu Lys Thr Phe Lys Ala Gly
545                 550                 555                 560

Asp Lys Asp Asn Ser Leu Asn Thr Gly Lys Leu Lys Asn Asp Lys Ile
                565                 570                 575

Ser Arg Phe Asp Phe Val Gln Lys Ile Glu Val Asp Gly Gln Thr Ile
                580                 585                 590

Thr Leu Ala Ser Gly Glu Phe Gln Ile Tyr Lys Gln Asn His Ser Ala
            595                 600                 605

Val Val Ala Leu Gln Ile Glu Lys Ile Asn Asn Pro Asp Lys Thr Asp
610                 615                 620

Ser Leu Ile Asn Gln Arg Ser Phe Leu Val Ser Gly Leu Gly Gly Glu
625                 630                 635                 640

His Thr Ala Phe Asn Gln Leu Pro Gly Gly Lys Ala Glu Tyr His Gly
                645                 650                 655

Lys Ala Phe Ser Ser Asp Asp Pro Asn Gly Arg Leu His Tyr Ser Ile
                660                 665                 670

Asp Phe Thr Lys Lys Gln Gly Tyr Gly Arg Ile Glu His Leu Lys Thr
                675                 680                 685

Leu Glu Gln Asn Val Glu Leu Ala Ala Ala Glu Leu Lys Ala Asp Glu
            690                 695                 700

Lys Ser His Ala Val Ile Leu Gly Asp Thr Arg Tyr Gly Ser Glu Glu
705                 710                 715                 720

Lys Gly Thr Tyr His Leu Ala Leu Phe Gly Asp Arg Ala Gln Glu Ile
                725                 730                 735

Ala Gly Ser Ala Thr Val Lys Ile Gly Glu Lys Val His Glu Ile Gly
                740                 745                 750

Ile Ala Gly Lys Gln
            755

<210> SEQ ID NO 70
<211> LENGTH: 405
<212> TYPE: PRT
<213> ORGANISM: Neisseria meningitidis

<400> SEQUENCE: 70

Met Lys His Phe Pro Ser Lys Val Leu Thr Thr Ala Ile Leu Ala Thr
1               5                   10                  15

Phe Cys Ser Gly Ala Leu Ala Ala Thr Asn Asp Asp Val Lys Lys
                20                  25                  30

Ala Ala Thr Val Ala Ile Ala Ala Tyr Asn Asn Gly Gln Glu Ile
            35                  40                  45

Asn Gly Phe Lys Ala Gly Glu Thr Ile Tyr Asp Ile Asp Glu Asp Gly
            50                  55                  60

Thr Ile Thr Lys Lys Asp Ala Thr Ala Ala Asp Val Glu Ala Asp Asp
65                  70                  75                  80
```

```
Phe Lys Gly Leu Gly Leu Lys Lys Val Val Thr Asn Leu Thr Lys Thr
                85                  90                  95
Val Asn Glu Asn Lys Gln Asn Val Asp Ala Lys Val Lys Ala Ala Glu
            100                 105                 110
Ser Glu Ile Glu Lys Leu Thr Thr Lys Leu Ala Asp Thr Asp Ala Ala
        115                 120                 125
Leu Ala Asp Thr Asp Ala Ala Leu Asp Ala Thr Thr Asn Ala Leu Asn
    130                 135                 140
Lys Leu Gly Glu Asn Ile Thr Thr Phe Ala Glu Thr Lys Thr Asn
145                 150                 155                 160
Ile Val Lys Ile Asp Glu Lys Leu Glu Ala Val Ala Asp Thr Val Asp
                165                 170                 175
Lys His Ala Glu Ala Phe Asn Asp Ile Ala Asp Ser Leu Asp Glu Thr
            180                 185                 190
Asn Thr Lys Ala Asp Glu Ala Val Lys Thr Ala Asn Glu Ala Lys Gln
        195                 200                 205
Thr Ala Glu Glu Thr Lys Gln Asn Val Asp Ala Lys Val Lys Ala Ala
    210                 215                 220
Glu Thr Ala Ala Gly Lys Ala Glu Ala Ala Gly Thr Ala Asn Thr
225                 230                 235                 240
Ala Ala Asp Lys Ala Glu Ala Val Ala Ala Lys Val Thr Asp Ile Lys
                245                 250                 255
Ala Asp Ile Ala Thr Asn Lys Asp Asn Ile Ala Lys Lys Ala Asn Ser
            260                 265                 270
Ala Asp Val Tyr Thr Arg Glu Glu Ser Asp Ser Lys Phe Val Arg Ile
        275                 280                 285
Asp Gly Leu Asn Ala Thr Thr Glu Lys Leu Asp Thr Arg Leu Ala Ser
    290                 295                 300
Ala Glu Lys Ser Ile Thr Glu His Gly Thr Arg Leu Asn Gly Leu Asp
305                 310                 315                 320
Arg Thr Val Ser Asp Leu Arg Lys Glu Thr Arg Gln Gly Leu Ala Glu
                325                 330                 335
Gln Ala Ala Leu Ser Gly Leu Phe Gln Pro Tyr Asn Val Gly Arg Phe
            340                 345                 350
Asn Val Thr Ala Ala Val Gly Gly Tyr Lys Ser Glu Ser Ala Val Ala
        355                 360                 365
Ile Gly Thr Gly Phe Arg Phe Thr Glu Asn Phe Ala Ala Lys Ala Gly
    370                 375                 380
Val Ala Val Gly Thr Ser Ser Gly Ser Ser Ala Ala Tyr His Val Gly
385                 390                 395                 400
Val Asn Tyr Glu Trp
                405

<210> SEQ ID NO 71
<211> LENGTH: 6
<212> TYPE: PRT
<213> ORGANISM: Artificial sequence
<220> FEATURE:
<223> OTHER INFORMATION: Synthetic polypeptide sequence

<400> SEQUENCE: 71

Gly Ser Gly Gly Gly Gly
1               5

<210> SEQ ID NO 72
```

```
<211> LENGTH: 29
<212> TYPE: DNA
<213> ORGANISM: Artificial sequence
<220> FEATURE:
<223> OTHER INFORMATION: Synthetic nucleic acid sequence

<400> SEQUENCE: 72
atcggcatgc gccgttcgga cgacatttg                                  29

<210> SEQ ID NO 73
<211> LENGTH: 30
<212> TYPE: DNA
<213> ORGANISM: Artificial sequence
<220> FEATURE:
<223> OTHER INFORMATION: Synthetic nucleic acid sequence

<400> SEQUENCE: 73
aagaaggcct ttattgcttg gcggcaaggc                                 30

<210> SEQ ID NO 74
<211> LENGTH: 274
<212> TYPE: PRT
<213> ORGANISM: Neisseria meningitidis

<400> SEQUENCE: 74
```

Val Asn Arg Thr Ala Phe Cys Cys Leu Ser Leu Thr Thr Ala Leu Ile
1               5                   10                  15

Leu Thr Ala Cys Ser Ser Gly Gly Gly Val Ala Ala Asp Ile

<210> SEQ ID NO 75
<211> LENGTH: 273
<212> TYPE: PRT
<213> ORGANISM: Neisseria meningitidis

<400> SEQUENCE: 75

Val Asn Arg Thr Ala Phe Cys Cys Leu Ser Leu Thr Ala Ala Leu Ile
1               5                   10                  15
Leu Thr Ala Cys Ser Ser Gly Gly Gly Gly Val Ala Ala Asp Ile Gly
            20                  25                  30
Ala Gly Leu Ala Asp Ala Leu Thr Ala Pro Leu Asp His Lys Asp Lys
        35                  40                  45
Ser Leu Gln Ser Leu Thr Leu Asp Gln Ser Val Arg Lys Asn Glu Lys
    50                  55                  60
Leu Lys Leu Ala Ala Gln Gly Ala Glu Lys Thr Tyr Gly Asn Gly Asp
65                  70                  75                  80
Ser Leu Asn Thr Gly Lys Leu Lys Asn Asp Lys Val Ser Arg Phe Asp
                85                  90                  95
Phe Ile Arg Gln Ile Glu Val Asp Gly Gln Leu Ile Thr Leu Glu Ser
            100                 105                 110
Gly Glu Phe Gln Ile Tyr Lys Gln Asp His Ser Ala Val Val Ala Glu
        115                 120                 125
Gln Thr Glu Lys Ile Asn Asn Pro Asp Lys Ile Asp Ser Leu Ile Asn
    130                 135                 140
Gln Arg Ser Phe Leu Val Ser Gly Leu Gly Gly Glu His Thr Ala Phe
145                 150                 155                 160
Asn Gln Leu Pro Asp Gly Lys Ala Glu Tyr His Gly Lys Ala Phe Ser
                165                 170                 175
Ser Asp Asp Ala Gly Gly Lys Leu Thr Tyr Thr Ile Asp Phe Ala Ala
            180                 185                 190
Lys Gln Gly His Gly Lys Ile Glu His Leu Lys Thr Pro Glu Gln Asn
        195                 200                 205
Val Glu Leu Ala Ala Ala Glu Leu Lys Ala Asp Glu Lys Ser His Ala
    210                 215                 220
Val Ile Leu Gly Asp Thr Arg Tyr Gly Ser Glu Lys Gly Thr Tyr
225                 230                 235                 240
His Leu Ala Leu Phe Gly Asp Arg Ala Gln Glu Ile Ala Gly Ser Ala
                245                 250                 255
Thr Val Lys Ile Gly Glu Lys Val His Glu Ile Gly Ile Ala Gly Lys
            260                 265                 270
Gln

<210> SEQ ID NO 76
<211> LENGTH: 281
<212> TYPE: PRT
<213> ORGANISM: Neisseria meningitidis

<400> SEQUENCE: 76

Val Asn Arg Thr Ala Phe Cys Cys Leu Ser Leu Thr Thr Ala Leu Ile
1               5                   10                  15
Leu Thr Ala Cys Ser Ser Gly Gly Gly Gly Ser Gly Gly Gly Val
            20                  25                  30

```
Ala Ala Asp Ile Gly Thr Gly Leu Ala Asp Ala Leu Thr Ala Pro Leu
         35                  40                  45

Asp His Lys Asp Lys Ser Leu Lys Ser Leu Thr Leu Glu Asp Ser Ile
 50                  55                  60

Pro Gln Asn Gly Thr Leu Thr Leu Ser Ala Gln Gly Ala Glu Lys Thr
 65                  70                  75                  80

Phe Lys Ala Gly Asp Lys Asp Asn Ser Leu Asn Thr Gly Lys Leu Lys
                 85                  90                  95

Asn Asp Lys Ile Ser Arg Phe Asp Phe Val Gln Lys Ile Glu Val Asp
             100                 105                 110

Gly Gln Thr Ile Thr Leu Ala Ser Gly Glu Phe Gln Ile Tyr Lys Gln
         115                 120                 125

Asn His Ser Ala Val Val Ala Leu Gln Ile Glu Lys Ile Asn Asn Pro
 130                 135                 140

Asp Lys Thr Asp Ser Leu Ile Asn Gln Arg Ser Phe Leu Val Ser Gly
145                 150                 155                 160

Leu Gly Gly Glu His Thr Ala Phe Asn Gln Leu Pro Gly Gly Lys Ala
                165                 170                 175

Glu Tyr His Gly Lys Ala Phe Ser Ser Asp Pro Asn Gly Arg Leu
            180                 185                 190

His Tyr Ser Ile Asp Phe Thr Lys Lys Gln Gly Tyr Gly Arg Ile Glu
        195                 200                 205

His Leu Lys Thr Leu Glu Gln Asn Val Glu Leu Ala Ala Glu Leu
    210                 215                 220

Lys Ala Asp Glu Lys Ser His Ala Val Ile Leu Gly Asp Thr Arg Tyr
225                 230                 235                 240

Gly Ser Glu Glu Lys Gly Thr Tyr His Leu Ala Leu Phe Gly Asp Arg
                245                 250                 255

Ala Gln Glu Ile Ala Gly Ser Ala Thr Val Lys Ile Gly Glu Lys Val
            260                 265                 270

His Glu Ile Gly Ile Ala Gly Lys Gln
        275                 280

<210> SEQ ID NO 77
<211> LENGTH: 274
<212> TYPE: PRT
<213> ORGANISM: Neisseria meningitidis

<400> SEQUENCE: 77

Val Asn Arg Thr Ala Phe Cys Cys Leu Ser Leu Thr Thr Ala Leu Ile
 1               5                  10                  15

Leu Thr Ala Cys Ser Ser Gly Gly Gly Cys Ala Ala Asp Ile Gly
             20                  25                  30

Ala Gly Leu Ala Asp Ala Leu Thr Ala Pro Leu Asp His Lys Asp Lys
         35                  40                  45

Gly Leu Gln Ser Leu Thr Leu Asp Gln Ser Val Arg Lys Asn Glu Lys
 50                  55                  60

Leu Lys Leu Ala Ala Gln Gly Ala Glu Lys Thr Tyr Gly Asn Gly Asp
 65                  70                  75                  80

Ser Leu Asn Thr Gly Lys Leu Lys Asn Asp Lys Val Ser Arg Phe Asp
                 85                  90                  95

Phe Ile Arg Gln Ile Glu Val Asp Gly Gln Leu Ile Thr Leu Glu Ser
             100                 105                 110

Gly Glu Phe Gln Val Tyr Lys Gln Ser His Ser Ala Leu Thr Ala Phe
         115                 120                 125
```

Gln Thr Glu Gln Ile Gln Asp Ser Glu His Ser Gly Lys Met Val Ala
    130                 135                 140

Lys Arg Gln Phe Arg Ile Gly Asp Ile Ala Gly Glu His Thr Ser Phe
145                 150                 155                 160

Asp Lys Leu Pro Glu Gly Gly Arg Ala Thr Tyr Arg Gly Thr Ala Phe
                165                 170                 175

Gly Ser Asp Asp Ala Gly Gly Lys Leu Thr Tyr Thr Ile Asp Phe Ala
            180                 185                 190

Ala Lys Gln Gly Asn Gly Lys Ile Glu His Leu Lys Ser Pro Glu Leu
        195                 200                 205

Asn Val Asp Leu Ala Ala Asp Ile Lys Pro Asp Gly Lys Arg His
210                 215                 220

Ala Val Ile Ser Gly Ser Val Leu Tyr Asn Gln Ala Glu Lys Gly Ser
225                 230                 235                 240

Tyr Ser Leu Gly Ile Phe Gly Gly Lys Ala Gln Glu Val Ala Gly Ser
                245                 250                 255

Ala Glu Val Lys Thr Val Asn Gly Ile Arg His Ile Gly Leu Ala Ala
            260                 265                 270

Lys Gln

<210> SEQ ID NO 78
<211> LENGTH: 274
<212> TYPE: PRT
<213> ORGANISM: Neisseria meningitidis

<400> SEQUENCE: 78

Val Asn Arg Thr Ala Phe Cys Cys Leu Ser Leu Thr Thr Ala Leu Ile
1               5                   10                  15

Leu Thr Ala Cys Ser Ser Gly Gly Gly Cys Ala Ala Asp Ile Gly
            20                  25                  30

Ala Gly Leu Ala Asp Ala Leu Thr Ala Pro Leu Asp His Lys Asp Lys
        35                  40                  45

Gly Leu Gln Ser Leu Met Leu Asp Gln Ser Val Arg Lys Asn Glu Lys
    50                  55                  60

Leu Lys Leu Ala Ala Gln Gly Ala Glu Lys Thr Tyr Gly Asn Gly Asp
65                  70                  75                  80

Ser Leu Asn Thr Gly Lys Leu Lys Asn Asp Lys Val Ser Arg Phe Asp
                85                  90                  95

Phe Ile Arg Gln Ile Glu Val Asp Gly Gln Leu Ile Thr Leu Glu Ser
            100                 105                 110

Gly Glu Phe Gln Val Tyr Lys Gln Ser His Ser Ala Leu Thr Ala Leu
        115                 120                 125

Gln Thr Glu Gln Val Gln Asp Ser Glu Asp Ser Gly Lys Met Val Ala
    130                 135                 140

Lys Arg Gln Phe Arg Ile Gly Asp Ile Ala Gly Glu His Thr Ser Phe
145                 150                 155                 160

Asp Lys Leu Pro Lys Asp Val Met Ala Thr Tyr Arg Gly Thr Ala Phe
                165                 170                 175

Gly Ser Asp Asp Ala Gly Gly Lys Leu Thr Tyr Thr Ile Asp Phe Ala
            180                 185                 190

Ala Lys Gln Gly His Gly Lys Ile Glu His Leu Lys Ser Pro Glu Leu
        195                 200                 205

Asn Val Asp Leu Ala Ala Ala Tyr Ile Lys Pro Asp Glu Lys His His
210                 215                 220

```
Ala Val Ile Ser Gly Ser Val Leu Tyr Asn Gln Ala Glu Lys Gly Ser
225                 230                 235                 240

Tyr Ser Leu Gly Ile Phe Gly Gly Lys Ala Gln Glu Val Ala Gly Ser
                245                 250                 255

Ala Glu Val Lys Thr Val Asn Gly Ile Arg His Ile Gly Leu Ala Ala
            260                 265                 270

Lys Gln

<210> SEQ ID NO 79
<211> LENGTH: 274
<212> TYPE: PRT
<213> ORGANISM: Neisseria meningitidis

<400> SEQUENCE: 79

Val Asn Arg Thr Thr Phe Cys Cys Leu Ser Leu Thr Ala Ala Leu Ile
1               5                   10                  15

Leu Thr Ala Cys Ser Ser Gly Gly Gly Cys Ala Ala Asp Ile Gly
            20                  25                  30

Ala Gly Leu Ala Asp Ala Leu Thr Ala Pro Leu Asp His Lys Asp Lys
        35                  40                  45

Gly Leu Gln Ser Leu Thr Leu Asp Gln Ser Val Arg Lys Asn Glu Lys
    50                  55                  60

Leu Lys Leu Ala Ala Gln Gly Ala Glu Lys Thr Tyr Gly Asn Gly Asp
65                  70                  75                  80

Ser Leu Asn Thr Gly Lys Leu Lys Asn Asp Lys Val Ser Arg Phe Asp
                85                  90                  95

Phe Ile Arg Gln Ile Glu Val Asn Gly Gln Leu Ile Thr Leu Glu Ser
            100                 105                 110

Gly Glu Phe Gln Val Tyr Lys Gln Ser His Ser Ala Leu Thr Ala Leu
        115                 120                 125

Gln Thr Glu Gln Val Gln Asp Ser Glu His Ser Arg Lys Met Val Ala
    130                 135                 140

Lys Arg Gln Phe Arg Ile Gly Asp Ile Ala Gly Glu His Thr Ser Phe
145                 150                 155                 160

Asp Lys Leu Pro Lys Gly Asp Ser Ala Thr Tyr Arg Gly Thr Ala Phe
                165                 170                 175

Gly Ser Asp Asp Ala Gly Gly Lys Leu Thr Tyr Thr Ile Asp Phe Ala
            180                 185                 190

Ala Lys Gln Gly Tyr Gly Lys Ile Glu His Leu Lys Ser Pro Glu Leu
        195                 200                 205

Asn Val Asp Leu Ala Ala Ala Tyr Ile Lys Pro Asp Glu Lys His His
    210                 215                 220

Ala Val Ile Ser Gly Ser Val Leu Tyr Asn Gln Asp Glu Lys Gly Ser
225                 230                 235                 240

Tyr Ser Leu Gly Ile Phe Gly Gly Gln Ala Gln Glu Val Ala Gly Ser
                245                 250                 255

Ala Glu Val Lys Thr Ala Asn Gly Ile Arg His Ile Gly Leu Ala Ala
            260                 265                 270

Lys Gln

<210> SEQ ID NO 80
<211> LENGTH: 274
<212> TYPE: PRT
<213> ORGANISM: Neisseria meningitidis
```

<400> SEQUENCE: 80

```
Val Asn Arg Thr Thr Phe Cys Cys Phe Ser Leu Thr Ala Ala Leu Ile
1               5                   10                  15

Leu Thr Ala Cys Ser Ser Gly Gly Gly Cys Ala Ala Asp Ile Gly
            20                  25                  30

Ala Gly Leu Ala Asp Ala Leu Thr Ala Pro Leu Asp His Lys Asp Lys
        35                  40                  45

Ser Leu Gln Ser Leu Thr Leu Asp Gln Ser Val Arg Lys Asn Glu Lys
    50                  55                  60

Leu Lys Leu Ala Ala Gln Gly Ala Glu Lys Thr Tyr Gly Asn Gly Asp
65                  70                  75                  80

Ser Leu Asn Thr Gly Lys Leu Lys Asn Asp Lys Val Ser Arg Phe Asp
                85                  90                  95

Phe Ile Arg Gln Ile Glu Val Asp Gly Gln Leu Ile Thr Leu Glu Ser
            100                 105                 110

Gly Glu Phe Gln Val Tyr Lys Gln Ser His Ser Ala Leu Thr Ala Leu
        115                 120                 125

Gln Thr Glu Gln Glu Gln Asp Pro Glu His Ser Gly Lys Met Val Ala
    130                 135                 140

Lys Arg Arg Phe Lys Ile Gly Asp Ile Ala Gly Glu His Thr Ser Phe
145                 150                 155                 160

Asp Lys Leu Pro Lys Asp Val Met Ala Thr Tyr Arg Gly Thr Ala Phe
                165                 170                 175

Gly Ser Asp Asp Ala Gly Gly Lys Leu Thr Tyr Thr Ile Asp Phe Ala
            180                 185                 190

Ala Lys Gln Gly His Gly Lys Ile Glu His Leu Lys Ser Pro Glu Leu
        195                 200                 205

Asn Val Glu Leu Ala Thr Ala Tyr Ile Lys Pro Asp Glu Lys His His
    210                 215                 220

Ala Val Ile Ser Gly Ser Val Leu Tyr Asn Gln Asp Glu Lys Gly Ser
225                 230                 235                 240

Tyr Ser Leu Gly Ile Phe Gly Gly Gln Ala Gln Glu Val Ala Gly Ser
                245                 250                 255

Ala Glu Val Glu Thr Ala Asn Gly Ile His His Ile Gly Leu Ala Ala
            260                 265                 270

Lys Gln
```

<210> SEQ ID NO 81
<211> LENGTH: 274
<212> TYPE: PRT
<213> ORGANISM: Neisseria meningitidis

<400> SEQUENCE: 81

```
Val Asn Arg Thr Thr Phe Cys Cys Phe Ser Leu Thr Ala Ala Leu Ile
1               5                   10                  15

Leu Thr Ala Cys Ser Ser Gly Gly Gly Cys Ala Ala Asp Ile Gly
            20                  25                  30

Ala Gly Leu Ala Asp Ala Leu Thr Ala Pro Leu Asp His Lys Asp Lys
        35                  40                  45

Ser Leu Gln Ser Leu Thr Leu Asp Gln Ser Val Arg Lys Asn Glu Lys
    50                  55                  60

Leu Lys Leu Ala Ala Gln Gly Ala Glu Lys Thr Tyr Gly Asn Gly Asp
65                  70                  75                  80

Ser Leu Asn Thr Gly Lys Leu Lys Asn Asp Lys Val Ser Arg Phe Asp
```

```
                    85                  90                  95
Phe Ile Arg Gln Ile Glu Val Asp Gly Gln Leu Ile Thr Leu Glu Ser
                100                 105                 110
Gly Glu Phe Gln Val Tyr Lys Gln Ser His Ser Ala Leu Thr Ala Leu
            115                 120                 125
Gln Thr Glu Gln Val Gln Asp Ser Glu His Ser Gly Lys Met Val Ala
        130                 135                 140
Lys Arg Gln Phe Arg Ile Gly Asp Ile Ala Gly Glu His Thr Ser Phe
145                 150                 155                 160
Asp Lys Leu Pro Glu Gly Gly Arg Ala Thr Tyr Arg Gly Thr Ala Phe
                165                 170                 175
Gly Ser Asp Asp Ala Ser Gly Lys Leu Thr Tyr Thr Ile Asp Phe Ala
            180                 185                 190
Ala Lys Gln Gly His Gly Lys Ile Glu His Leu Lys Ser Pro Glu Leu
        195                 200                 205
Asn Val Asp Leu Ala Ala Ser Asp Ile Lys Pro Asp Lys Lys Arg His
    210                 215                 220
Ala Val Ile Ser Gly Ser Val Leu Tyr Asn Gln Ala Glu Lys Gly Ser
225                 230                 235                 240
Tyr Ser Leu Gly Ile Phe Gly Gly Gln Ala Gln Glu Val Ala Gly Ser
                245                 250                 255
Ala Glu Val Glu Thr Ala Asn Gly Ile Arg His Ile Gly Leu Ala Ala
            260                 265                 270
Lys Gln

<210> SEQ ID NO 82
<211> LENGTH: 274
<212> TYPE: PRT
<213> ORGANISM: Neisseria meningitidis

<400> SEQUENCE: 82

Val Asn Arg Thr Thr Phe Cys Cys Phe Ser Leu Thr Ala Ala Leu Ile
1               5                   10                  15
Leu Thr Ala Cys Ser Ser Gly Gly Gly Cys Ala Ala Asp Ile Gly
            20                  25                  30
Ala Gly Leu Ala Asp Ala Leu Thr Ala Pro Leu Asp His Lys Asp Lys
        35                  40                  45
Ser Leu Gln Ser Leu Thr Leu Asp Gln Ser Val Arg Lys Asn Glu Lys
    50                  55                  60
Leu Lys Leu Ala Ala Gln Gly Ala Glu Lys Thr Tyr Gly Asn Gly Asp
65                  70                  75                  80
Ser Leu Asn Thr Gly Lys Leu Lys Asn Asp Lys Val Ser Arg Phe Asp
                85                  90                  95
Phe Ile Arg Gln Ile Glu Val Asp Gly Gln Leu Ile Thr Leu Glu Ser
                100                 105                 110
Gly Glu Phe Gln Ile Tyr Lys Gln Asp His Ser Ala Val Val Ala Leu
            115                 120                 125
Gln Ile Glu Lys Ile Asn Asn Pro Asp Lys Ile Asp Ser Leu Ile Asn
        130                 135                 140
Gln His Gly Lys Ile Glu Arg Ser Phe Leu Val Ser Gly Leu Gly Gly
145                 150                 155                 160
Glu His Thr Ala Phe Asn Gln Leu Pro Asp Gly Gly Lys Ala Glu Tyr
                165                 170                 175
His Gly Lys Ala Phe Ser Ser Asp Asp Ala Gly Gly Lys Leu Thr Tyr
```

```
                    180                 185                 190
Thr Ile Asp Phe Ala Ala Lys Gln Gly His Leu Lys Thr Pro Glu Gln
                195                 200                 205

Asn Val Glu Leu Ala Ala Ala Glu Leu Lys Ala Asp Glu Lys Ser His
            210                 215                 220

Ala Val Ile Leu Gly Asp Thr Arg Tyr Gly Ser Glu Lys Gly Thr
225                 230                 235                 240

Tyr His Leu Ala Leu Phe Gly Asp Arg Ala Gln Glu Ile Ala Gly Ser
                245                 250                 255

Ala Thr Val Lys Ile Gly Glu Lys Val His Glu Ile Gly Ile Ala Gly
                260                 265                 270

Lys Gln

<210> SEQ ID NO 83
<211> LENGTH: 274
<212> TYPE: PRT
<213> ORGANISM: Neisseria meningitidis

<400> SEQUENCE: 83

Val Asn Arg Thr Ala Phe Cys Cys Leu Ser Leu Thr Thr Ala Leu Ile
1               5                   10                  15

Leu Thr Ala Cys Ser Ser Gly Gly Gly Val Ala Ala Asp Ile Gly
                20                  25                  30

Ala Gly Leu Ala Asp Ala Leu Thr Ala Pro Leu Asp His Lys Asp Lys
            35                  40                  45

Gly Leu Gln Ser Leu Thr Leu Asp Gln Ser Val Arg Lys Asn Glu Lys
        50                  55                  60

Leu Lys Leu Ala Ala Gln Gly Arg Glu Lys Thr Tyr Gly Asn Gly Asp
65                  70                  75                  80

Ser Leu Asn Thr Gly Lys Leu Lys Asn Asp Lys Val Ser Arg Phe Asp
                85                  90                  95

Phe Ile Arg Gln Ile Glu Val Asp Gly Gln Leu Ile Thr Leu Glu Ser
                100                 105                 110

Gly Glu Phe Gln Val Tyr Lys Gln Ser His Ser Ala Leu Thr Ala Phe
            115                 120                 125

Gln Thr Glu Gln Ile Gln Asp Ser Glu His Ser Gly Lys Met Val Ala
130                 135                 140

Lys Arg Gln Phe Arg Ile Gly Asp Ile Ala Gly Glu His Thr Ser Phe
145                 150                 155                 160

Asp Lys Leu Pro Glu Gly Gly Arg Ala Thr Tyr Arg Gly Thr Ala Phe
                165                 170                 175

Gly Ser Asp Asp Ala Gly Gly Lys Leu Thr Tyr Thr Ile Asp Phe Ala
            180                 185                 190

Ala Lys Gln Gly Asn Gly Lys Ile Glu His Leu Lys Ser Pro Glu Leu
        195                 200                 205

Asn Val Asp Leu Ala Ala Ala Asp Ile Lys Pro Asp Gly Lys Arg His
    210                 215                 220

Ala Val Ile Ser Gly Ser Val Leu Tyr Asn Gln Ala Glu Lys Gly Ser
225                 230                 235                 240

Tyr Ser Leu Gly Ile Phe Gly Gly Lys Ala Gln Glu Val Ala Gly Ser
                245                 250                 255

Ala Glu Val Lys Thr Val Asn Gly Ile Arg His Ile Gly Leu Ala Ala
            260                 265                 270

Lys Gln
```

<210> SEQ ID NO 84
<211> LENGTH: 274
<212> TYPE: PRT
<213> ORGANISM: Neisseria meningitidis

<400> SEQUENCE: 84

Met Asn Arg Thr Ala Phe Cys Cys Leu Ser Leu Thr Ala Ala Leu Ile
1               5                   10                  15

Leu Thr Ala Cys Ser Ser Gly Gly Gly Val Ala Ala Asp Ile Gly
            20                  25                  30

Ala Gly Leu Ala Asp Ala Leu Thr Ala Pro Leu Asp His Lys Asp Lys
        35                  40                  45

Ser Leu Gln Ser Leu Thr Leu Asp Gln Ser Val Arg Lys Asn Glu Lys
    50                  55                  60

Leu Lys Leu Ala Ala Gln Gly Arg Glu Lys Thr Tyr Gly Asn Gly Asp
65                  70                  75                  80

Ser Leu Asn Thr Gly Lys Leu Lys Asn Asp Lys Val Ser Arg Phe Asp
                85                  90                  95

Phe Ile Arg Gln Ile Glu Val Asp Gly Gln Leu Ile Thr Leu Glu Ser
            100                 105                 110

Gly Glu Phe Gln Val Tyr Lys Gln Ser His Ser Ala Leu Thr Ala Leu
        115                 120                 125

Gln Thr Glu Gln Val Gln Asp Ser Glu His Ser Gly Lys Met Val Ala
    130                 135                 140

Lys Arg Gln Phe Arg Ile Gly Asp Ile Ala Gly Glu His Thr Ser Phe
145                 150                 155                 160

Asp Lys Leu Pro Glu Gly Gly Arg Ala Thr Tyr Arg Gly Thr Ala Phe
                165                 170                 175

Gly Ser Asp Asp Ala Ser Gly Lys Leu Thr Tyr Thr Ile Asp Phe Ala
            180                 185                 190

Ala Lys Gln Gly His Gly Lys Ile Glu His Leu Lys Ser Pro Glu Leu
        195                 200                 205

Asn Val Asp Leu Ala Ala Ser Asp Ile Lys Pro Asp Lys Lys Arg His
    210                 215                 220

Ala Val Ile Ser Gly Ser Val Leu Tyr Asn Gln Ala Glu Lys Gly Ser
225                 230                 235                 240

Tyr Ser Leu Gly Ile Phe Gly Gly Gln Ala Gln Glu Val Ala Gly Ser
                245                 250                 255

Ala Glu Val Glu Thr Ala Asn Gly Ile Arg His Ile Gly Leu Ala Ala
            260                 265                 270

Lys Gln

<210> SEQ ID NO 85
<211> LENGTH: 12
<212> TYPE: PRT
<213> ORGANISM: Neisseria meningitidis

<400> SEQUENCE: 85

Pro Leu Gln Asn Ile Gln Pro Gln Val Thr Lys Arg
1               5                   10

<210> SEQ ID NO 86
<211> LENGTH: 20
<212> TYPE: PRT
<213> ORGANISM: Neisseria meningitidis

```
<400> SEQUENCE: 86

Ala Gln Ala Ala Asn Gly Gly Ala Ser Gly Gln Val Lys Val Thr Lys
1               5                   10                  15

Val Thr Lys Ala
            20

<210> SEQ ID NO 87
<211> LENGTH: 18
<212> TYPE: PRT
<213> ORGANISM: Neisseria meningitidis

<400> SEQUENCE: 87

Lys Leu Ser Ser Thr Asn Ala Lys Thr Gly Asn Lys Val Glu Val Thr
1               5                   10                  15

Lys Ala

<210> SEQ ID NO 88
<211> LENGTH: 14
<212> TYPE: PRT
<213> ORGANISM: Neisseria meningitidis

<400> SEQUENCE: 88

Pro Pro Gln Lys Asn Gln Ser Gln Pro Val Val Thr Lys Ala
1               5                   10

<210> SEQ ID NO 89
<211> LENGTH: 14
<212> TYPE: PRT
<213> ORGANISM: Neisseria meningitidis

<400> SEQUENCE: 89

Pro Pro Ser Lys Gly Gln Thr Gly Asn Lys Val Thr Lys Gly
1               5                   10

<210> SEQ ID NO 90
<211> LENGTH: 14
<212> TYPE: PRT
<213> ORGANISM: Neisseria meningitidis

<400> SEQUENCE: 90

Pro Pro Ser Lys Ser Gln Pro Gln Val Lys Val Thr Lys Ala
1               5                   10

<210> SEQ ID NO 91
<211> LENGTH: 18
<212> TYPE: PRT
<213> ORGANISM: Neisseria meningitidis

<400> SEQUENCE: 91

Gln Pro Gln Thr Ala Asn Thr Gln Gln Gly Gly Lys Val Lys Val Thr
1               5                   10                  15

Lys Ala

<210> SEQ ID NO 92
<211> LENGTH: 18
<212> TYPE: PRT
<213> ORGANISM: Neisseria meningitidis

<400> SEQUENCE: 92

Gln Pro Gln Val Thr Asn Gly Val Gln Gly Asn Gln Val Lys Val Thr
1               5                   10                  15

Lys Ala
```

```
<210> SEQ ID NO 93
<211> LENGTH: 18
<212> TYPE: PRT
<213> ORGANISM: Neisseria meningitidis

<400> SEQUENCE: 93

Gln Pro Ser Lys Ala Gln Gly Gln Thr Asn Asn Gln Val Lys Val Thr
1               5                   10                  15

Lys Ala

<210> SEQ ID NO 94
<211> LENGTH: 20
<212> TYPE: PRT
<213> ORGANISM: Neisseria meningitidis

<400> SEQUENCE: 94

Pro Pro Ser Ser Asn Gln Gly Lys Asn Gln Ala Gln Thr Gly Asn Thr
1               5                   10                  15

Val Thr Lys Ala
            20

<210> SEQ ID NO 95
<211> LENGTH: 13
<212> TYPE: PRT
<213> ORGANISM: Neisseria meningitidis

<400> SEQUENCE: 95

Tyr Val Ala Val Glu Asn Gly Val Ala Lys Lys Val Ala
1               5                   10

<210> SEQ ID NO 96
<211> LENGTH: 15
<212> TYPE: PRT
<213> ORGANISM: Neisseria meningitidis

<400> SEQUENCE: 96

His Phe Val Gln Gln Thr Pro Lys Ser Gln Pro Thr Leu Val Pro
1               5                   10                  15

<210> SEQ ID NO 97
<211> LENGTH: 14
<212> TYPE: PRT
<213> ORGANISM: Neisseria meningitidis

<400> SEQUENCE: 97

Thr Leu Ala Asn Gly Ala Asn Asn Thr Ile Ile Arg Val Pro
1               5                   10

<210> SEQ ID NO 98
<211> LENGTH: 13
<212> TYPE: PRT
<213> ORGANISM: Neisseria meningitidis

<400> SEQUENCE: 98

His Val Val Val Asn Asn Lys Val Ala Thr His Val Pro
1               5                   10

<210> SEQ ID NO 99
<211> LENGTH: 10
<212> TYPE: PRT
<213> ORGANISM: Neisseria meningitidis
```

```
<400> SEQUENCE: 99

Tyr Val Asp Glu Gln Ser Lys Tyr His Ala
1               5                   10

<210> SEQ ID NO 100
<211> LENGTH: 15
<212> TYPE: PRT
<213> ORGANISM: Neisseria meningitidis

<400> SEQUENCE: 100

His Phe Val Gln Asn Lys Gln Asn Gln Arg Pro Thr Leu Val Pro
1               5                   10                  15

<210> SEQ ID NO 101
<211> LENGTH: 18
<212> TYPE: PRT
<213> ORGANISM: Neisseria meningitidis

<400> SEQUENCE: 101

Tyr Trp Thr Thr Val Asn Thr Gly Ser Ala Thr Thr Thr Thr Phe
1               5                   10                  15

Val Pro

<210> SEQ ID NO 102
<211> LENGTH: 10
<212> TYPE: PRT
<213> ORGANISM: Neisseria meningitidis

<400> SEQUENCE: 102

Tyr Val Asp Glu Lys Lys Met Val His Ala
1               5                   10

<210> SEQ ID NO 103
<211> LENGTH: 13
<212> TYPE: PRT
<213> ORGANISM: Neisseria meningitidis

<400> SEQUENCE: 103

His Tyr Thr Arg Gln Asn Asn Ala Asp Val Phe Val Pro
1               5                   10

<210> SEQ ID NO 104
<211> LENGTH: 14
<212> TYPE: PRT
<213> ORGANISM: Neisseria meningitidis

<400> SEQUENCE: 104

Tyr Tyr Thr Lys Asp Thr Asn Asn Asn Leu Thr Leu Val Pro
1               5                   10

<210> SEQ ID NO 105
<211> LENGTH: 17
<212> TYPE: PRT
<213> ORGANISM: Neisseria meningitidis

<400> SEQUENCE: 105

His Trp Asn Thr Val Tyr Asn Thr Asn Gly Thr Thr Thr Thr Phe Val
1               5                   10                  15

Pro
```

```
<210> SEQ ID NO 106
<211> LENGTH: 14
<212> TYPE: PRT
<213> ORGANISM: Neisseria meningitidis

<400> SEQUENCE: 106

Thr Tyr Thr Val Asp Ser Ser Gly Val Val Thr Pro Val Pro
1               5                   10

<210> SEQ ID NO 107
<211> LENGTH: 14
<212> TYPE: PRT
<213> ORGANISM: Neisseria meningitidis

<400> SEQUENCE: 107

His Phe Val Ala Asp Ser Gln Gly Lys Ile Thr Arg Val Pro
1               5                   10

<210> SEQ ID NO 108
<211> LENGTH: 17
<212> TYPE: PRT
<213> ORGANISM: Neisseria meningitidis

<400> SEQUENCE: 108

Tyr Tyr Tyr Thr Thr Ala Thr Asn Ser Ser Thr Ser Thr Thr Phe Val
1               5                   10                  15
Pro

<210> SEQ ID NO 109
<211> LENGTH: 17
<212> TYPE: PRT
<213> ORGANISM: Neisseria meningitidis

<400> SEQUENCE: 109

His Tyr Thr Thr Val Tyr Asn Ala Thr Thr Thr Thr Thr Thr Phe Val
1               5                   10                  15
Pro

<210> SEQ ID NO 110
<211> LENGTH: 11
<212> TYPE: PRT
<213> ORGANISM: Neisseria meningitidis

<400> SEQUENCE: 110

Tyr Val Asp Asp Gln Gly Lys Val Lys Gly Pro
1               5                   10

<210> SEQ ID NO 111
<211> LENGTH: 13
<212> TYPE: PRT
<213> ORGANISM: Neisseria meningitidis

<400> SEQUENCE: 111

Thr Phe Thr Leu Glu Ser Asn Gln Met Lys Pro Val Pro
1               5                   10
```